(12) United States Patent
Satoh et al.

(10) Patent No.: US 7,429,599 B2
(45) Date of Patent: *Sep. 30, 2008

(54) METHODS FOR TREATING OR PREVENTING AN INFLAMMATORY OR METABOLIC CONDITION OR INHIBITING JNK

(75) Inventors: Yoshitaka Satoh, San Diego, CA (US); Shripad S. Bhagwat, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 711 days.

This patent is subject to a terminal disclaimer.

(21) Appl. No.: 10/395,811

(22) Filed: Mar. 24, 2003

(65) Prior Publication Data
US 2004/0106634 A1   Jun. 3, 2004

Related U.S. Application Data

(63) Continuation-in-part of application No. 10/004,645, filed on Dec. 4, 2001, now Pat. No. 7,129,242.

(60) Provisional application No. 60/251,904, filed on Dec. 6, 2000.

(51) Int. Cl.
*A61K 31/505* (2006.01)
*A61K 31/50* (2006.01)
*A61K 31/497* (2006.01)

(52) U.S. Cl. .................. 514/275; 514/247; 514/253.01; 514/256

(58) Field of Classification Search .................. 514/247, 514/253, 256
See application file for complete search history.

(56) References Cited

U.S. PATENT DOCUMENTS

| | | | |
|---|---|---|---|
| 3,994,890 A | | 11/1976 | Fujimura |
| 4,415,569 A | | 11/1983 | Yasuo et al. |
| 4,788,195 A | * | 11/1988 | Torley et al. ........... 514/252.18 |
| 4,876,252 A | | 10/1989 | Torley et al. |
| 5,516,775 A | * | 5/1996 | Zimmermann et al. ... 514/224.2 |
| 6,114,333 A | | 9/2000 | Davis et al. |
| 6,162,613 A | | 12/2000 | Su et al. |
| 6,361,760 B1 | | 3/2002 | Murata et al. |
| 6,531,491 B1 | | 3/2003 | Kania et al. |
| 6,534,524 B1 | | 3/2003 | Kania et al. |

FOREIGN PATENT DOCUMENTS

| | | |
|---|---|---|
| DE | 12 66 763 B | 4/1968 |
| EP | 0 494 774 | 7/1992 |
| EP | 0 518 805 | 12/1992 |
| GB | 1293557 | 9/1970 |
| GB | 2 345 486 A | 7/2000 |
| WO | WO 98/43969 | 10/1998 |
| WO | WO 99/53927 | 10/1999 |
| WO | WO 01/12609 | 2/2001 |
| WO | WO 01/12621 A1 | 2/2001 |
| WO | WO 02/46170 A2 | 6/2002 |
| WO | WO 02/085396 | 10/2002 |

OTHER PUBLICATIONS

Adam et al., 1999, J. of Vascular Surgery 30/4:641-650.
Aspenström et al., 1996, "Two GTPases, Cdc42 and Rac, bind directly to a protein implicated in the immunodeficiency disorder Wiskott-Aldrich syndrome", Curr. Biol. 6:70-75.
Chen et al., 1996, "Activation and inhibition of the AP-1 complex in human breast cancer cells", Mol. Carcinogenesis 15:215-226.
Dong et al., 1998, "Defective T cell differentiation in the absence of Jnk1", Science 282:2092-2095.
Faris et al., 1996, "Regulation of interleukin-2 transcription by inducible stabile expression of dominant negative and dominant active mitogen-activated protein kinase kinase kinase in Jurkat T cells", J. Biol. Chem. 271:27366-27373.
Gum et al., 1997, "Regulation of 92 kDa type IV collagenase expression by the jun aminoterminal kinase- and the extracellular signal-regulated kinase- dependent signaling cascades", Oncogene 14:1481-1493.
Han et al., 1999, "Jun N-terminal kinase in rheumatoid arthritis", J. Pharmacol. Exp. Therap. 291:124-130.
Hibi et al., 1993, "Identification of an oncoprotein- and UV-responsive protein kinase that binds and potentiates the c-Jun activation domain", Genes Dev. 7:2135-2148.
Ishizuka et al., 1997, "Mast cell tumor necrosis factor α production is regulated by MEK kinases", Proc. Natl. Acad. Sci. USA 94:6358-6363.
Karin et al., 1997, "AP-1 function and regulation", Curr. Opin. Cell. Biol. U9:240-246.
Lange-Carter et al., 1993, "A divergence in the MAP kinase regulatory network defined by MEK kinase and Raf", Science 260:315-319.

(Continued)

*Primary Examiner*—Jennifer Kim
(74) *Attorney, Agent, or Firm*—Jones Day

(57) ABSTRACT

This invention generally relates to methods for treating or preventing a condition responsive to JNK inhibition, such as a metabolic condition, comprising administering to a patient in need thereof an effective amount of an Anilinopyrimidine Derivative having the following structure:

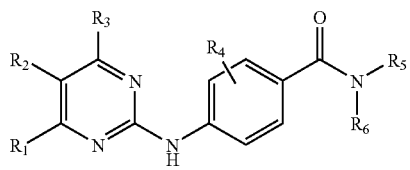

or a pharmaceutically acceptable salt thereof, wherein $R_1$ through $R_6$ are as defined herein.

4 Claims, No Drawings

OTHER PUBLICATIONS

Li et al., 1996, "Blocked signal transduction to the ERK and JNK protein kinases in anergic CD4+ T cells", Science 271:1272-1276.

Li et al., 1996, "The Ras-JNK pathway is involved in shear-induced gene expression", Mol. Cell. Biol. 16:5947-5954.

Lin et al., 1995, "Identification of a dual specificity kinase that activates the Jun kinases and p38-Mpk2", Science 268:286-290.

Manning and Mercurio, 1997, "Transcription inhibitors in inflammation", Exp. Opin. Invest. Drugs 6:555-567.

Milne et al., 1995, "p53 is phosphorylated in vitro and in vivo by an ultraviolet radiation-induced protein kinase characteristic of the c-Jun kinase, JNK1", J. Biol. Chem. 270:5511-5518.

Mohit et al., 1995, "p493F12 kinase: a novel MAP kinase expressed in a subset of neurons in the human nervous system", Neuron 14:67-78.

Nishina et al., 1997, "Impaired CD28-mediated interleukin 2 production and proliferation in stress kinase SAPK/ERK1 kinase (SEK1)/mitogen-activated protein kinase kinase 4 (MKK4)-deficient T lymphocytes", J. Exp. Med. 186:941-953.

Okamoto et al., 1997, "Selective activation of the JNK/AP-1 pathway in Fas-mediated apoptosis of rheumatoid arthritis synoviocytes", Arthritis & Rheumatism 40:919-926.

Pombo et al., 1994, "The stress-activated protein kinases are major c-Jun amino-terminal kinases activated by ischemia and reperfusion", J. Biol. Chem. 269:26546-26551.

Raitano et al., 1995, "The Bcr-Abl leukemia oncogene activates Jun kinase and requires Jun for transformation", Proc.Natl. Acad. Sci. USA 92:11746-11750.

Sabapathy et al., 1999, "JNK2 is required for efficient T-cell activation and apoptosis but not for normal lymphocyte development", Curr. Biol. 9:116-125.

Su et al., 1994, "JNK is involved in signal integration during costimulation of T lymphocytes", Cell 77:727-736.

Swantek et al., 1997, "Jun N-terminal kinase/stress-activated protein kinase (JNK/SAPK) is required for lipopolysaccharide stimulation of tumor necrosis factor alpha (TNF-$\alpha$) translation: glucocorticoids inhibit TNF-$\alpha$ translation by blocking JNK/SAPK", Mol. Cell. Biol. 17:6274-6282.

Szabo et al., 1996, "Altered cJUN expression: an early event in human lung carcinogenesis", Cancer Res. 56:305-315.

Tournier et al., 1997, "Mitogen-activated protein kinase kinase 7 is an activator of the c-Jun NH2-terminal kinase", Proc. Natl. Acad. Sci. USA 94:7337-7342.

Whitmarsh and Davis, 1996, "Transcription factor AP-1 regulation by mitogen-activated protein kinase signal transduction pathways", Mol. Med. 74:589-607.

Yan et al., 1994, "Activation of stress-activated protein kinase by MEKK1 phosphorylation of its activator SEK1", Nature 372:798-800.

Yang et al., 1998, "Differentiation of CD4+ T cells to Th1 cells requires MAP kinase JNK2", Immunity 9:575-585.

Yin et al., 1997, "Tissue-specific pattern of stress kinase activation in ischemic/reperfused heart and kidney", J. Biol. Chem. 272:19943-19950.

Spiegelman et al., 1993 "Regulation of Adipocyte Gene Expression in Differentiation and Syndromes of Obesity/Diabetes", *J. of Biol. Chem. 268*:6823-6826.

Hirosumi et al., 2002 "A central role for JNK in obesity and insulin resistance", *Letters to Nature 420*:333-336.

* cited by examiner

METHODS FOR TREATING OR PREVENTING AN INFLAMMATORY OR METABOLIC CONDITION OR INHIBITING JNK

This application is a continuation-in-part of U.S. application Ser. No. 10/004,645 filed Dec. 4, 2001 now U.S. Pat. No. 7,129,242 which claims the benefit of U.S. Provisional Application No. 60/251,904, filed Dec. 6, 2000, each of which is incorporated by reference herein in its entirety.

1. FIELD OF THE INVENTION

This invention is generally directed to Anilinopyrimidines and derivatives thereof which have utility over a wide range of indications, including activity as Jun N-terminal kinase inhibitors, and related compositions and methods.

2. BACKGROUND OF THE INVENTION

The Jun N-terminal kinase (JNK) pathway is activated by exposure of cells to environment stress or by treatment of cells with pro-inflammatory cytokines. Targets of the JNK pathway include the transcription factors c-jun and ATF-2 (Whitmarsh A. J., and Davis R. J. *J. Mol. Med.* 74:589-607, 1996). These transcription factors are members of the basic leucine zipper (bZIP) group that bind as homo- and heterodimeric complexes to AP-1 and AP-1-like sites in the promoters of many genes (Karin M., Liu Z. G. and Zandi E. *Curr Opin Cell Biol* 9:240-246, 1997). JNK binds to the N-terminal region of c-jun and ATF-2 and phosphorylates two sites within the activation domain of each transcription factor (Hibi M., Lin A., Smeal T., Minden A., Karin M. *Genes Dev.* 7:2135-2148, 1993; Mohit A. A., Martin M. H., and Miller C. A. *Neuron* 14:67-75, 1995). Three JNK enzymes have been identified as products of distinct genes (Hibi et al, supra; Mohit et al., supra). Ten different isoforms of JNK have been identified. These represent alternatively spliced forms of three different genes: JNK1, JNK2 and JNK3. JNK1 and 2 are ubiquitously expressed in human tissues, whereas JNK3 is selectively expressed in the brain, heart and testis (Dong, C., Yang, D., Wysk, M., Whitmarsh, A., Davis, R., Flavell, R. *Science* 270:1-4, 1998). Gene transcripts are alternatively spliced to produce four-JNK1 isoformns, four-JNK2 isoforms and two-JNK3 isoforms. JNK1 and 2 are expressed widely in mammalian tissues, whereas JNK3 is expressed almost exclusively in the brain. Selectivity of JNK signaling is achieved via specific interactions of JNK pathway components and by use of scaffold proteins that selectively bind multiple components of the signaling cascade. JIP-1 (JNK-interacting protein-1) selectively binds the MAPK module, MLK→JNKK2→JNK.12,13. It has no binding affinity for a variety of other MAPK cascade enzymes. Different scaffold proteins are likely to exist for other MAPK signaling cascades to preserve substrate specificity.

JNKs are activated by dual phosphorylation on Thr-183 and Tyr-185. JNKK1 (also own as MKK-4) and JNKK2 (MKK-7), two MAPKK level enzymes, can mediate JNK activation in cells (Lin A., Minden A., Martinetto H., Claret F.-Z., Lange-Carter C., Mercurio F., Johnson G. L., and Karin M. *Science* 268:286-289, 1995; Tournier C., Whitmarsh A. J., Cavanagh J., Barrett T., and Davis R. J. *Proc. Nat. Acad. Sci. USA* 94:7337-7342, 1997). JNKK2 specifically phosphorylates JNK, whereas JNKK1 can also phosphorylate and activate p38. Both JNKK1 and JNKK2 are widely expressed in mammalian tissues. JNKK1 and JNKK2 are activated by the MAPKKK enzymes, MEKK-1, MEKK-2, MEKK-3 and MLK-3 (Lange-Carter C. A., Pleiman C. M., Gardner A. M., Blumer K. J., and Johnson G. L. *Science* 260:315-319, 1993; Yan M., Dai J. C., Deak J. C., Kyriakis J. M., Zon L. I., Woodgett J. R., and Templeton D. J. *Nature* 372:798-781, 1994; Deacon, K. and Blank, J., *J. Biol. Chem.* 274:16604-16610, 1999; Teramoto, H., Coso, O., Miyata, H., Igishi, T., Miki, T. and Gutkind, S., *J. Biol. Chem.* 271:27225-27228, 1996). Both MEKK-1 and MEKK-2 are widely expressed in mammalian tissues.

Activation of the JNK pathway has been documented in a number of disease settings, providing the rationale for targeting this pathway for drug discovery. In addition, molecular genetic approaches have validated the pathogenic role of this pathway in several diseases. For example, autoimmune and inflammatory diseases arise from the over-activation of the immune system. Activated immune cells express many genes encoding inflammatory molecules, including cytokines, growth factors, cell surface receptors, cell adhesion molecules and degradative enzymes. Many of these genes are regulated by the JNK pathway, through activation of the transcription factors AP-1 and ATF-2, including TNFα, IL-2, E-selectin and matrix metalloproteinases such as collagenase-1 (Manning A. M. and Mecurio F. *Exp. Opin. Invest. Drugs* 6: 555-567, 1997). Monocytes, tissue macrophages and tissue mast cells are key sources of TNFα production. The JNK pathway regulates TNFα production in bacterial lipopolysaccharide-stimulated macrophages, and in mast cells stimulated through the FceRII receptor (Swantek J. L., Cobb M. H., Geppert T. D. *Mol. Cell. Biol.* 17:6274-6282, 1997; Ishizuka, T., Tereda N., Gerwins, P., Hamelmann E., Oshiba A., Fanger G. R., Johnson G. L., and Gelfland E. W. *Proc. Nat. Acad. Sci. USA* 94:6358-6363, 1997). Inhibition of JNK activation effectively modulates TNFα secretion from these cells. The JNK pathway therefore regulates production of this key pro-inflammatory cytokine. International Publication No. WO 98/18782 to Celltech Therapeutics Limited discloses 4-pyridyl-pyrimidine compounds which are allegedly useful in the prophylaxis and treatment of immune diseases, allergic diseases involving mast cells or eosinophils, and diseases involving inappropriate platelet activation. Matrix metalloproteinases (MMPs) promote cartilage and bone erosion in rheumatoid arthritis, and generalized tissue destruction in other autoimmune diseases. Inducible expression of MMPs, including MMP-3 and MMP-9, type II and IV collagenases, are regulated via activation of the JNK pathway and AP-1 (Gum, R., Wang, H., Lengyel, E., Jurez, J., and Boyd, D. *Oncogene* 14:1481-1493, 1997). In human rheumatoid synoviocytes activated with TNFα, IL-1, or Fas ligand the JNK pathway is activated (Han Z., Boyle D. L., Aupperle K. R., Bennett B., Manning A. M., Firestein G. S. *J. Pharm. Exp. Therap.* 291:1-7, 1999; Okamoto K., Fujisawa K., Hasunuma T., Kobata T., Sumida T., and Nishioka K. *Arth & Rheum* 40: 919-92615, 1997). Inhibition of JNK activation results in decreased AP-1 activation and collagenase-1 expression (Han et al., supra). The JNK pathway therefore regulates MMP expression in cells involved in rheumatoid arthritis.

Inappropriate activation of T lymphocytes initiates and perpetuates many autoimmune diseases, including asthma, inflammatory bowel disease and multiple sclerosis. The JNK pathway is activated in T cells by antigen stimulation and CD28 receptor co-stimulation and regulates production of the growth factor IL-2 and cellular proliferation (Su B., Jacinto E., Hibi M., Kallunki T., Karin M., Ben-Neriah Y. *Cell* 77:727-736, 1994; Fans M., Kokot N., Lee L., and Nel A. E. *J. Biol. Chem.* 271:27366-27373, 1996). Peripheral T cells from mice genetically deficient in JNKK1 show decreased proliferation and IL-2 production after CD28 co-stimulation and PMA/Ca2+ ionophore activation, providing important validation for the role of the JNK pathway in these cells (Nishina H., Bachmann M., Oliveria-dos-Santos A. J., et al. *J. Exp. Med.* 186:941-953, 1997). It is known that T cells activated by antigen receptor stimulation in the absence of accessory cell-derived co-stimulatory signals lose the capacity to synthesize IL-2, a state called clonal anergy. This is an important process by which auto-reactive T cell populations are eliminated from the peripheral circulation. Of note, anergic T cells fail to activate the JNK pathway in response to CD3- and CD28-receptor co-stimulation, even though expression of the JNK enzymes is unchanged (Li W., Whaley C. D., Mondino A., and Mueller D. L. *Science* 271: 1272-1276, 1996). Recently, the examination of JNK-deficient mice revealed that the JNK pathway plays a key role in T cell activation and differentiation to T helper 1 and 2 cell types. JNK1 or JNK2 knockout mice develop normally and are phenotypically unremarkable. Activated naive CD4+ T cells from these mice fail to produce IL-2 and do not proliferate well (Sabapathy, K, Hu, Y, Kallunki, T, Schreiber, M, David, J-P, Jochum, W, Wagner, E, Karin, M. *Curr Biol* 9:116-125, 1999). It is possible to induce T cell differentiation in T cells from these mice, generating Th1 cells (producer of IFN-g and TNFβ) and Th2 effector cells (producers of IL-4, IL-5, IL-6, IL-10 and IL-13) [22,23]. Deletion of either JNK1 or JNK2 in mice resulted in a selective defect in the ability of Th1 effector cells to express IFNg. This suggests that JNK1 and JNK2 do not have redundant functions in T cells and that they play different roles in the control of cell growth, differentiation and death. The JNK pathway therefore, is an important point for regulation of T cell responses to antigen.

Cardiovascular disease (CVD) accounts for nearly one quarter of total annual deaths worldwide. Vascular disorders such as atherosclerosis and restenosis result from dysregulated growth of the vessel wall, restricting blood flow to vital organs. The JNK pathway is activated by atherogenic stimuli and regulates local cytokine and growth factor production in vascular cells (Yang, D D, Conze, D, Whitmarsh, A J, et al, *Immunity*, 9:575, 1998). In addition, alterations in blood flow, hemodynamic forces and blood volume lead to JNK activation in vascular endothelium, leading to AP-1 activation and pro-atherosclerotic gene expression (Aspenstrom P., Lindberg U., and Hall A. *Curr. Biol*. 6:70-77, 1996). Ischemia and ischemia coupled with reperfusion in the heart, kidney or brain results in cell death and scar formation, which can ultimately lead to congestive heart failure, renal failure or cerebral dysfunction. In organ transplantation, reperfusion of previously ischemic donor organs results in acute leukocyte-mediated tissue injury and delay of graft function. The JNK pathway is activated by ischemia and reperfusion (Li Y., Shyy J., Li S., Lee J., Su B., Karin M., Chien S *Mol. Cell. Biol*. 16:5947-5954, 1996), leading to the activation of JNK-responsive genes and leukocyte-mediated tissue damage. In a number of different settings JNK activation can be either pro- or anti-apoptotic. JNK activation is correlated with enhanced apoptosis in cardiac tissues following ischemia and reperfusion (Pombo C M, Bonventre J V, Avruch J, Woodgett J R, Kyriakis J. M, Force T. *J. Biol. Chem*. 26 :26546-26551, 1994).

Cancer is characterized by uncontrolled growth, proliferation and migration of cells. Cancer is the second leading cause of death with 500,000 deaths and an estimated 1.3 million new cases in the United States in 1996. The role of signal transduction pathways contributing to cell transformation and cancer is a generally accepted concept. The JNK pathway leading to AP-1 appears to play a critical role in cancer. Expression of c-jun is altered in early lung cancer and may mediate growth factor signaling in non-small cell lung cancer (Yin T., Sandhu G., Wolfgang C. D., Burrier A., Webb R. L., Rigel D. F. Hai T., and Whelan J. *J. Biol. Chem*. 272:19943-19950, 1997). Indeed, over-expression of c-jun in cells results in transformation, and blocking c-jun activity inhibits MCF-7 colony formation (Szabo E., Riffe M., Steinberg S. M., Birrer M. J., Linnoila R. I. *Cancer Res*. 56:305-315, 196). DNA-damaging agents, ionizing radiation and tumor necrosis factor activate the pathway. In addition to regulating c-jun production and activity, JNK activation can regulate phosphorylation of p53, and thus can modulate cell cycle progression (Chen T. K., Smith L. M., Gebhardt D. K., Birrer M. J., Brown P. H. *Mol. Carcinogenesis* 15:215-226, 1996). The oncogene BCR-Ab1, associated with t(9,22) Philadelphia chromosome translocation of chronic myelogenous leukemia, activates JNK and leads to transformation of hematopoietic cells (Milne D. M., Campbell L. E., Campbell D. G., Meek D W. *J. Biol. Chem*. 270:5511-5518, 1995). Selective inhibition of JNK activation by naturally occurring JNK inhibitory protein, called JIP-1, blocks cellular transformation caused by BCR-Ab1 expression (Raitano A. B., Halpern J. R., Hambuch T. M., Sawyers C. L. *Proc. Nat. Acad. Sci USA* 92:11746-11750, 1995). Thus, JNK inhibitors may block transformation and tumor cell growth.

The involvement of JNK in insulin mediated diseases such as Type II diabetes and obesity has also been confirmed (Hirosumi, J. et al *Nature* 420:333-336, 2002; International Publication No. WO 02/085396). Without being limited by theory, it is thought that phosphorylation at Ser 307 of insulin receptor substrate ("IRS-1") is responsible for TNF-α-induced and FFA-induced insulin resistance (Hotamisigil, G. H. *Science* 271:665-668, 1996). This was demonstrated in a cellular model of insulin resistance in liver cells where increased Ser 307 phosphorylation of IRS-1 was seen in cells treated with TNF-α (Hirosumi, J. Id.). It was also shown that the TNF-α-induced Ser 307 phosphorylation was completely prevented by an inhibitor of JNK (Id.). Additional studies have demonstrated that inhibition of the JNK pathway inhibits TNF-α lipolysis which has been implicated in diseases characterized by insulin resistance (International Publication No. WO 99/53927).

Accordingly, there is a need in the art for inhibitors of the JNK pathway. In addition, there is a need for pharmaceutical compositions comprising one or more inhibitors, as well as to methods for treating conditions in animals which are responsive to such inhibitors. The present invention fulfills these needs, and provides further related advantages. Citation of any reference in Section 2 of this application is not an admission that the reference is prior art to the application.

3. SUMMARY OF THE INVENTION

In brief, the present invention generally relates to methods for treating or preventing a condition responsive to JNK inhibition, comprising administering to a patient in need thereof an effective amount of a compound having the following formula (I):

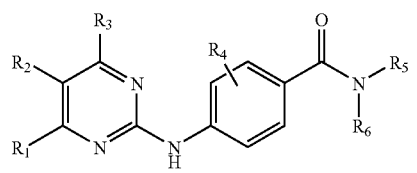

wherein $R_1$ though $R_6$ are as defined below, and including isomers, prodrugs and pharmaceutically acceptable salts thereof.

A compound of formula (I), or a pharmaceutically acceptable salt thereof, is hereinafter referred to as an "Anilinopyrimidine Derivative."

In general, the present invention is directed to methods for treating or preventing a condition responsive to inhibition of the JNK pathway, comprising administering to a patient in need thereof an effective amount of an Anilinopyrimidine Derivative.

Anilinopyrimidine Derivatives are useful for treating or preventing a metabolic condition including, but not limited to: diabetes (such as Type II diabetes, Type I diabetes, diabetes insipidus, diabetes mellitus, maturity-onset diabetes, juvenile diabetes, insulin-dependant diabetes, non-insulin dependant diabetes, malnutrition-related diabetes, ketosis-prone diabetes or ketosis-resistant diabetes);or obesity (such as hereditary obesity, dietary obesity, hormone related obesity or obesity related to the administration of medication).

Anilinopyrimidine Derivatives are useful for treating or preventing an inflammatory condition including, but not limited to: hearing loss (such as that from otitis externa or acute otitis media); fibrosis related diseases (such as pulmonary interstitial fibrosis, renal fibrosis, cystic fibrosis, liver fibrosis, wound-healing or burn-healing, wherein the burn is a first-, second- or third-degree burn and/or a thermal, chemical or electrical burn); arthritis (such as rheumatoid arthritis, rheumatoid spondylitis, osteoarthritis or gout); an allergy; allergic rhinitis; acute respiratory distress syndrome; asthma; bronchitis; an inflammatory bowel disease (such as irritable bowel syndrome, mucous colitis, ulcerative colitis, Crohn's disease, gastritis, esophagitis, pancreatitis or peritonitis); or an autoimmune disease (such as scleroderma, systemic lupus erythematosus, myasthenia gravis, transplant rejection, endotoxin shock, sepsis, psoriasis, eczema, dermatitis or multiple sclerosis).

Anilinopyrimidine Derivatives are also useful for treating or preventing a liver disease (such as hepatitis, alcohol-induced liver disease, toxin-induced liver disease, steatosis or sclerosis); a cardiovascular disease (such as atherosclerosis, restenosis following angioplasty, left ventricular hypertrophy, myocardial infarction, chronic obstructive pulmonary disease or stroke); ischemic damage (such as to the heart, kidney, liver or brain); ischemia-reperfusion injury (such as that caused by transplant, surgical trauma, hypotension, thrombosis or trauma injury); neurodegenerative disease (such as epilepsy, Alzheimer's disease, Huntington's disease, Amyotrophic lateral sclerosis, peripheral neuropathies, spinal cord damage or Parkinson's disease); or cancer (such as cancer of the head, neck, eye, mouth, throat, esophagus, chest, bone, lung, colon, rectum, stomach, prostate, breast, ovaries, testicles or other reproductive organs, skin, thyroid, blood, lymph nodes, kidney, liver, pancreas, and brain or central nervous system).

In one embodiment, the present methods for treating or preventing further comprise the administration of an effective amount of another therapeutic agent useful for treating or preventing the diseases or disorders disclosed herein. In this embodiment, the time in which the therapeutic effect of the other therapeutic agent is exerted overlaps with the time in which the therapeutic effect of the Anilinopyrimidine Derivative is exerted.

In one embodiment, the present methods for treating or preventing a metabolic condition an inflammatory condition, a liver disease, a cardiovascular disease, ischemic damage, a neurodegenerative disease or cancer comprise inhibiting JNK in vivo.

In one embodiment, inhibiting JNK in vivo comprises inhibiting TNF-α in vivo.

In one embodiment the JNK is JNK1. In another embodiment the JNK is JNK2. In another embodiment the JNK is JNK3.

These and other aspects of this invention will be evident upon reference to the following detailed description and illustrative examples, which are intended to exemplify non-limiting embodiments of the invention. Certain patent and other documents are cited herein to more specifically set forth various aspects of this invention. Each of these documents are hereby incorporated by reference in their entirety.

4. DETAILED DESCRIPTION OF THE INVENTION

4.1 Definitions

As used herein, the terms used above having following meaning:

"Alkyl" means a straight chain or branched, saturated or unsaturated alkyl, cyclic or non-cyclic hydrocarbon having from 1 to 10 carbon atoms, while "lower alkyl" has the same meaning but only has from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclopentane or cyclohexane) fused to one or more aromatic (such as phenyl) or non-aromatic (such as cyclohexane) carbocyclic rings.

"Halogen" means fluorine, chlorine, bromine or iodine.

"Keto" means a carbonyl group (i.e., =O).

"Aryl" means an aromatic carbocyclic moiety such as phenyl or naphthyl.

"Arylalkyl" means an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" means a heterocyclic ring containing from 5 to 10 ring atoms

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (i.e., aryl, arylalkyl, heterocycle and heterocyclealkyl) wherein at least one hydrogen atom is replaced with a substituent. In the case of a keto substituent ("C(=O)") two hydrogen atoms are replaced. Substituents include halogen, hydroxy, alkyl, substituted alkyl (such as haloalkyl, mono- or di-substituted aminoalkyl, alkyloxyalkyl, and the like, aryl, substituted aryl, arylalkyl, substituted arylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —NR$_a$SO$_2$R$_b$, or a radical of the formula —Y—Z—R$_a$ where Y is alkanediyl, substitute alkanediyl, or a direct bond, Z is —O—, —S—, —S(=O)—, —S(=O)$_2$—, —N(R$_b$)—, —C(=O)—, —C(=O)O—, —OC(=O)—, —N(R$_b$)C(=O)—, —C(=O)N(R$_b$)— or a direct bond, wherein R$_a$ and R$_b$ are the same or different and independently hydrogen, amino, alkyl, substituted alkyl (including halogenated alkyl), aryl, substituted aryl, arylalkyl, substituted arylalkyl, heterocycle, substituted heterocycle, heterocylealkyl or substituted heterocyclealkyl, or wherein R$_a$ and R$_b$ taken together with the nitrogen atom to which they are attached form a heterocycle or substituted heterocycle.

"Haloalkyl" means alkyl having one or more hydrogen atoms replaced with halogen, such as —CF$_3$.

"Hydroxyalkyl" means alkyl having one or more hydrogen atoms replaced with hydroxy, such as —CH$_2$OH "Sulfonylalkyl" means —SO$_2$-(alkyl);
"Sulfinylalkyl" means —SO-(alkyl);
"Thioalkyl" means —S-(alkyl);
"Carboxyl" means —COOH.
"Alkoxy" means —O-(alkyl), such as methoxy, ethoxy, n-propyloxy, iso-propyloxy, n-butyloxy, iso-butyloxy, and the like.

"Patient" means an animal, including, but not limited to, an animal such as a cow, monkey, horse, sheep, pig, chicken, turkey, quail, cat, dog, mouse, rat, rabbit, and guinea pig, and is more preferably a mammal, and most preferably a human.

"Acyl" means alkyl(C=O).

"Nitrogen-containing non-aromatic heterocycle" means morpholinyl, thiomorpholinyl, pyrrolidinonyl, pyrrolidinyl, piperidinyl, homopiperidinyl, piperazinyl, homopiperazinyl, hydantoinyl, tetrahydropyrindinyl, tetrahydropyrimidinyl, oxazolidinyl, thiazolidinyl, indolinyl, isoindolinyl, tetrahydroquinolinyl, tetrahydroisoquinolinyl and the like.

An "effective amount" when used in connection with an Anilinopyrimidine Derivative is an amount effective for treating or preventing a condition, such as those described herein that can be treated or prevented by administering a JNK inhibitor.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In certain embodiments, the patient is an infant, child, adolescent or adult.

As used herein, the term "prodrug" refers to any derivative of the Anilinopyrimidine Derivatives that are metabolized or otherwise converted into an active form upon introduction into the body of an animal. Prodrugs are well known to those skilled in the art of pharmaceutical chemistry, and provide benefits such as increased adsorption and half-life. Prodrugs of this invention may be formed when, for example, hydroxy groups are esterified or alkylated, or when carboxyl groups are esterified. Those skilled in the art of drug delivery will readily appreciate that the pharmacokinetic properties of Anilinopyrimidine Derivatives may be controlled by an appropriate choice of moieties to produce prodrug derivatives.

4.2 Compounds of the Invention

As mentioned above, the present invention is related to methods for treating or preventing a condition responsive to JNK inhibition, comprising administering to a patient in need thereof an effective amount of a Anilinopyrimidine Derivative of formula (I):

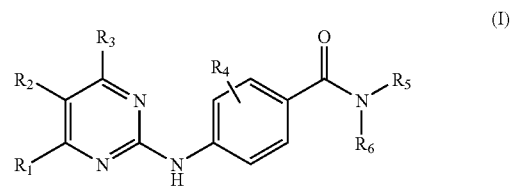

(I)

including isomers, prodrugs and pharmaceutically acceptable salts thereof, wherein:

R$_1$ is aryl or heteroaryl optionally substituted with one to four substituents independently selected from R$_7$;

R$_2$ is hydrogen;

R$_3$ is hydrogen or lower alkyl;

R$_4$ represents one to four optional substituents, wherein each substituent is the same or different and independently selected from halogen, hydroxy, lower alkyl and lower alkoxy;

R$_5$ and R$_6$ are the same or different and independently —R$_8$, —(CH$_2$)$_a$C(=O)R$_9$, —(CH$_2$)$_a$C(=O)OR$_9$, —(CH$_2$)$_a$C(=O)NR$_9$R$_{10}$, —(CH$_2$)$_a$C(=O)NR$_9$(CH$_2$)$_b$C(=O)R$_{10}$, —(CH$_2$)$_a$NR$_9$C(=O)R$_{10}$, (CH$_2$)$_a$NR$_{11}$C(=O)NR$_9$R$_{10}$, —(CH$_2$)$_a$NR$_9$R$_{10}$, —(CH$_2$)$_a$OR$_9$, —(CH$_2$)$_a$SO$_c$R$_9$ or —(CH)$_a$SO$_2$NR$_9$R$_{10}$;

or R$_5$ and R$_6$ taken together with the nitrogen atom to which they are attached to form a heterocycle or substituted heterocycle;

R$_7$ is at each occurrence independently halogen, hydroxy, cyano, nitro. carboxy, alkyl, alkoxy, haloalkyl, acyloxy, thioalkyl, sulfinylalkyl, sulfonylalkyl, hydroxyalkyl, aryl, substituted aryl, aralkyl, substituted aralkyl, heterocycle, substituted heterocycle, heterocyclealkyl, substituted heterocyclealkyl, —C(=O)OR$_8$, —OC(=O)R$_8$, —C(=O)NR$_8$R$_9$, —C(=O)NR$_8$OR$_9$, —SO$_c$R$_8$, —SO$_c$NR$_8$R$_9$, —NR$_8$SO$_c$R$_9$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

R$_8$, R$_9$, R$_{10}$ and R$_{11}$ are the same or different and at each occurrence independently hydrogen, alkyl, substituted alkyl, aryl, substituted aryl, aralkyl, substituted arylalkyl, heterocycle, substituted heterocycle, heterocyclealkyl or substituted heterocyclealkyl;

or $R_8$ and $R_9$ taken together with the atom or atoms to which they are attached to form a heterocycle or substituted heterocycle;

a and b are the same or different and at each occurrence independently selected from 0, 1, 2, 3 or 4; and c is at each occurrence 0, 1 or 2.

In one embodiment of the invention, in the Anilinopyrimidine Derivatives of structure (I), $R_1$ is a substituted or unsubstituted aryl or heteroaryl with the proviso that the heteroaryl is not pyridyl. When $R_1$ is substituted, it is substituted with one or more substituents defined below. Preferably, when substituted, $R_1$ is substituted with a halogen, sulfone or sulfonamide.

In another embodiment of the invention, in the Anilinopyrimidine Derivatives of structure (I), $R_1$ is substituted or unsubstituted aryl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl or quinazolinyl.

In another embodiment of the invention, in the Anilinopyrimidine Derivatives of structure (I), $R_1$ is substituted or unsubstituted aryl or heteroaryl with the proviso that the heteroaryl is not imidazo[1,2a]pyrid-3-yl or pyrazolo[2,3a]pyrid-3-yl. When $R_1$ is substituted, it is substituted with one or more substituents defined below. Preferably, when substituted, $R_1$ is substituted with a halogen, sulfone or sulfonamide.

In another embodiment of the invention, in the Anilinopyrimidine Derivatives of structure (I), $R_1$ is substituted or unsubstituted aryl, preferably phenyl. When $R_1$ is a substituted aryl, the substituents are defined below. Preferably, when substituted, $R_1$ is substituted with a halogen, sulfone or sulfonamide.

In another embodiment of the invention, in the Anilinopyrimidine Derivatives of structure (I), $R_5$ and $R_6$, taken together with the nitrogen atom to which they are attached form a substituted or unsubstituted nitrogen-containing non-aromatic heterocycle, preferably piperazinyl, piperidinyl or morpholinyl.

When $R_5$ and $R_6$, taken together with the nitrogen atom to which they are attached form substituted piperazinyl, piperadinyl or morpholinyl, the piperazinyl, piperadinyl or morpholinyl is substituted with one or more substituents defined below. Preferably, when substituted, the substituent is alkyl, amino, alkylamino, alkylether, acyl, pyrrolidinyl or piperidinyl.

In one embodiment of the invention, in the Anilinopyrimidine Derivatives of formula (I), $R_3$ is hydrogen and $R_4$ is not present, and the compounds of this invention have the following formula (II):

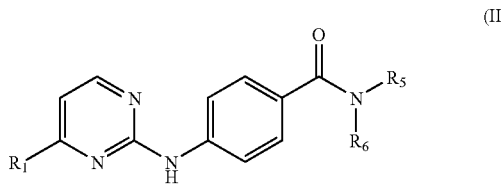

(II)

In a more specific embodiment of the invention, in the Anilinopyrimidine Derivatives of formula (II), $R_1$ is phenyl optionally substituted with $R_7$, and having the following formula (III):

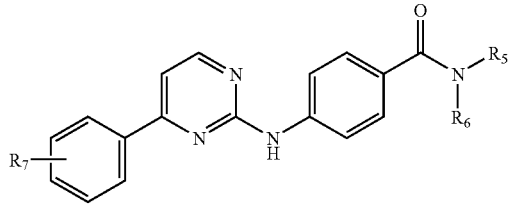

(III)

In still a further embodiment of the invention, in the Anilinopyrimidine Derivatives of formula (III), $R_7$ is at the para position relative to the pyrimidine, as represented by the following formula (IV):

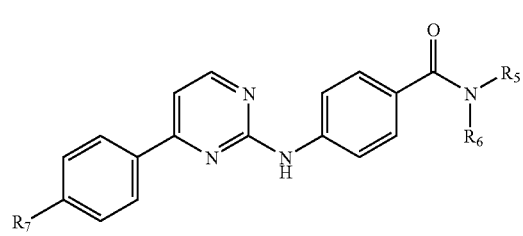

(IV)

4.3 Preparation of Compounds of the Invention

The Anilinopyrimidine Derivatives can generally be obtained using organic synthesis techniques known to those skilled in the art, as well as by the following general techniques and the procedures set forth in the Examples. To that end, the Anilinopyrimidine Derivatives can be made according to the following Reaction Schemes 1 through 9:

Reaction Scheme 1

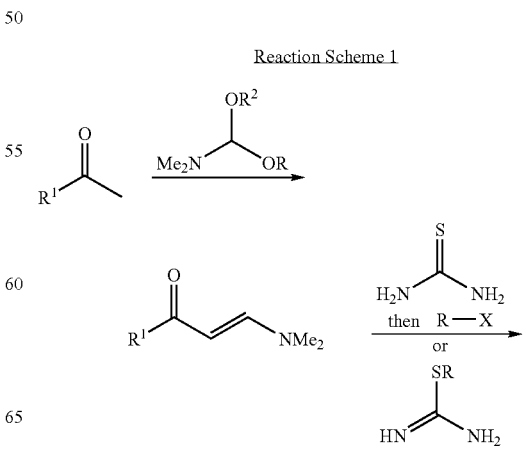

-continued

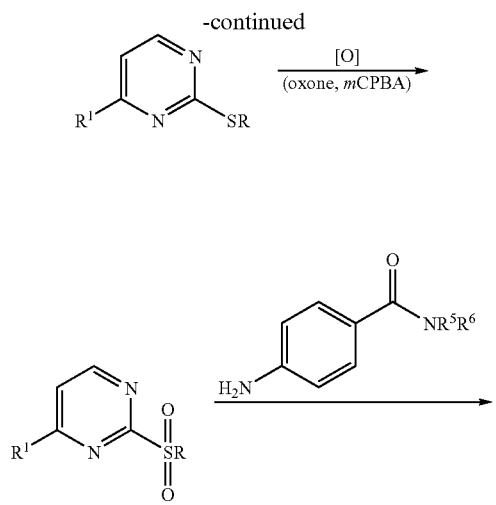

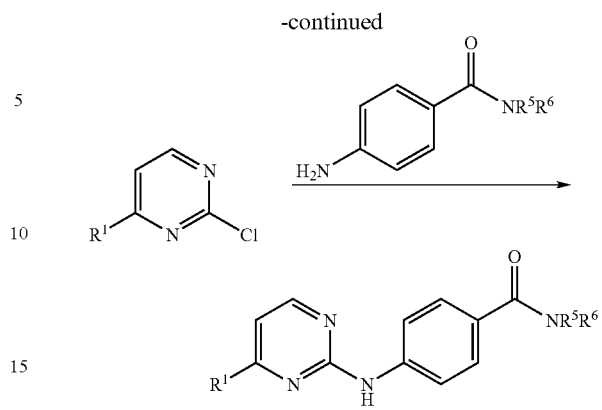

Similarly, the Anilinopyrimidine Derivatives may be prepared from the 2-chloropyrimidine derivatives. Thus, condensation of the β-dimethylaminobutenones with urea followed by the treatment with chlorinating agent such as phosphorus oxychloride gives 4-substituted 2-chloropyrimidines. Further treatment with substituted anilines affords the desired Anilinopyrimidine Derivatives.

Reaction Scheme 3

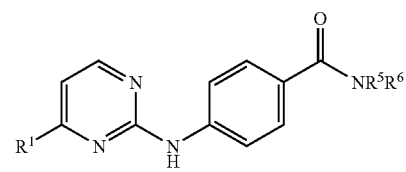

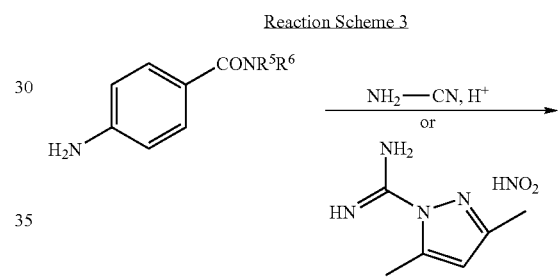

Appropriately substituted methylketones may be treated with a dimethylformamide acetal, such as dimethylformamide dimethylacetal or dimethylformamide diethylacetal, to afford the corresponding β-dimethylaminobutenones. Treatment of the aminobutenones with thiourea in the presence of a base such as sodium methoxide, followed by alkylation with an alkyl halide, such as methyl iodide, gives 4-substituted 2-alkylthiopyrimidines. Oxidation of the thioether with organic and inorganic oxidizing agents, such as m-chloroperbenzoic acid or oxone, yields the sulfones which, upon condensation with p-aminocarbonylanilines, give rise to the formation of the desired anilinopyrimidine derivatives.

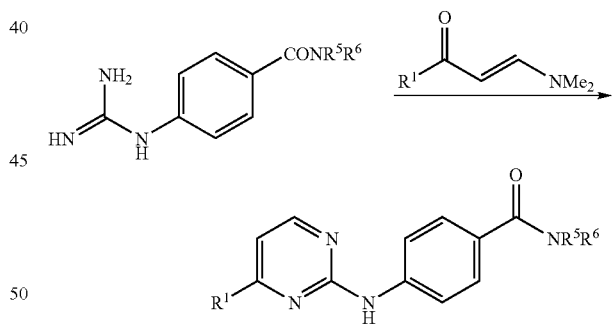

The Anilinopyrimidine Derivatives can also be prepared by condensation of the β-dimethylaminobutenones with appropriately substituted guanidines. The requisite guanidines may be synthesized by the reaction of the aniline with cyanamide in the presence of an acid, or with a pyrazoloamidine.

Reaction Scheme 2

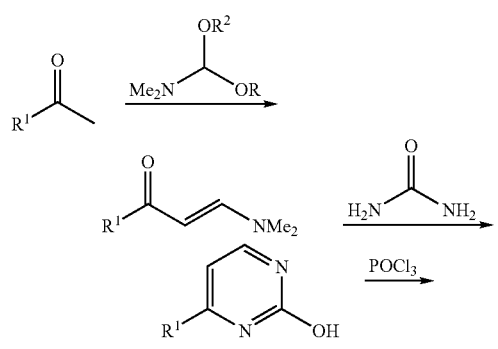

Reaction Scheme 4

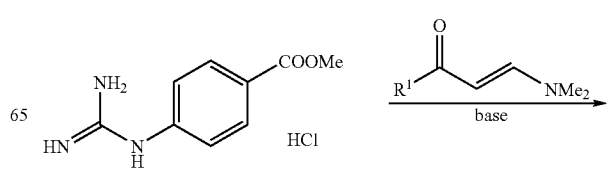

-continued

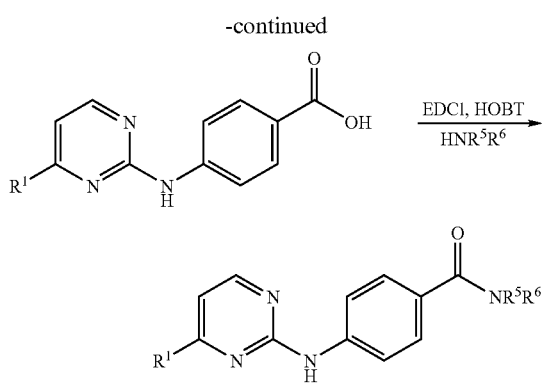

Cyclization of alkoxycarbonylphenylguanidines with the b-aminoketones gives 4-substituted 2-(4-carboxyphenyl) aminopyrimidines. Condensation of the benzoic acid derivatives with appropriate amines affords the desired amides.

Reaction Scheme 5

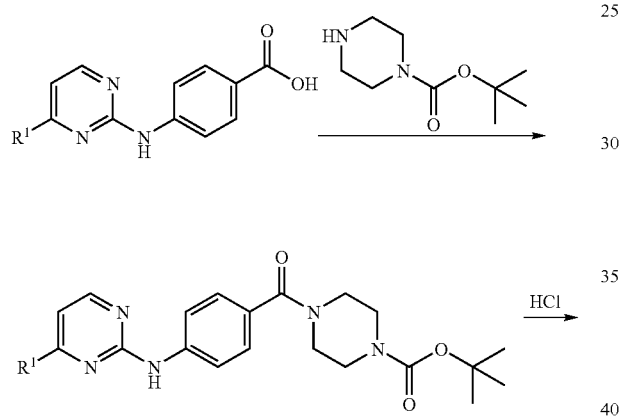

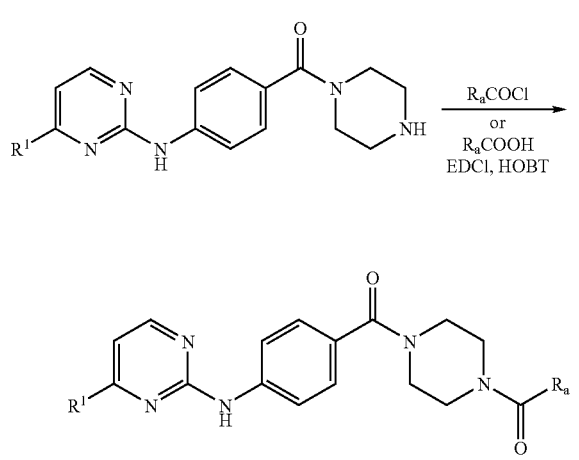

Condensation of the benzoic acids with N-Boc-piperazine followed by deprotection of the tert-butoxycarbonyl group with an acid such as hydrochloric acid yields piperazineamides. Subsequent condensation with carboxylic acid derivatives yields bisacylpiperazines Reaction Scheme 6

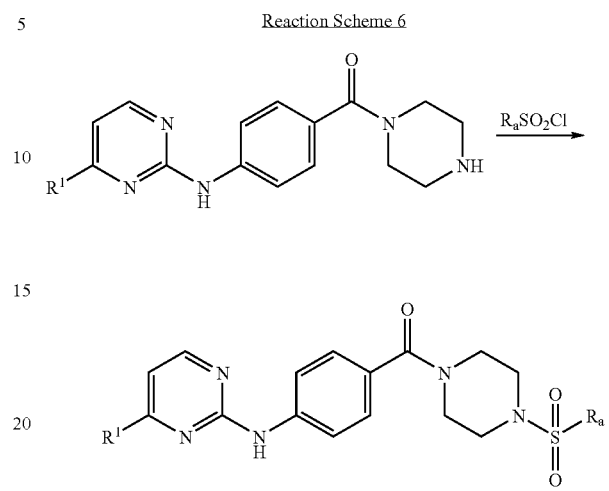

Similar reaction with sulfonyl chlorides gives the corresponding sulfonamides.

Reaction Scheme 7

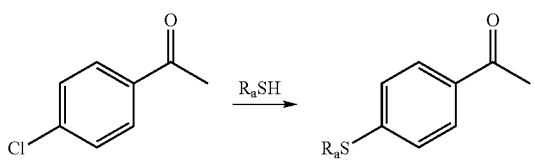

Acetophenones with p-alkyl- and arylthio groups may be prepared by the reaction of p-chloroacetophenone with alkyl and arylthiols.

Reaction Scheme 8

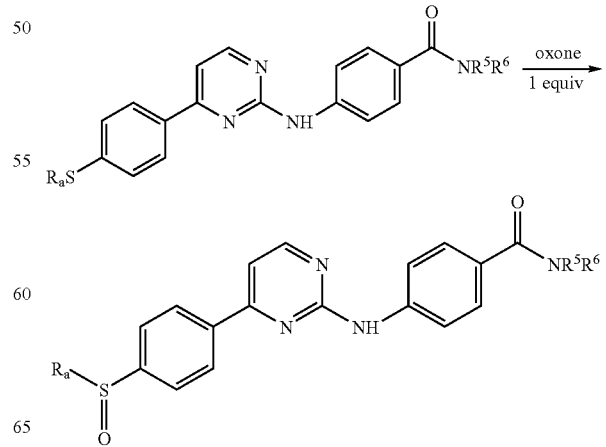

Anilinopyrimidine Derivatives with the p-alkyl- and arylsulfinyl groups may be prepared by controlled oxidation of the sulfides with an oxidizing agent such as oxone.

Reaction Scheme 9

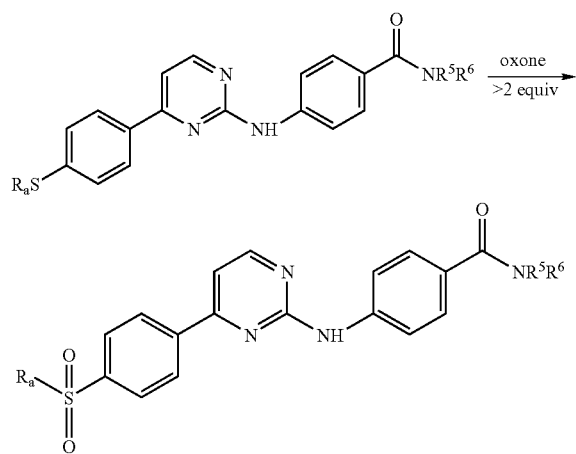

Anilinopyrimidine Derivatives having p-alkyl- and arylsulfonyl groups may be prepared by oxidation of the sulfides with an oxidizing agent such as oxone.

The Anilinopyrimidine Derivatives can be in the form of a pharmaceutically acceptable salt or free base. Acid addition salts of the free base can be prepared by methods well known in the art, and may be formed from organic and inorganic acids. Suitable organic acids include maleic, fumaric, benzoic, ascorbic, succinic, methanesulfonic acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic sulfuric, phosphoric, and nitric acids. Additional salts include sulfate, citrate, acetate, oxalate, chloride, bromide, iodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" is intended to encompass any and all acceptable salt forms.

Pharmaceutically acceptable salts can be formed by conventional and known techniques, such as by reacting a compound of this invention with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Anilinopyrimidine Derivative is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

The Anilinopyrimidine Derivatives can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound, including tautomeric forms of the compound.

4.4 Methods of Use

Conditions that may be treated using an Anilinopyrimidine Derivative, or using a pharmaceutical composition containing the same, include any condition that is responsive to JNK pathway inhibition, and thereby benefit from administration of such an inhibitor.

In one embodiment, the invention relates to methods for treating or preventing a metabolic condition including, but not limited to: diabetes (such as Type II diabetes, Type I diabetes, diabetes insipidus, diabetes mellitus, maturity-onset diabetes, juvenile diabetes, insulin-dependant diabetes, non-insulin dependant diabetes, malnutrition-related diabetes, ketosis-prone diabetes or ketosis-resistant diabetes); or obesity (such as hereditary obesity, dietary obesity, hormone related obesity or obesity related to the administration of medication) comprising administering to a patient in need thereof an effective amount of an Anilinopyrimidine Derivative.

In another embodiment, the invention relates to methods for treating or preventing an inflammatory condition including, but not, limited to: hearing loss (such as that from otitis externa or acute otitis media); fibrosis related diseases (such as pulmonary interstitial fibrosis, renal fibrosis, cystic fibrosis, litter fibrosis, wound-healing or burn-healing, wherein the burn is a first-, second- or third-degree burn and/or a thermal, chemical or electrical burn); arthritis (such as rheumatoid arthritis, rheumatoid spondylitis, osteoarthritis or gout); an allergy; allergic rhinitis; acute respiratory distress syndrome; asthma; bronchitis; an inflammatory bowel disease (such as irritable bowel syndrome, mucous colitis, ulcerative colitis, Crohn's disease, gastritis, esophagitis, pancreatitis or peritonitis); or an autoimmune disease (such as scleroderma, systemic lupus erythematosus, myasthenia gravis, transplant rejection, endotoxin shock, sepsis, psoriasis, eczema, dermatitis or multiple sclerosis) comprising administering to a patient in need thereof an effective amount of an Anilinopyrimidine Derivative.

In another embodiment, the invention relates to methods for treating or preventing a liver disease (such as hepatitis, alcohol-induced liver disease, toxin-induced liver disease, steatosis or sclerosis); a cardiovascular disease (such as atherosclerosis, restenosis following angioplasty, left ventricular hypertrophy, myocardial infarction, chronic obstructive pulmonary disease or stroke); ischemic damage (such as to the heart, kidney, liver or brain); ischemia-reperfusion injury (such as that caused by transplant, surgical trauma, hypotension, thrombosis or trauma injury); neurodegenerative disease (such as epilepsy, Alzheimer's disease, Huntington's disease, Amyotrophic lateral sclerosis, peripheral neuropathies, spinal cord damage or Parkinson's disease); or cancer (such as cancer of the head, neck, eye, mouth, throat, esophagus, chest, bone, lung, colon, rectum, stomach, prostate, breast, ovaries, testicles or other reproductive organs, skin, thyroid, blood, lymph nodes, kidney, liver, pancreas, and brain or central nervous system) comprising administering to a patient in need thereof an effective amount of an Anilinopyrimidine Derivative.

In another embodiment, the invention relates to methods for treating or preventing otitis externa, acute otitis media, hearing loss, pulmonary interstitial fibrosis, liver fibrosis, renal fibrosis, wound-healing or burn-healing (wherein the burn is a first-, second- or third-degree burn and/or a thermal, chemical or electrical burn), chronic obstructive pulmonary disease, allergic rhinitis, acute respiratory distress syndrome, systemic lupus erythematosus, nephropathy, pancreatitis, peritonitis, sepsis, alcohol or toxin-induced liver disease, sclerosis, steatosis or ischemia-reperfusion injury comprising administering to a patient in need thereof an effective amount of an Anilinopyrimidine Derivative.

In one embodiment, the present methods for treating or preventing further comprise the administration of an effective amount of another therapeutic agent useful for treating or preventing the diseases or disorders disclosed herein. In this embodiment, the time in which the therapeutic effect of the other therapeutic agent is exerted overlaps with the time in which the therapeutic effect of the Anilinopyrimidine Derivative is exerted.

In one embodiment, the methods for treating or preventing a metabolic condition an inflammatory condition, a liver disease, a cardiovascular disease, ischemic damage, a neurodegenerative disease or cancer comprise inhibiting JNK in vivo.

In one embodiment, inhibiting JNK in vivo comprises inhibiting TNF-α in vivo.

In one embodiment the JNK is JNK1. In another embodiment the JNK is JNK2. In another embodiment the JNK is JNK3.

In another embodiment of the present methods, in the Anilinopyrimidine Derivatives of structure (I), $R_1$ is a substituted or unsubstituted aryl or heteroaryl with the proviso that the heteroaryl is not pyridyl. When $R_1$ is substituted, it is substituted with one or more substituents defined above. Preferably, when substituted, $R_1$ is substituted with a halogen, sulfone or sulfonamide.

In another embodiment of the present methods, in the Anilinopyrimidine Derivatives of structure (I), $R_1$ is substituted or unsubstituted aryl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl or quinazolinyl.

In another embodiment of the present methods, in the Anilinopyrimidine Derivatives of structure (I), $R_1$ is substituted or unsubstituted aryl or heteroaryl with the proviso that the heteroaryl is not imidazo[1,2a]pyrid-3-yl or pyrazolo[2,3a]pyrid-3-yl. When $R_1$ is substituted, it is substituted with one or more substituents defined above. Preferably, when substituted, $R_1$ is substituted with a halogen, sulfone or sulfonamide.

In another embodiment of the present methods, in the Anilinopyrimidine Derivatives of structure (I), $R_1$ is substituted or unsubstituted aryl, preferably phenyl or naphthyl. When $R_1$ is a substituted aryl, it is substituted with one or more substituents defined above. Preferably, when substituted, $R_1$ is substituted with a halogen, sulfone or sulfonamide.

In another embodiment of the present methods, in the Anilinopyrimidine Derivatives of structure (I), $R_5$ and $R_6$ taken together with the nitrogen atom to which they are attached form a substituted or unsubstituted nitrogen containing non-aromatic heterocycle.

In another embodiment of the present methods, the nitrogen-containing non-aromatic heterocycle is piperazinyl, piperadinyl or morpholinyl. When the nitrogen-containing non-aromatic heterocycle is a substituted piperazinyl, piperadinyl or morpholinyl ring, the substituents are defined above. Preferably, when substituted, the substituent is alkyl, amino, alkylamino, alkylether, acyl, pyrrolidinyl or piperidinyl.

When used in the present methods, the Anilinopyrimidine Derivatives of this invention can be administered as a component of a composition that optionally comprises a pharmaceutically acceptable carrier or vehicle.

The Anilinopyrimidine Derivatives can also be used in cancer adjuvant therapy in combination with a cytotoxic agent or with radiation therapy.

4.5 Administration and Pharmaceutical Compositions

The Anilinopyrimidine Derivatives can be administered to a patient orally or parenterally in conventional and well known preparations, such as capsules, microcapsules, tablets, granules, powder, troches, pills, suppositories, injections, suspensions and syrups. Prior to administration, the Anilinopyrimidine Derivatives are typically formulated as a pharmaceutical composition that contains an effective dosage amount of one or more of such compounds in combination with one (or more) pharmaceutically acceptable carrier(s). Suitable formulations in this regard may be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethyl cellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous sicilic acid, talc or sodium lauryl sulfate), a flavoring agent (e.g., citric acid, menthol, glycine or orange powder) a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and/or a base wax (e.g. cocoa butter, white petrolatum or polyethylene glycol).

The amount of an Anilinopyrimidine Derivative in a dosage form may differ depending on factors such as, but not limited to, the route by which it is to be administered to patients. However, typical dosage forms of the invention comprise an Anilinopyrimidine Derivative in an amount of from about 0.10 mg to about 3500 mg, from about 1 mg to about 2500 mg, from about 10 mg to about 500 mg, from about 25 mg to about 250 mg, from about 50 mg to about 100 mg. Typical dosage forms comprise an Anilinopyrimidine Derivative in an amount of about 0.1, 1, 2, 5, 7.5, 10, 12.5, 15, 17.5, 20, 25, 50, 100, 150, 200, 250, 500, 750, 1000, 1500, 2000, 2500, 3000 or 3500 mg. In a particular embodiment, a dosage form comprises a Pyrazoloanthrone Derivative in an amount of about 1, 2, 5, 10, 25, 50, 100, 250 or 500 mg. In a specific embodiment, a dosage form comprises an amount of about 5, 10, 25 or 50 mg of an Anilinopyrimidine Derivative.

Further, the effect of the Anilinopyrimidine Derivative can be delayed or prolonged by proper formulation. For example, a slowly soluble pellet of the Anilinopyrimidine Derivative may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

In certain embodiments, the Anilinopyrimidine Derivatives can be used in combination, e.g., as an adjunct therapy, with at least one other therapeutic agent. An Anilinopyrimidine Derivative and the other therapeutic agent can act additively or, more preferably, synergistically. In a preferred embodiment, an Anilinopyrimidine Derivative is administered concurrently with the administration of another therapeutic agent, which can be part of the same composition as or in a different composition from that comprising the Anilinopyrimidine Derivative. In another embodiment, an Anilinopyrimidine Derivative is administered prior or subsequent to administration of another therapeutic agent. As many of the disorders for which the Anilinopyrimidine Derivatives are useful in treating are chronic, in one embodiment combination therapy involves alternating between administering an Anilinopyrimidine Derivative and another therapeutic agent. The duration of administration of the Anilinopyrimidine Derivative or the other therapeutic agent can be, e.g., one month, three months, six months, a year, or for more extended periods, such as the patient's lifetime. In certain embodiments, when a composition of the invention is administered concurrently with another therapeutic agent that potentially produces adverse side effects including, but not limited to, toxicity, the other therapeutic agent can advantageously be administered at a dose that falls below the threshold at which the adverse side effect is elicited.

The other therapeutic agent can be an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone. Anti-inflammatory agents particularly useful for treating arthritis, including rhumatiod arthritis, include enbrel, infliximab, anarkinra, celecoxib and rofecoxib.

The other therapeutic agent can be an anti-cancer agent. Useful anti-cancer agents include, but are not limited to, nitrogen mustards, such as cyclophosphamide, Ifosfamide, trofosfamide and Chlorambucil; nitrosoureas, such as carmustine (BCNU) and Lomustine (CCNU); alkylsulphonates, such as busulfan and Treosulfan; triazenes, such as Dacarbazine; platinum-containing compounds, such as Cisplatin and carboplatin; vinca alkaloids, such as vincristine, Vinblastine, Vindesine and Vinorelbine; taxoids, such as paclitaxel and Docetaxol; epipodophyllins, such as etoposide, Teniposide, Topotecan, 9-aminocamptothecin, camptoirinotecan and crisnatol; mytomycins, such as mytomycin C; DHFR inhibitors, such as methotrexate and Trimetrexate; IMP-dehydrogenase inhibitors, such as mycophenolic acid, Tiazofurin, Ribavirin and EICAR; ribonuclotide-reductase inhibitors, such as hydroxyurea and deferoxamine; uracil analogs, such as 5-fluorouracil, Floxuridine, Doxifluridine and Ratitrexed; cytosine analogs, such as cytarabine (ara C), cytosine arabinoside and fludarabine; purine analogs, such as mercaptopurine and thioguanine; anti-estrogens, such as Tamoxifen, Raloxifene and megestrol; LHRH agonists, such as goscrclin and Leuprolide acetate; anti-androgens, such as flutamide and bicalutamide; vitamin D3 analogs, such as B 1089, CB 1093 and KH 1060; photodynamic therapeutic agents, such as vertoporfin (BPD-MA), Phthalocyanine, photosensitizer Pc4 and demethoxyhypocrellin A (2BA-2-DMHA); cytokines, such as interferon-α, interferon-γ and tumor-necrosis factor; isoprenylation inhibitors such as Lovastatin; dopaminergic neurotoxins, such as 1-methyl-4-phenylpyridinium ion; cell-cycle inhibitors, such as staurosporine: actinomycins, such as Actinomycin D and Dactinomycin; bleomycins, such as bleomycin A2, Bleomycin B2 and Peplomycin; anthracyclines, such as daunorubicin, Doxorubicin (adriamycin), Idarubicin, Epirubicin, Pirarubicin, Zorubicin and Mitoxantrone; MDR inhibitors, such as verapamil; and $Ca^{2+}$ATPase inhibitors, such as thapsigargin The other therapeutic agent can also be an antiobiotic (e.g., vancomycin, penicillin, amoxicillin, ampicillin, cefotaxime, ceftriaxone, cefixime, rifampin, metronidazole, doxycycline or streptomycin). The other, therapeutic agent can also be a PDE4 inhibitor (e.g., roflumilast or rolipram). The other therapeutic agent can also be an antihistamine (e.g., cyclizine, hydroxyzine, promethazine or diphenhydramine). The other therapeutic agent can also be an anti-malarial (e.g., artemisinin, artemether, artsunate, chloroquine phosphate, mefloquine hydrochloride, doxycycline hyclate, proguanil hydrochloride, atovaquone or halofantrine). The ether therapeutic agent can also be drotrecogin alfa.

The following examples are offered by way of illustration, not limitation. To this end, it should be noted that one or more hydrogen atoms may be omitted from the drawn structure consistent with accepted shorthand notation of such organic compounds, and that one skilled in the art would readily appreciate their presence.

Retention time data for the following examples was obtained by one of two methods detailed as follows:

Method A

Column: YMC Pro C-18, 3.0µ spherical silica gel, 4.0×50 mm, pore size 120 Å.
Gradient: 0-10 min, 20% A-90% A linear binary gradient.
Flow rate: 2.0 mL/min.
Mobile Phase: A, 0.1% formic acid in acetonitrile; B, 0.1% trifluoroacetic acid in water.

Method B

Column: YMC ODS-A, 5.0µ spherical silica gel, 4.6×250 mm, pore size 120 Å.
Gradient: 0-10 min, 20% A-90% A linear binary gradient followed by 10-25 min, 100% A.
Flow rate: 1.0 mL/min.
Mobile Phase: A, 0.1% trifluoroacetic acid in acetonitrile; B, 0.1% trifluoroacetic acid in water.

4.6 EXAMPLES

Example 1

Synthesis of 4-{[4-(4-Chlorophenyl)pyrimidin-2-yl]amino}benzamide

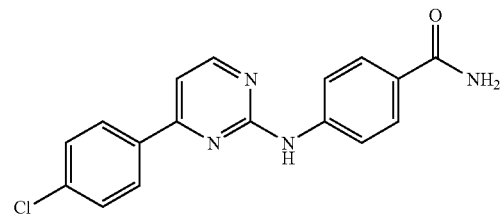

(2E)-3-(Dimethylamino)-1-(4-chlorophenyl)prop-2-en-1-one

A solution of 1-(4-chlorophenyl)ethan-1-one (3.0 g, 19.3 mmol) and N,N, dimethylformamide diisopropylacetal (20 ml) was heated at 150° C. for 16 hours. The reaction mixture was cooled to 0° C. and treated with hexanes (20 ml). The resulting solid was collected via filtration and washed with hexanes to provide the title compound: EI-MS (m/z) 209 [M+1]$^+$.

4-(4-Chlorophenyl)pyrimidine-2-thiol

To a solution of (2E)-3-(dimethylamino)-1-(4-chlorophenyl)prop-2-en-1-one (1.5 g, 7.2 mmol) in ethanol (25 ml) was added thiourea (0.60 g, 7.9 mmol) and potassium carbonate (K$_2$CO$_3$) (1.19 g. 8.63 mmol). The resulting suspension was heated to 85° C. for 12 hours then cooled to ambient temperature. The resulting solid was collected and thoroughly washed with water and hexanes to provide a beige solid: EI-MS (m/z) 222 [M+1]$^+$.

4-(4 Chlorophenyl)-2-methylthiopyrimidine 4-(4-Chlorophenyl)pyrimidine-2-thiol (1.2 g, 5.39 mmol) was taken in 10 ml of an aqueous potassium hydroxide (0.453 g, 5.39 mmol) solution. Iodomethane (503 µl, 5.39 mmol) was added at ambient temperature and the reaction mixture was allowed to stir for 30 minutes. The resulting white solid was collected via filtration and washed with minimal water and hexanes to provide the title compound: EI-MS (m/z) 237 [M+1]$^+$.

4-(4-chlorophenyl)-2-(methylsulfonyl)pyrimidine

To a solution of 4-(4-chlorophenyl)-2-methylthiopyrimidine (1.1 g, 4.65 mmol) in acetone (30 ml) and water (10 ml) was added oxone (7.14 g, 11.62 mmol). The reaction mixture was stirred for 18 hours then diluted with water and extracted into dichloromethane. The extracts were dried over magnesium sulfate, filtered and concentrated to provide a white solid: EI-MS (m/z) 269 [M+1]$^+$.

4-{(4-(4-chlorophenyl)pyrimidin-2-yl)amino}benzamide

To a solution of 4-(4-chlorophenyl)-2-(methylsulfonyl)pyrimidine (0.10 g, 0.37 mmol) and 4-aminobenzamide in 2-propanol (3 ml) was heated to 120° C. in a sealed vessel for 14 hours. The crude material was concentrated and purified by preparative HPLC to provide the title compound as a beige solid: LC/MS Retention Time; 6.30 min (Method A), M+1; 325.

Example 2

Alternative Synthesis of 4-{[4-(4-Chlorophenyl)pyrimidin-2-yl]amino}benzamide

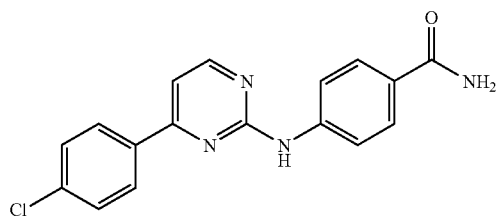

N-{(4-Aminocarbonyl)phenyl}guanidine nitrate

To a stirred suspension of 4-aminocarbonylaniline (20 g, 147 mmol) and cyanamide (14.2 g, 338 mmol) in 70 mL of ethanol was added concentrated nitric acid (20 mL) dropwise. The reaction mixture was heated at reflux overnight, and cooled. Volatile matters were evaporated to give a thick oil. The residue was taken up in methylene chloride and methanol to afford yellow solid. This material was filtered, washed with ether and water and dried in vacuo at 50° C. to afford the desired product (17.5 g, 66% yield): LC/MS Retention Time; 0.63 min (Method A), M+1; 179.

4-{(4-(4-Chlorophenyl)pyridin-2-yl)amino}benzamide

To a solution of (2E)-3-(dimethylamino)-1-(4-chlorophenyl)prop-2-en-1-one (0.10 g, 0.48 mmol), 4-(amidinoamino)benzamide nitrate (0.116 g, 0.48 mmol), and potassium carbonate (0.132 g, 0.96 mmol) in ethanol (10 ml) with was heated to 120° C. overnight in a sealed vessel. The reaction mixture was cooled to room temperature and the resulting solid was collected then washed with ethanol, water, and diethyl ether to provide the title compound as a beige solid, identical in all respects with the compound prepared in Example 1.

Example 3

Synthesis of Representative Compounds

The compounds listed below were prepared according to the procedure of Example 2 using the appropriate methylketone as the starting material.

| Compound Number | Structure | MOL. WEIGHT | RT, min | M + 1 |
|---|---|---|---|---|
| 3-1 | 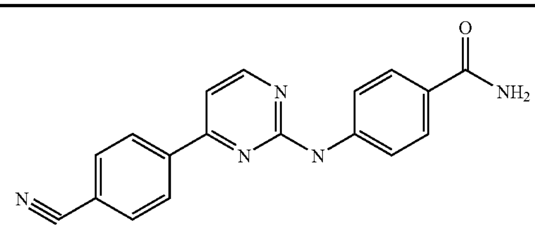 | 315.335 | 5.67 | 316 |

-continued

| Compound Number | Structure | MOL. WEIGHT | RT, min | M + 1 |
| --- | --- | --- | --- | --- |
| 3-2 | 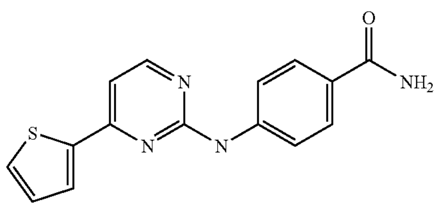 | 296.353 | 5.53 | 296 |
| 3-3 | 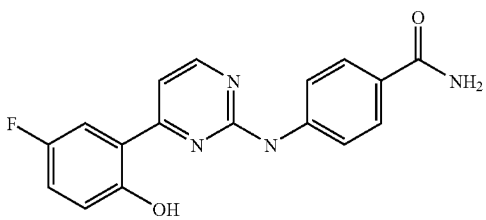 | 324.314 | 5.93 | 325 |
| 3-4 | 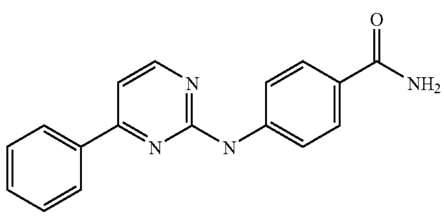 | 290.325 | 5.77 | 291 |
| 3-5 | 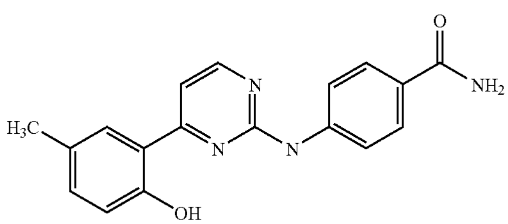 | 320.35 | 6.07 | 321 |
| 3-6 | 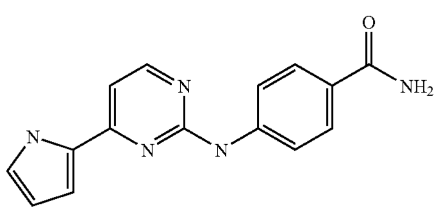 | 279.302 | 4.8 | 280 |
| 3-7 | 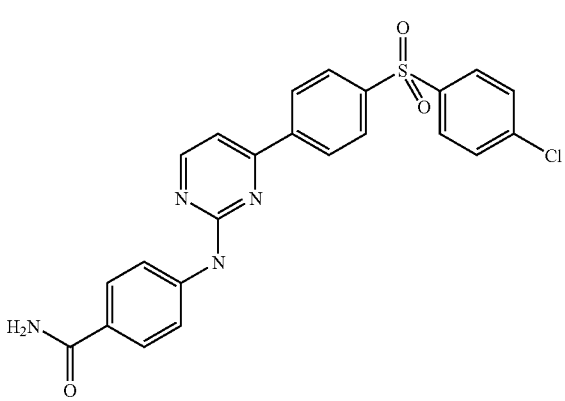 | 464.931 | 6.47 | 4.65 |

-continued

| Compound Number | Structure | MOL. WEIGHT | RT, min | M + 1 |
|---|---|---|---|---|
| 3-8 | 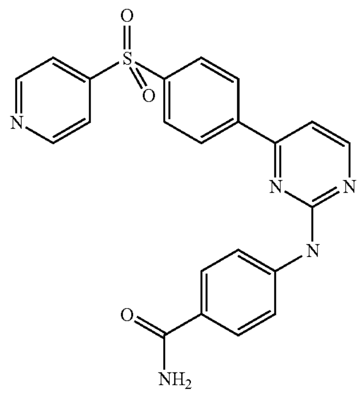 | 431.474 | 5.53 | 432 |
| 3-9 | 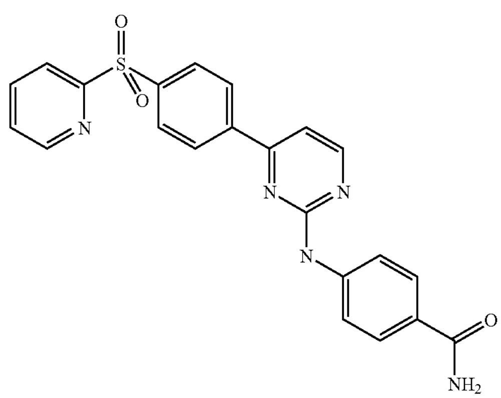 | 431.474 | 5.58 | 432 |
| 3-10 | 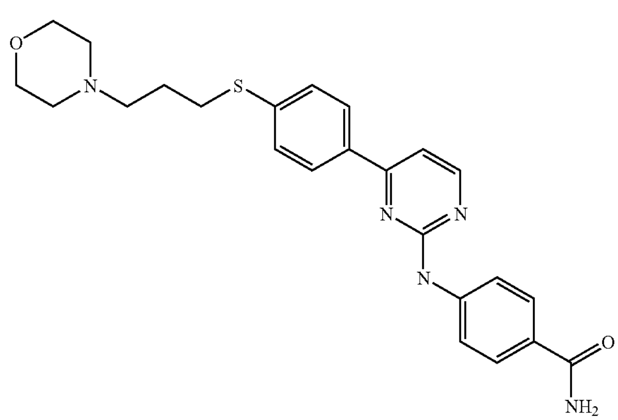 | 449.576 | 4.62 | 450 |

-continued

| Compound Number | Structure | MOL. WEIGHT | RT, min | M + 1 |
| --- | --- | --- | --- | --- |
| 3-11 | 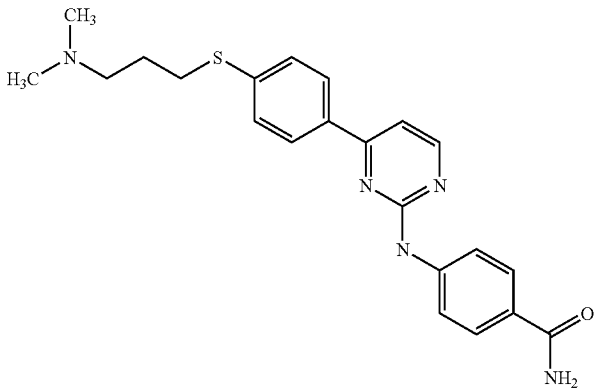 | 407.539 | 4.62 | 408 |
| 3-12 | 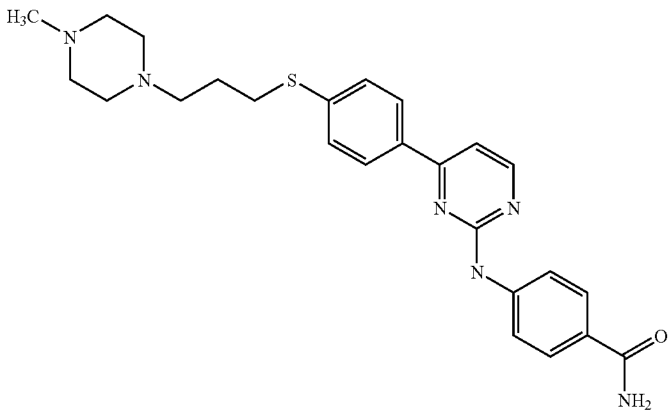 | 462.619 | 4.47 | 463 |
| 3-13 | 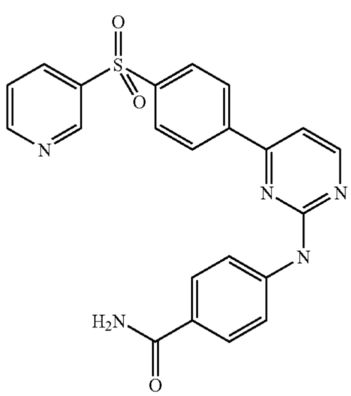 | 431.474 | 5.53 | 432 |
| 3-14 | 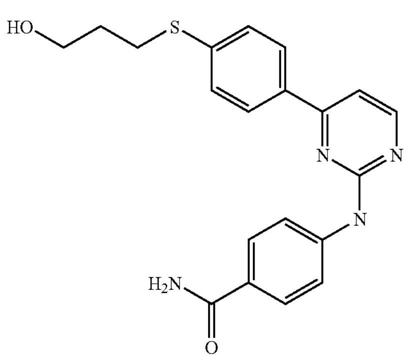 | 380.47 | 5.55 | 381 |

-continued

| Compound Number | Structure | MOL. WEIGHT | RT, min | M + 1 |
|---|---|---|---|---|
| 3-15 | 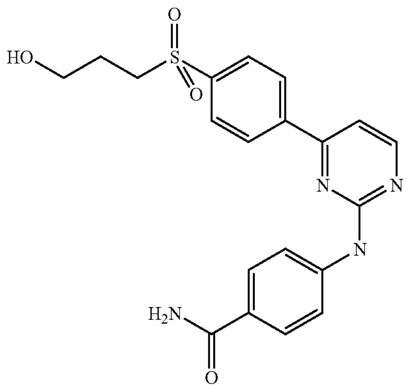 | 412.468 | 5.04 | 413 |
| 3-16 | 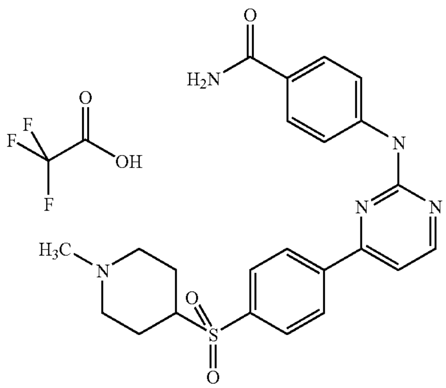 | 565.57 | 1.97 | 452 |
| 3-17 | 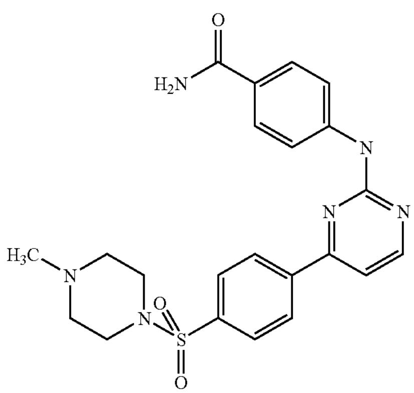 | 452.537 | 5.48 | 453 |
| 3-18 | 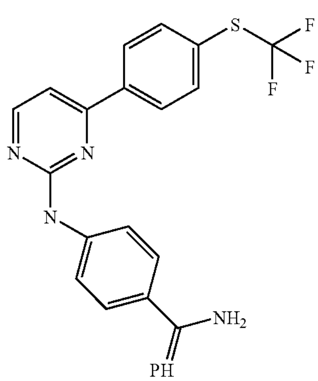 | 390.388 | 7.18 | 391 |

-continued

| Compound Number | Structure | MOL. WEIGHT | RT, min | M + 1 |
|---|---|---|---|---|
| 3-19 | (4-butylphenyl-pyrimidin-2-yl)-aminobenzamide | 346.432 | 7.43 | 347 |
| 3-20 | (4-(phenylthio)phenyl-pyrimidin-2-yl)-aminobenzamide | 398.488 | 7.4 | 399 |
| 3-21 | (4-(phenylsulfonyl)phenyl-pyrimidin-2-yl)-aminobenzamide | 430.486 | 6.64 | 431 |
| 3-22 | (4-bromophenyl-pyrimidin-2-yl)-aminobenzamide | 369.221 | 6.88 | 369 |

-continued

| Compound Number | Structure | MOL. WEIGHT | RT, min | M + 1 |
|---|---|---|---|---|
| 3-23 | 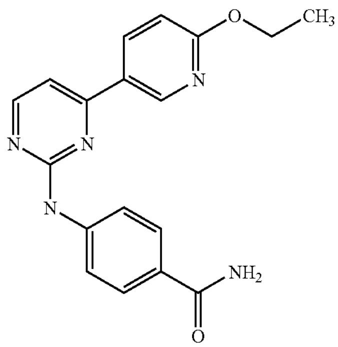 | 335.365 | 5.8 | 336 |
| 3-24 | 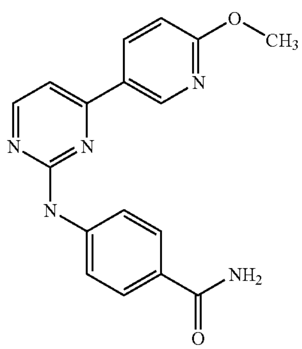 | 321.339 | 5.5 | 322 |
| 3-25 | 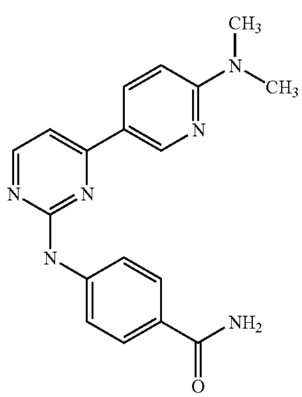 | 334.381 | 4.04 | 335 |
| 3-26 | 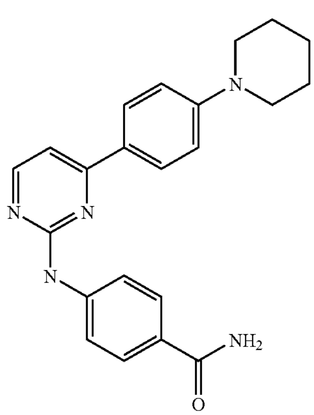 | 373.458 | 5.57 | 374 |

-continued
| Compound Number | Structure | MOL. WEIGHT | RT, min | M + 1 |
|---|---|---|---|---|
| 3-27 | 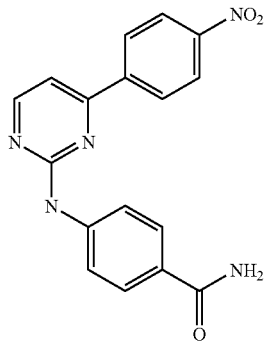 | 335.322 | 5.87 | 336 |
| 3-28 | 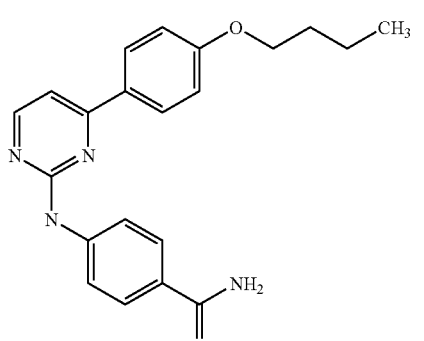 | 362.431 | 6.77 | 363 |
| 3-29 | 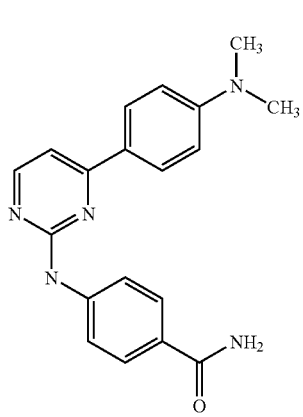 | 333.393 | 5.07 | 334 |
| 3-30 | 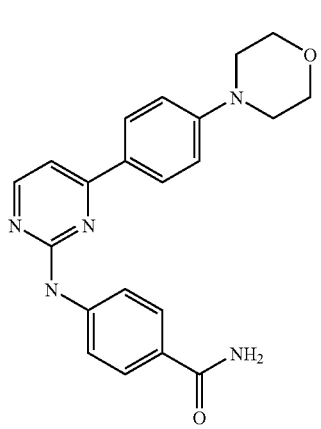 | 375.43 | 5.47 | 376 |

-continued

| Compound Number | Structure | MOL. WEIGHT | RT, min | M + 1 |
|---|---|---|---|---|
| 3-31 | 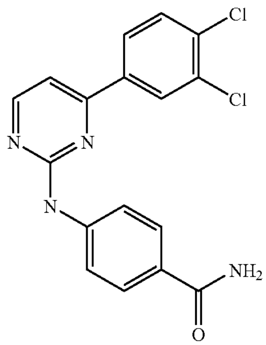 | 359.215 | 6.57 | 359 |
| 3-32 | 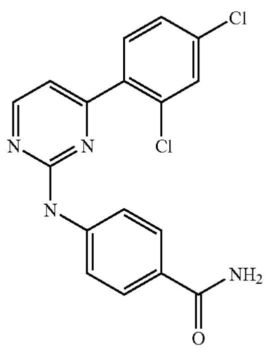 | 359.215 | 6.47 | 359 |
| 3-33 | 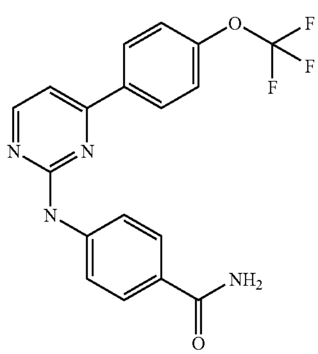 | 374.321 | 6.43 | 375 |
| 3-34 | 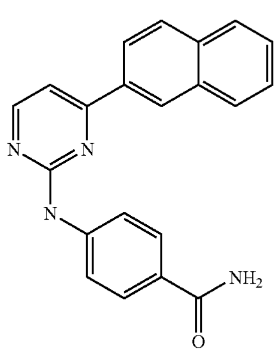 | 340.384 | 6.33 | 341 |

-continued

| Compound Number | Structure | MOL. WEIGHT | RT, min | M + 1 |
| --- | --- | --- | --- | --- |
| 3-35 | 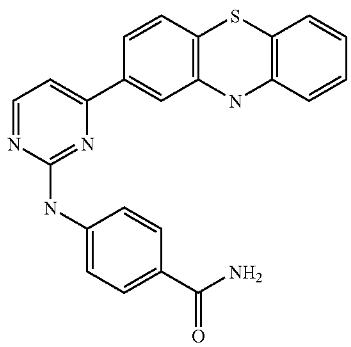 | 411.487 | 6.73 | 412 |
| 3-36 | 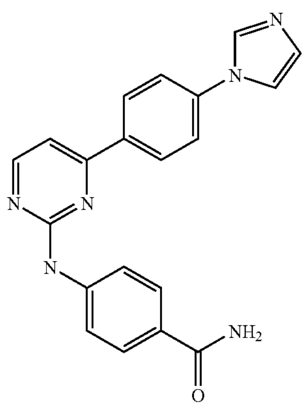 | 356.387 | 4.27 | 357 |
| 3-37 | 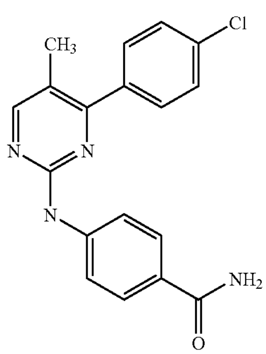 | 338.797 | 6.37 | 339 |
| 3-38 | 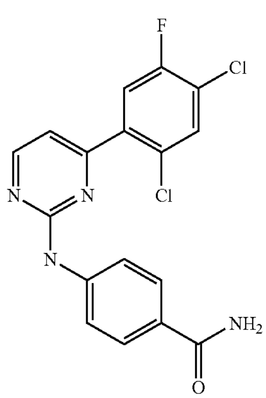 | 377.205 | 6.50 | 377 |

-continued

| Compound Number | Structure | MOL. WEIGHT | RT, min | M + 1 |
|---|---|---|---|---|
| 3-39 | 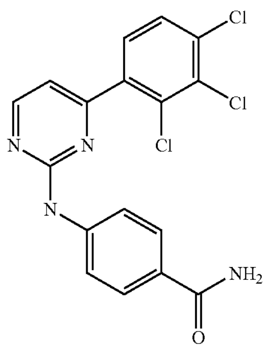 | 393.66 | 6.67 | 393 |
| 3-40 | 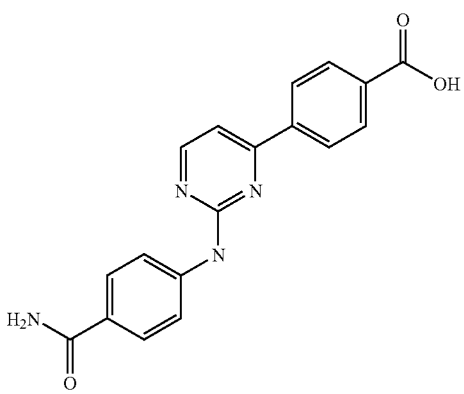 | 334.334 | 4.7 | 335 |
| 3-41 | 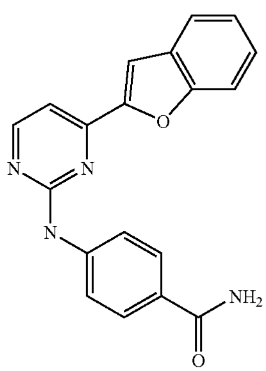 | 330.346 | 11.176 | 331 |
| 3-42 | 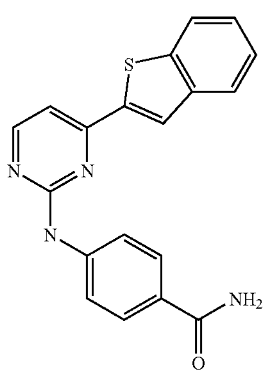 | 346.413 | 10.288 | 347 |

-continued

| Compound Number | Structure | MOL. WEIGHT | RT, min | M + 1 |
|---|---|---|---|---|
| 3-43 | 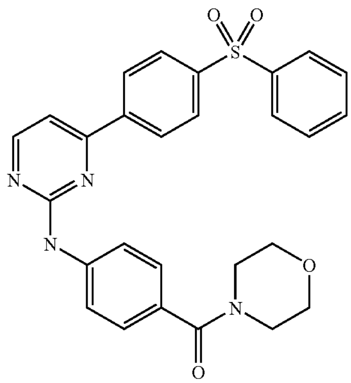 | 500.577 | 10.48 | 501.3 |
| 3-44 | 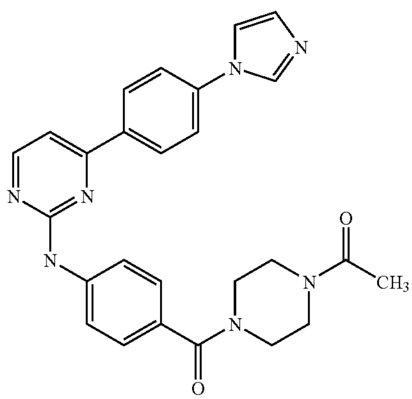 | 467.53 | 9.956 | 468.3 |
| 3-45 | 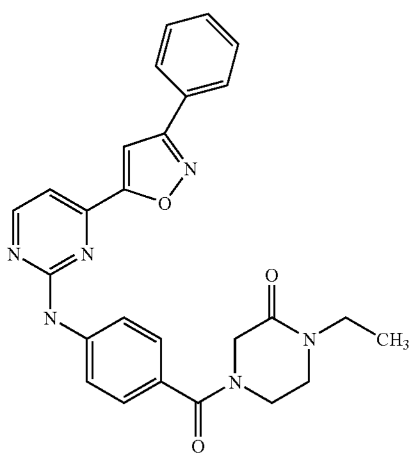 | 468.515 | 11.268 | 469.3 |
| 3-46 | 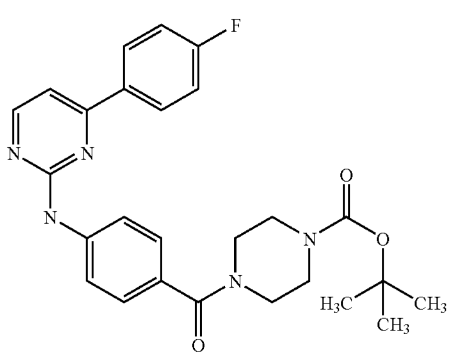 | 477.5372 | 12.74 | 478.3 |

-continued

| Compound Number | Structure | MOL. WEIGHT | RT, min | M + 1 |
|---|---|---|---|---|
| 3-47 | 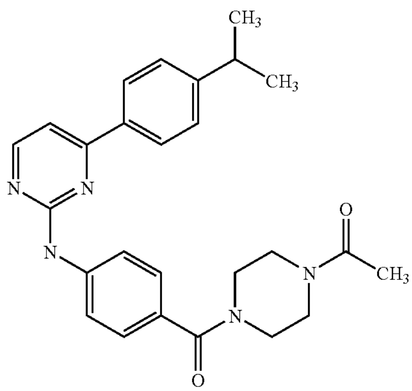 | 443.5481 | 11.292 | 444.6 |
| 3-48 | 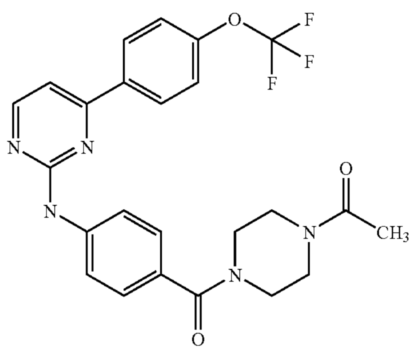 | 485.4638 | 11.396 | 486.3 |
| 3-49 | 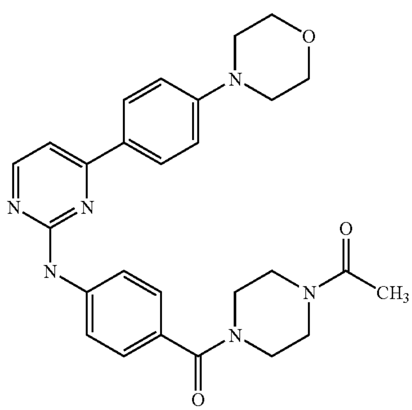 | 486.573 | 8.548 | 487.3 |
| 3-50 | 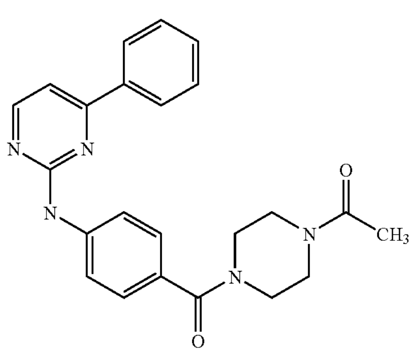 | 401.4677 | 9.664 | 402 |

-continued

| Compound Number | Structure | MOL. WEIGHT | RT, min | M + 1 |
|---|---|---|---|---|
| 3-51 | (4-fluorophenyl)-pyrimidin-2-yl-amino-phenyl-piperazine, 2 HCl | 450.3428 | 8.684 | 378.4 |
| 3-52 | [4-(trifluoromethyl)phenyl]-pyrimidin-2-yl-amino-phenyl-(4-acetylpiperazin-1-yl)methanone | 469.4648 | 11.36 | 470.3 |
| 3-53 | [4-(trifluoromethyl)phenyl]-pyrimidin-2-yl-amino-phenyl-[4-(furan-2-carbonyl)piperazin-1-yl]methanone | 521.4968 | 12.204 | 522.3 |
| 3-54 | [4-(trifluoromethylthio)phenyl]-pyrimidin-2-yl-amino-phenyl-(4-acetylpiperazin-1-yl)methanone | 501.5308 | 12.072 | 502.3 |

-continued

| Compound Number | Structure | MOL. WEIGHT | RT, min | M + 1 |
|---|---|---|---|---|
| 3-55 | 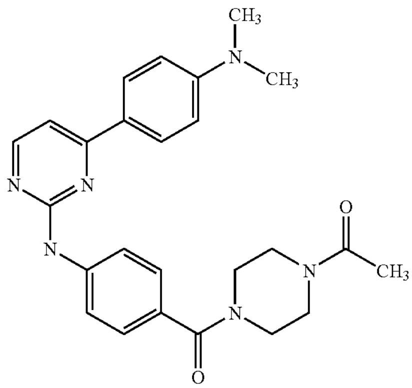 | 444.5362 | 8.696 | 445.4 |
| 3-56 | 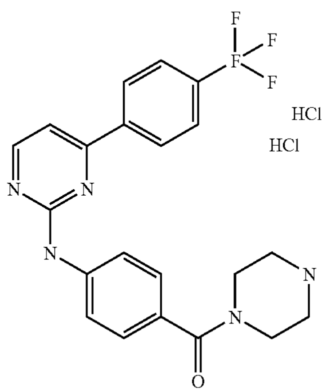 | 500.3498 | 9.74 | 428.4 |
| 3-57 | 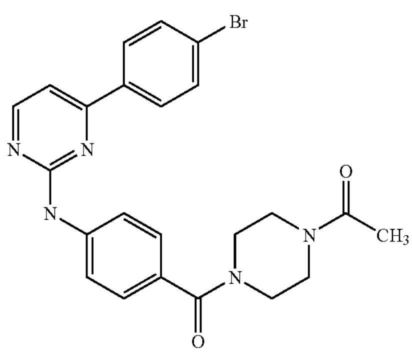 | 480.3638 | 11.084 | 482.2 |
| 3-58 | 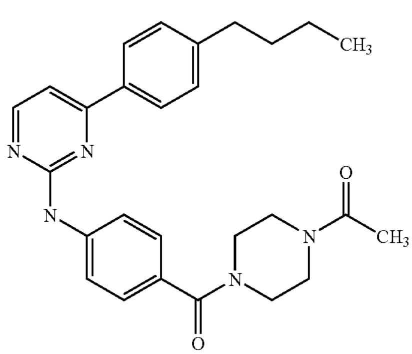 | 457.5749 | 12.344 | 458.3 |

-continued

| Compound Number | Structure | MOL. WEIGHT | RT, min | M + 1 |
|---|---|---|---|---|
| 3-59 | 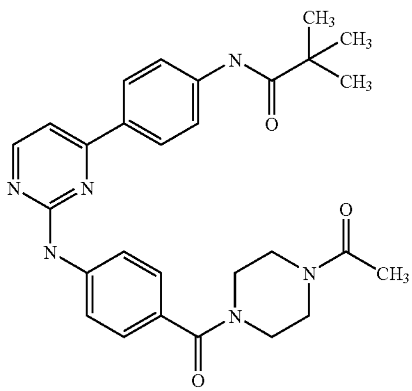 | 500.5998 | 9.924 | 501.5 |
| 3-60 | 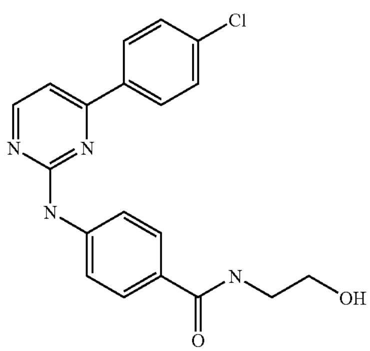 | 368.8223 | 10.624 | 369.2 |
| 3-61 | 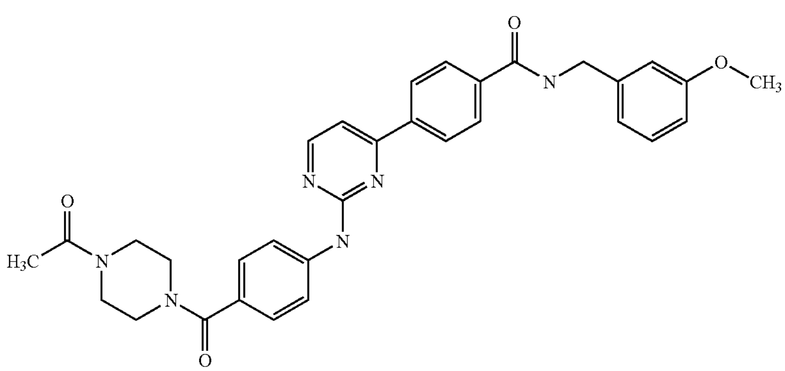 | 564.6428 | 6.49 | 565.4 |
| 3-62 | 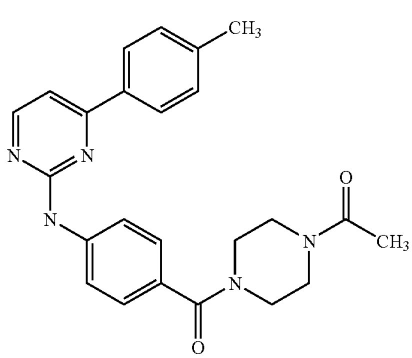 | 415.4945 | 10.268 | 416.3 |

| Compound Number | Structure | MOL. WEIGHT | RT, min | M + 1 |
|---|---|---|---|---|
| 3-63 | 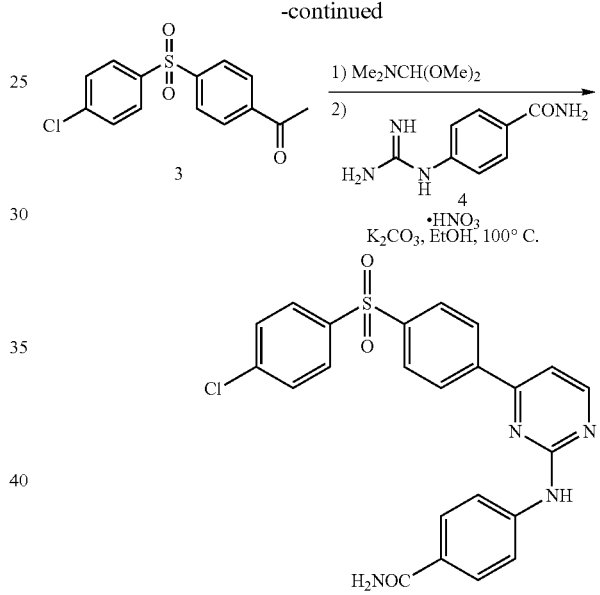 | 470.3579 | 12.05 | 470.3 |

Example 4

Synthesis of 4-[(4-{4-[(4-Chlorophenyl)sulfonyl]phenyl}pyrimidin-2-yl)amino]benzamide

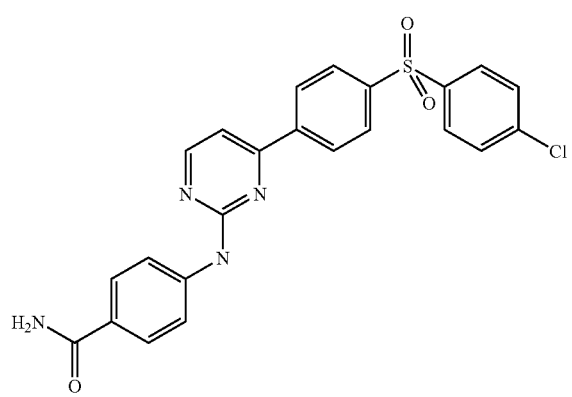

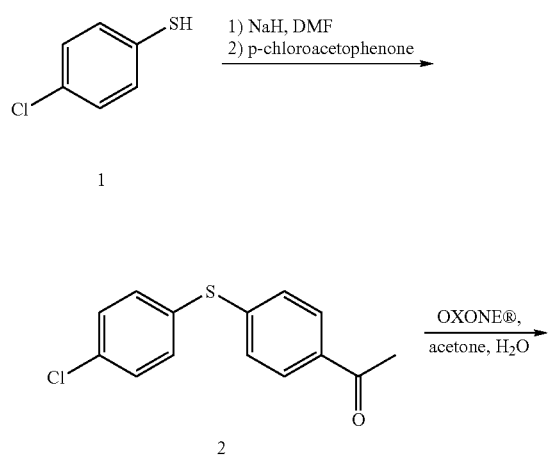

To a stirred solution of p-chlorobenzenethiol (1) (3.2 g, 0.022 mol) in DMF (40 mL) was added NaH (60% dispersion in mineral oil, 0.8 g). After the effervescence had ceased, p-chlorobenzenethiol (0.011 mol, 0.55 equiv) was added. The solution was then stirred at 110° C. for 3 h. The mixture was cooled to room temperature and then diluted with ether (150 mL). The ethereal suspension was washed with 5% NaOH (aq, 50 mL.), 3% HCl (aq, 2×50 mL), filtered, and concentrated to afford 2.88 g of p-chlorophenylthioacetophenone (2) (100%). Biarylsulfide (2) was then dissolved in acetone/water (4:1, v/v, 100 mL). OXONE (13.5 g, 2.2 equiv) was added to the solution. The reaction was stirred 4 h at room temperature. After this time, the acetone was removed in vacuo. The mixture was diluted in ether (100 mL) and water (100 mL). The mixture was shaken and the layers separated. The ether layer was dried (MgSO$_4$), filtered and concentrated to afford 2.02 g (62%) of sulfone 3. Sulfone (3) was then dissolved in dimethylformamide dimethyl acetal (15 mL) and heated to 110° C. for 12 h. The reaction mixture was then concentrated to remove excess in dimethylformamide dimethyl aceteal. A portion of the intermediate ene-amino ketone (0.38 g, 1.09 mmol) was taken up in ethanol (20 mL). To this solution was added K$_2$CO$_3$ (0.45 g, 3 equiv) and 4-guanadinobenzamide (4) (0.26 g, 1 equiv). The reaction mixture was heated in a sealed tube at 100° C. for 12 h. The mixture was then cooled to room temperature, diluted with water (30 mL), and then filtered. The solid was washed with water and ethanol. A portion of the material was purified by preparatory HPLC to afford 15 mg of the desired compound, which was found to be 100% pure by analytical HPLC. LCMS (M+H=465.0 @ 6.47 min.(Method A)).

Example 5

Synthesis of 4-({4-[4-(4-Pyridylsulfonyl)phenyl]pyrimidin-2-yl}amino)benzamide

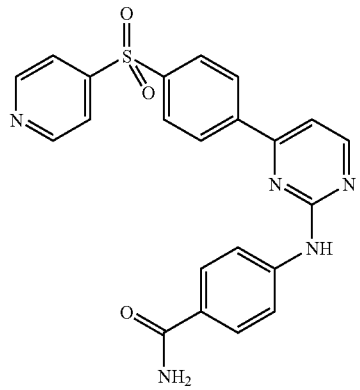

The above compound was made according to the procedure of Example 4 from 2-mercaptopyridine and the appropriate thiol as the starting materials. LCMS: (M+H=432.1, @ 5.50 min.(Method B)).

Example 6

Synthesis of 4-({4-[4-(2-Pyridylsulfonyl)phenyl]}pyrimidin-2-yl}amino)benzamide

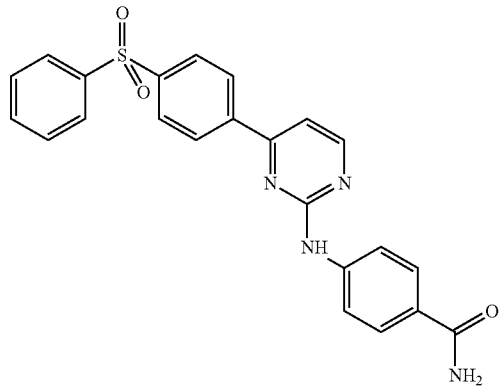

The above compound was made according to the procedure of Example 4 from 2-mercaptopyridine and the appropriate thiol as the starting materials. LCMS (M+H=432.0 @ 5.58 min.(Method B)).

Example 7

Synthesis of 4-({4-[4-(3-Pyridylsulfonyl)phenyl]pyrimidin-2-yl}amino)benzamide

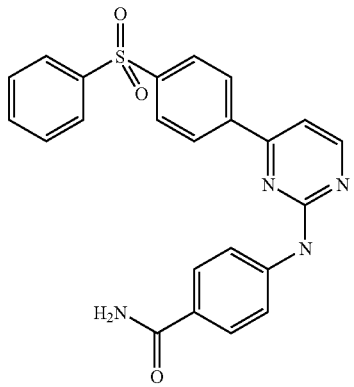

The above compound was made according to the procedure of Example 4 from 3-mercaptopyridine and the appropriate thiol as the starting materials. LCMS (M+H=432.1 @ 5.55 min.(Method B)).

Example 8

Synthesis of 4-({4-[4-(3-Hydroxypropylthio)phenyl]pyrimidin-2-yl}amino)benzamide

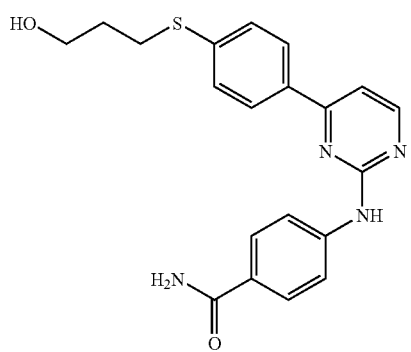

The above compound was made according to the procedure (if Example 4 from 3-mercaptopropanol and the appropriate thiol as the starting materials. LCMS (M+H=381.0 @ 5.55 min.(Method B)).

Example 9

Synthesis of 4-[(4-{4-[(3-Hydroxypropyl)sulfonyl]phenyl}pyrimidin-2-yl)amino]benzamide

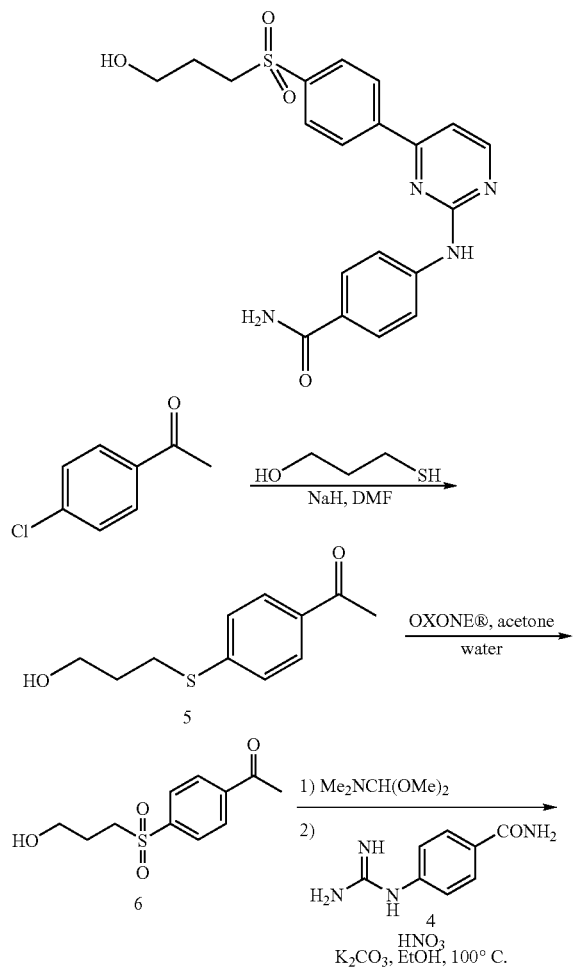

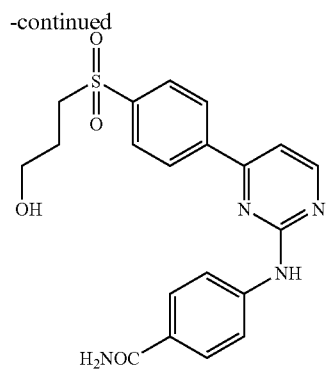

To a solution of 3-mercaptopropanol (5 g, 0.054 mol) in DMF (40 mL) was added NaH (2.2 g, 60% dispersion in mineral oil). After the bubbling had ceased, p-chloroacetophenone (5.25 mL, 0.041 mol, 0.75 equiv) was added and the mixture was stirred at 100° C. for 3 h. The reaction was cooled, diluted with ether (200 mL), and washed with 5% HCl (aq) (2×30 mL), water (2×50 mL), and then brine (40 mL). The ether layer was dried (MgSO$_4$), filtered, and concentrated to afford thioaryl ketone (5) (6.1 g, 0.29 mol, 72%). Ketone (5) (0.72 g, 3.4 mmol) was dissolved in acetone/water (4:1 v/v, 20 mL). OXONE® (4.2 g) was added and the mixture was stirred for 2 h. The mixture was then concentrated, diluted with ether (75 mL), washed with water (3×50 mL), and then brine (50 mL). The ether layer was then dried (MgSO$_4$), filtered, and concentrated to afford to aryl sulfone (6). The title compound was prepared as previously described in Example 4 from ketone (6) to afford 39 mg (3%) of analytically pure material. LCMS: (M+H=413.0 @ 5.04 min. (Method A)).

Example 10

Synthesis of 4-({4-[4-(3-Morpholin-4-ylprophylthio)phenyl]pyrimidin-2-yl}amino)benzamide

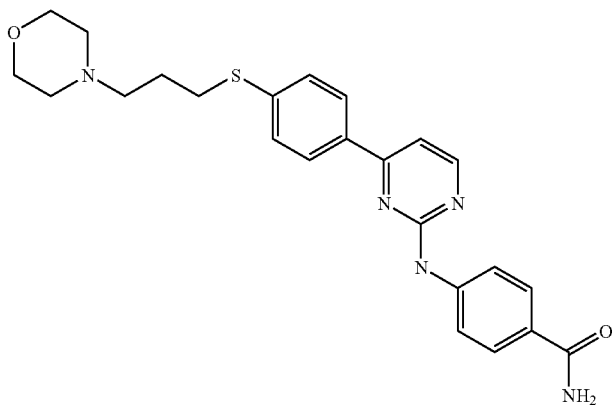

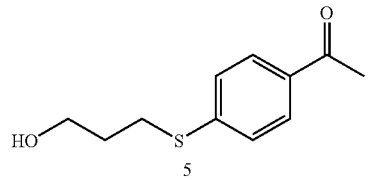 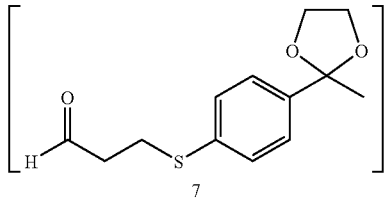

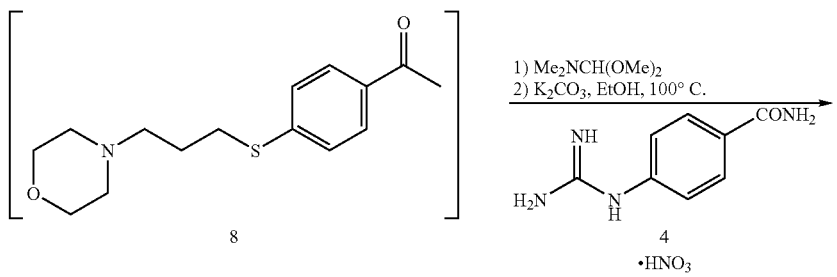

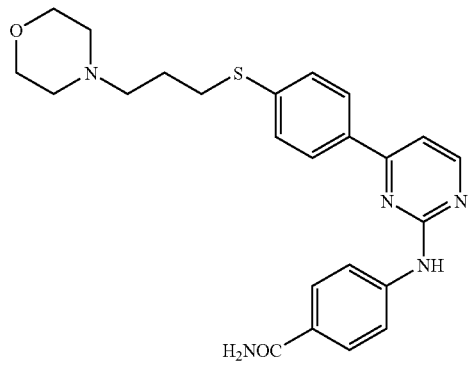

Acetophenone (5) was then taken up on toluene (50 mL). To this solution was added ethylene glycol (2.6 mL, 2 equiv) and p-toluenesulfonic acid (0.7 g). The reaction was refluxed with a Dean Stark trap for 2-3 h. After azeotropic removal of water, the reaction was cooled and then washed with 10% $NaHCO_3$ (aq, 50 mL), water (50 mL), and brine (50 mL). The organic extract was dried ($MgSO_4$), filtered, and concentrated. The crude acetal was then taken up in $CH_2CL_2$ (20 mL). In a separate flask, $(COCl)_2$ (2.26 mL, 26.0 mmol) was dissolved in $CH_2CL_2$ (20 mL) and cooled to −78° C. DMSO (3.7 mL, 52.0 mmol) in $CH_2CL_2$ (5 mL) was then added to the cold solution dropwise. This mixture was stirred for 2 min, after which the crude acetal was added in $CH_2CL_2$ (20 mL). After stirring 15 min, $Et_3N$ (16.5 mL, 5 equiv) was added slowly. The resulting mixture was stirred 5 min, and then let warm to room temperature over 1 h. The mixture was then poured into a separatory funnel and washed with 5% $NaHCO_3$ (100 mL). The organic layer was then washed with brine (50 mL), dried ($Na_2SO_4$), filtered, and concentrated to afford crude aldehyde (7). Aldehyde (7)(0.5 g) was then taken up in MeOH/AcOH (10 mL). To this solution was added morpholine (0.21 mL). The mixture was stirred 10 min. after which time $NaBH_3CN$ (0.19 g) was added. After 30 min, the reaction mixture was concentrated, basified with 3 M NaOH, and extracted with $CH_2CL_2$ (3×15 mL). The organic extracts were concentrated and then taken up in acetone/water (9:1 v/v, 20 mL). P-TsOH (0.1 g) was then added to the solution and the mixture was stirred 12 h. After this time, the mixture was concentrated, basified with 1 M NaOH, and extracted with $CH_2Cl_2$ (3×15 mL). The organic extracts were then dried ($Na_2SO_4$), filtered, and concentrated to afford crude aryl ketone (8), which was taken up in dimethylformamide dimethyl acetal (15 mL) and heated to 100° C. for 12 h. The mixture was then concentrated down and taken up in EtOH (15 mL). To this solution was added $K_2CO_3$ (0.31 g) and 4-guanadinobenzamide (4) (0.14). The reaction mixture was heated in a sealed tube at 100° C. for 12 h. The mixture was then cooled to room temperature, diluted with water (30 mL), and then filtered, The solid was flashed with water and ethanol. The material was purified by preparatory HPLC to afford the titled compound (33 mg, 4%): LCMS 4.62 min. (Method A), M+H=450.

Example 11

Synthesis of 4-[(4-{4-[3-(Dimethylamino)propylthio]phenyl}pyrimidin-2-yl)amino]benzamide

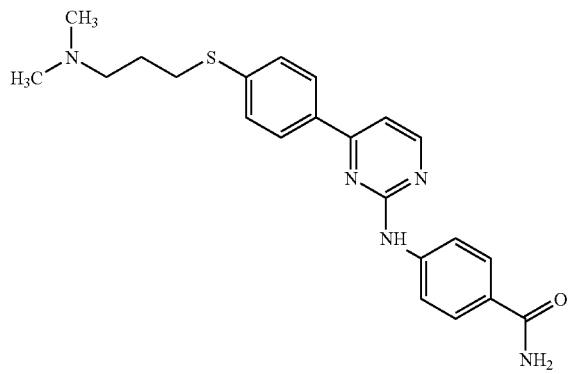

The titled compound was prepared by the procedure of Example 10, except dimethylamine was used in place of morpholine during the reductive amination of aldehyde (7). LCMS (M+H=408.0 @ 4.62 min.(Method B)).

Example 12

Synthesis of 4-[(4-{4-[3-(4-Methylpiperazinyl)propylthio]phenyl}pyrimidin-2-yl)amino]benzamide

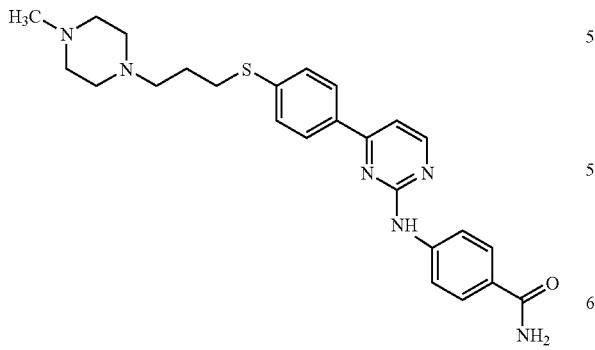

The titled compound was prepared by the procedure of Example 10, except N-methylpiperizine was used in place of morpholine in the reductive amination of aldehyde (7). LCMS (M+H=463.0 @ 4.47 min.(Method B)).

Example 13

Synthesis of 4-[4-{4-[(1-Methyl-4-piperidyl)sulfonyl]phenyl}pyrimidin-2-yl)amino]benzamide

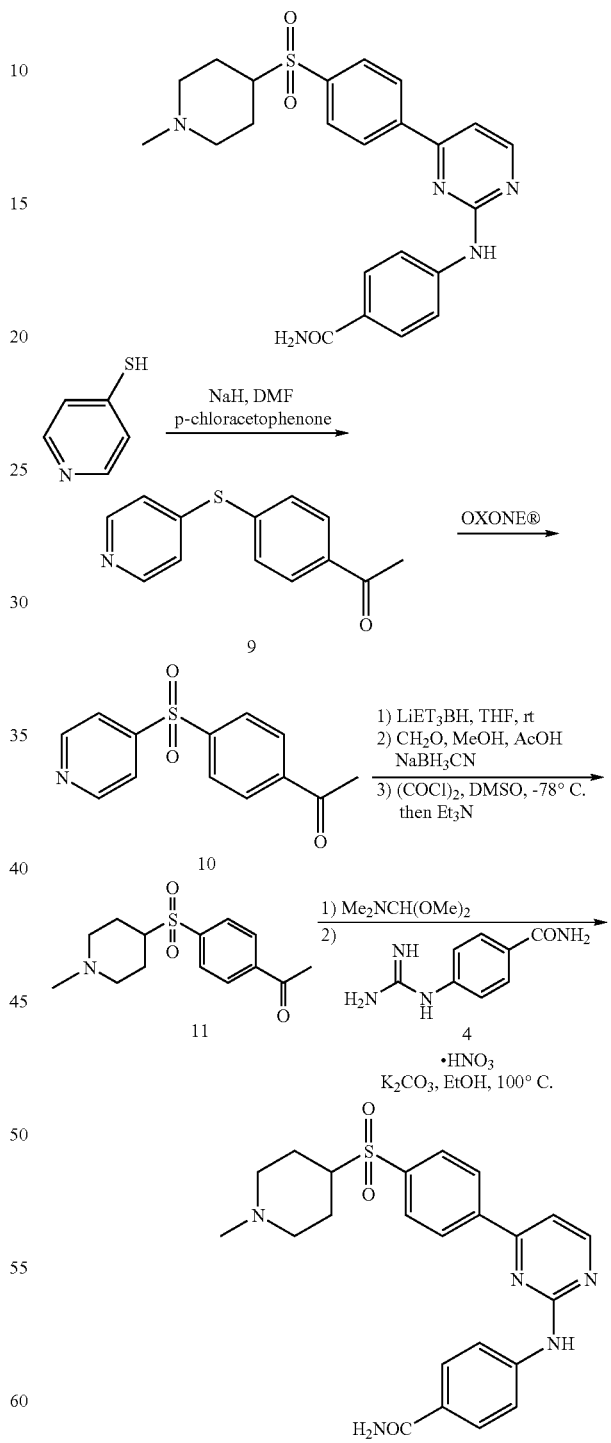

4-mercaptopyridine (2.8 g, 25,0 mmol) was dissolved in DMF (25 mL). NaH (1 g, 60% dispersion in mineral oil) was then added to the solution. After the effervescence had ceased, p-chloroacetophenone (1.4 mL, 11 mmol) was added and the mixture was heated to 110° C. for 14 h. After this time, the mixture was cooled, diluted with ether (100 mL). The mixture was washed with 5% NaOH (2×50 mL), water (2×50 mL), and brine 50 mL). The ethereal extract was dried (MgSO$_4$), filtered, and concentrated. The resulting oil was purified by flash chromatography (9:1 to 7:3 hexanes/ethyl acetate gradient). Concentration of the desired fractions afforded 1.37 g (54%) of thioacetophenone (9). Sulfide (9) (1.37 g) was then dissolved in acetone/water (9:1 v/v, 35 mL). To this solution was added OXONE® (7.4 g, 2 equiv). The mixture was stirred for 2 h. The mixture was then concentrated, neutralized with 10% NaHCO$_3$, and extracted with CH$_2$Cl$_2$ (3×50 mL). The organic extracts were dried (Na$_2$SO$_4$), filtered, and concentrated to afford diarylsulfone (10) (1.25 g, 80%). Sulfone (10) (0.53 g. 2.0 mmol) was dissolved in THF (7 mL). To this solution was added Super Hydride® (6.3 mL, 1 M in THF) at room temperature. The solution was stirred at room temperature for 1 h, followed by quenching with MeOH (0.6 mL). The mixture was then concentrated. The residue was taken up in 1 N HCl (50 mL). The aqueous mixture was extracted with ether (3×50 mL). The organic layers were discarded. The aqueous layer was basified and extracted with CH$_2$Cl$_2$ (3×15 mL). The organic layers were concentrated. The residue was taken up in AcOH/MeOH (1:1 v/v, 10 mL). CH$_2$O (37% aq, 1 mL) and NaBH$_3$CN (0.1 g) were added. The mixture was stirred 30 min. The mixture was then concentrated basified with 10% NaOH (aq) and extracted with CH$_2$Cl$_2$ (3×15 mL). The organic extracts were dried (Na$_2$SO$_4$), filtered, and concentrated to afford crude ketone (11). Aryl ketone (10) was refluxed in dimethylformamide dimethyl acetal (15 mL) and heated to 100° C. for 12 h. The mixture was then concentrated down and taken up in EtOH (15 mL). To this solution was added K$_2$CO$_3$ (0.31 g) and 4-guanadinobenzamide (4) (0.14 g). The reaction mixture was heated in a sealed tube at 100° C. for 12 h. The mixture was then cooled to room temperature, diluted with water (30 mL), and then filtered. The solid was washed with water and ethanol. The material was purified by preparatory HPLC to afford 6.0 mg (0.5% from sulfone (10)) of the title compound. LCMS (M+H=452 @ 6.13 min. (Method A)).

Example 14

Synthesis of 4-[(4-{4-[(4-Methylpiperazinyl)sulfonyl]phenyl}pyridin-2-yl)amino]benzamide

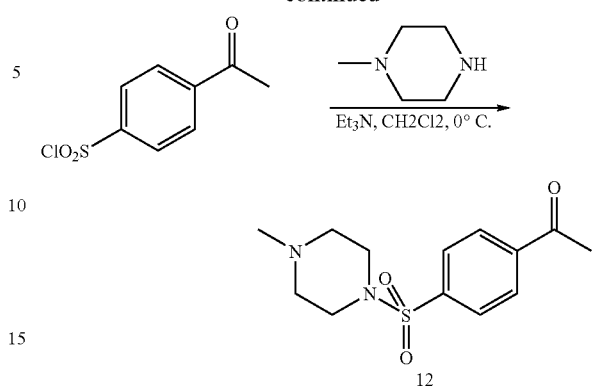

N-Methylpiperizine (1.16 mL, 0.01 mol) was dissolved in CH$_2$Cl$_2$ (30 mL) and Et$_3$N (4.4 mL, 0.033 mol). The solution was cooled to 0° C. and 4-acetylbenzenesulfonyl chloride (2.29 g, 0.01 mol) was added at once. The reaction was stirred for 15 min., poured into a separatory funnel, and extracted with water (3×20 mL) and then brine (10 mL). The organic layer was dried (Na$_2$SO$_4$), filtered, and concentrated to afford aryl ketone (12). Ketone (12) was carried on without purification to make the title compound as described in Example 13. An analytical sample was purified by preparatory HPLC (0.028 mg, 0.6%): LCMS (M+H=453.2 @ 5.48 min.(Method A)).

Example 15

Synthesis of 4-{2-[(4-Carbamoylphenyl)amino]pyrimidin-4-yl}benzoic acid

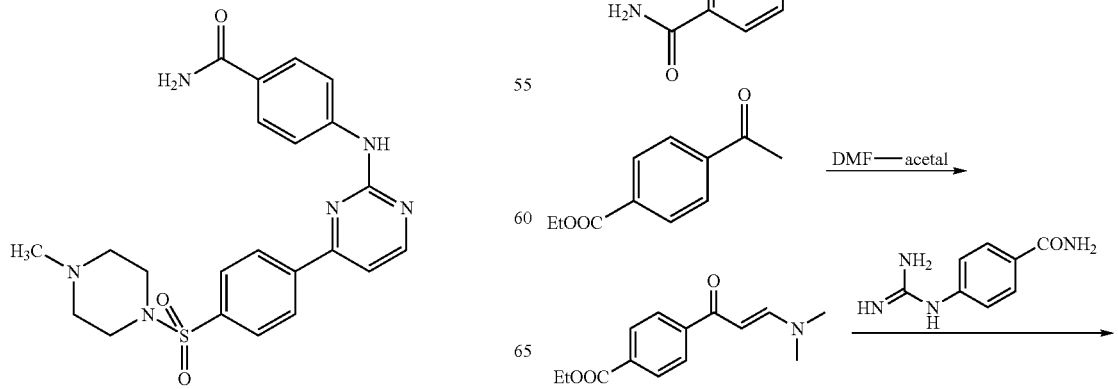

-continued

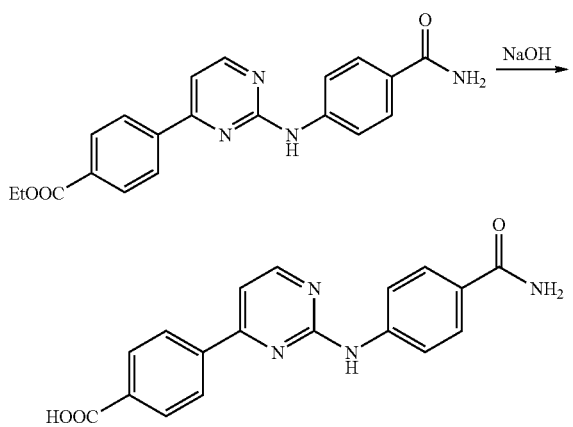

A mixture of ethyl 4-acetylbenzoate (3.00 g, 15.62 mmol) and N,N-dimethylformamide dimethyl acetal (6.2 g, 52.10 mmol) was refluxed for 18 hours, cooled and concentrated to give ethyl 4-[(2E)-3-(dimethylamino)prop-2-enoyl]benzoate quantitatively. A solution of ethyl 4-[(2E)-3-(dimethylamino) prop-2-enoyl]benzoate, potassium carbonate (3.55 g, 25.74 mmol), and 4-(amidinoamino)benzamide (3.10 g, 12.87 mmol) in ETOH (120 mL) was refluxed for 18 hours. The mixture was cooled, filtered, and washed with ETOH, water, then ether respectively to give ethyl 4-{2-[(4-carbamoylphenyl)amino]pyrimidin-4-yl}benzoate (2.60 g, 46% yield). This compound was refluxed for 2 hours in ETOH (30 mL), water (20 mL), and NaOH (0.640 g, 16 mmol). The reaction mixture was cooled, acidified to pH 3, and filtered to give 1.00 gram (42% yield) of the titled compound. HPLC/ES-MS (20-100% acetonitrile): R.T. 4.7 min.(Method A); (m/z) 335 [M+1]$^+$.

Example 16

Synthesis of (4-{[4-(4-Chlorophenyl)pyridin-2-yl]amino}phenyl)-N,N-dimethyl carboxamide

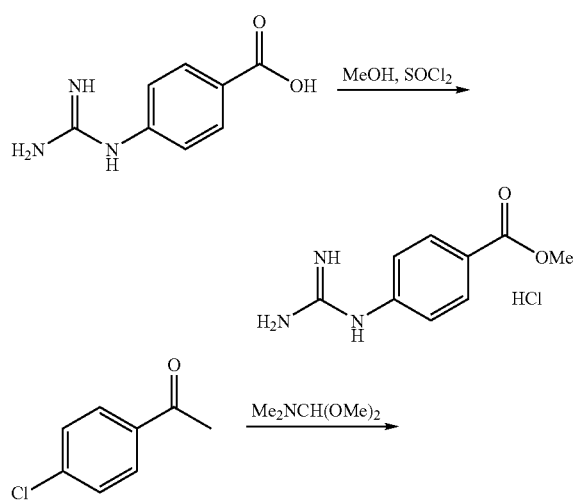

-continued

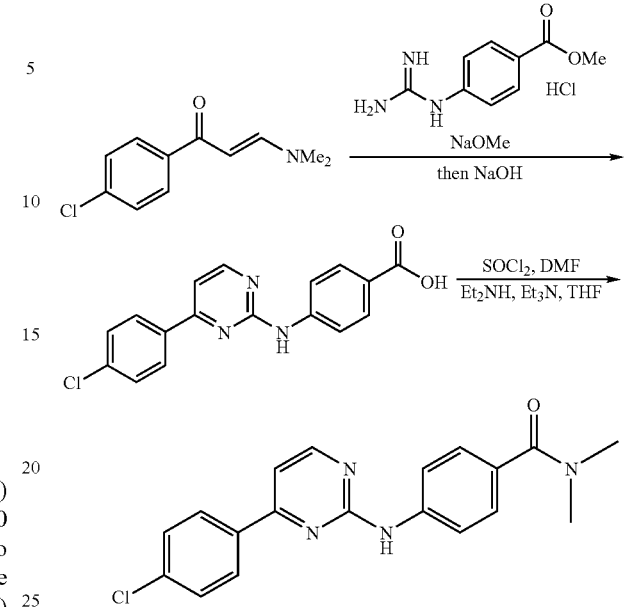

4-Guanidino-benzoic Acid Methyl Ester

To a stirred suspension of 4-guanidino benzoic acid (20.0 g, 93 mmol) in methanol (600 mL) was added thionyl chloride (12 mL) drop wise. The reaction mixture was stirred at room temperature overnight. The reaction was concentrated in vacuo to give a white powder. The crude material was dissolved in dichloromethane and evaporated to provide the title compound as a white powder (17.95 g, 100% yield): HPLC Retention Time; 1.27 min (Method A). M+1; 193.

(2E)-3-Dimethylamino-1-(4-chlorophenyl)prop-2-en-1-one

A solution of 1-(4-chlorophenyl)ethane-1-one (35.0 g, 226 mmol) and N,N Dimethylformamide diisopropylacetal (35 mL) was heated to reflux for 16 hours. The reaction mixture was cooled to room temperature and treated with hexanes (50 mL). The resulting solid was collected via filtration and washed with hexanes to provide the title compound as a yellow solid (47.12 g, 99% yield): HPLC Retention Time; 6.45 min (Method B). M+1; 209.

4-[4-(4-Cholorophenyl)-pyrimidin-2-ylamino]benzoic Acid

A Solution of 4-guanidino-benzoic acid methyl ester (17.95, g, 93 mmol), (2E) 3-dimethylamino-1-(4-chlorophenyl)prop-2-en-1-one (19.44 g, 93 mmol, and potassium carbonate (38.50 g, 279 mmol) in 1-propanol was heated to reflux for 24 hours. The reaction mixture was cooled to room temperature. The resulting solid was collected via filtration and washed with ethanol to provide the title compound which was used without further purification. EI MS(m/z) 339 [M+1]$^+$. To a suspension of 4-[4-(4-chlorophenyl)-pyrimidin-2-ylamino]benzoic acid methyl ester in methanol (100 mL) was added 5N NaOH (100 mL). The reaction mixture was heated to reflux for 4 hours and then cooled to room temperature. The resulting solid was collected via filtration, washed with hexanes, and dried in vacuo to provide the title compound as a yellow solid (27.36 g, 100% yield): HPLC Retention Time; 7.29 min (Method A). M+1; 325.

(4-{[4-(4-Chlorophenyl)-pyrimidin-2-yl]amino}phenyl)-N,N-dimethyl carboxamide

To 4-{[4-(4-chlorophenyl)pyrimidin-2-yl]amino}benzoic acid (200 mg, 0.615 mmol) is added thionyl chloride (4 mL) along with a catalytic amount of DMF at room temperature. The resulting suspension is then refluxed for a period of 1 hour resulting in a clear pale yellow solution which was concentrated in vacuo. To the flask was then added a solution of dimethylamine (615 µL of a 2.0 M solution in THF, 1.23 mmol) and triethylamine (124 mg, 1.23 mmol) in tetrahydrofuran (4.5 mL). The solution was then stirred for 18 hours at room temperature, diluted with water (5 mL) and filtered. Purification of the remaining solid by preparative HPLC yielded the title compound. HPLC/ES-MS: RT 6.74 min. (Method A); (m/z) 353 [M+1]$^+$.

Example 17

Synthesis of Further Representative Compounds

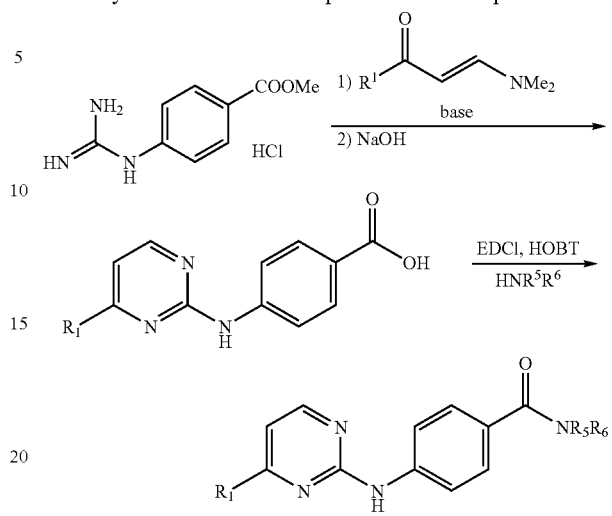

Compounds listed below were prepared according to the above procedure:

| Compound Number | Structure | MOL. WEIGHT | RT, min | M + 1 |
|---|---|---|---|---|
| 17-1 | 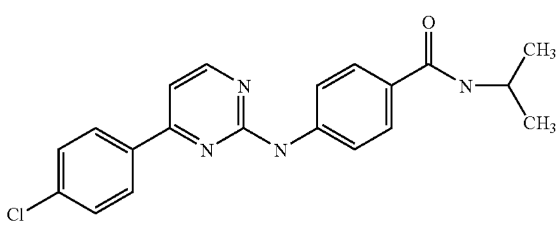 | 366.85 | 7.02 | 367 |
| 17-2 | 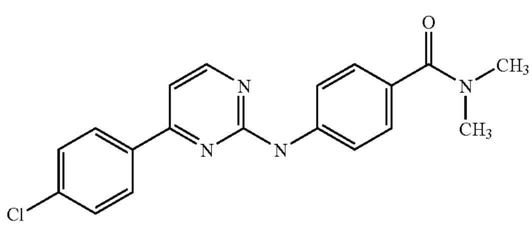 | 352.823 | 6.74 | 353 |
| 17-3 | 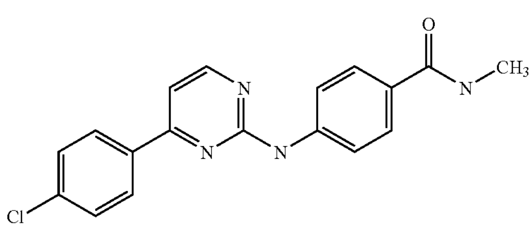 | 338.797 | 6.43 | 339 |
| 17-4 | 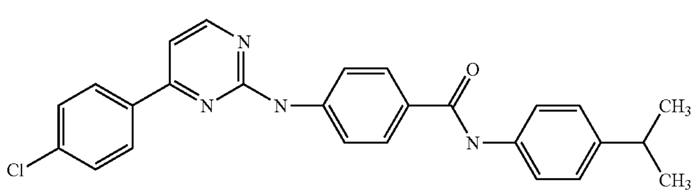 | 442.948 | 7.97 | 443 |

-continued

| Compound Number | Structure | MOL. WEIGHT | RT, min | M + 1 |
|---|---|---|---|---|
| 17-5 | 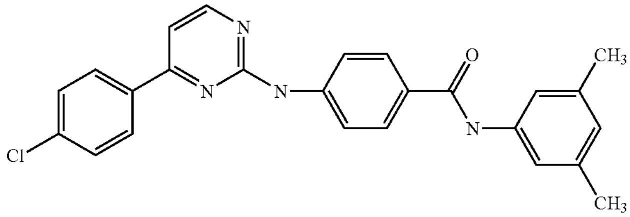 | 428.921 | 7.83 | 429 |
| 17-6 | 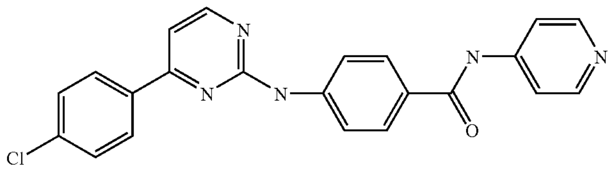 | 418.857 | 7.53 | 419 |
| 17-7 | 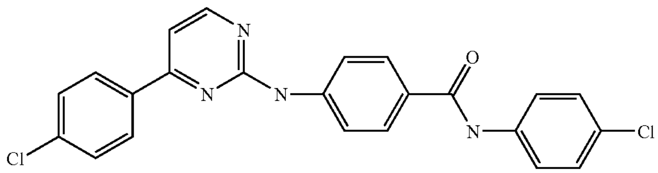 | 435.312 | 7.80 | 436 |
| 17-8 | 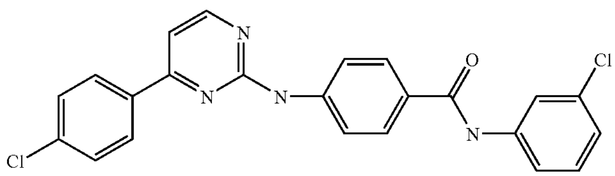 | 435.312 | 7.80 | 436 |
| 17-9 | 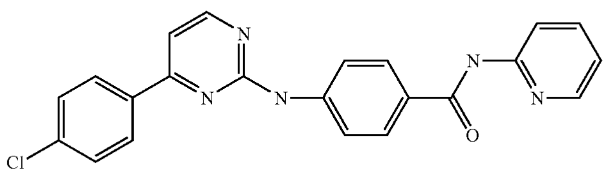 | 401.855 | 6.82 | 402 |
| 17-10 | 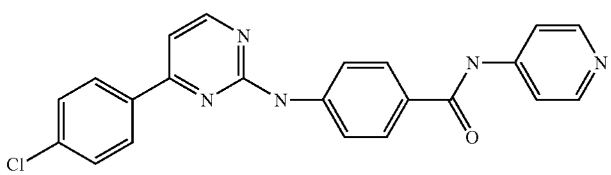 | 401.855 | 6.82 | 402 |
| 17-11 | 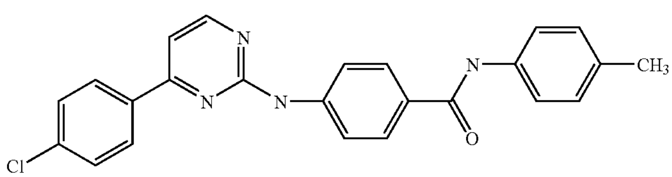 | 414.894 | 7.67 | 415 |
| 17-12 | 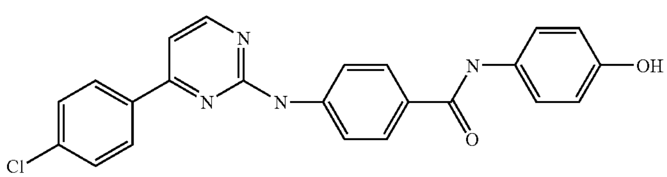 | 416.866 | 6.87 | 417 |

| Compound Number | Structure | MOL. WEIGHT | RT, min | M + 1 |
|---|---|---|---|---|
| 17-13 | 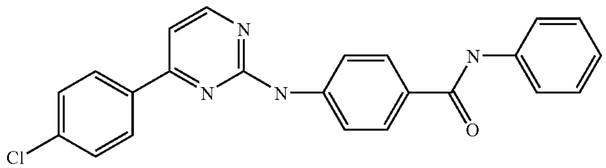 | 400.867 | 7.53 | 401 |
| 17-14 | 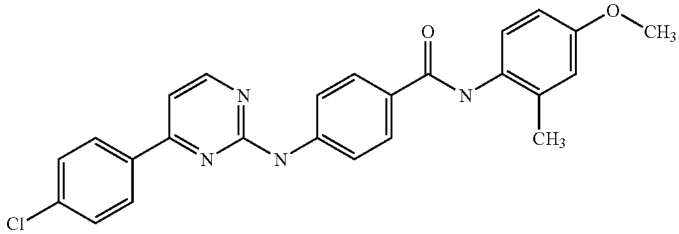 | 444.92 | 7.40 | 445 |
| 17-15 | 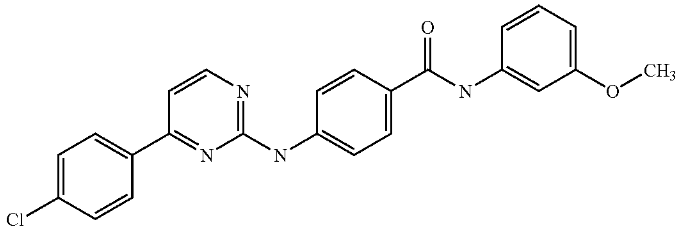 | 430.893 | 7.50 | 431 |
| 17-16 | 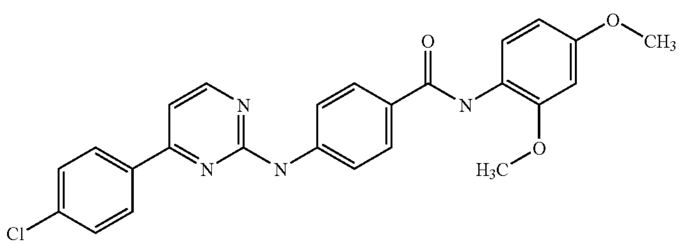 | 460.919 | 7.60 | 461 |
| 17-17 | 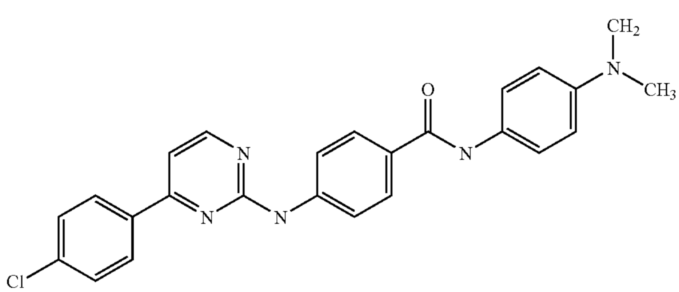 | 443.936 | 5.97 | 444 |
| 17-18 | 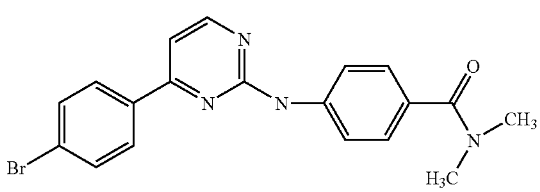 | 397.274 | 6.77 | 397 |

-continued

| Compound Number | Structure | MOL. WEIGHT | RT, min | M + 1 |
| --- | --- | --- | --- | --- |
| 17-19 | 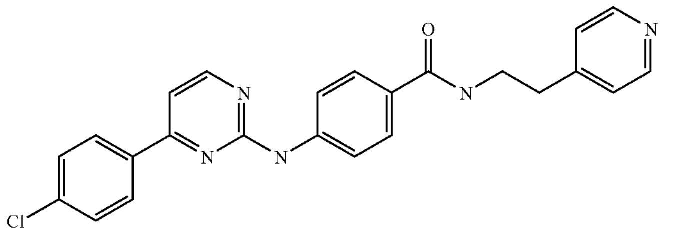 | 429.909 | 5.07 | 430 |
| 17-20 | 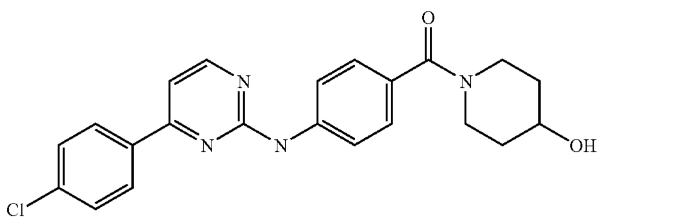 | 408.887 | 6.1 | 409 |
| 17-21 | 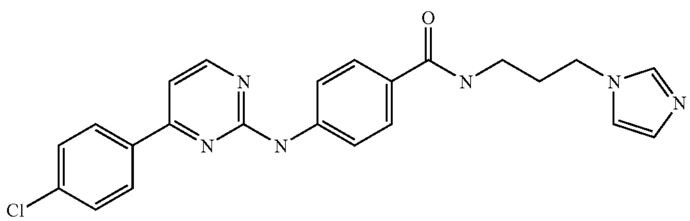 | 432.913 | 4.53 | 433 |
| 17-22 | 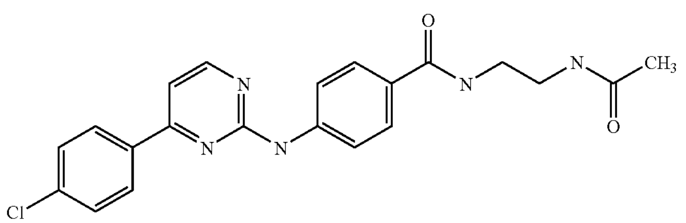 | 409.875 | 5.57 | 410 |
| 17-23 | 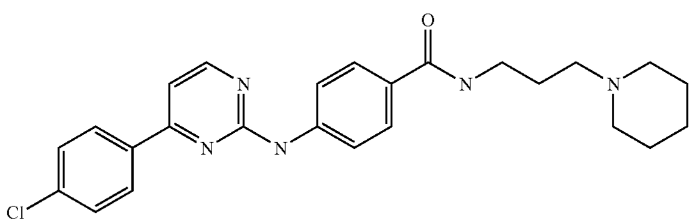 | 449.983 | 4.73 | 450 |
| 17-24 | 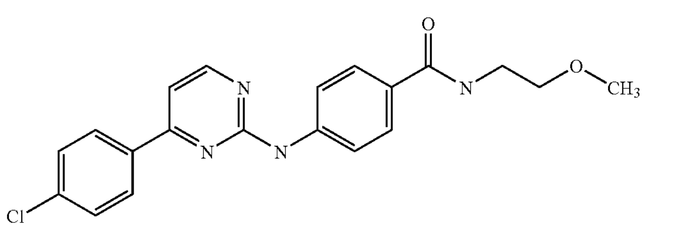 | 382.849 | 6.17 | 383 |

-continued
| Compound Number | Structure | MOL. WEIGHT | RT, min | M + 1 |
|---|---|---|---|---|
| 17-25 | 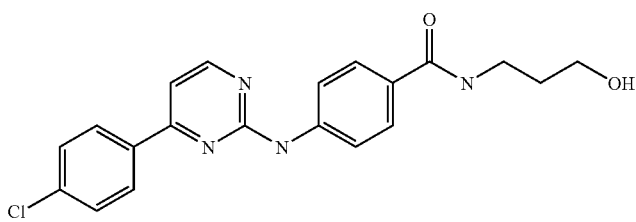 | 382.849 | 6.1 | 383 |
| 17-26 | 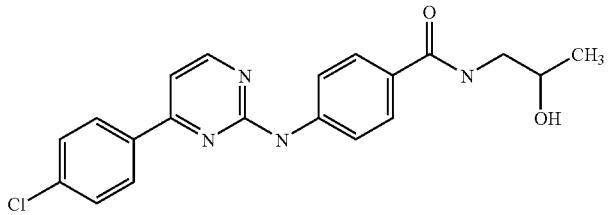 | 382.849 | 6.17 | 383 |
| 17-27 | 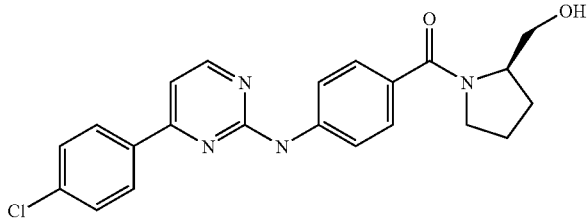 | 408.887 | 6.28 | 409 |
| 17-28 | 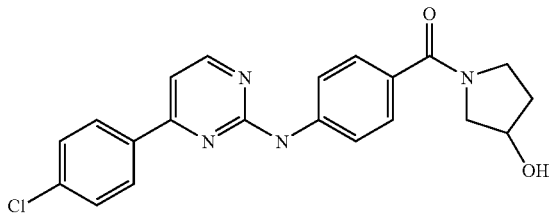 | 394.86 | 5.87 | 395 |
| 17-29 | 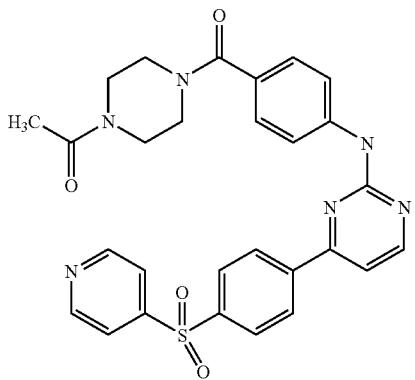 | 542.617 | 5.9 | 543 |

-continued

| Compound Number | Structure | MOL. WEIGHT | RT, min | M + 1 |
|---|---|---|---|---|
| 17-30 | 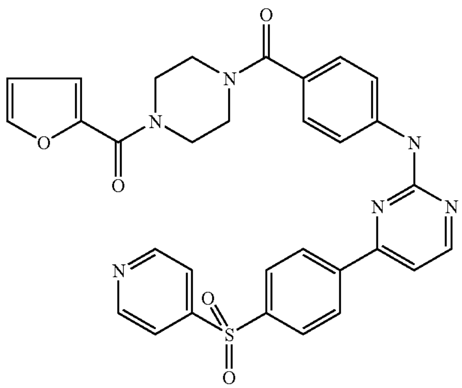 | 594.649 | 5.86 | 595 |
| 17-31 | 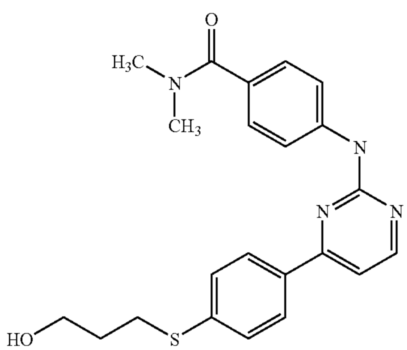 | 408.524 | 5.58 | 409 |
| 17-32 | 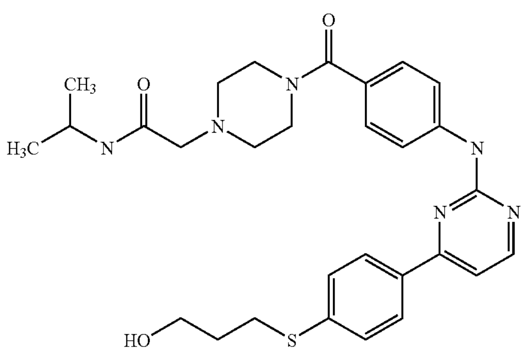 | 548.708 | 5.89 | 549 |
| 17-33 | 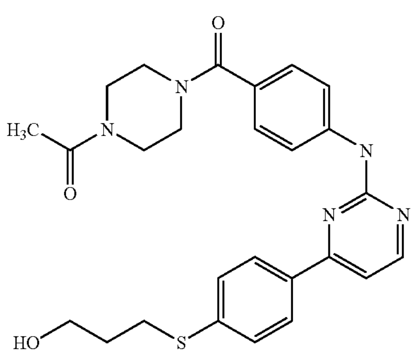 | 491.613 | 5.32 | 492 |

| Compound Number | Structure | MOL. WEIGHT | RT, min | M + 1 |
|---|---|---|---|---|
| 17-34 | 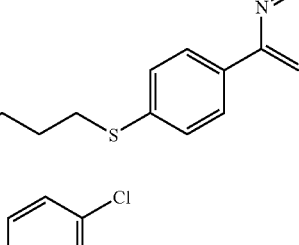 | 543.645 | 6.73 | 544 |
| 17-35 | 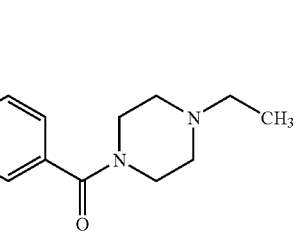 | 421.922 | 5.92 | 422 |
| 17-36 | 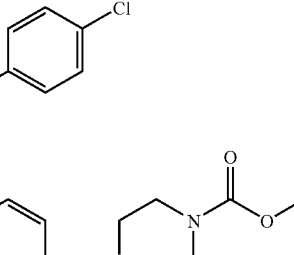 | 493.992 | 8.04 | 494 |
| 17-37 | 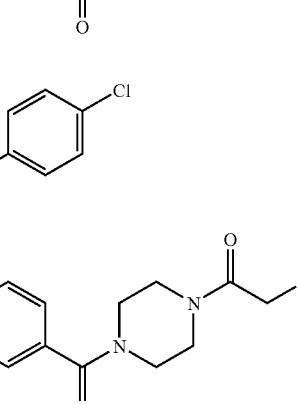 | 449.933 | 11.2 | 450 |

-continued

| Compound Number | Structure | MOL. WEIGHT | RT, min | M + 1 |
|---|---|---|---|---|
| 17-38 | 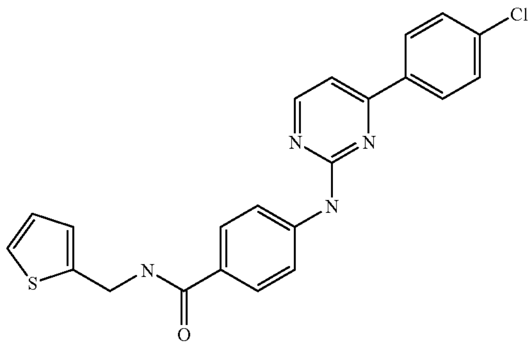 | 420.922 | 7.7 | 421 |
| 17-39 | 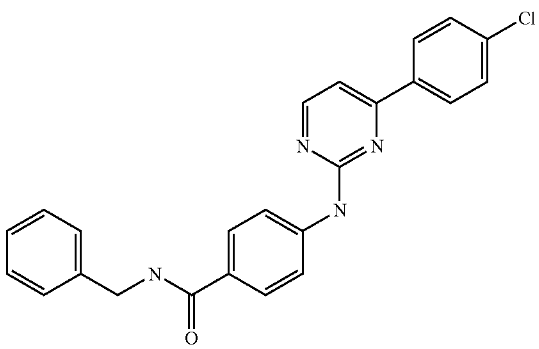 | 414.894 | 7.8 | 415 |
| 17-40 | 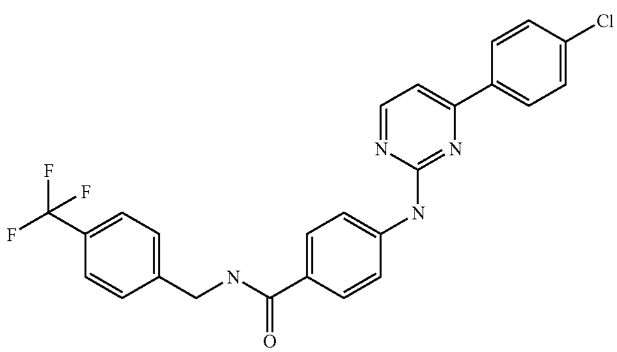 | 482.891 | 8.1 | 483 |
| 17-41 | 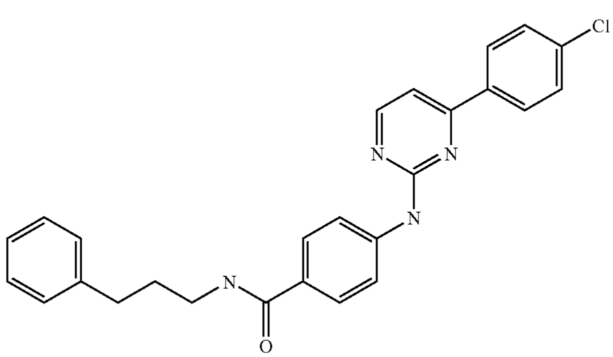 | 442.948 | 8.07 | 443 |

-continued

| Compound Number | Structure | MOL. WEIGHT | RT, min | M + 1 |
|---|---|---|---|---|
| 17-42 | 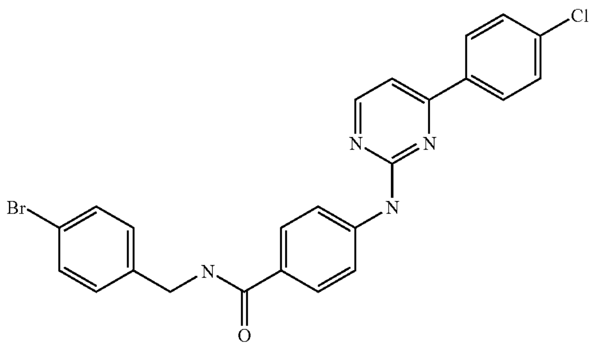 | 493.79 | 8 | 495 |
| 17-43 | 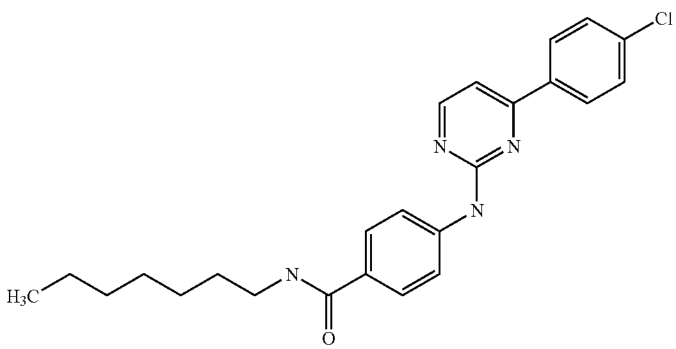 | 422.957 | 8.4 | 423 |
| 17-44 | 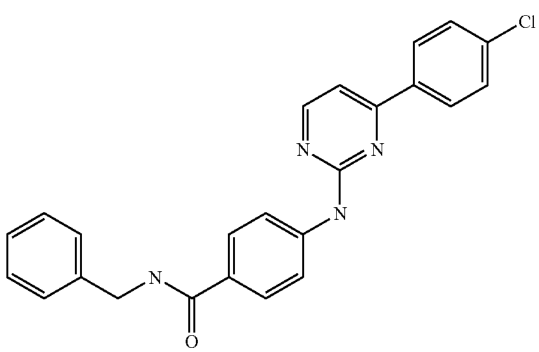 | 406.915 | 7.9 | 407 |
| 17-45 | 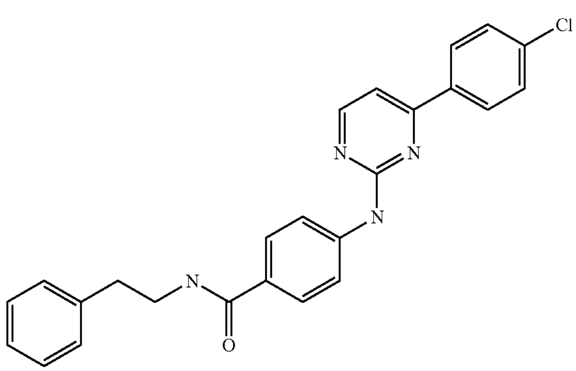 | 428.921 | 7.8 | 429 |

-continued
| Compound Number | Structure | MOL. WEIGHT | RT, min | M + 1 |
|---|---|---|---|---|
| 17-46 | 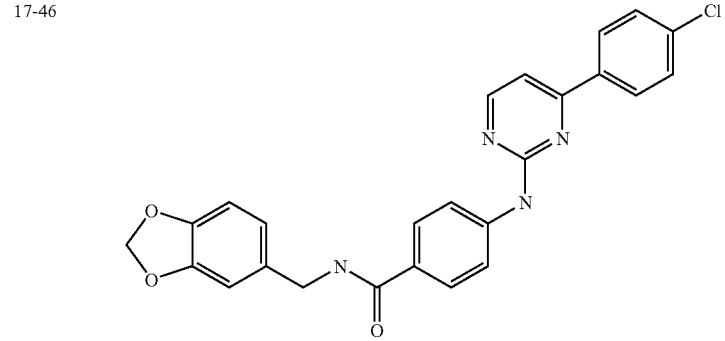 | 458.903 | 7.7 | 459 |
| 17-47 | 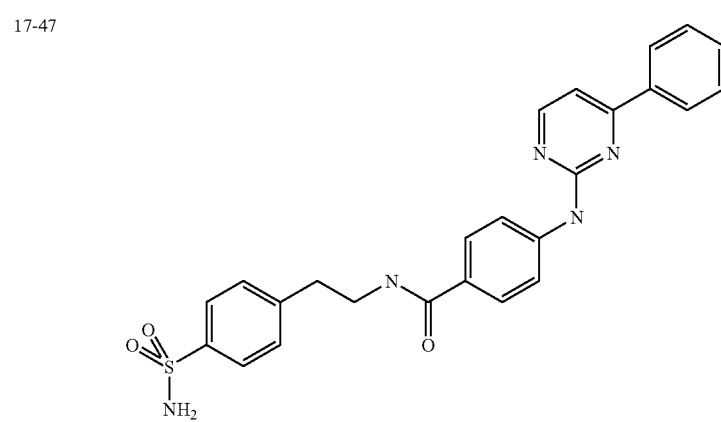 | 508 | 6.2 | 508 |
| 17-48 | 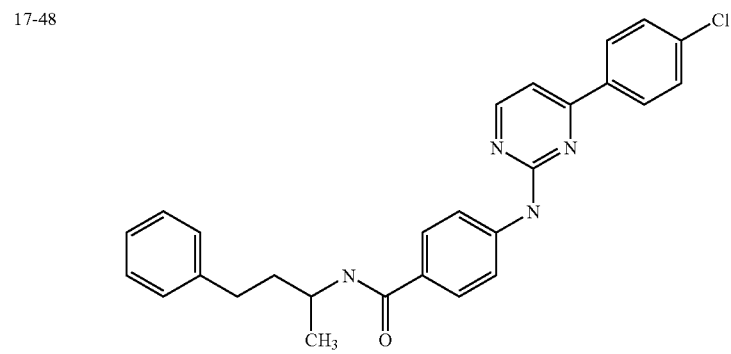 | 456.974 | 7.5 | 457 |
| 17-49 | 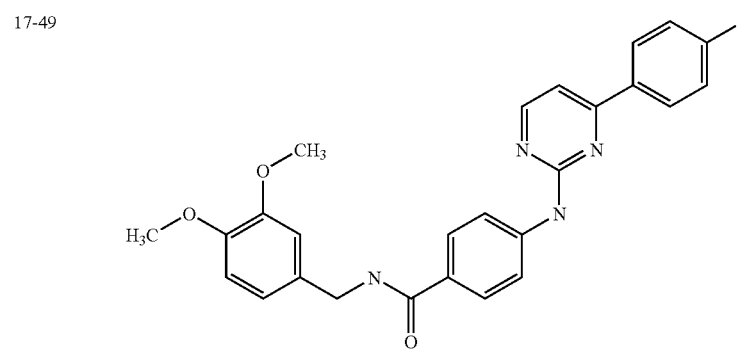 | 474.946 | 6.7 | 475 |

| Compound Number | Structure | MOL. WEIGHT | RT, min | M + 1 |
|---|---|---|---|---|
| 17-50 | 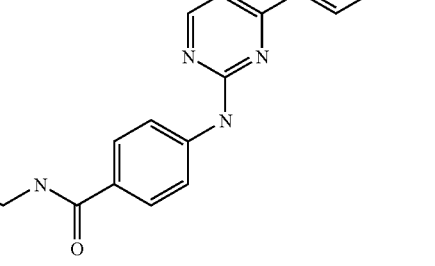 | 467.954 | 6.7 | 468 |
| 17-51 | 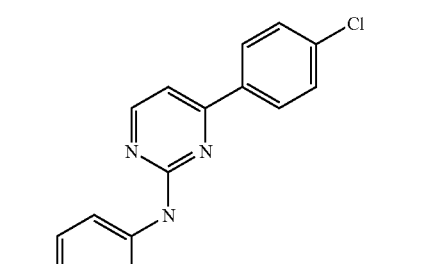 | 488.973 | 7.6 | 489 |
| 17-52 | 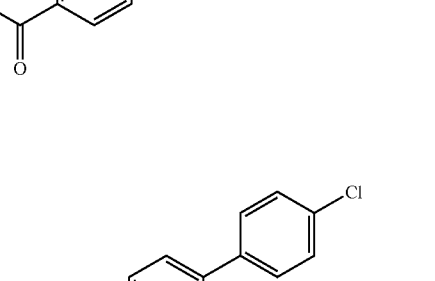 | 550.888 | 8.5 | 551 |
| 17-53 | 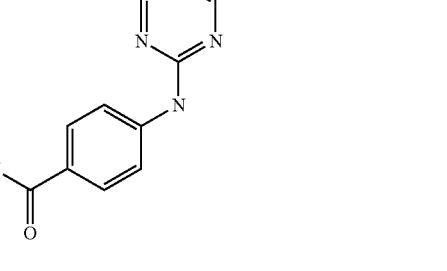 | 505.018 | 7.8 | 505 |

-continued
| Compound Number | Structure | MOL. WEIGHT | RT, min | M + 1 |
|---|---|---|---|---|
| 17-54 | 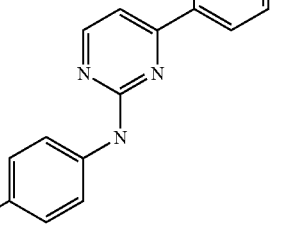 | 449.94 | 5.9 | 450 |
| 17-55 | 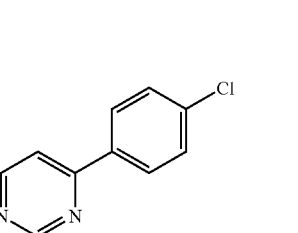 | 420.941 | 8.2 | 421 |
| 17-56 | 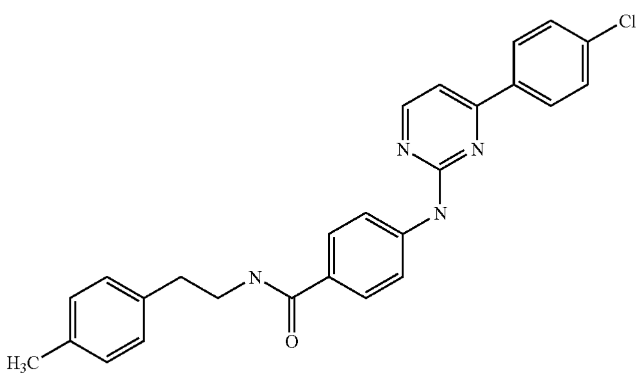 | 442.948 | 8 | 443 |
| 17-57 | 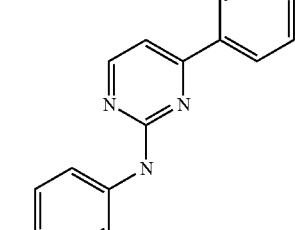 | 432.953 | 8.2 | 433 |

-continued
| Compound Number | Structure | MOL. WEIGHT | RT, min | M + 1 |
|---|---|---|---|---|
| 17-58 | 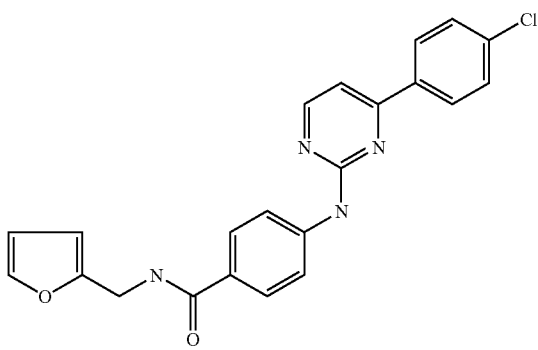 | 404.855 | 7.5 | 405 |
| 17-59 | 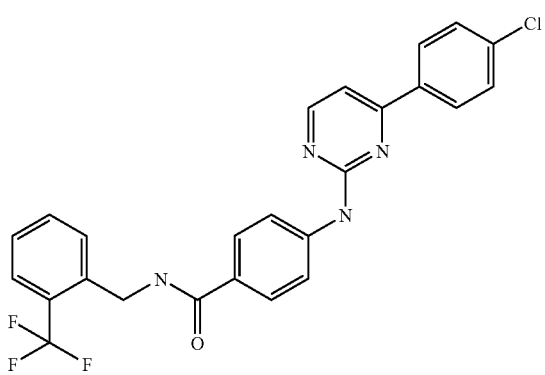 | 482.891 | 8.1 | 483 |
| 17-60 | 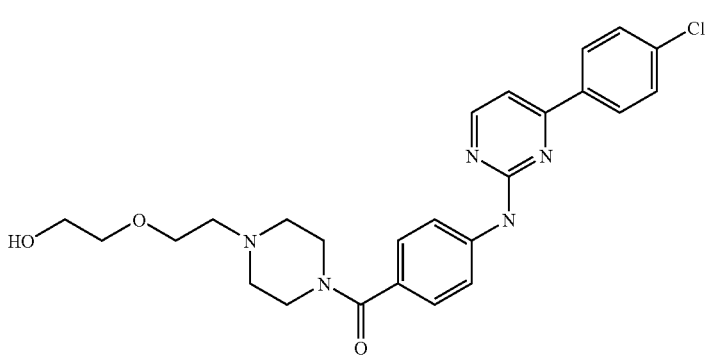 | 504.971 | 7.6 | 505 |
| 17-61 | 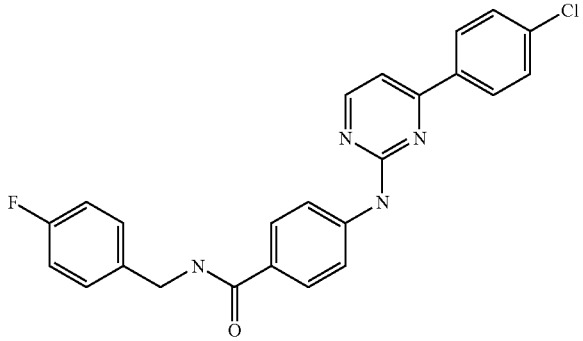 | 432.884 | 7.8 | 433 |

-continued

| Compound Number | Structure | MOL. WEIGHT | RT, min | M + 1 |
|---|---|---|---|---|
| 17-62 | 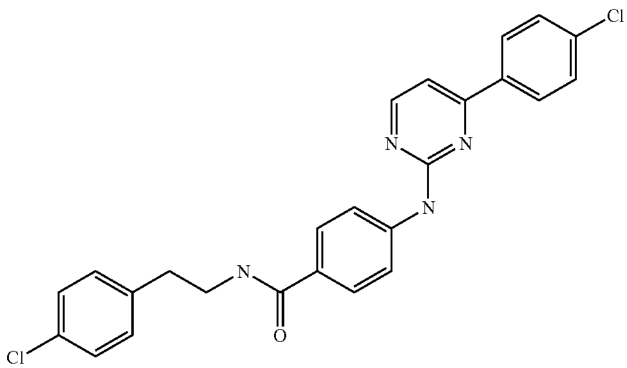 | 463.366 | 8.1 | 463 |
| 17-63 | 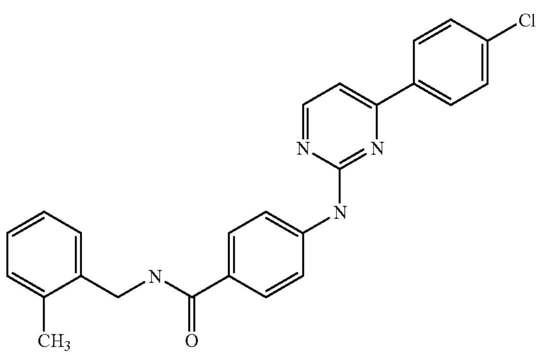 | 428.921 | 7.9 | 429 |
| 17-64 | 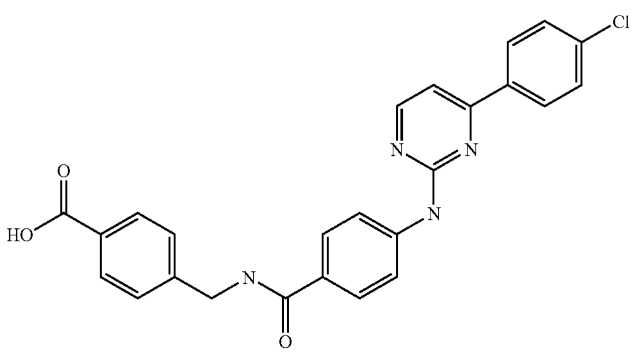 | 458.903 | 7.8 | 460 |
| 17-65 | 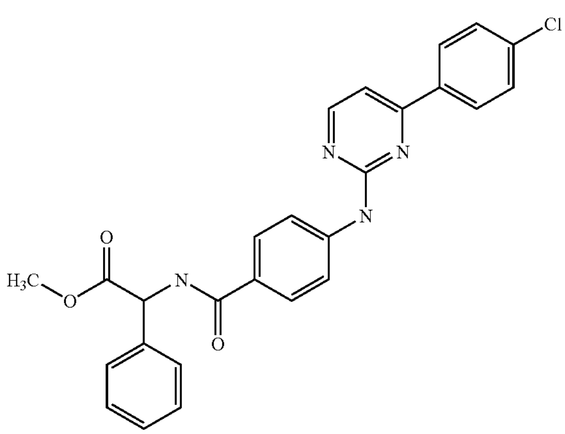 | 472.93 | 7.8 | 473 |

-continued
| Compound Number | Structure | MOL. WEIGHT | RT, min | M + 1 |
|---|---|---|---|---|
| 17-66 | 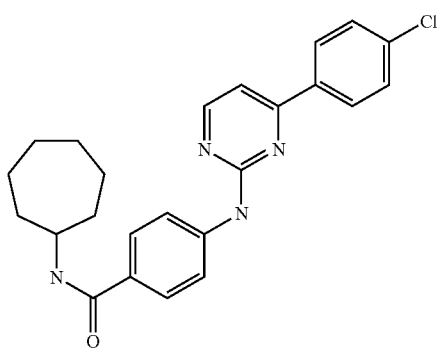 | 420.941 | 8.1 | 421 |
| 17-67 | 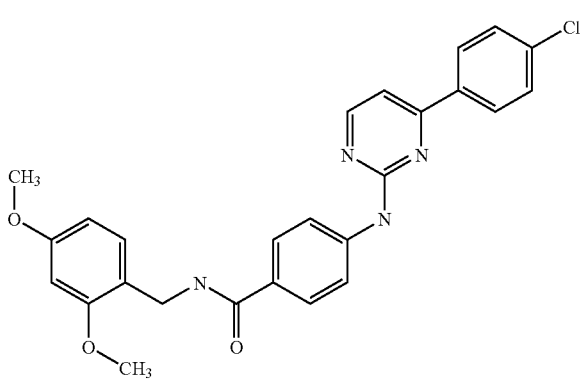 | 474.946 | 7.8 | 475 |
| 17-68 | 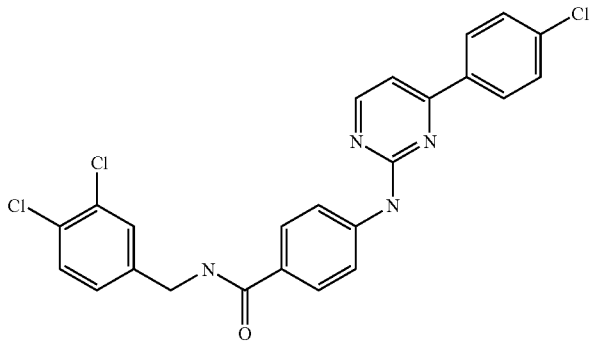 | 483.784 | 8.2 | 483 |
| 17-69 | 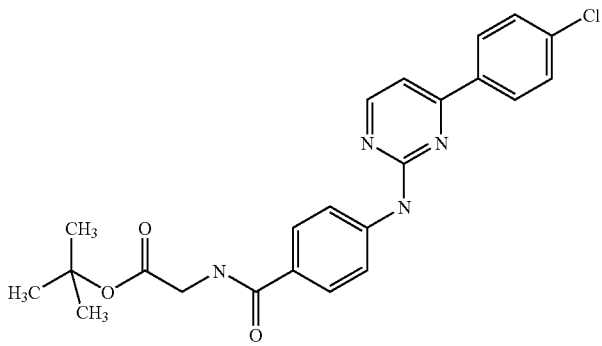 | 438.913 | 7.8 | 439 |

-continued

| Compound Number | Structure | MOL. WEIGHT | RT, min | M + 1 |
|---|---|---|---|---|
| 17-70 | 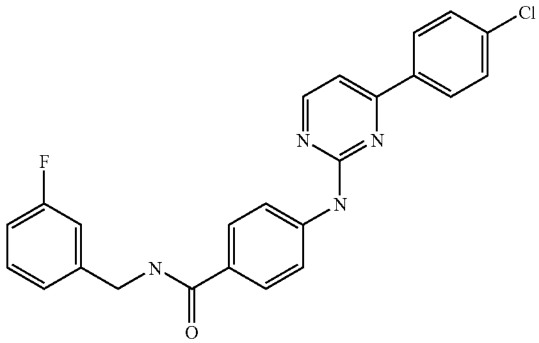 | 432.884 | 7.1 | 433 |
| 17-71 | 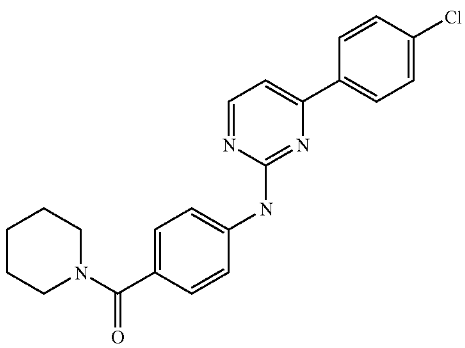 | 392.888 | 7.8 | 393 |
| 17-72 | 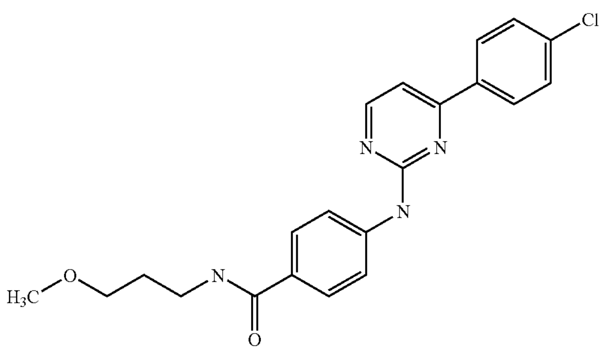 | 396.876 | 7.2 | 397 |
| 17-73 | 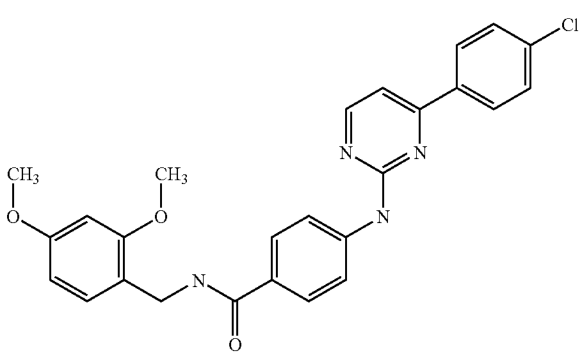 | 474.946 | 7.8 | 475 |

-continued

| Compound Number | Structure | MOL. WEIGHT | RT, min | M + 1 |
|---|---|---|---|---|
| 17-74 | 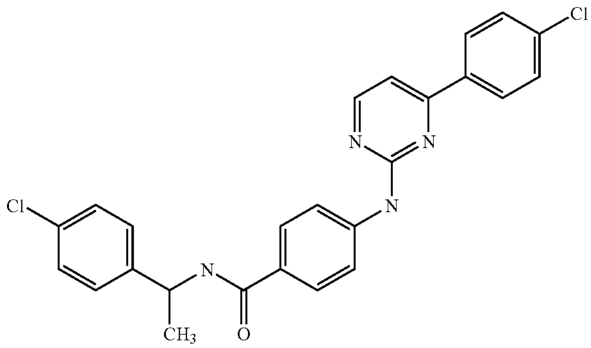 | 463.366 | 8.2 | 463 |
| 17-75 | 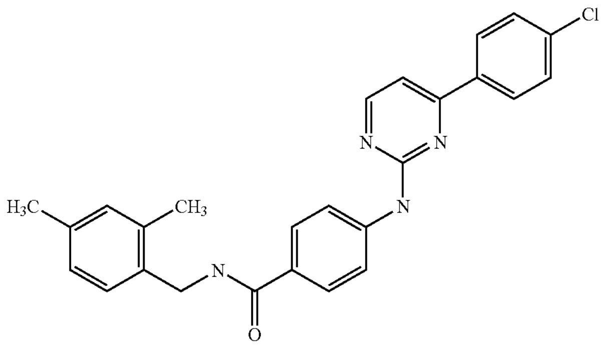 | 442.948 | 8.1 | 443 |
| 17-76 | 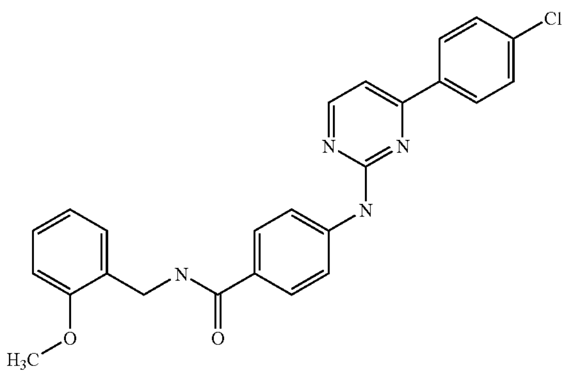 | 444.92 | 7.8 | 445 |
| 17-77 | 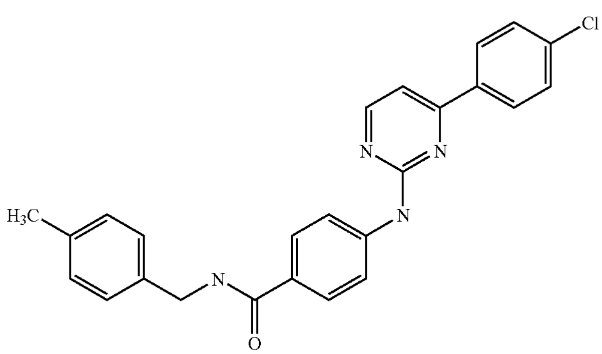 | 428.921 | 7.9 | 429 |

-continued

| Compound Number | Structure | MOL. WEIGHT | RT, min | M + 1 |
|---|---|---|---|---|
| 17-78 | 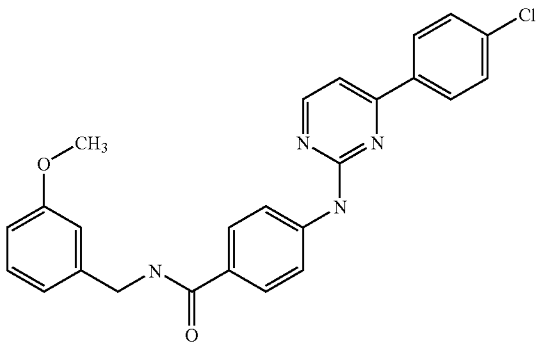 | 444.92 | 5.7 | 445 |
| 17-79 | 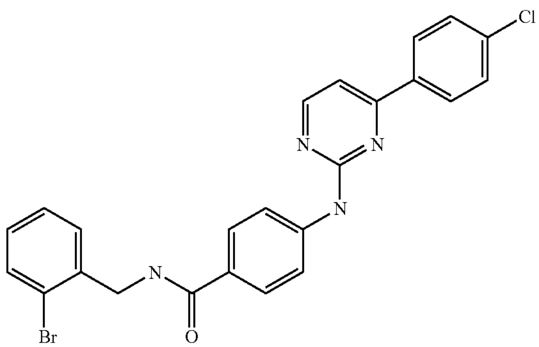 | 493.79 | 8 | 495 |
| 17-80 | 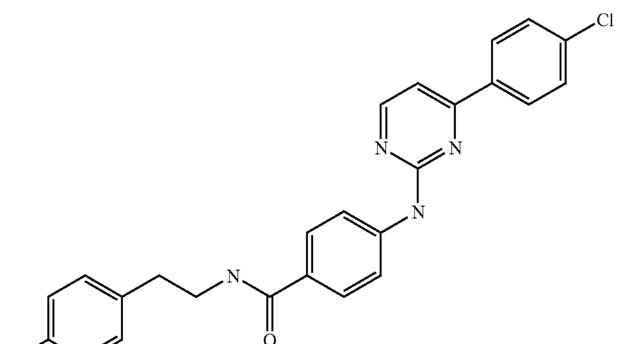 | 446.911 | 7.9 | 447 |
| 17-81 | 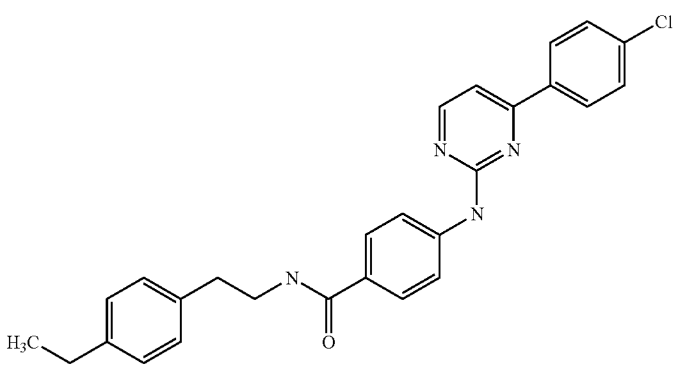 | 456.974 | 8.2 | 457 |

-continued

| Compound Number | Structure | MOL. WEIGHT | RT, min | M + 1 |
|---|---|---|---|---|
| 17-82 | 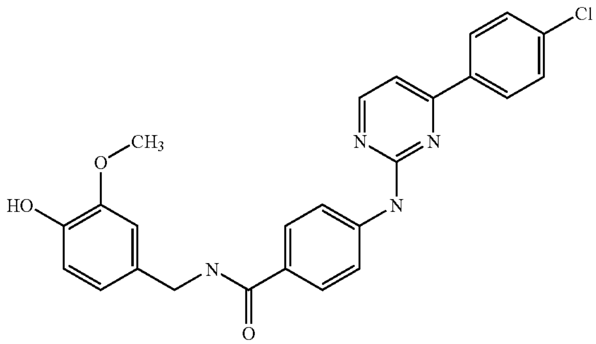 | 460.919 | 7.3 | 461 |
| 17-83 | 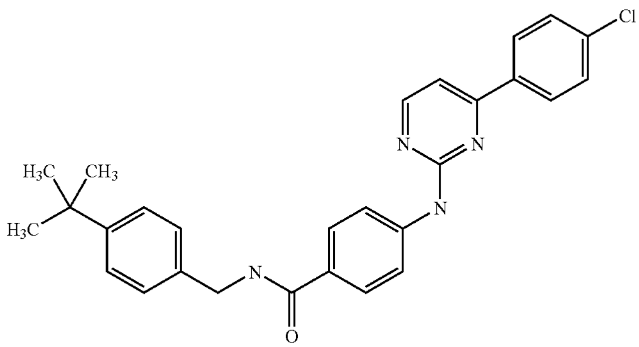 | 471.001 | 8.5 | 471 |
| 17-84 | 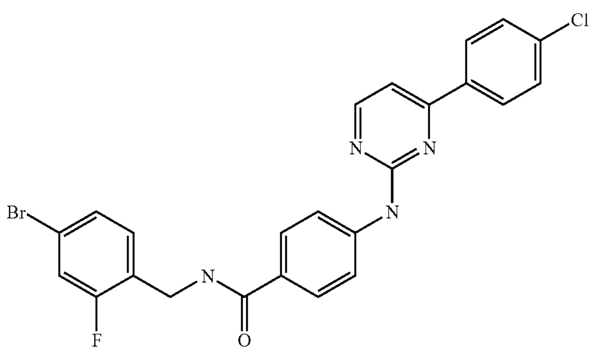 | 511.78 | 8.2 | 513 |
| 17-85 | 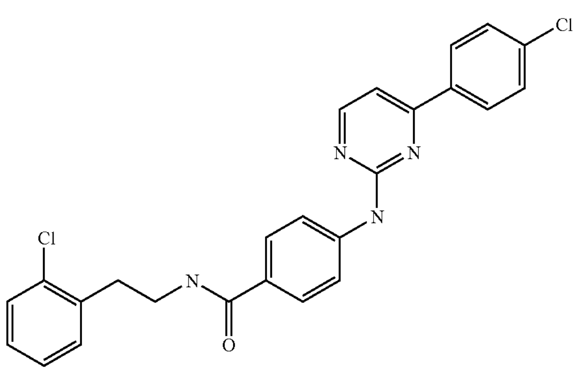 | 463.366 | 8 | 463 |

-continued
| Compound Number | Structure | MOL. WEIGHT | RT, min | M + 1 |
|---|---|---|---|---|
| 17-86 | 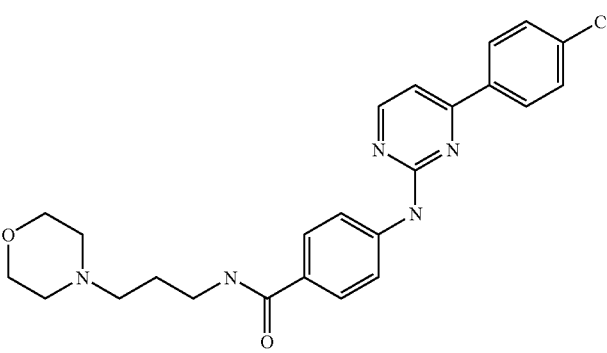 | 451.955 | 5.9 | 452 |
| 17-87 | 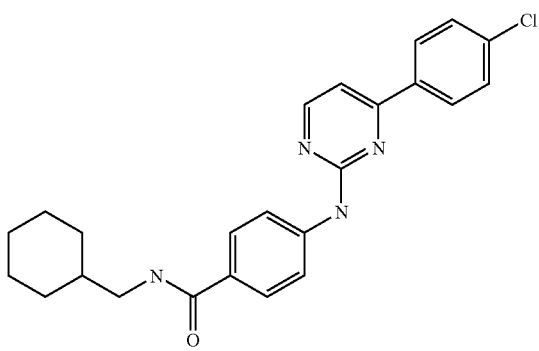 | 420.941 | 8.1 | 421 |
| 17-88 | 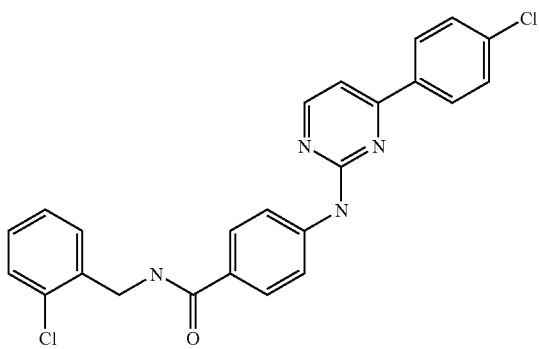 | 449.339 | 7.9 | 449 |
| 17-89 | 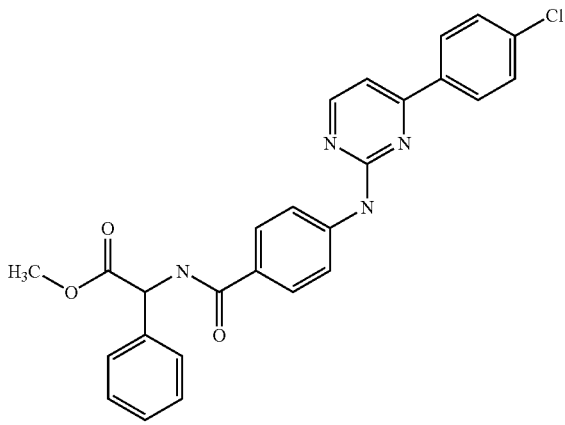 | 472.93 | 7.8 | 473 |

-continued

| Compound Number | Structure | MOL. WEIGHT | RT, min | M + 1 |
| --- | --- | --- | --- | --- |
| 17-90 | 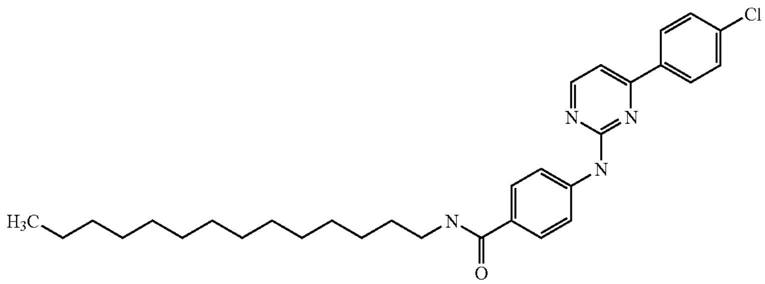 | 521.145 | 9.8 | 521 |
| 17-91 | 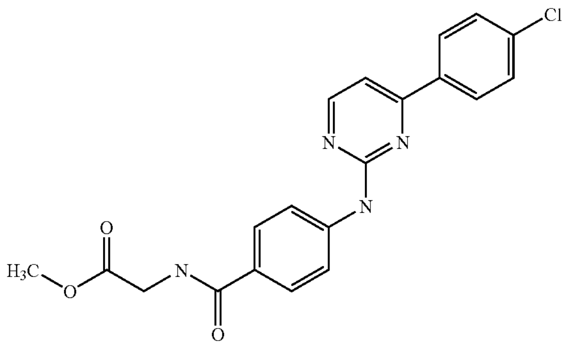 | 396.832 | 6.3 | 397 |
| 17-92 | 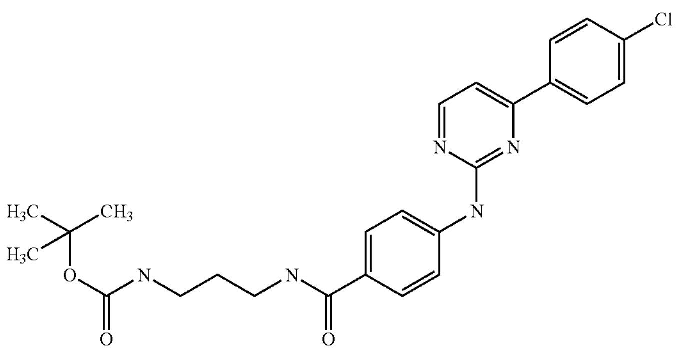 | 481.981 | 7.6 | 482 |
| 17-93 | 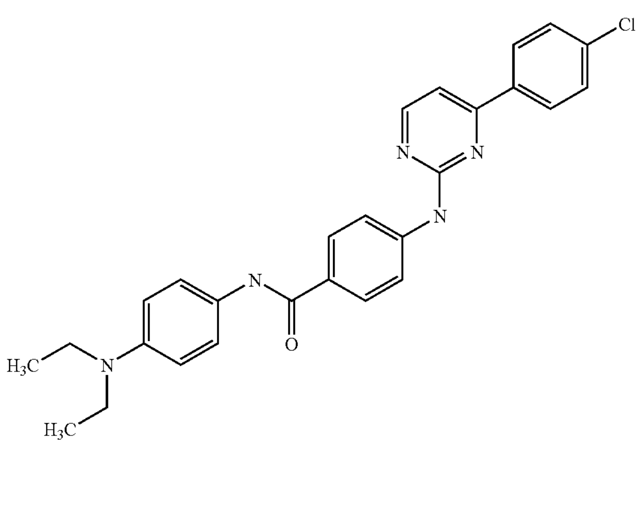 | 471.989 | 7.7 | 472 |

-continued
| Compound Number | Structure | MOL. WEIGHT | RT, min | M + 1 |
|---|---|---|---|---|
| 17-94 | 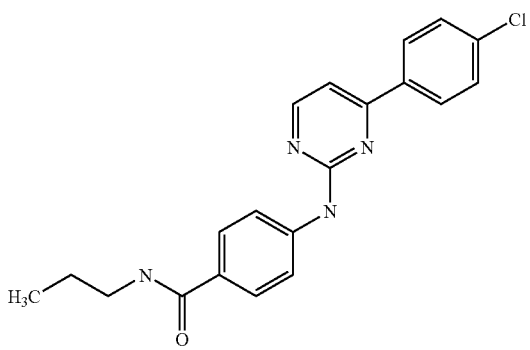 | 366.85 | 6.6 | 367 |
| 17-95 | 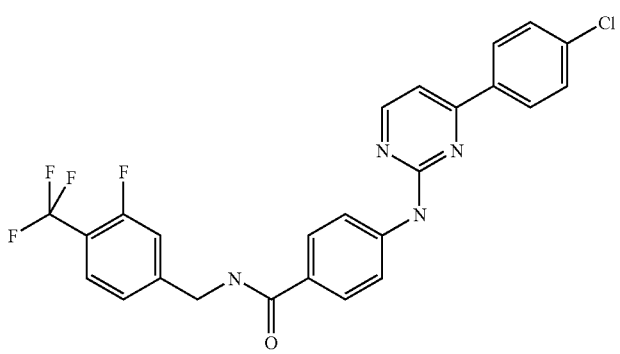 | 500.881 | 7.5 | 501 |
| 17-96 | 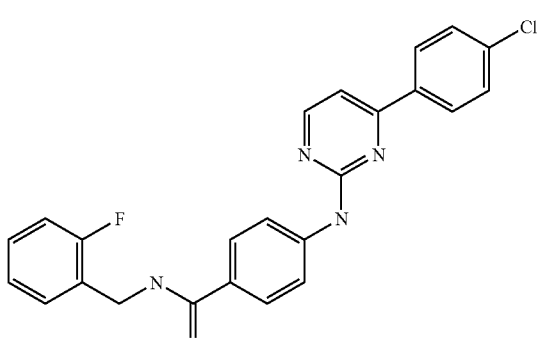 | 432.884 | 7.1 | 433 |
| 17-97 | 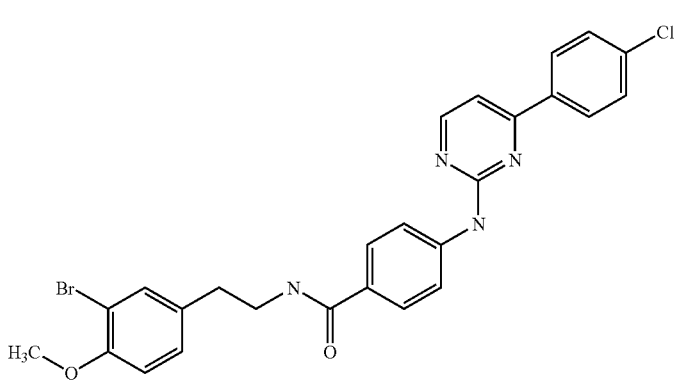 | 438.913 | 7.5 | 439 |

-continued

| Compound Number | Structure | MOL. WEIGHT | RT, min | M + 1 |
|---|---|---|---|---|
| 17-98 | 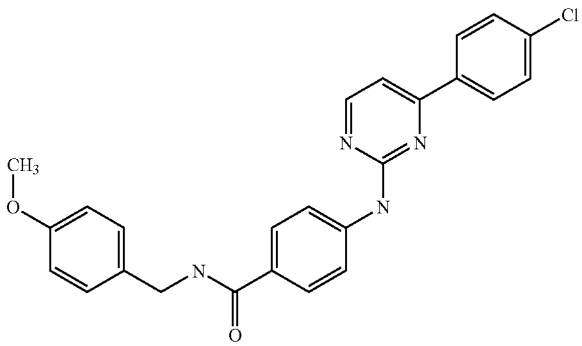 | 444.92 | 7.7 | 445 |
| 17-99 | 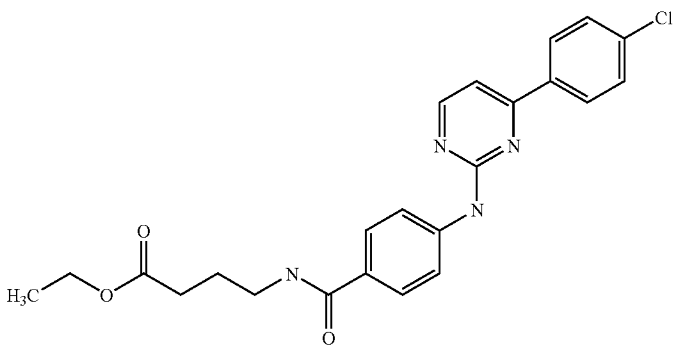 | 537.843 | 7.4 | 539 |
| 17-100 | 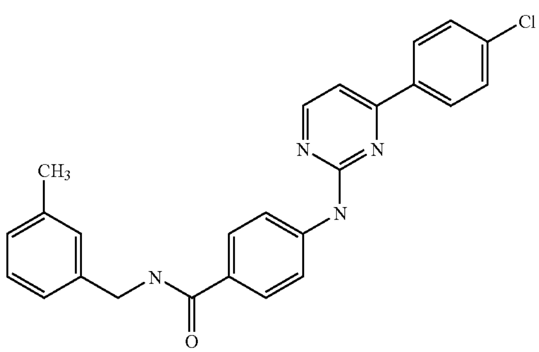 | 428.921 | 7.3 | 429 |
| 17-101 | 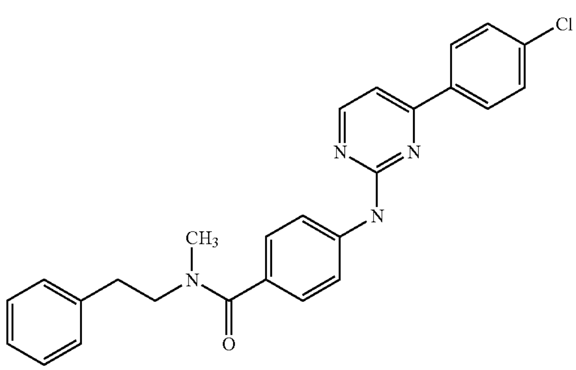 | 442.948 | 7.4 | 443 |

-continued
| Compound Number | Structure | MOL. WEIGHT | RT, min | M + 1 |
|---|---|---|---|---|
| 17-102 | 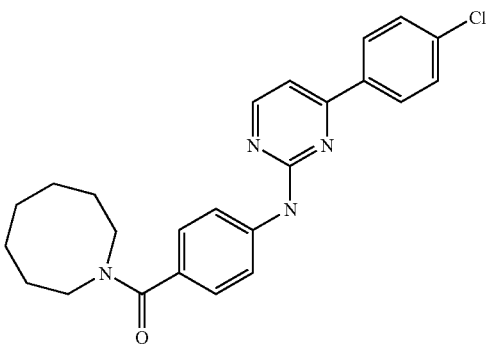 | 420.941 | 7.5 | 421 |
| 17-103 | 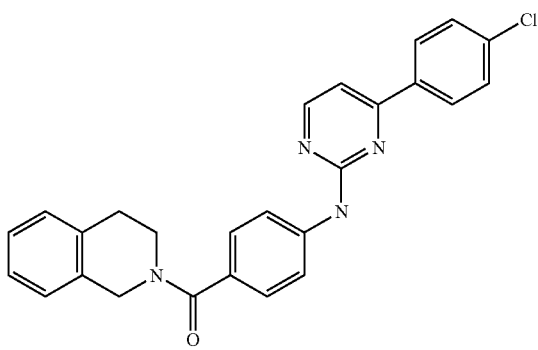 | 440.932 | 7.3 | 441 |
| 17-104 | 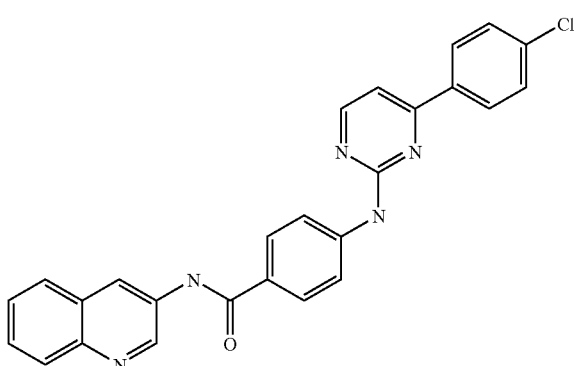 | 451.915 | 6.2 | 453 |
| 17-105 | 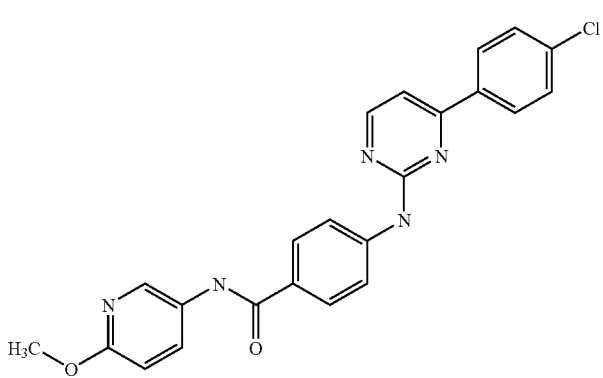 | 431.881 | 4.9 | 432 |

-continued

| Compound Number | Structure | MOL. WEIGHT | RT, min | M + 1 |
| --- | --- | --- | --- | --- |
| 17-106 | 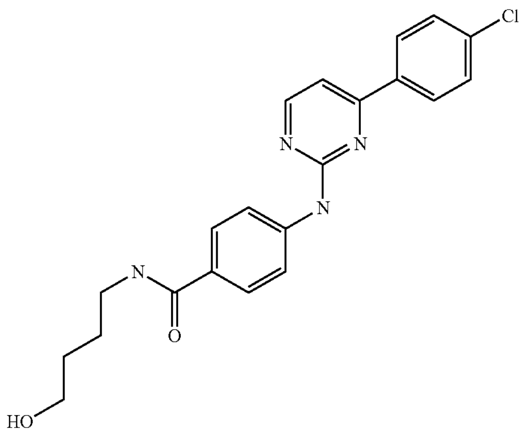 | 396.876 | 5.71 | 397 |
| 17-107 | 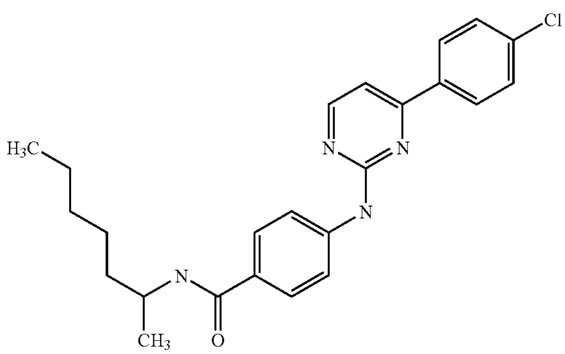 | 422.957 | 7.7 | 423 |
| 17-108 | 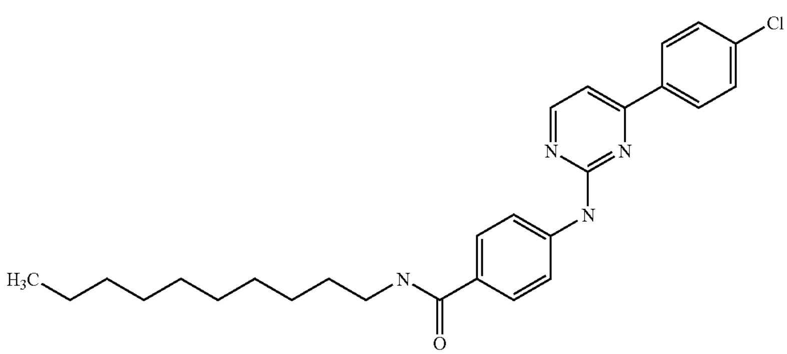 | 465.038 | 8.6 | 465 |
| 17-109 | 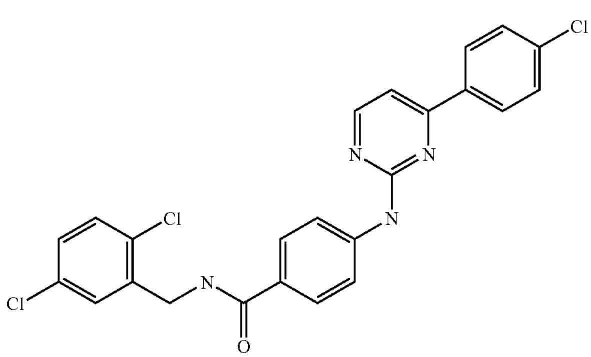 | 483.784 | 7.8 | 483 |

-continued
| Compound Number | Structure | MOL. WEIGHT | RT, min | M + 1 |
|---|---|---|---|---|
| 17-110 | 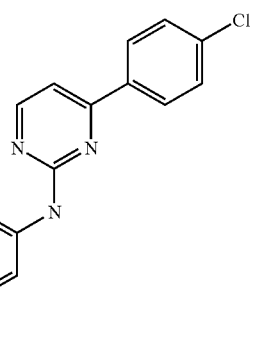 | 456.974 | 7.7 | 457 |
| 17-111 | 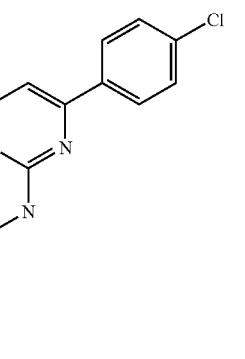 | 456.974 | 7.6 | 457 |
| 17-112 | 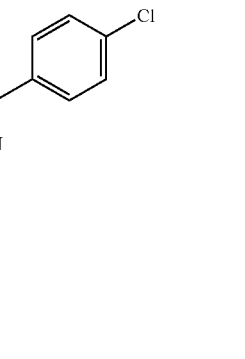 | 511.78 | 7.4 | 513 |
| 17-113 | 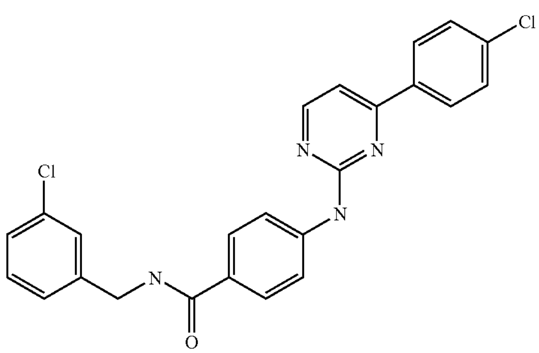 | 449.339 | 7.4 | 449 |

-continued

| Compound Number | Structure | MOL. WEIGHT | RT, min | M + 1 |
| --- | --- | --- | --- | --- |
| 17-114 | 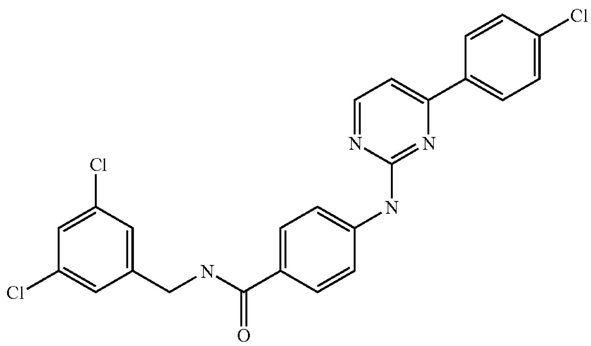 | 483.784 | 7.8 | 485 |
| 17-115 | 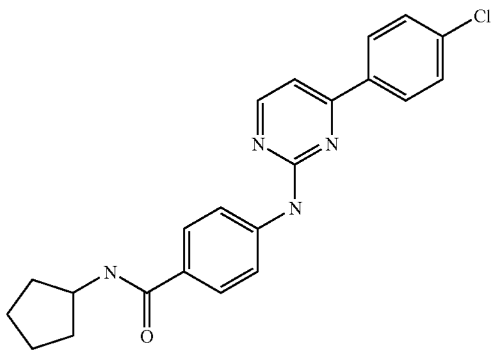 | 392.888 | 7.1 | 393 |
| 17-116 | 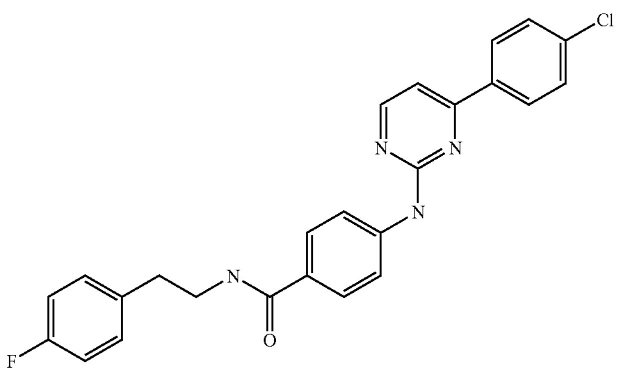 | 446.911 | 7.2 | 447 |
| 17-117 | 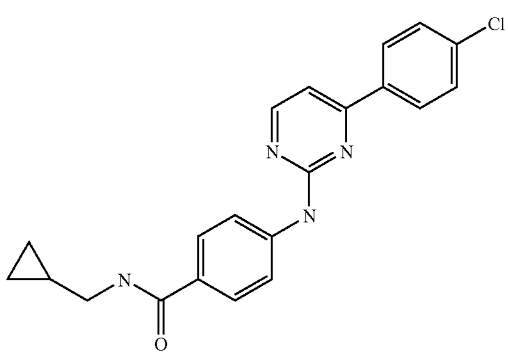 | 378.861 | 6.8 | 379 |

-continued

| Compound Number | Structure | MOL. WEIGHT | RT, min | M + 1 |
|---|---|---|---|---|
| 17-118 | 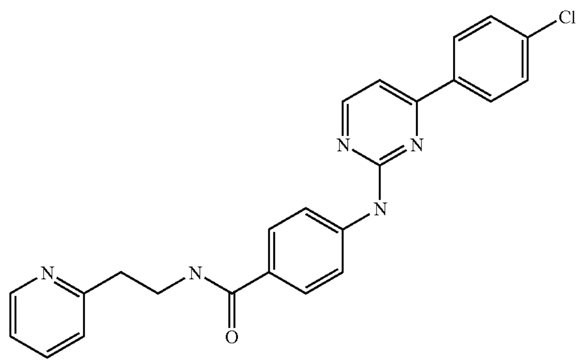 | 429.909 | 4.9 | 430 |
| 17-119 | 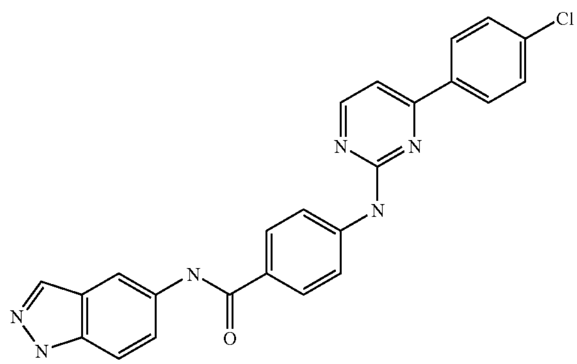 | 440.892 | 6.5 | 441 |
| 17-120 | 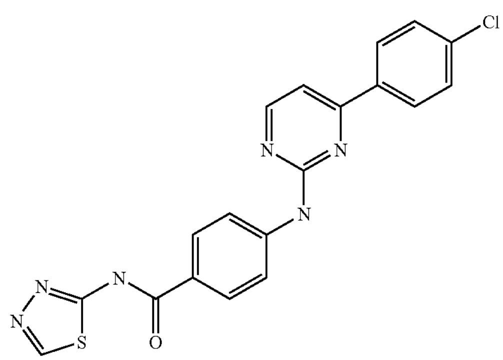 | 408.872 | 6.5 | 409 |
| 17-121 | 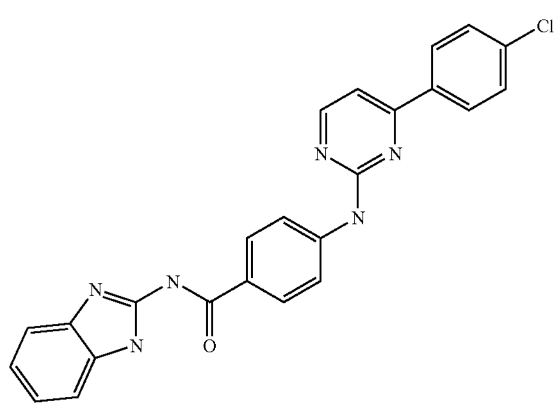 | 440.892 | 6.4 | 441 |

-continued

| Compound Number | Structure | MOL. WEIGHT | RT, min | M + 1 |
|---|---|---|---|---|
| 17-122 | 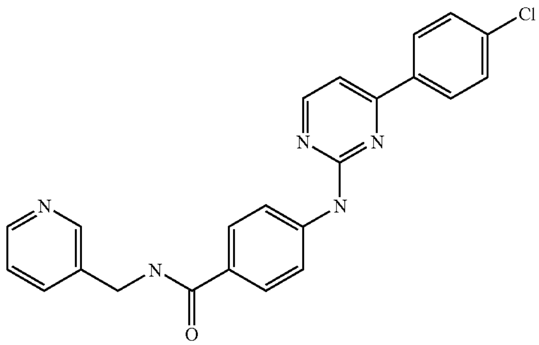 | 415.882 | 4.9 | 416 |
| 17-123 | 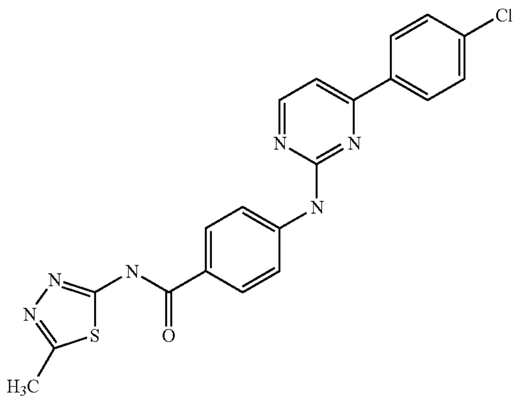 | 422.898 | 6.6 | 423 |
| 17-124 | 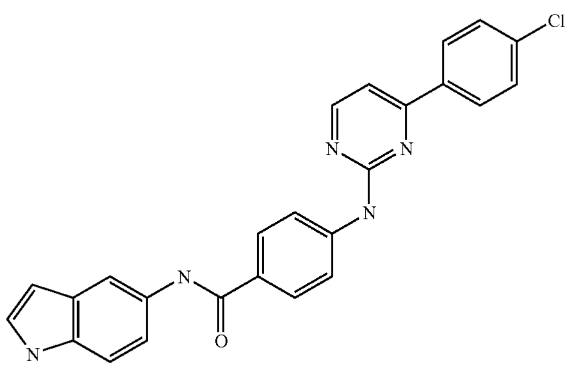 | 439.904 | 7.1 | 440 |
| 17-125 | 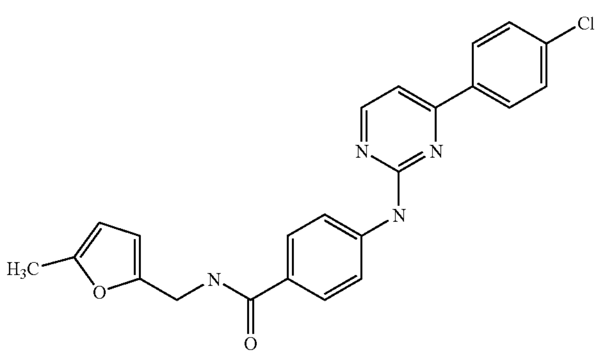 | 418.882 | 7.2 | 419 |

-continued

| Compound Number | Structure | MOL. WEIGHT | RT, min | M + 1 |
|---|---|---|---|---|
| 17-126 | 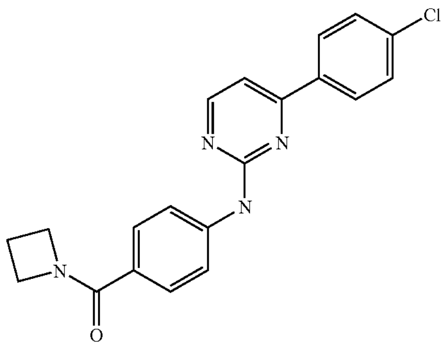 | 364.834 | 6.4 | 365 |
| 17-127 | 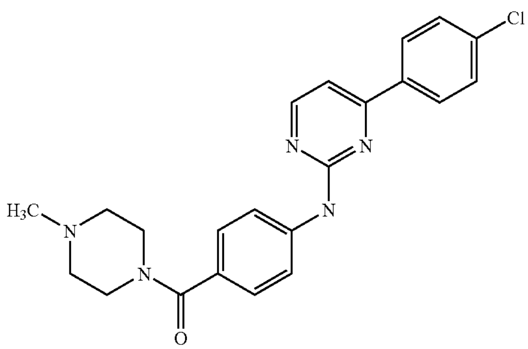 | 407.903 | 4.8 | 408 |
| 17-128 | 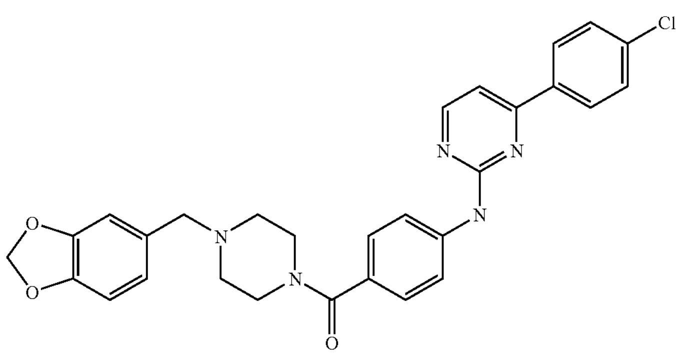 | 528.009 | 5.3 | 528 |
| 17-129 | 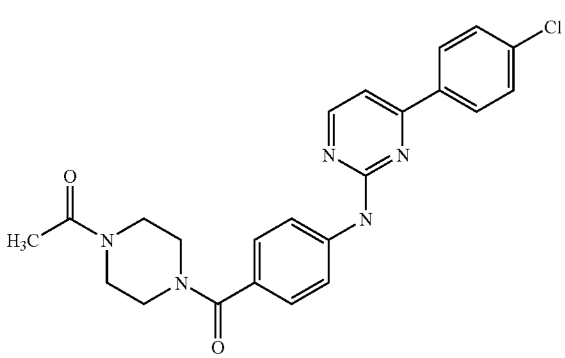 | 435.913 | 6.8 | 436 |

-continued

| Compound Number | Structure | MOL. WEIGHT | RT, min | M + 1 |
|---|---|---|---|---|
| 17-130 | 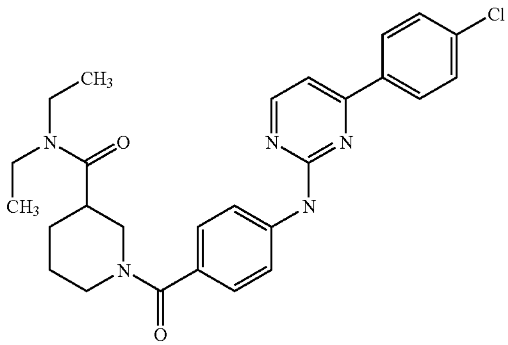 | 492.02 | 7.4 | 492 |
| 17-131 | 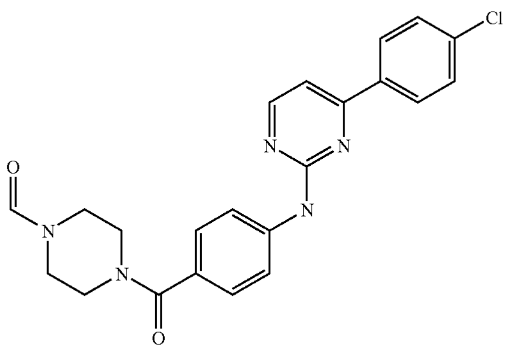 | 421.886 | 6.8 | 422 |
| 17-132 | 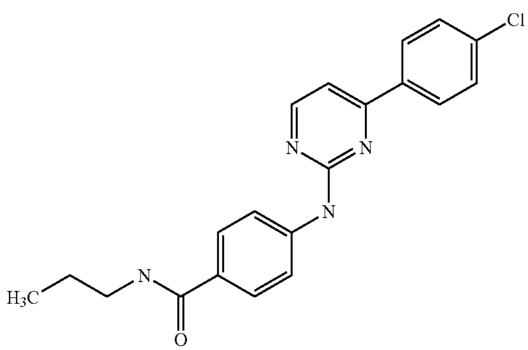 | 366.85 | 7.4 | 367 |
| 17-133 | 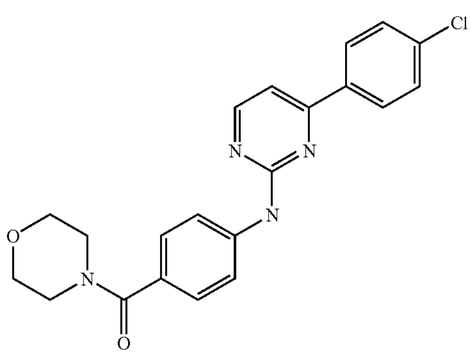 | 394.86 | 7.2 | 395 |

-continued

| Compound Number | Structure | MOL. WEIGHT | RT, min | M + 1 |
|---|---|---|---|---|
| 17-134 | 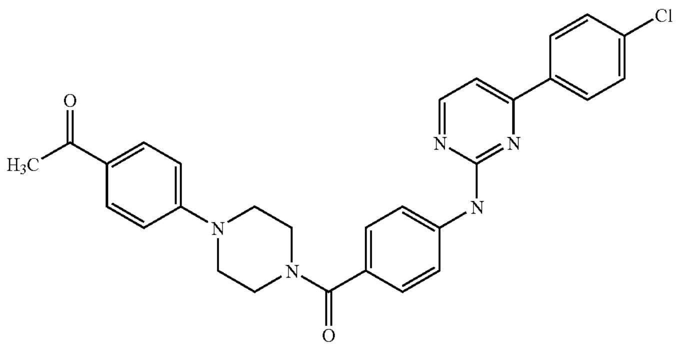 | 512.01 | 7.6 | 512 |
| 17-135 | 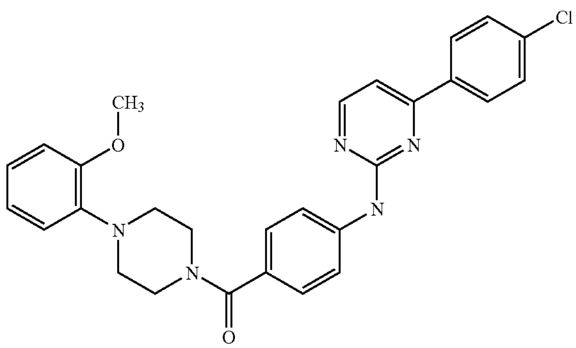 | 499.999 | 7.8 | 500 |
| 17-136 | 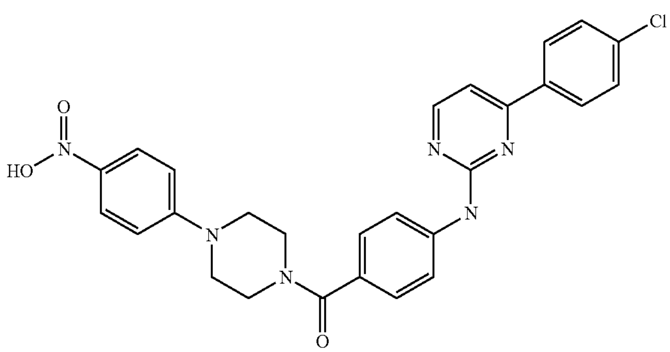 | 516.987 | 7.9 | 515 |
| 17-137 | 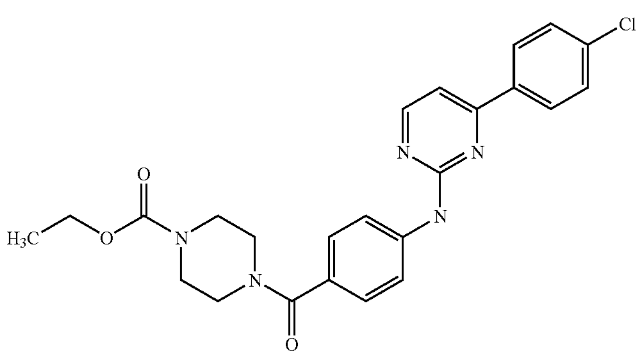 | 465.939 | 7.4 | 466 |

-continued
| Compound Number | Structure | MOL. WEIGHT | RT, min | M + 1 |
|---|---|---|---|---|
| 17-138 | 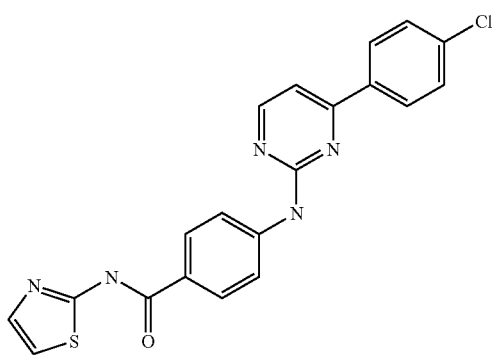 | 407.884 | 7.2 | 408 |
| 17-139 | 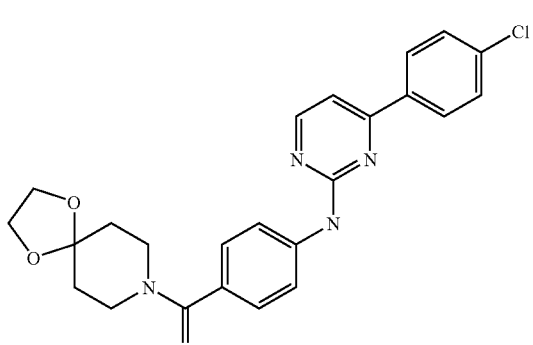 | 450.924 | 7.4 | 451 |
| 17-140 | 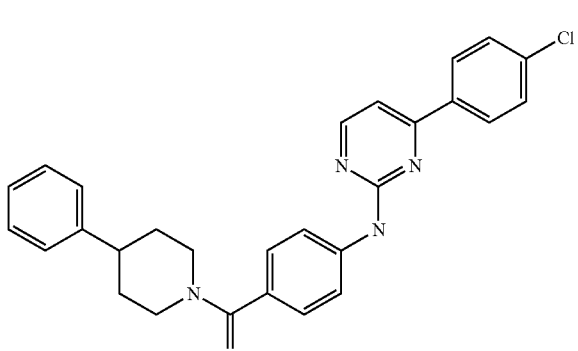 | 468.986 | 8.3 | 469 |
| 17-141 | 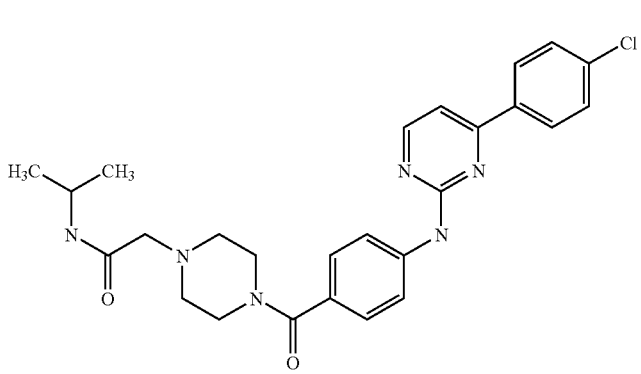 | 493.008 | 7.1 | 493 |

-continued

| Compound Number | Structure | MOL. WEIGHT | RT, min | M + 1 |
| --- | --- | --- | --- | --- |
| 17-142 | 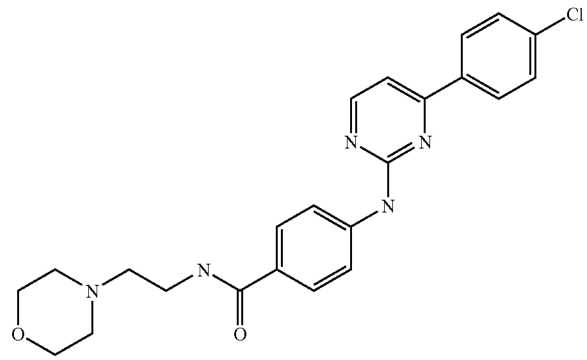 | 437.929 | 4.6 | 438 |
| 17-143 | 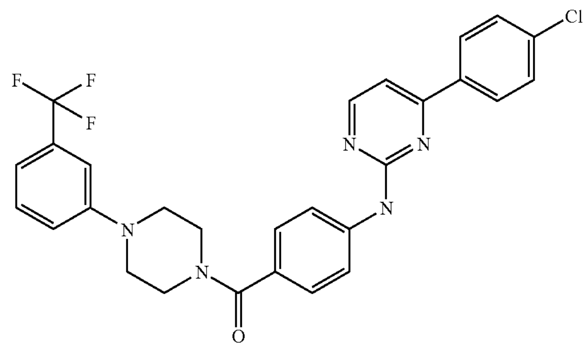 | 537.971 | 8.3 | 538 |
| 17-144 | 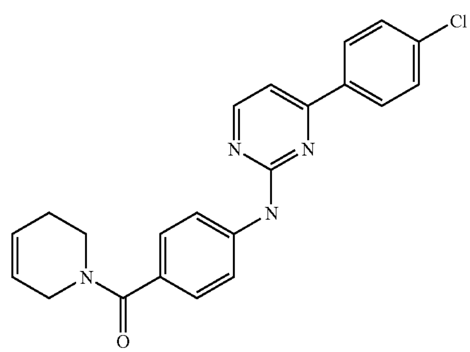 | 390.872 | 7.7 | 391 |
| 17-145 | 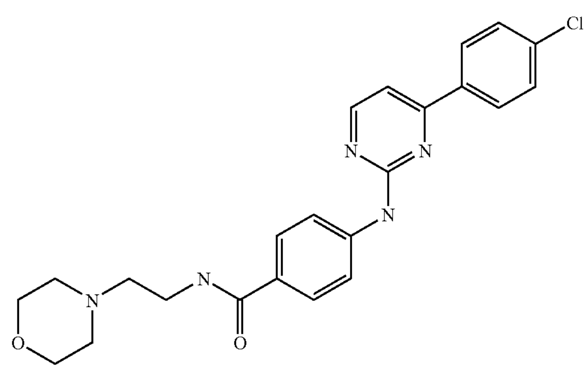 | 437.929 | 4.6 | 438 |

-continued

| Compound Number | Structure | MOL. WEIGHT | RT, min | M + 1 |
|---|---|---|---|---|
| 17-146 | 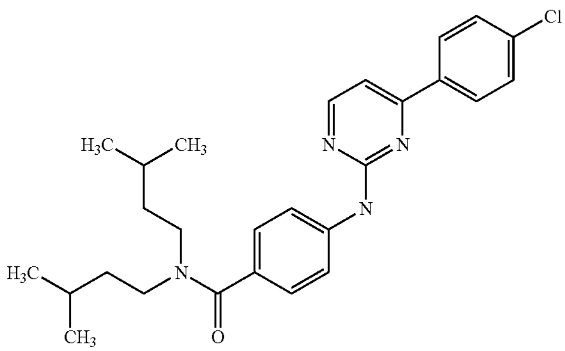 | 465.038 | 8.4 | 465 |
| 17-147 | 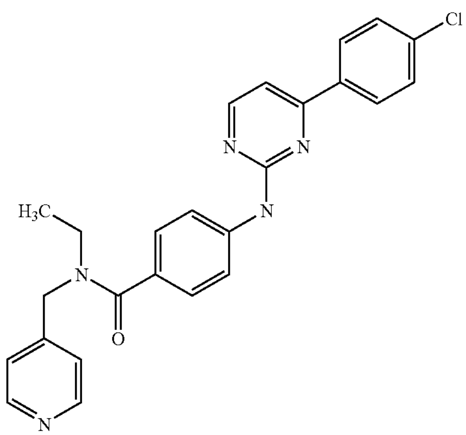 | 443.936 | 6.3 | 444 |
| 17-148 | 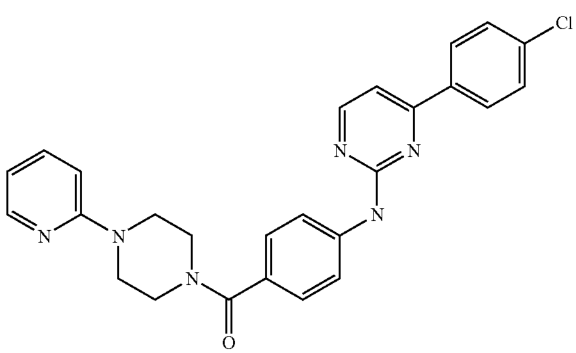 | 470.962 | 6.3 | 473 |
| 17-149 | 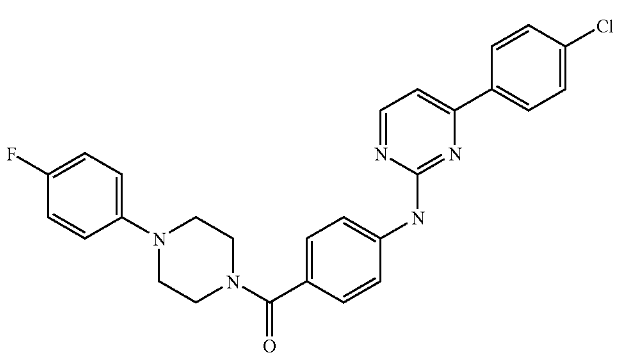 | 487.964 | 8 | 488 |

-continued

| Compound Number | Structure | MOL. WEIGHT | RT, min | M + 1 |
|---|---|---|---|---|
| 17-150 | 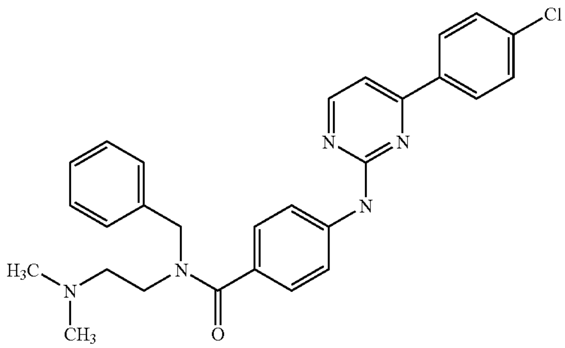 | 486.016 | 6.3 | 486 |
| 17-151 | 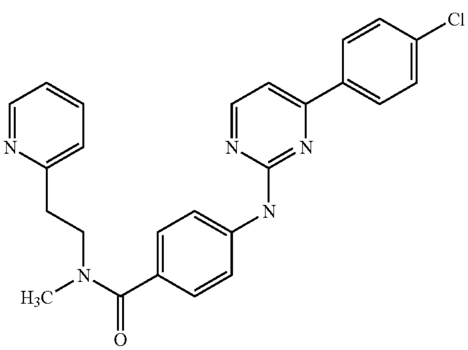 | 443.936 | 6.3 | 444 |
| 17-152 | 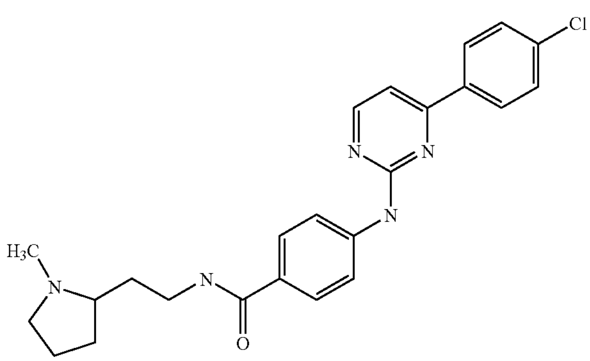 | 435.956 | 4.6 | 436 |
| 17-153 | 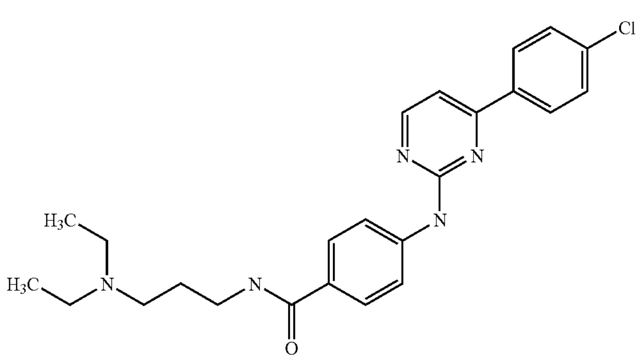 | 437.972 | 4.7 | 438 |

-continued

| Compound Number | Structure | MOL. WEIGHT | RT, min | M + 1 |
|---|---|---|---|---|
| 17-154 | 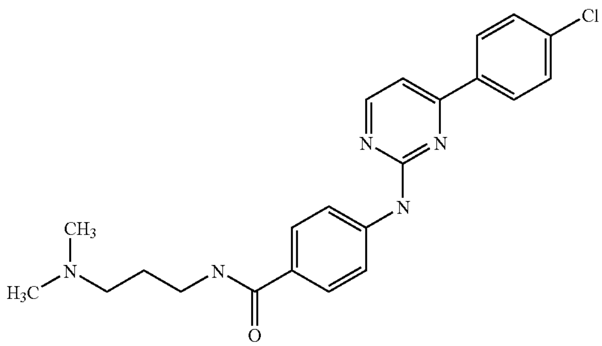 | 409.919 | 4.6 | 410 |
| 17-155 | 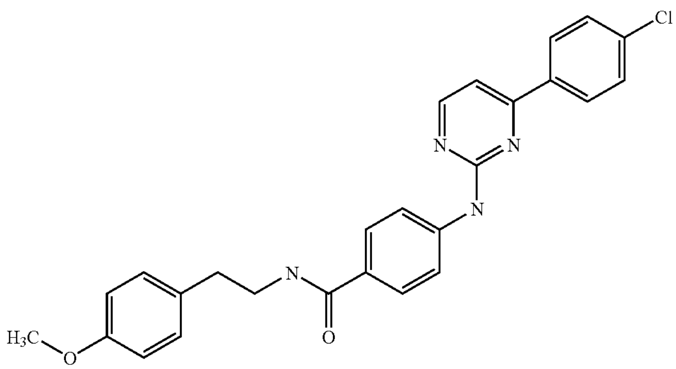 | 458.947 | 7.4 | 365 |
| 17-156 | 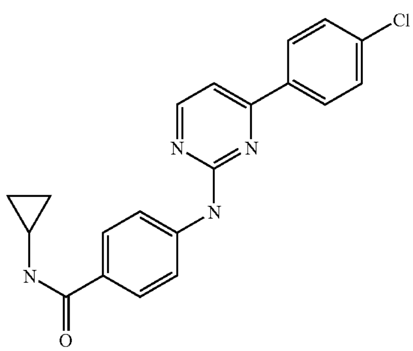 | 364.834 | 7.2 | 365 |
| 17-157 | 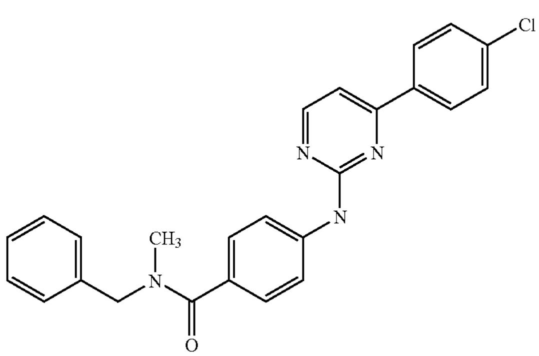 | 428.921 | 7.9 | 429 |

-continued

| Compound Number | Structure | MOL. WEIGHT | RT, min | M + 1 |
|---|---|---|---|---|
| 17-158 | 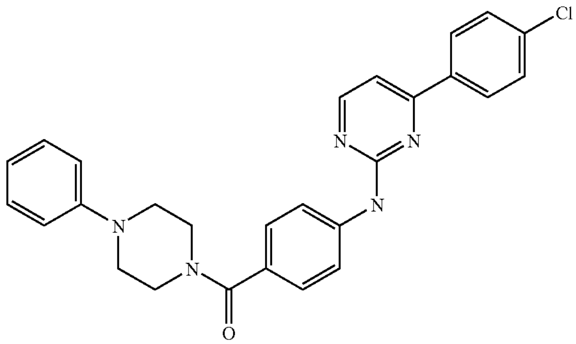 | 469.974 | 8 | 470 |
| 17-159 | 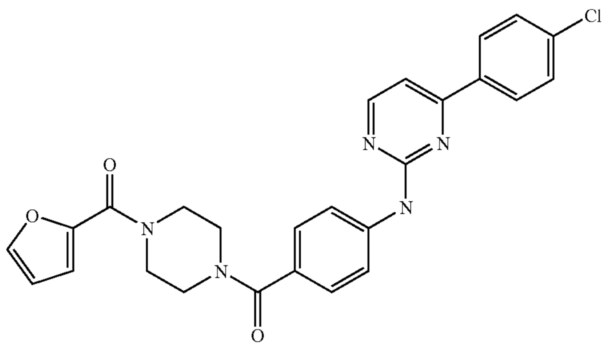 | 487.945 | 6.3 | 488 |
| 17-160 | 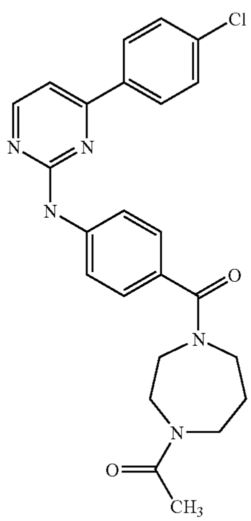 | 449.94 | 5.8 | 450 |
| 17-161 | 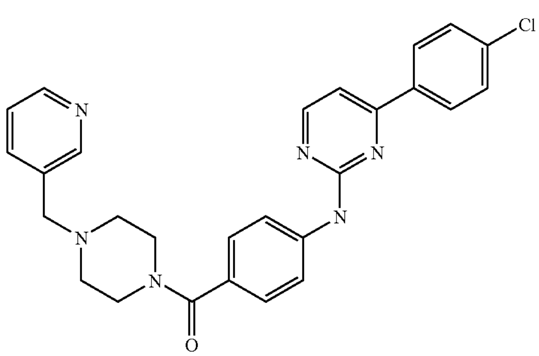 | 484.988 | 4.4 | 485 |

-continued

| Compound Number | Structure | MOL. WEIGHT | RT, min | M + 1 |
|---|---|---|---|---|
| 17-162 | 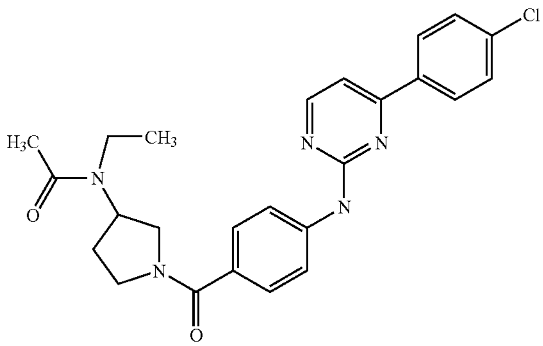 | 463.966 | 6 | 464 |
| 17-163 | 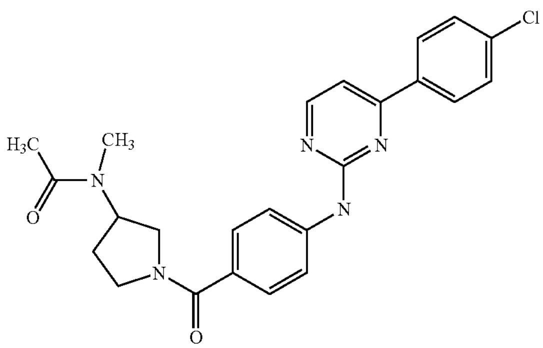 | 449.94 | 5.8 | 450 |
| 17-164 | 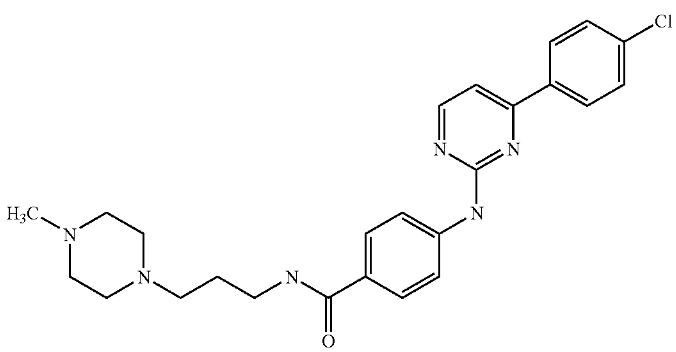 | 464.998 | 4.8 | 465 |
| 17-165 | 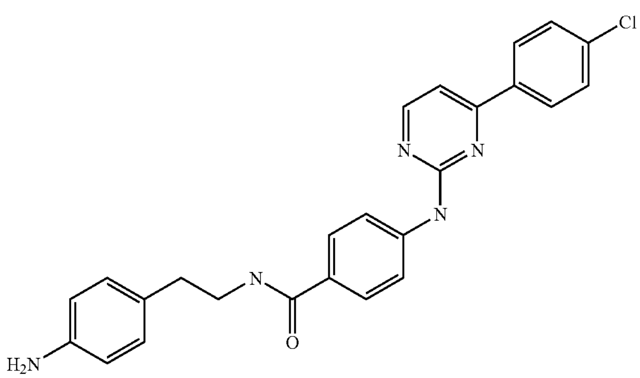 | 443.936 | 5.6 | 444 |

-continued

| Compound Number | Structure | MOL. WEIGHT | RT, min | M + 1 |
|---|---|---|---|---|
| 17-166 | 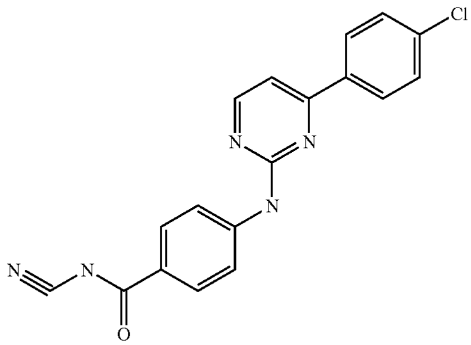 | 349.78 | 7.3 | 350 |
| 17-167 | 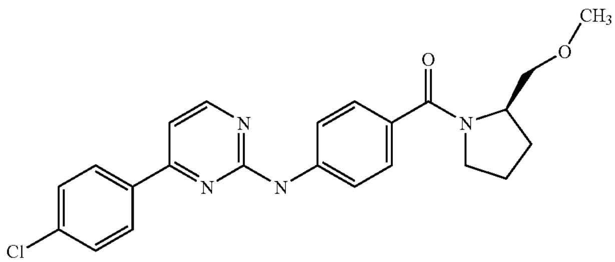 | 422.914 | 12.167 | 423.0 |
| 17-168 | 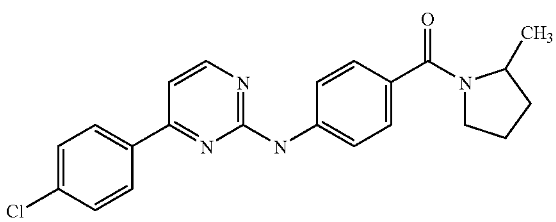 | 392.888 | 6.983 | 393.2 |
| 17-169 | 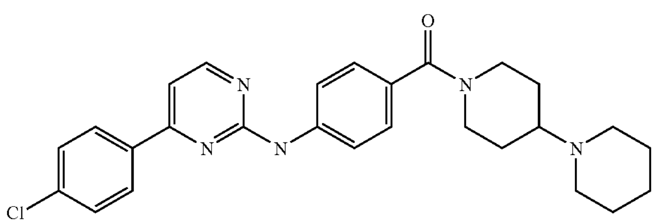 | 476.021 | 8.92 | 476.2 |
| 17-170 | 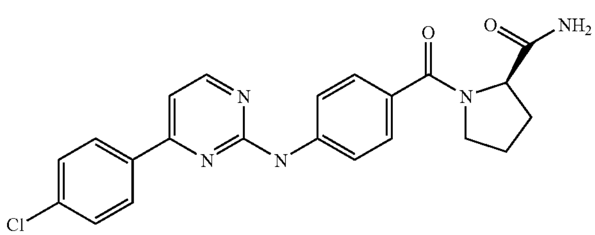 | 421.886 | 10.436 | 422.2 |
| 17-171 | 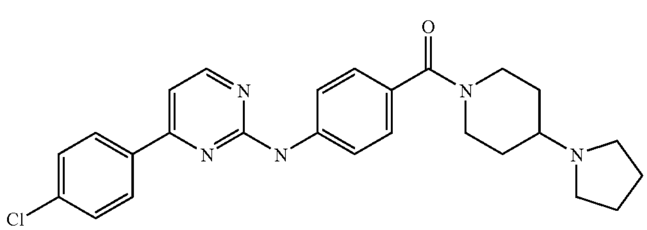 | 461.994 | 8.717 | 462.2 |

-continued

| Compound Number | Structure | MOL. WEIGHT | RT, min | M + 1 |
|---|---|---|---|---|
| 17-172 | 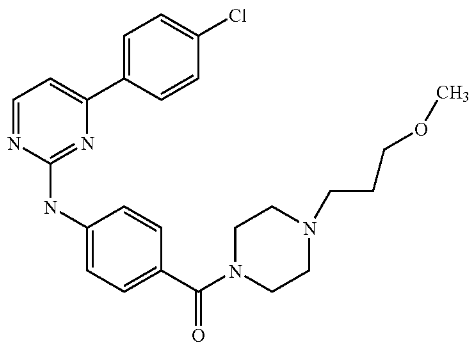 | 465.9822 | 8.45 | 466.9 |
| 17-173 | 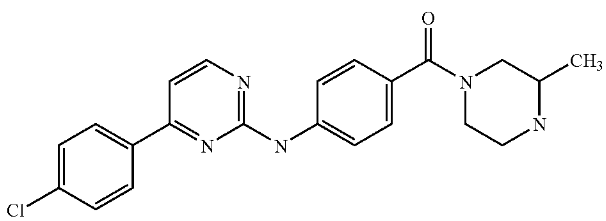 | 407.903 | 9.38 | 408 |
| 17-174 | 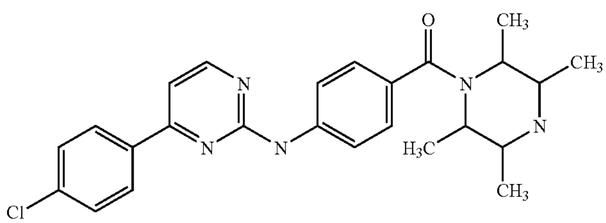 | 449.983 | 10.27 | 450 |
| 17-175 | 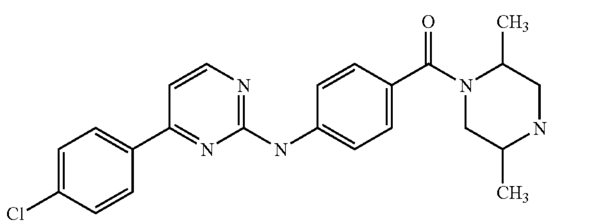 | 421.93 | 9.37 | 422 |
| 17-176 | 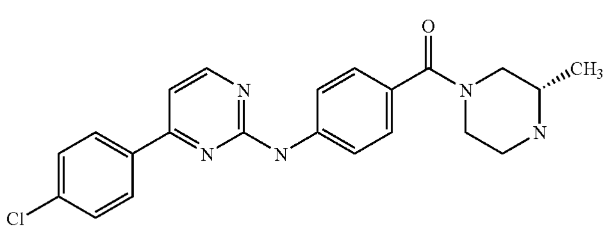 | 407.903 | 9.37 | 408 |
| 17-177 | 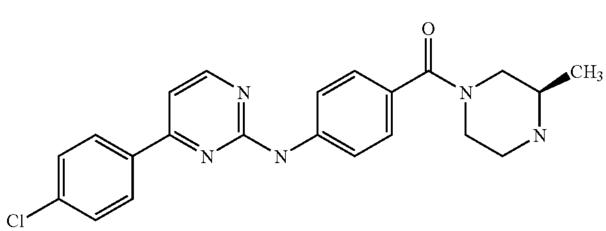 | 407.903 | 9.42 | 408 |

| Compound Number | Structure | MOL. WEIGHT | RT, min | M + 1 |
|---|---|---|---|---|
| 17-178 | 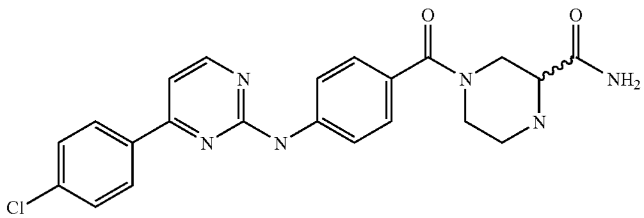 | 436.901 | 9.09 | 437 |
| 17-179 | 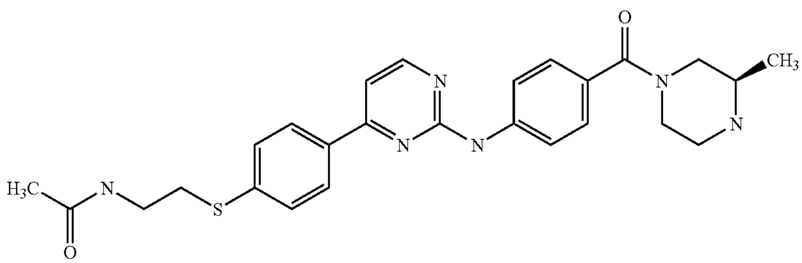 | 490.629 | 8.02 | 491 |
| 17-180 | 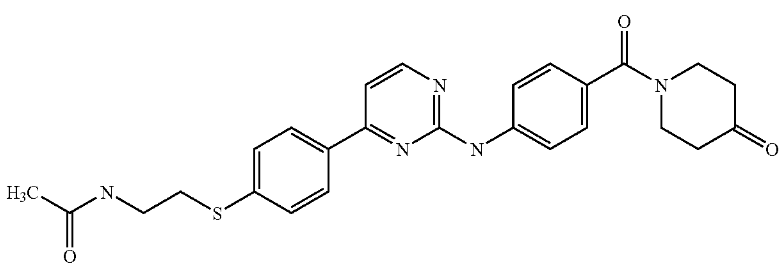 | 489.597 | 8.17 | 490 |
| 17-181 | 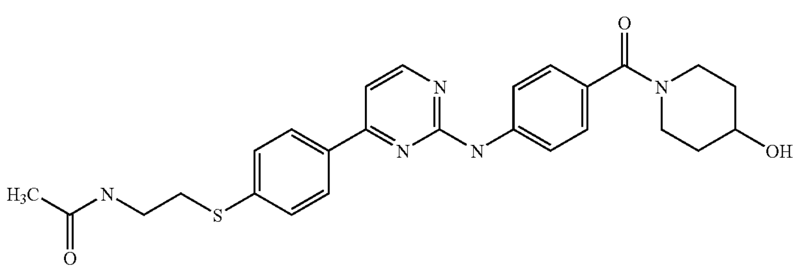 | 491.613 | 8.42 | 492 |
| 17-182 | 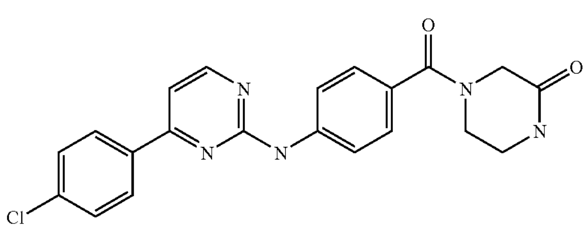 | 407.859 | 10.23 | 408 |
| 17-183 | 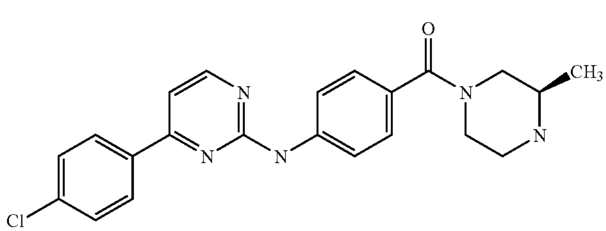 | 407.903 | 9.42 | 408 |

-continued

| Compound Number | Structure | MOL. WEIGHT | RT, min | M + 1 |
|---|---|---|---|---|
| 17-184 | | 449.94 | 11.07 | 450 |
| 17-184 | | 405.887 | 9.3 | 406 |
| 17-186 | 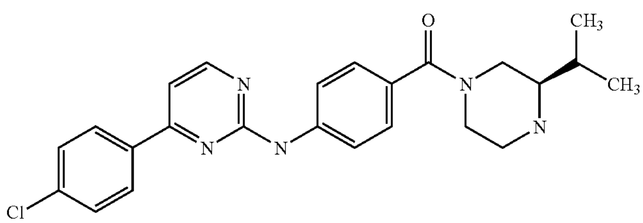 | 435.956 | 9.86 | 436 |
| 17-187 | 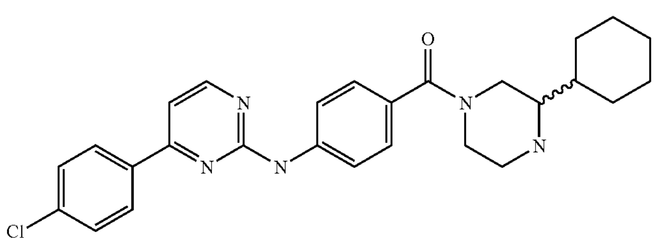 | 476.021 | 10.66 | 477 |
| 17-188 | 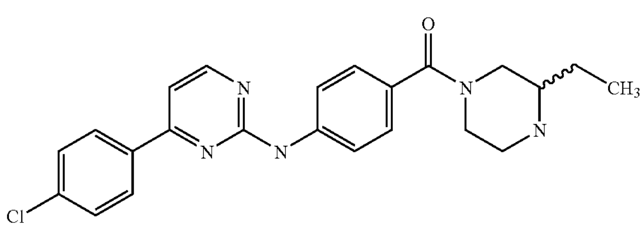 | 421.9296 | 10.63 | 422 |
| 17-189 | 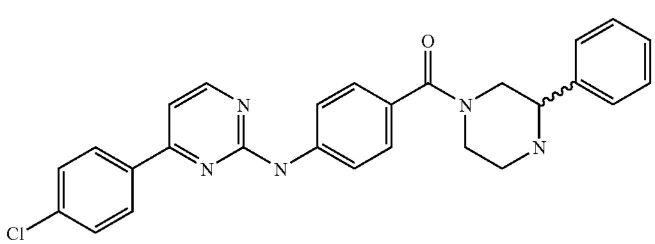 | 469.9736 | 10.57 | 470 |

-continued

| Compound Number | Structure | MOL. WEIGHT | RT, min | M + 1 |
|---|---|---|---|---|
| 17-190 | 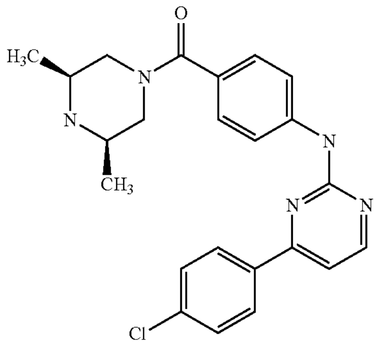 | 421.9296 | | |
| 17-191 | 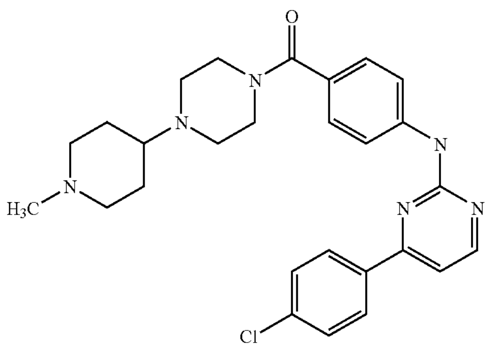 | 491.0359 | 9.03 | 491.3 |
| 17-192 | 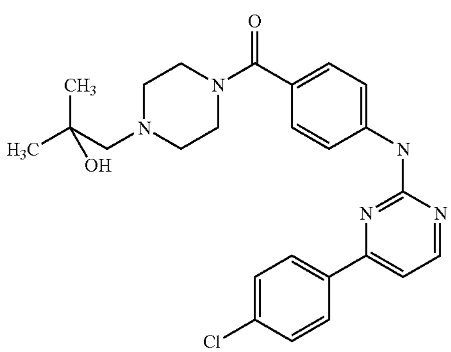 | 465.9822 | 9.88 | 466.3 |
| 17-193 | 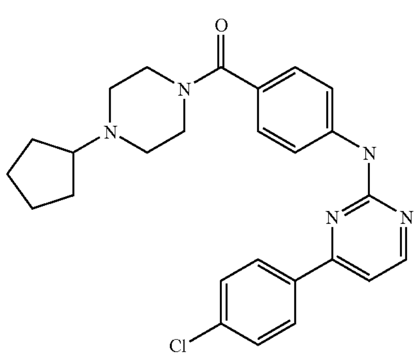 | 461.9942 | 10.48 | 462.3 |

-continued

| Compound Number | Structure | MOL. WEIGHT | RT, min | M + 1 |
|---|---|---|---|---|
| 17-194 | 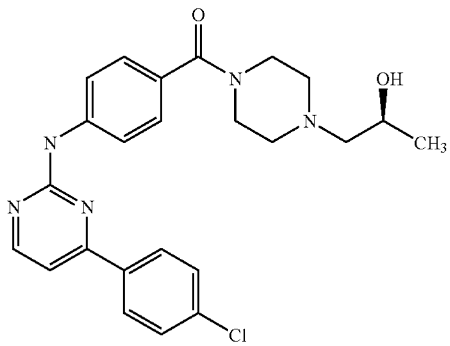 | 451.9554 | 9.7 | 452.3 |
| 17-195 | 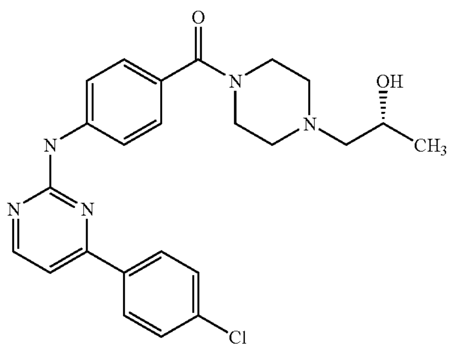 | 451.9554 | 9.7 | 452.3 |
| 17-196 | 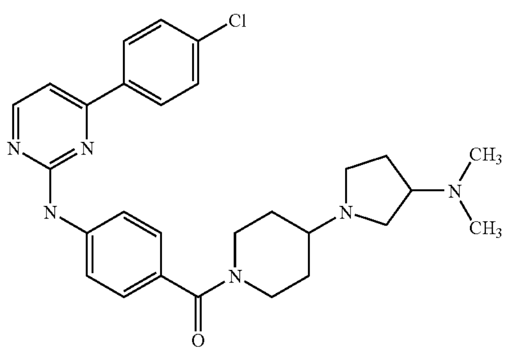 | 505.0627 | 505.4 | 11.976 |
| 17-197 | 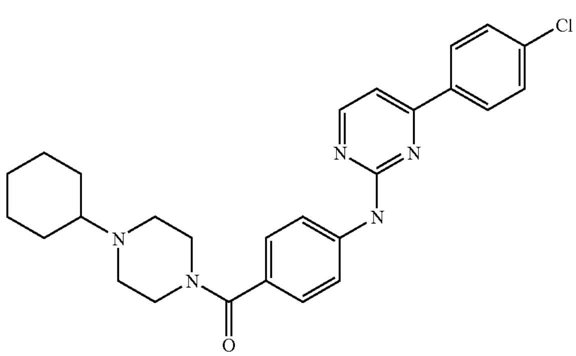 | 476.021 | 4.82 | 476.3 |

-continued

| Compound Number | Structure | MOL. WEIGHT | RT, min | M + 1 |
|---|---|---|---|---|
| 17-198 | 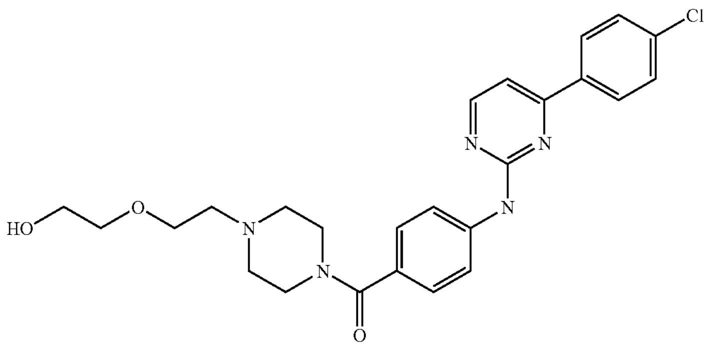 | 481.981 | 4.35 | 482 |
| 17-199 | 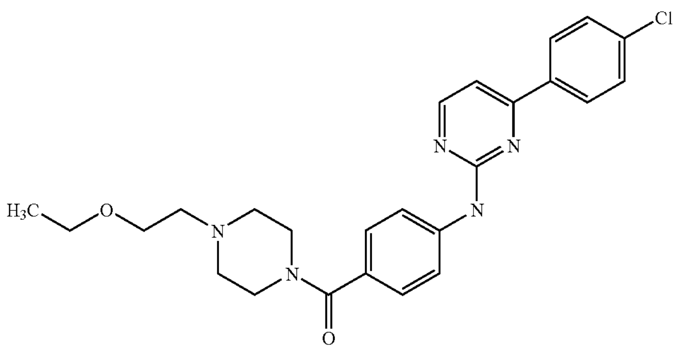 | 465.982 | 4.66 | 466.3 |
| 17-200 | 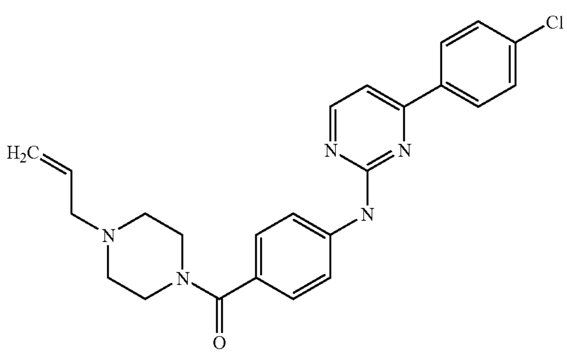 | 433.941 | 4.59 | 434 |
| 17-201 | 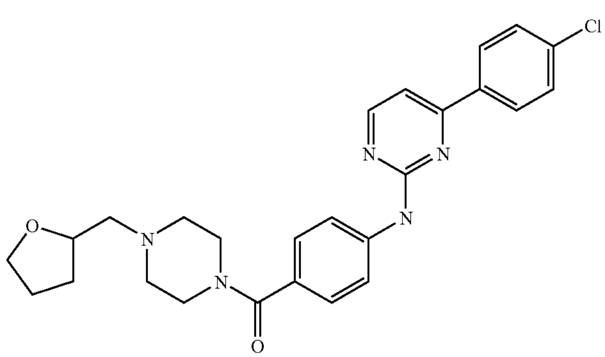 | 477.993 | 4.63 | 478.3 |

| Compound Number | Structure | MOL. WEIGHT | RT, min | M + 1 |
|---|---|---|---|---|
| 17-202 | 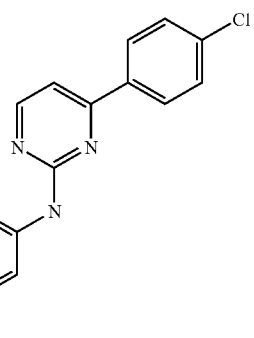 | 479.025 | 0.79 | 479.3 |
| 17-203 | 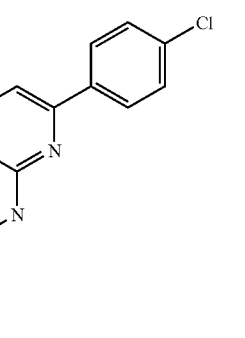 | 491.036 | 3.53 | 491.3 |
| 17-204 | 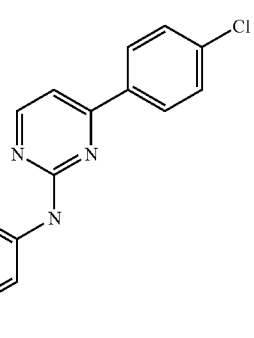 | 478.981 | 7.19 | 479.4 |
| 17-205 | 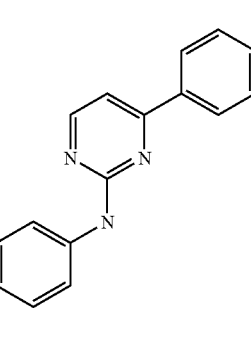 | 545.015 | 6.86 | 553.4 |

-continued

| Compound Number | Structure | MOL. WEIGHT | RT, min | M + 1 |
|---|---|---|---|---|
| 17-206 | 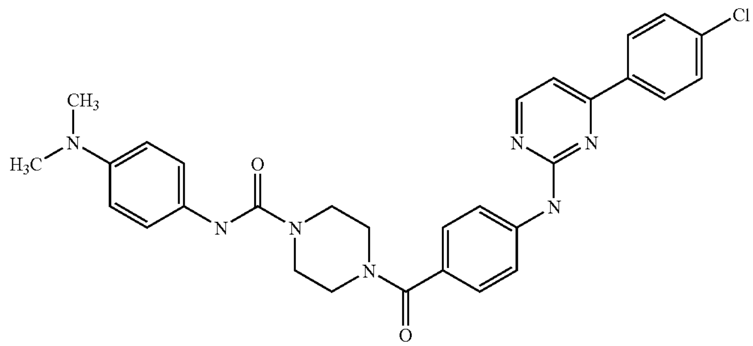 | 556.067 | 7.23 | 556.4 |
| 17-207 | 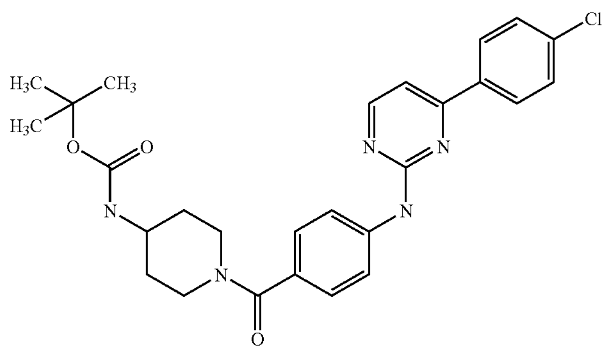 | 508.019 | 7.9 | 508.4 |
| 17-208 | 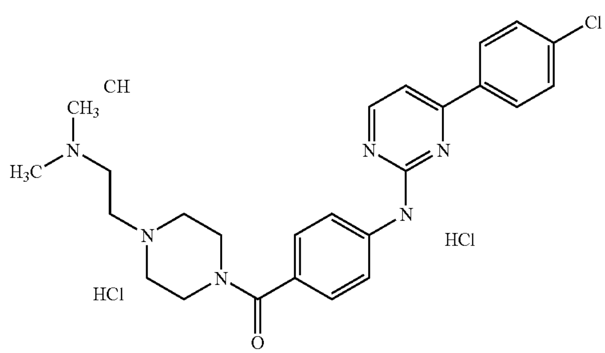 | 574.381 | 5.89 | 465.4 |
| 17-209 | 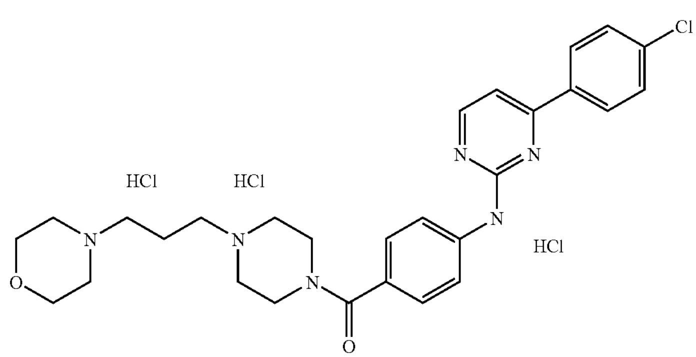 | 630.444 | 3.56 | 631.3 |

-continued

| Compound Number | Structure | MOL. WEIGHT | RT, min | M + 1 |
|---|---|---|---|---|
| 17-210 | 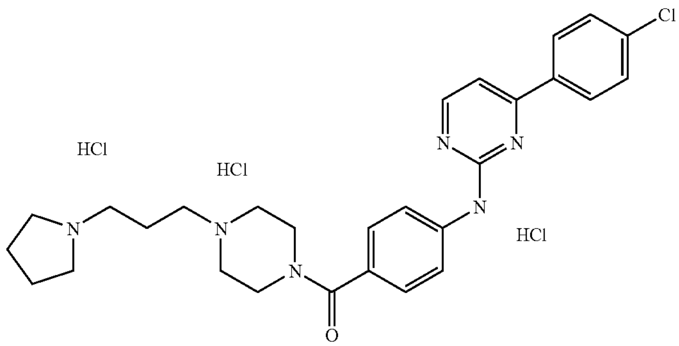 | 614.445 | 5.64 | 505.4 |
| 17-211 | 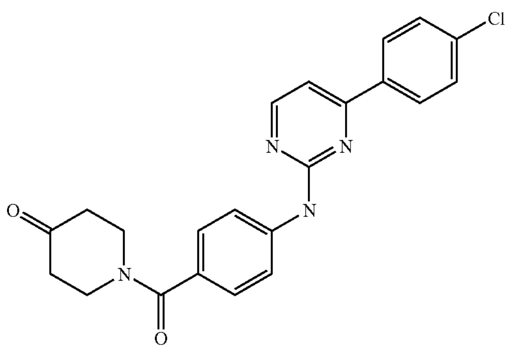 | 406.871 | 5.86 | 436.4 |
| 17-212 | 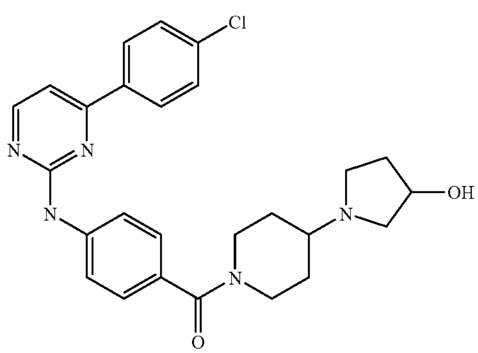 | 477.9932 | 478.5 | 7.583 |
| 17-213 | 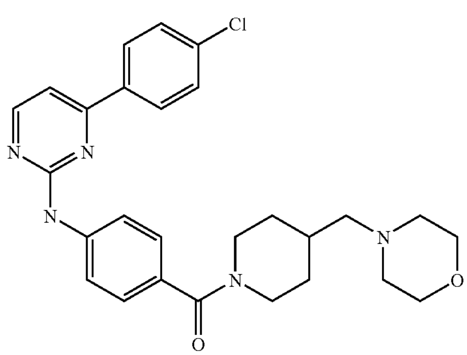 | 492.02 | 8.05 | 492.5 |

-continued

| Compound Number | Structure | MOL. WEIGHT | RT, min | M + 1 |
|---|---|---|---|---|
| 17-214 | 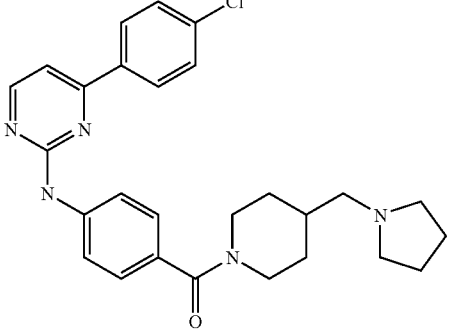 | 476.021 | 8.817 | 476.5 |
| 17-215 | 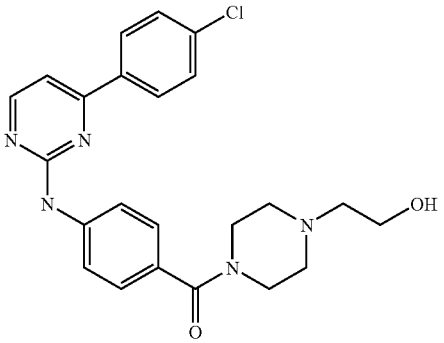 | 437.92 | | 438 |

Example 18

Synthesis of 4-{[4-(4-Chlorophenyl)pyrimidin-2-yl]amino}benzoic acid piperazine amide hydrochloride

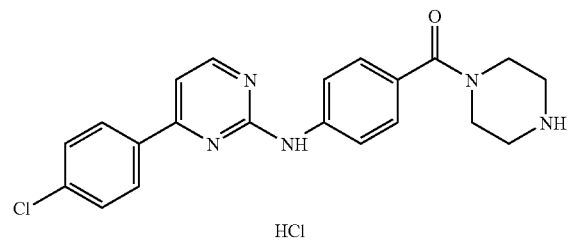

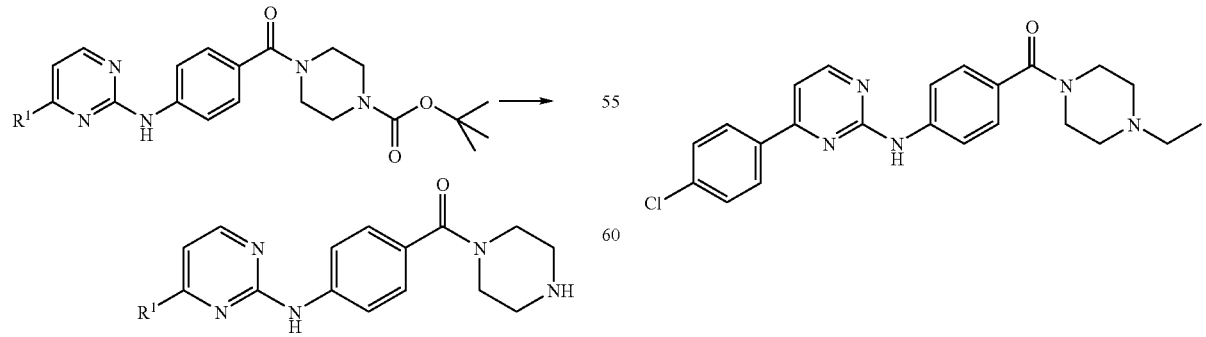

R¹ = 4-chlorophenyl

Hydrogen chloride gas was bubbled slowly in a solution of tert-butyl 4-{[4-(4-chlorophenyl)pyrimidin-2-yl]amino}benzoic acid piperazine amide (3.0 g, 6.1 mmol) in acetic acid (61 mL) for 20 minutes. The solution was concentrated and dried on a vacuum pump to give 2.6 g (99%) of the title compound; ES-MS, m/z 394 (M+1)⁺ LC/MS Retention Time, 5.84 min. (Method A).

Example 19

Synthesis of 4-{[4-(4-Chorophenyl)pyrimidin-2-yl]amino}benzoic acid 4-ethyl piperazine amide A solution of 4-{[4-(4-chlorophenyl)pyrimidin-2-yl]amino}Phenyl Piperazine Ketone (0.5 g, 1.54 mmol), N-ethylpiperazine (0.18 g, 1.54 mmol), 1-(3-dimethylaminopropyl)-3-ethyl carbodiimide hydrochloride (0.44 g, 2.31 mmol) and hydroxybenzotriazole (0.31 g, 2.31 mmol) in dimethylformamide (15 mL) was stirred for 18 h. Water (50 mL) was added and the solid was filtered. The solid was purified on preparatory HPLC (C-18 column, 30% acetonitrile to 100% acetonitrile in water-both containing 0.1% trifluoracetic acid) to give the titled compound, 0.27 g (42%) yield; ES-MS, m/z 422 (M+1)+ LC/MS Retention Time, 5.92 min. (Method A).

Example 20

Synthesis of 4-Acylaminopiperidines

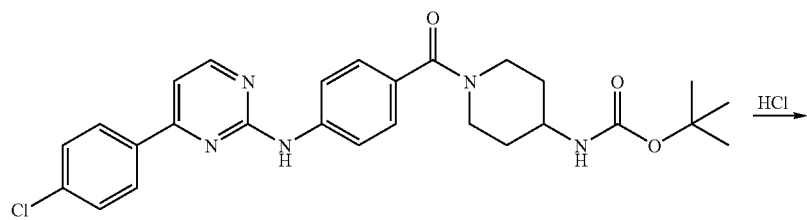

4-Aminopiperidyl 4-{[4-(4-chlorophenyl)pyrimidin-2-yl]amino}phenyl Ketone Hydrochloride (tert-Butoxy)-N-{1-[(4-{[4-(4-chlorophenyl)pyrimidin-2-yl]amino}phenyl)carbonyl](4-piperidyl)}carboxamide (4.00 g, 7.87 mmol) was stirred in 50 mL EtOH followed by addition of anhydrous HCl gas. The reaction was stirred for 30 min. then concentrated down to a residue. To this was added a small amount of EtOH followed by dilution with ether. A yellow solid formed which was filtered and dried to give 3.00 grams of 4-aminopiperidyl 4-{[4-(4-chlorophenyl)pyrimidin-2-yl]amino}phenyl ketone hydrochloride: HPLC Retention time; 5.89 min. (Method B) M+1; 408.4

N-{1-[(4-{[4-(4-Chlorophenyl)pyrimidin-2-yl]amino}phenyl)carbonyl]-4-piperidyl}acetamide Stirred 4-aminopiperidyl 4-{[4-(4-chlorophenyl)pyrimidin-2-yl]amino}phenyl ketone hydrochloride (300 mg, 0.582

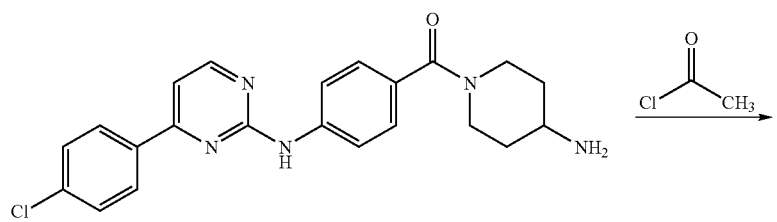

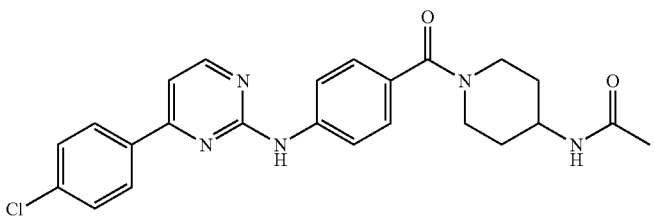

mmol) in 10 mL THF with triethylamine (0.293 mg, 2.91 mmol). Acetic anhydride (89 mg, 0.873 mmol) was added and the reaction was stirred for 40 minutes. The solution was concentrated down and purified by preperative HPLC to give N-{1-[(4-{[4-(4-chlorophenyl)pyrimidin-2-yl]amino}phenyl)carbonyl]-4-piperidyl}acetamide (0.120 g, 46% yield): HPLC Retention time; 6.92 min. (Method B) M+1; 450.4

Compounds listed below were prepared according to the above procedure.

| Compound Number | Structure | MW | RT, min | M + 1 |
|---|---|---|---|---|
| 20-1 | 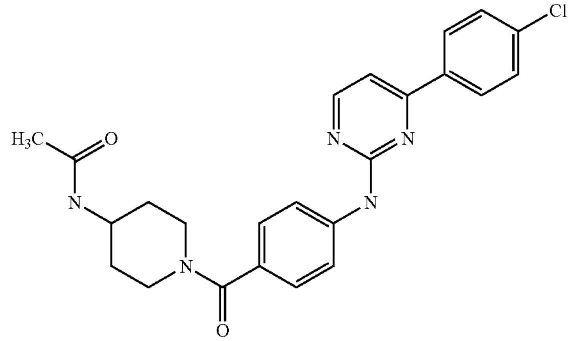 | 449.94 | 6.92 | 450.4 |
| 20-2 | 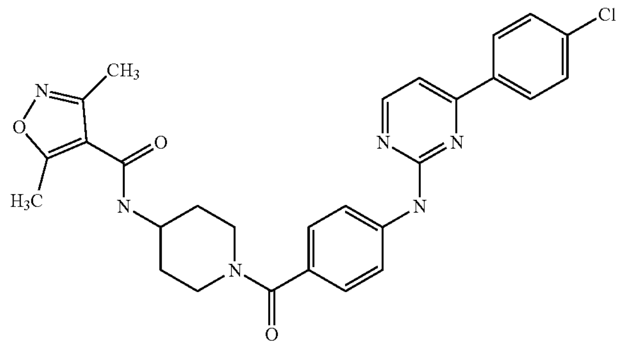 | 531.013 | 7.49 | 531.4 |
| 20-3 | 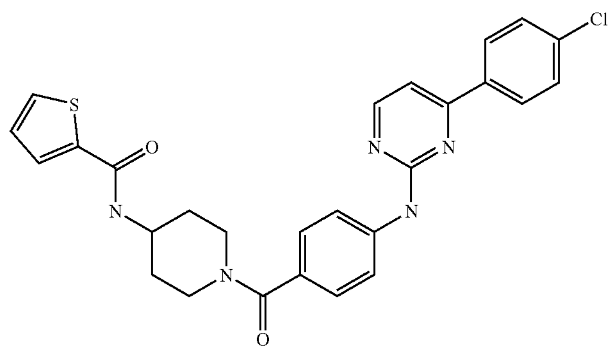 | 518.039 | 7.6 | 518.4 |
| 20-4 | 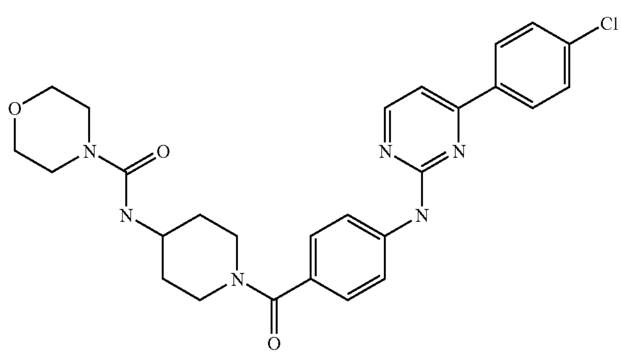 | 521.018 | 7.19 | 521.4 |

-continued

| Compound Number | Structure | MW | RT, min | M + 1 |
|---|---|---|---|---|
| 20-5 | 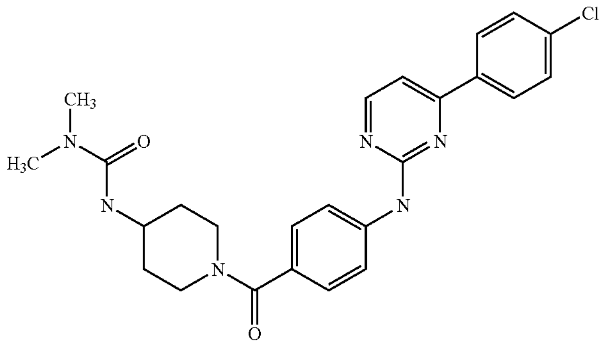 | 478.981 | 7.18 | 479.4 |
| 20-6 | 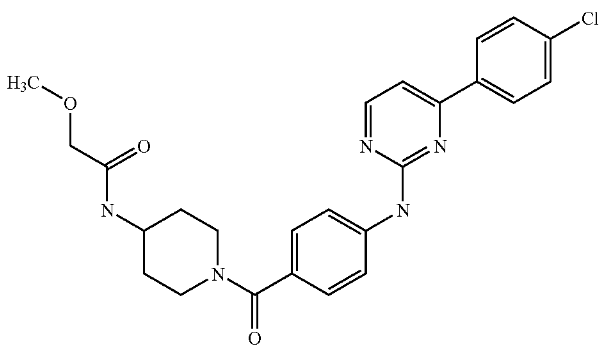 | 479.965 | 7.3 | 480.2 |
| 20-7 | 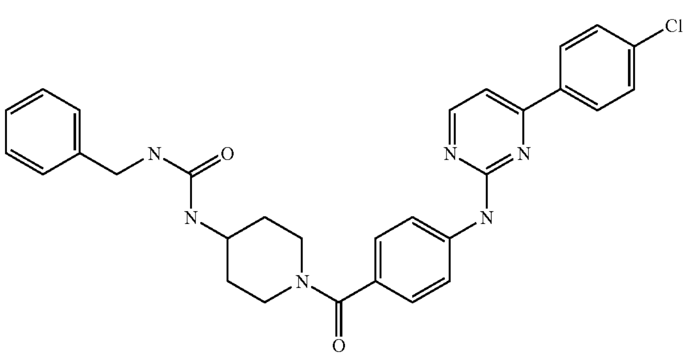 | 541.052 | 7.68 | 541.4 |

Example 21

Synthesis of Piperazineacetic Acid Amides

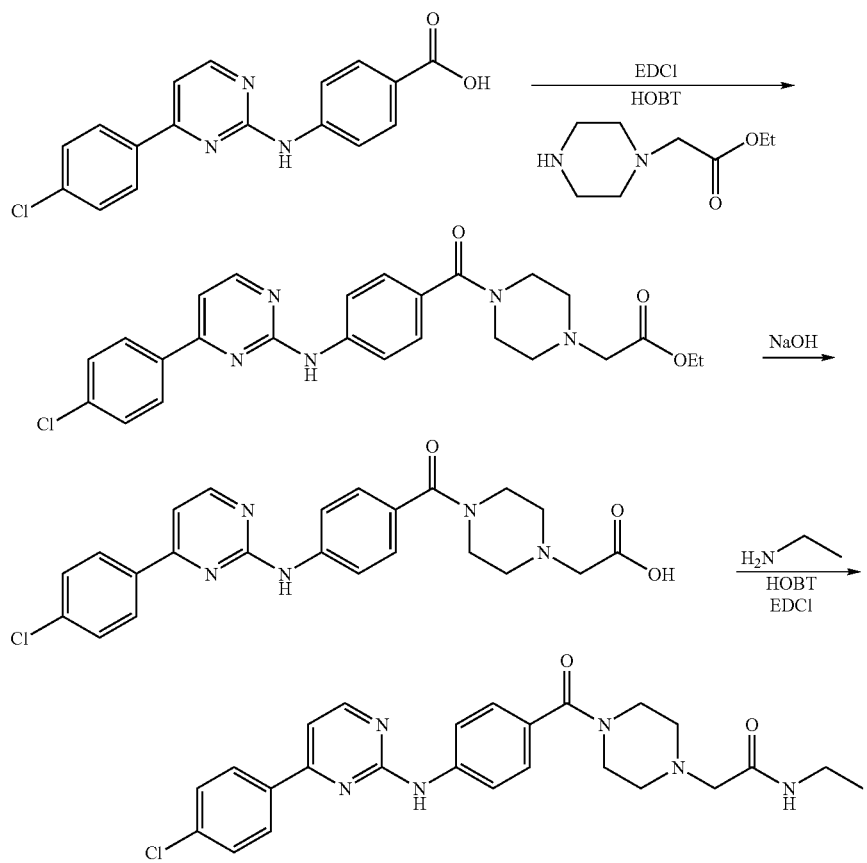

Ethyl 2-{4-[(4-{[4-(4-Chlorophenyl)pyrimidin-2-yl]amino}phenyl) carbonyl]piperazinyl}acetate 4-{[4-(4-chlorophenyl)pyrimidin-2-yl]amino}benzoic acid (5 g, 15.3 mmol) was dissolved in dimethylformamide. The HOBT(2.82 g, 18.4 mmol)] and EDCI(3.53 g, 18.4 mmol) were then added. The reaction stirred for 15 minutes then ethyl-2-piperazinylacetate (2.14 mL, 18.4 mmol) was added. The reaction was stirred overnight at room temperature. Water (150 mL) was added. The solid was collected by filtration, and purified by silica-gel column chromatography (90% EtOAc/Hexane, Rt=0.25) to yield 4.3 g (45% yield) of ethyl 2-{4-[(4-{[4(4-chlorophenyl)pyrimin-2-yl]amino}phenyl)carbonyl]piperazinyl}acetate: HPLC Retention time; 9.932 min. (Method B) M+1; 480.2

2-{4-[(4-{[4-(4-Chlorophenyl)pyrimidin-2-yl]amino}phenyl)carbonyl]piperazinyl}acetic Acid To ethyl 2-{4-[(4-{[4(4-chlorophenyl)pyrimin-2-yl]amino}phenyl) carbonyl]piperazinyl}acetate (5.0 g, 15.3 mmol was added ethanol (69 mL) and NaOH (1.14 g, 29.2 mmol, 4.1 eq) in 46 mL water. The reaction was heated at 75° C. for 1.5 hours. The reaction was acidified to pH=3, filtered, and dried, affording 4.3 g of the acid 2-{4-[(4-{[4-(4-chlorophenyl)pyrimidin-2-yl]amino}phenyl)carbonyl]piperazinyl}acetic acid (83.3%): HPLC Retention time; 9.260 min. (Method B) M+1; 452.3

2-{4-[(4-{[4-(4-Chlorophenyl)pyrimidin-2-yl]amino}phenyl)carbonyl]piperazinyl}N-ethylacetamide 2-{4-[(4-{[4-(4-Chlorophenyl)pyrimidin-2-yl]amino}phenyl) carbonyl]piperazinyl}acetic acid (0.200 g, 0.44 mmol) was dissolved in DMF then stirred for 15 minutes in ice-brine solution, then the HOBT (0.072 g, 0.53 mmol] then EDCI(0.102 g, 0.53 mmol) were added and stirred for another 30 minutes. Ethylamine (0.030 mL, 0.53 mmol) was added and the reaction was left to stir at room temp overnight. The reaction was quenched with 10 mL of water and a precipitate formed. The precipitate was colleted by filtration, and purified by preparative HPLC to yield 2-{4-[(4-{[4-(4-chlorophenyl)pyrimidin-2-yl]amino}phenyl)carbonyl]piperazinyl}N-ethylacetamide: HPLC Retention time; 9.508 min. (Method B) M+1; 479.2

Compounds listed below were prepared aqccording to the above procedure.

| Compound Number | Structure | MW | RT, min | M + 1 |
|---|---|---|---|---|
| 21-1 | 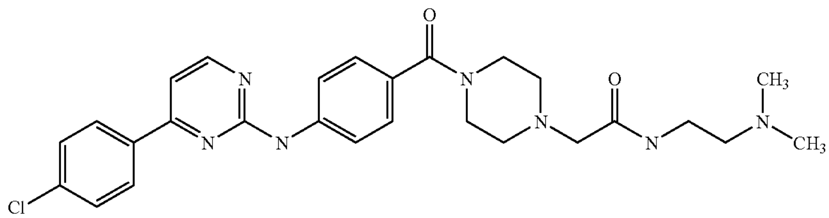 | 522.05 | 8.648 | 522.3 |
| 21-2 | 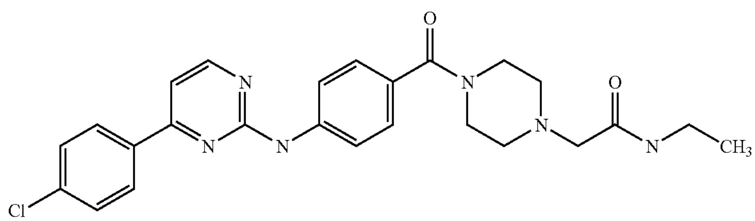 | 478.981 | 9.508 | 479.3 |
| 21-3 | 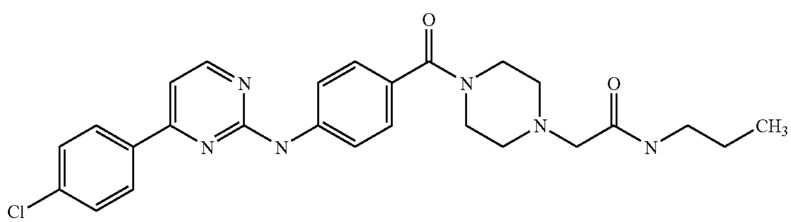 | 493.008 | 9.79 | 493.2 |
| 21-4 | 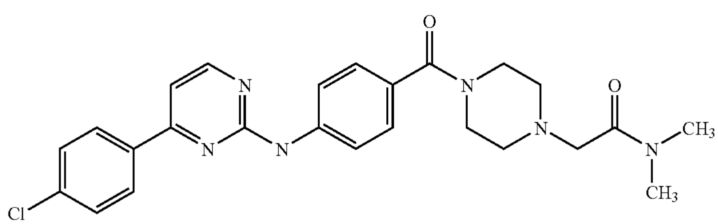 | 478.981 | 9.472 | 479.3 |
| 21-5 | 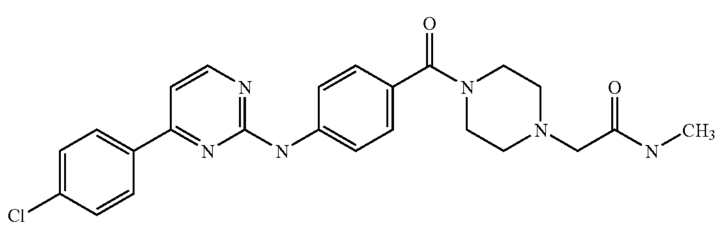 | 464.954 | 9.268 | 465.3 |
| 21-6 | 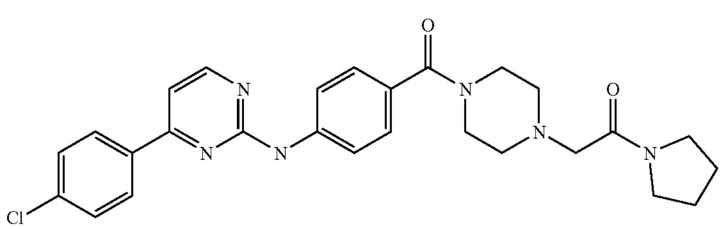 | 505.019 | 9.676 | 505.2 |

| Compound Number | Structure | MW | RT, min | M + 1 |
|---|---|---|---|---|
| 21-7 | 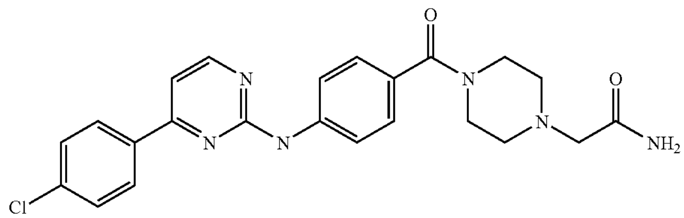 | 450.928 | 7.933 | 451.0 |
| 21-8 | 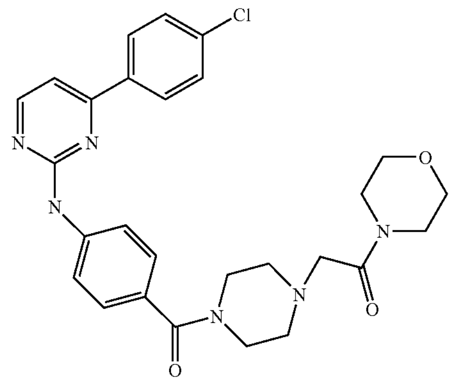 | 521.0181 | 9.644 | 521.6 |
| 21-9 | 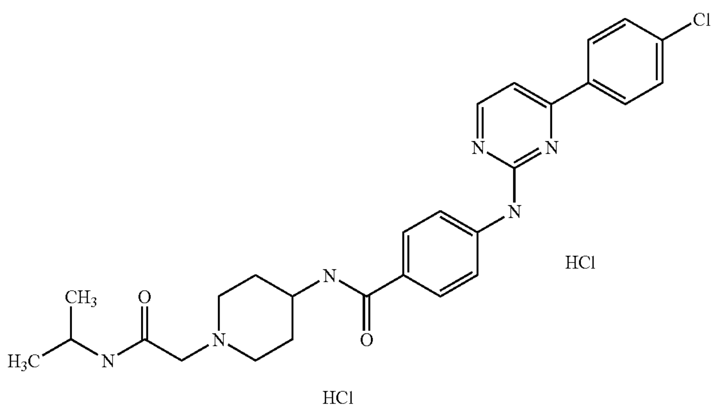 | 579.957 | 6.1 | 507.4 |
Example 22
Reductive Amination
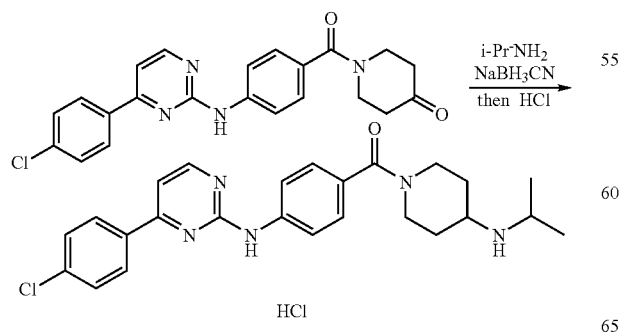

4-{[4-(4-chlorophenyl)pyrimidin-2-yl]amino}phenyl 4[(methylethyl)amino]piperidyl ketone hydrochloride 1-[(4-{[4-(4-chlorophenyl)pirimidin-2yl]amino}phenyl)carbonyl]piperidin-4-one (400 mg, 0.980 mmol) was dissolved in 10 mL EtOH along with isopropylamine (58 mg, 0.980 mmol). Sodium cyanoborohydride (62 mg, 0.986 mmol) was added and the mixture was stirred at room temperature for 18 hours. The reaction was quenched with water, extracted with ethyl acetate followed by flash chromatography (EtOAc/MeOH; 90:10) to give a residue. This was taken up in ETOH saturated (with HCl(g)), diluted with ether, filtered to give 4-{[4-(4-chlorophenyl)pyrimidin-2-yl]amino}phenyl 4-[(methylethyl)amino]piperidyl ketone hydrochloride (0.150 g, 30% yield): HPLC Retention time; 6.02 min. (Method B) M+1; 450.4.

Compounds listed below were prepared according to the above procedure.

| Compound Number | Structure | MW | RT, min | M + 1 |
|---|---|---|---|---|
| 22-1 | 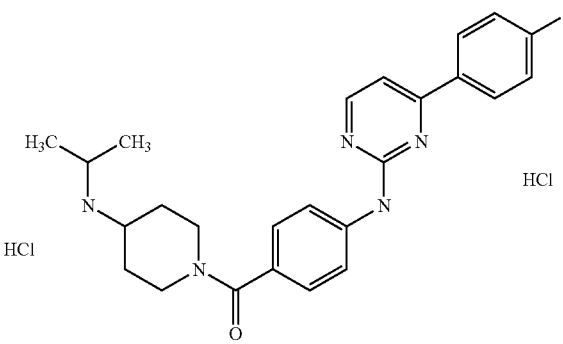 | 522.905 | 6.02 | 450.4 |
| 22-2 | 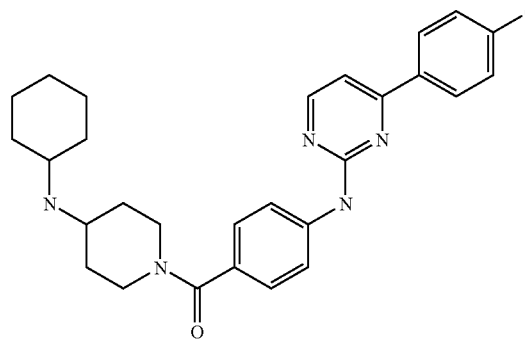 | 490.0478 | 10.612 | 490.3 |
| 22-3 | 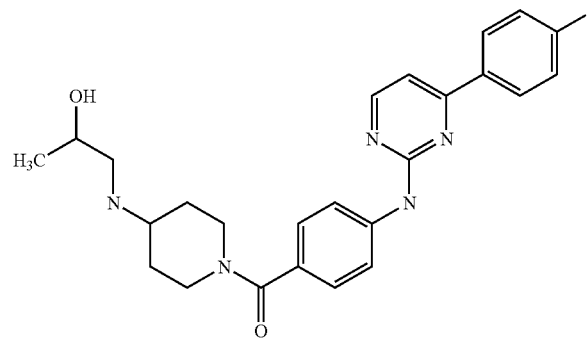 | 465.9822 | 9.644 | 466.3 |

-continued

| Compound Number | Structure | MW | RT, min | M + 1 |
|---|---|---|---|---|
| 22-4 | 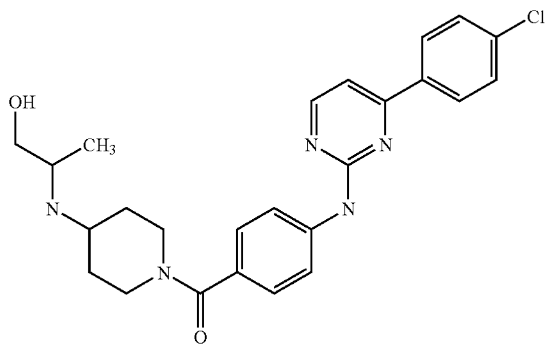 | 465.9822 | 9.604 | 466.3 |
| 22-5 | 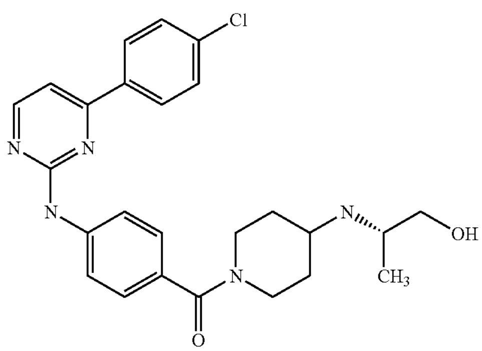 | 465.9822 | 9.52 | 466.4 |
| 22-6 | 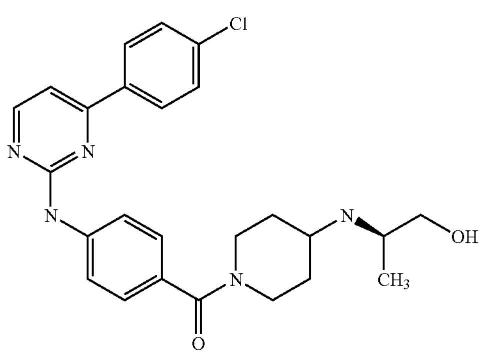 | 465.9822 | 9.584 | 466.4 |
| 22-7 | 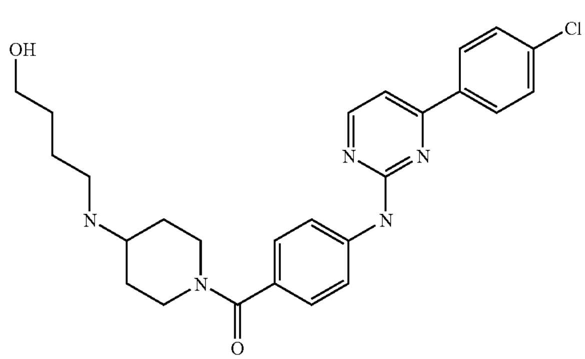 | 480.009 | 9.604 | 480.2 |

-continued

| Compound Number | Structure | MW | RT, min | M + 1 |
|---|---|---|---|---|
| 22-8 | 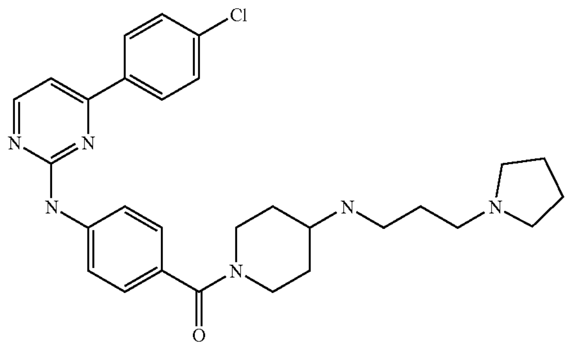 | 519.0895 | 9.172 | 519.4 |
| 22-9 | 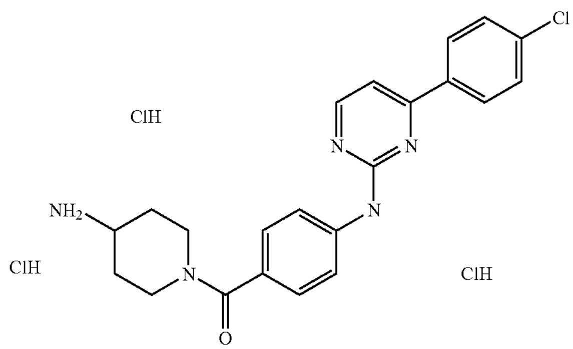 | 517.286 | 5.89 | 408.4 |
| 22-10 | 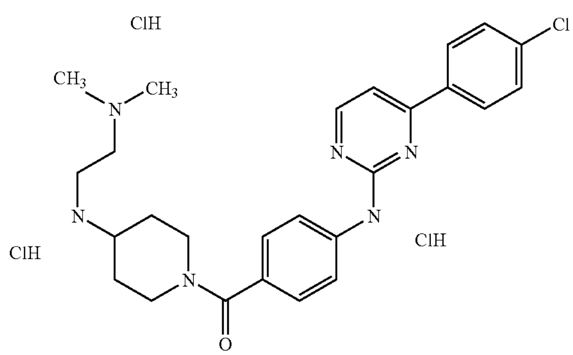 | 588.4076 | 5.43 | 479.4 |
| 22-11 | 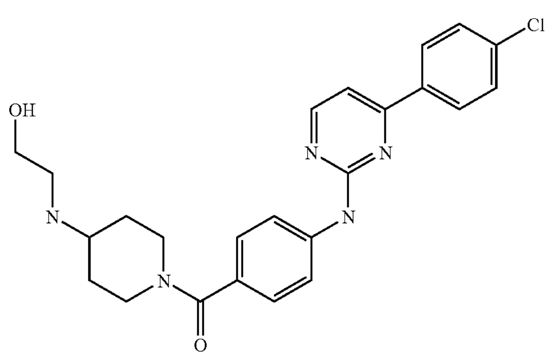 | 451.9554 | 6.12 | 452.4 |

-continued
| Compound Number | Structure | MW | RT, min | M + 1 |
|---|---|---|---|---|
| 22-12 | 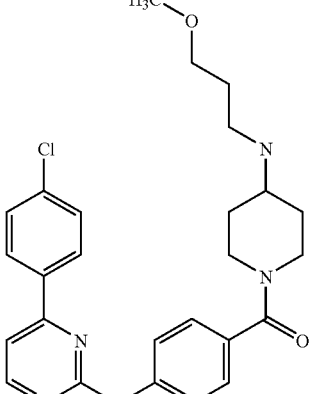 | 480.009 | 9.291 | 480.4 |
| 22-13 | 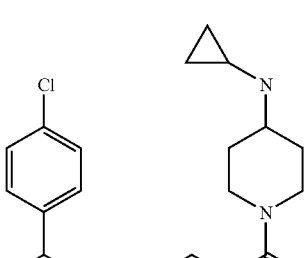 | 447.9674 | 9.976 | 448.4 |
Example 23
Synthesis of Reverse Sulfonamides
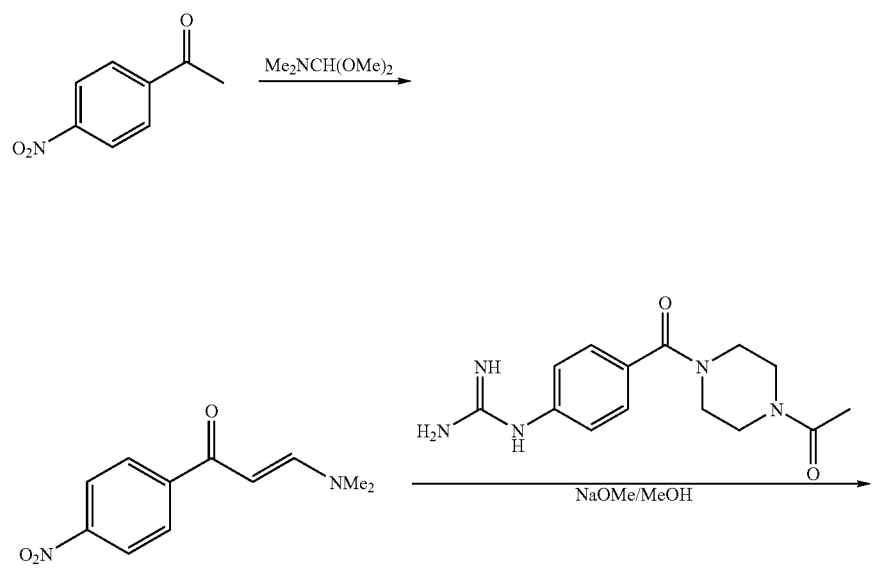

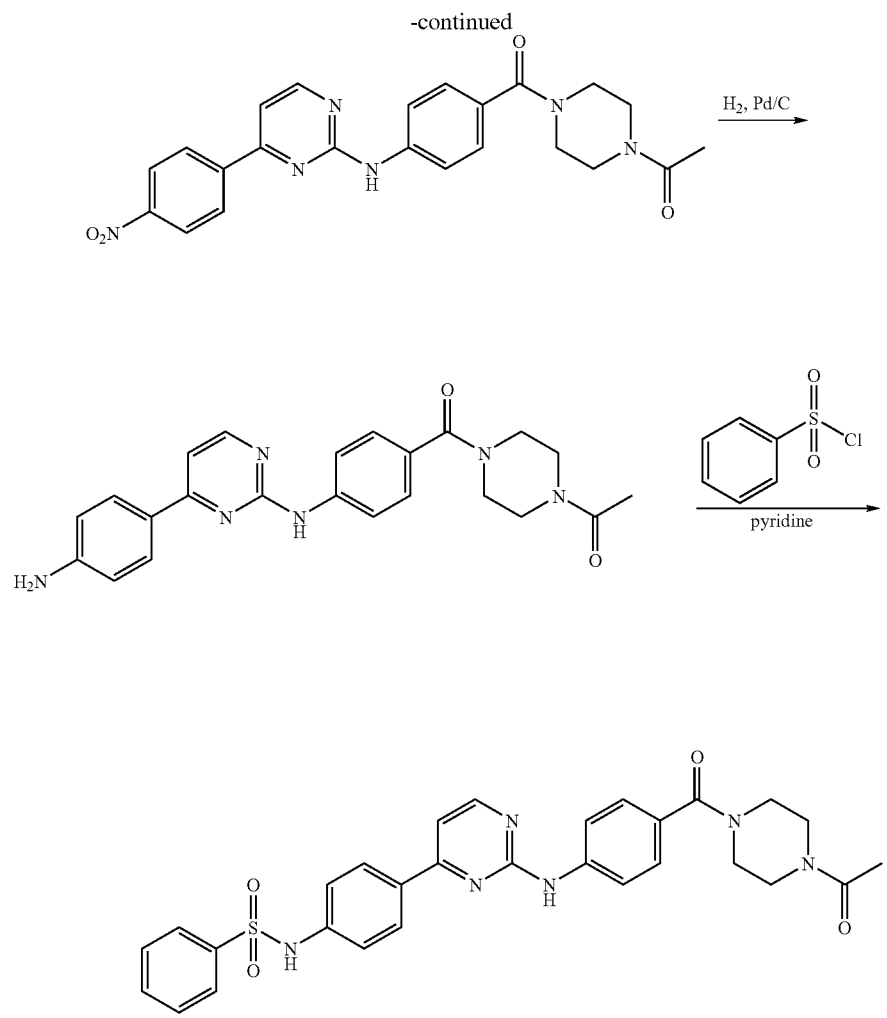

(2E)-1-(4-nitrophenyl)-3-dimethylamino)prop-2-en-1-one

A mixture of 4-nitroacetophenone (20.0 g, 121 mmol) and N,N-dimethylformamide dimethylacetal (200 ml) was refluxed for 18 hours, cooled and concentrated to give (2E)-1-(4-nitrophenyl)-3-dimethylamino)prop-2-en-1-one quantitatively.

1-Acetyl-4-[(4-{[4-(4-nitrophenyl)pyrimidin-2-yl}amino}phenyl)carbonyl}piperazine To a mixture of(2E)-1-(4-nitrophenyl)-3-dimethylamino) prop-2-en-1-one (250 mg, 1.14 mmol) and {4-{(4-acetylpiperazinyl)carbonyl]phenyl}aminocarboxamidine (394 mg, 1.36 mmol) in methanol (6 ml) is added 2 mL of a 2.0M solution of sodium methoxide in methanol. The reaction mixture is then refluxed for 18 hours then acidified to pH ~4 using 1N HCl. The solid which formed at this time was then filtered and purified by column chromatography using 10% methanol in chloroform to give 320 mg (69%) of the desired product.

1-Acetyl-4-[(4-{[4-(4-aminophenyl)pyrimidin-2-yl}amino}phenyl)carbonyl}piperazine To a solution of 1-acetyl-4-[(4-{[4-(4-nitrophenyl)pyrimidin-2-yl}amino}phenyl)carbonyl}piperazine (150 mg, 0.34 mmol) in methanol (5 mL) containing a few drops of acetic acid, is added 100 mg of 10% Palladium-Charcoal. The solution is then hydrogenated at 50 psi for 6 h at which time there remains no starting material. The solution is then filtered through a pad of Celite which gives 135 mg (95%) of essentially pure reduced material as a brown oil.

1-Acetyl-4-{[4-({4-[4-(phenylsulfonyl)aminophenyl] pyrimidin-2yl}amino)phenyl]carbonyl}piperazine To a solution of 1-acetyl-4-[(4-{[4-(4-aminophenyl)pyrimidin-2-yl}amino}phenyl)carbonyl}piperazine (100 mg, 0.24 mmol) in pyridine (5 mL) containing a catalytic amount of DMAP is added benzenesulfonyl chloride (50 mg, 0.29 mmol) and the solution is stirred overnight at room temperature. The pyridine is removed under vacuum and the residue extracted into methylene chloride and washed with 1N HCl. Evaporation of solvent provides the crude piperazine which is purified by preparative HPLC (10-60% $CH_3CN$ over 25 min.) to give an analytically pure sample as a yellow solid: M+1; 557.3. HPLC Retention Time; 9.59 min (Method B).

Compounds listed below were prepared according to the above procedure.

| Compound Number | Structure | MW | RT, min | M + 1 |
| --- | --- | --- | --- | --- |
| 23-1 | 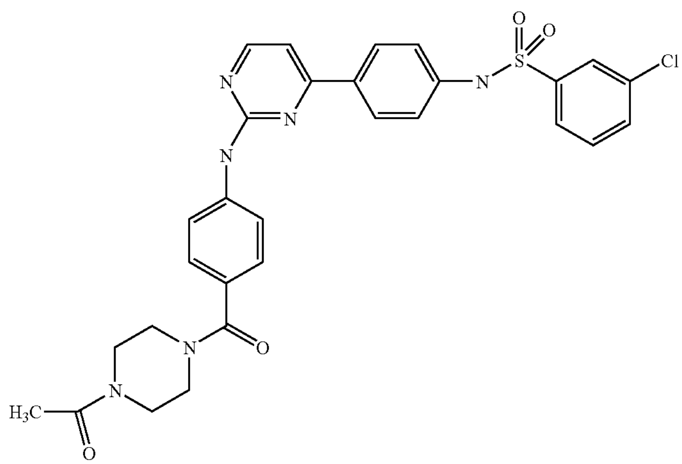 | 586 | 8.03 | 587.3 |
| 23-2 | 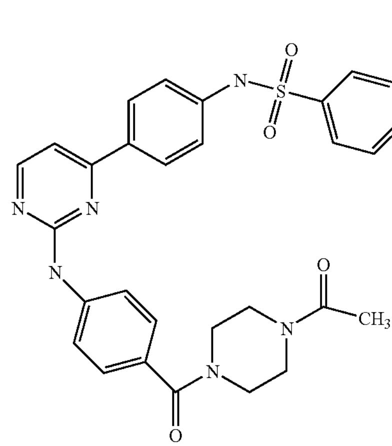 | 624.6413 | 9.53 | 625.3 |
| 23-3 | 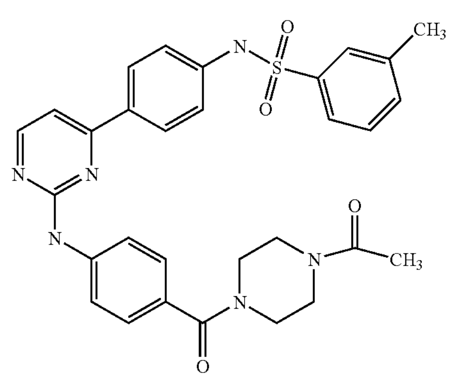 | 570.671 | 8.46 | 571.3 |

-continued

| Compound Number | Structure | MW | RT, min | M + 1 |
| --- | --- | --- | --- | --- |
| 23-4 | 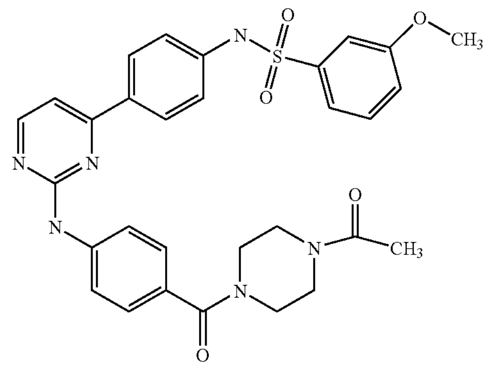 | 586.67 | 9 | 587.5 |
| 23-5 | 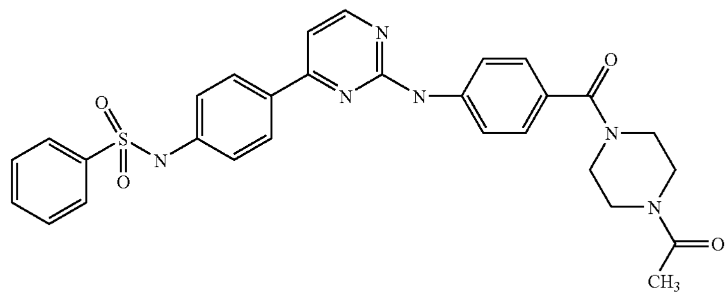 | 556.644 | 9.62 | 557.3 |
| 23-6 | 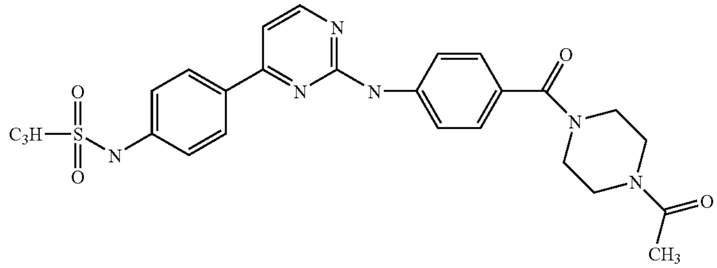 | 494.5734 | 8.35 | 495.3 |
| 23-7 | 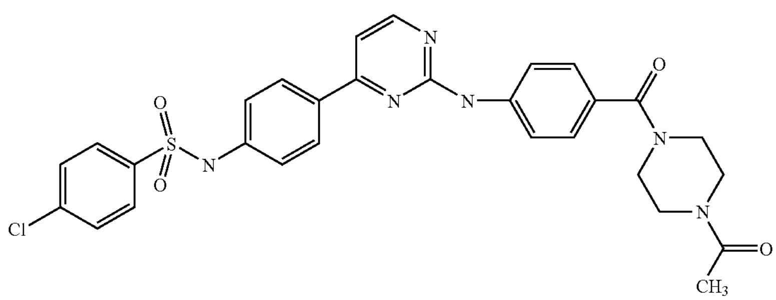 | 591.0893 | 10.14 | 591.3 |
| 23-8 | 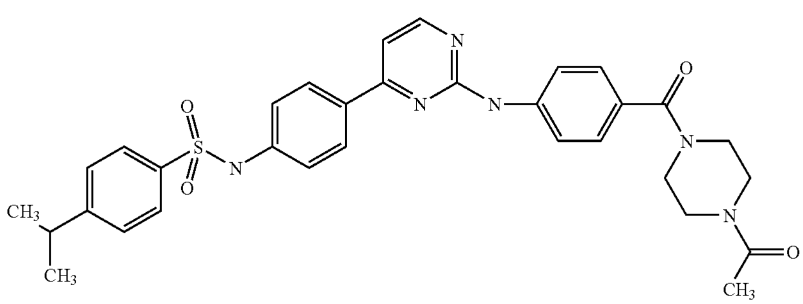 | 598.7246 | 10.25 | 599.5 |

-continued

| Compound Number | Structure | MW | RT, min | M + 1 |
|---|---|---|---|---|
| 23-9 | 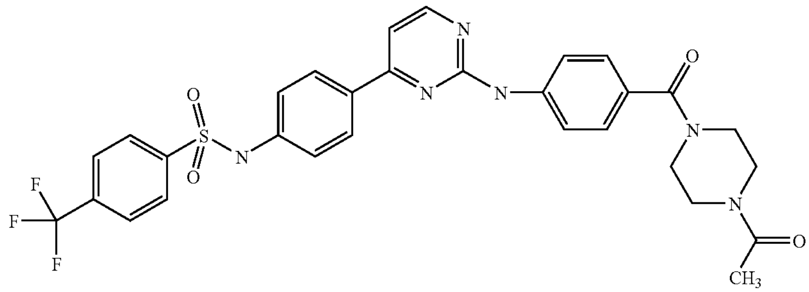 | 624.6413 | 10.58 | 625.3 |
| 23-10 | 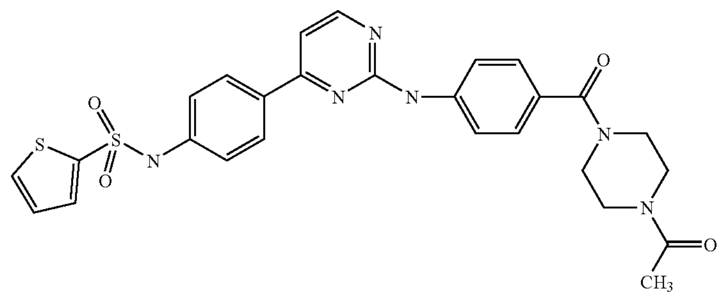 | 562.6724 | 9.56 | 563.3 |
| 23-11 | 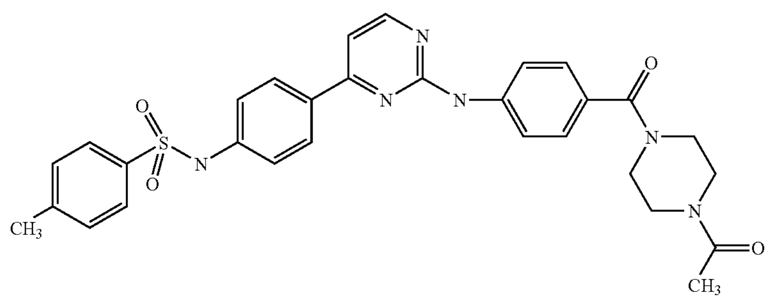 | 570.671 | 10.02 | 571.3 |
| 23-12 | 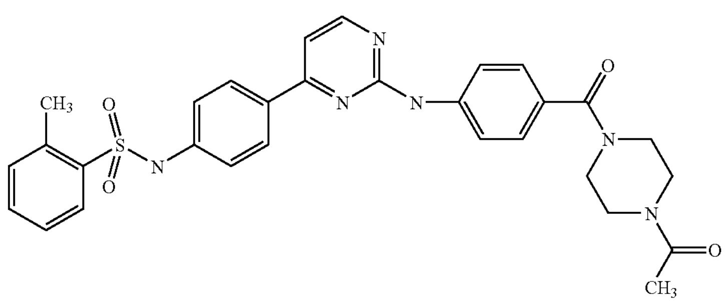 | 570.671 | 9.79 | 571.3 |
| 23-13 | 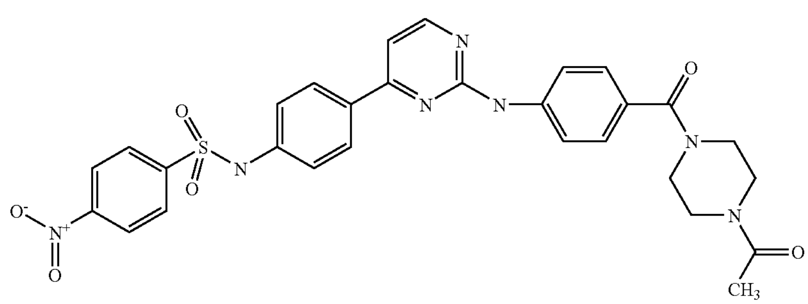 | 601.6413 | 7.15 | 602.5 |

-continued

| Compound Number | Structure | MW | RT, min | M + 1 |
|---|---|---|---|---|
| 23-14 | 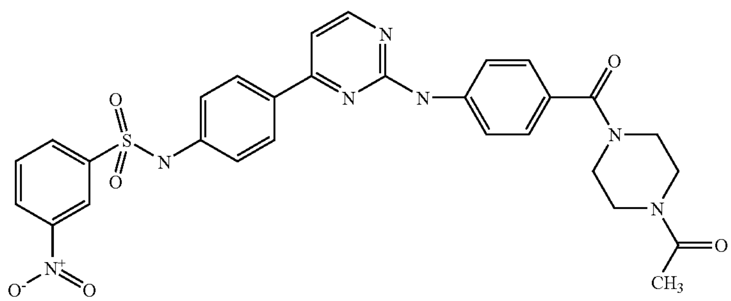 | 601.6413 | 8.57 | 602.3 |
| 23-15 | 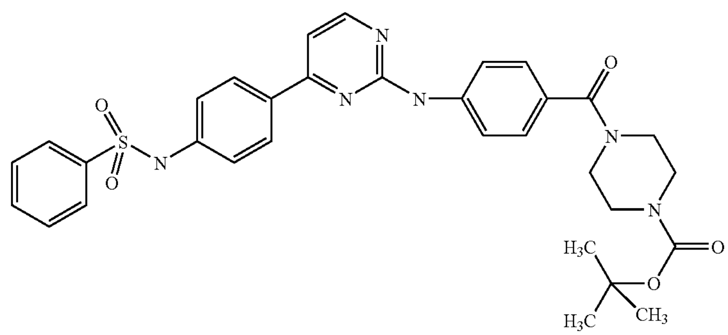 | 614.7236 | 8.23 | 615.5 |
| 23-16 | 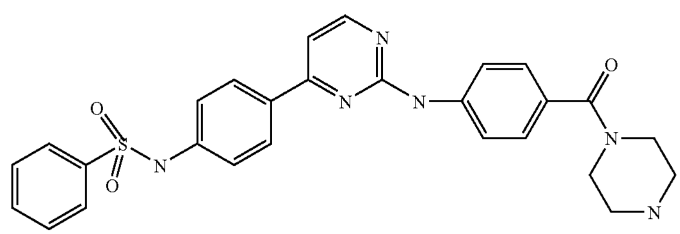 | 514.6074 | 4.55 | 515.3 |
| 23-17 | 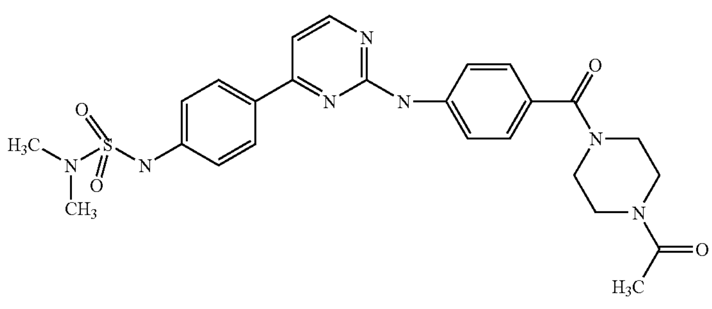 | 523.6151 | 8.85 | 524.3 |
| 23-18 | 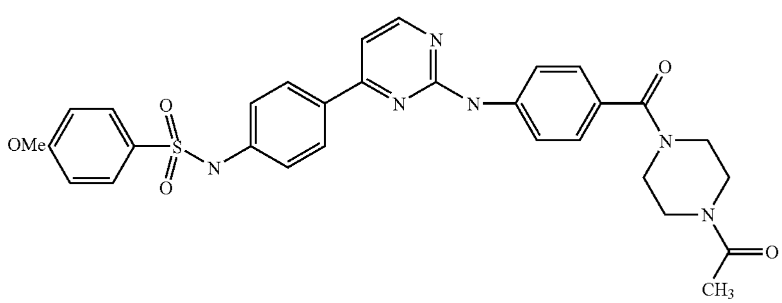 | 586.67 | 9.72 | 587.3 |

-continued

| Compound Number | Structure | MW | RT, min | M + 1 |
|---|---|---|---|---|
| 23-19 | 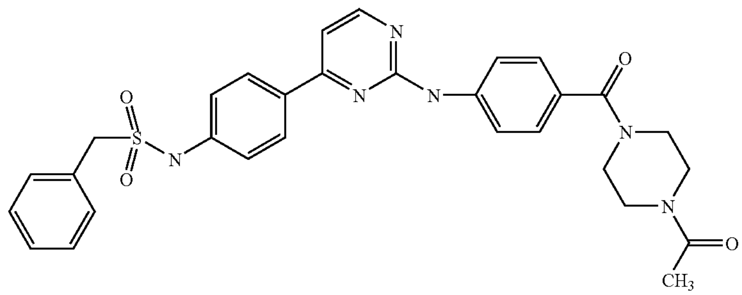 | 570.671 | 9.82 | 571.3 |
| 23-20 | 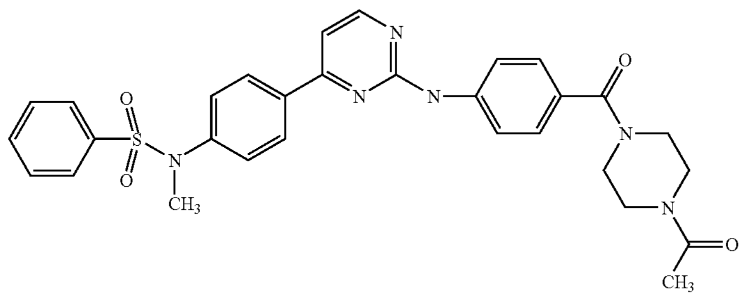 | 570.671 | 10.68 | 571.5 |
| 23-21 | 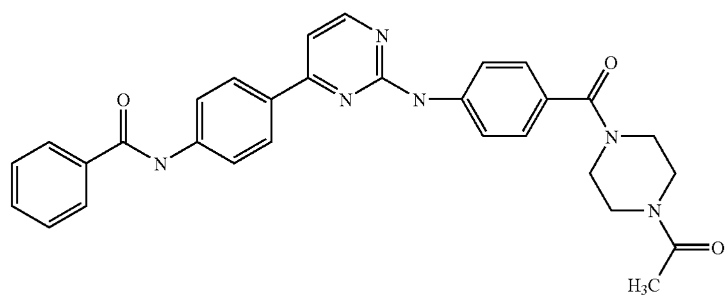 | 520.5902 | 9.89 | 521.3 |
| 23-22 | 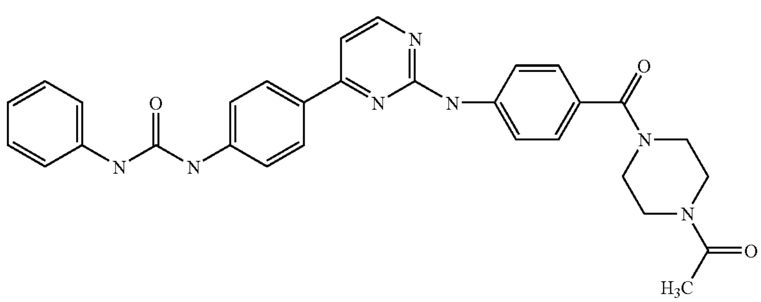 | 535.6051 | 7.58 | 536.3 |
| 23-23 | 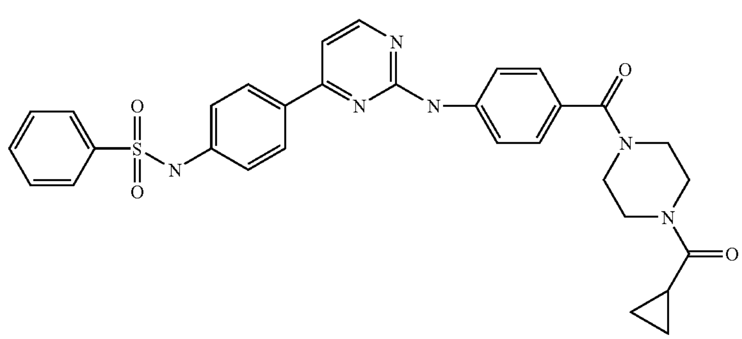 | 582.682 | 9.18 | 583.5 |

| Compound Number | Structure | MW | RT, min | M + 1 |
|---|---|---|---|---|
| 23-24 | 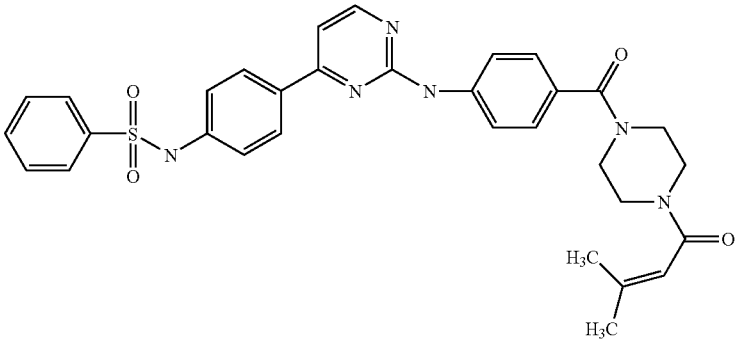 | 596.7088 | 9.76 | 597.5 |
| 23-25 | 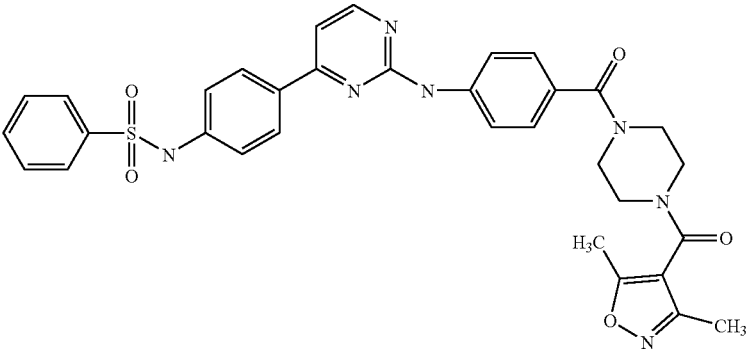 | 637.7179 | 9.8 | 638.3 |
| 23-26 | 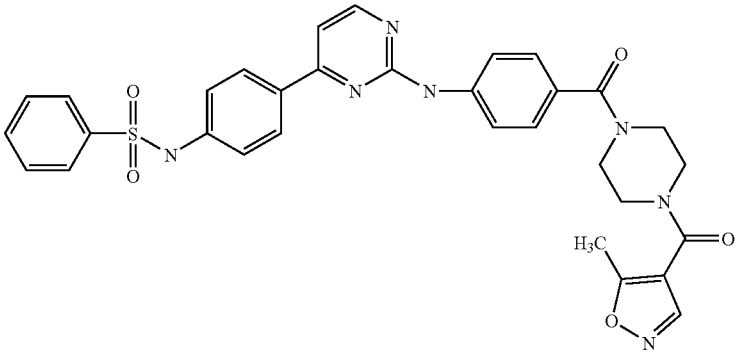 | 623.6911 | 9.2 | 624.5 |
| 23-27 | 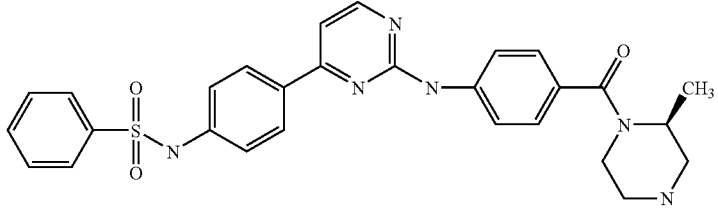 | 528.6342 | 5.92 | 529.3 |

Example 24
Synthesis of Further Representative Compounds
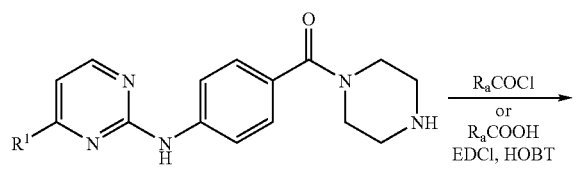
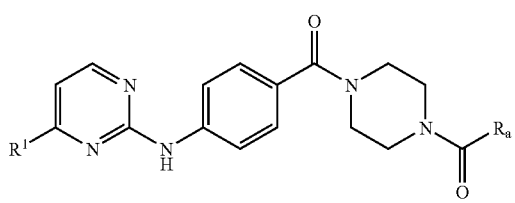
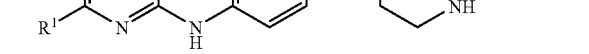
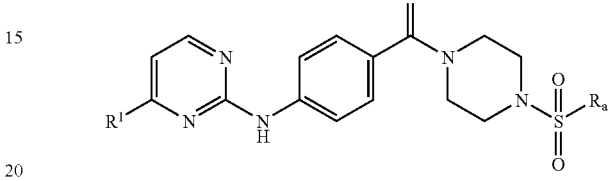
The compounds of Example 18, with the desired $R_1$ moiety, may be modified according to the above procedures to yield further representative compounds of this invention. For example, the following compounds were made according to the above procedures.
| Compound Number | Structure | MW | RT, min | M + 1 |
|---|---|---|---|---|
| 24-1 | 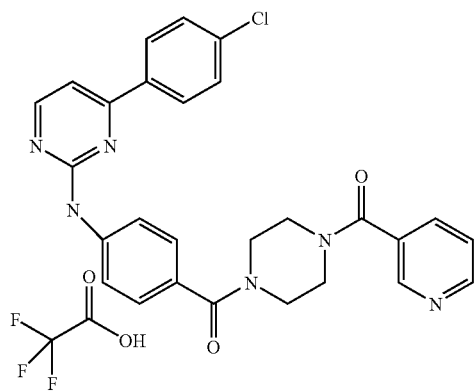 | 498.963 | 9.7 | 499 |
| 24-2 | 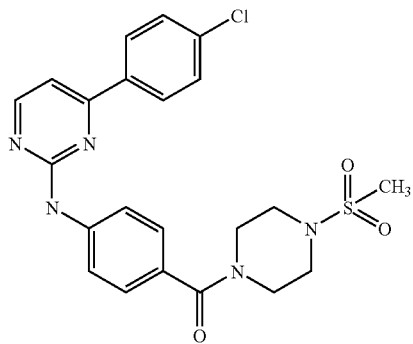 | 471.967 | 7.19 | 472 |

-continued

| Compound Number | Structure | MW | RT, min | M + 1 |
|---|---|---|---|---|
| 24-3 | 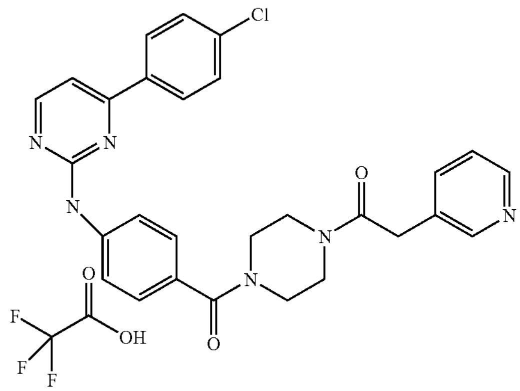 | 512.990 | 6.24 | 513 |
| 24-4 | 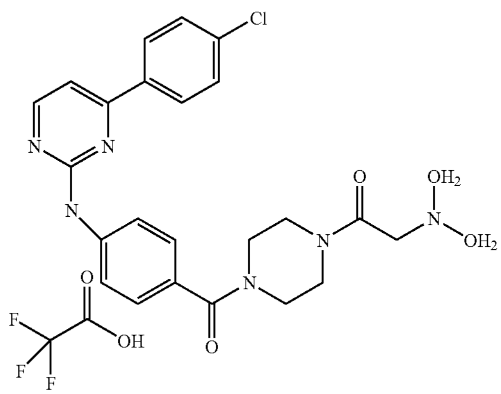 | 478.974 | 5.92 | 479 |
| 24-5 | 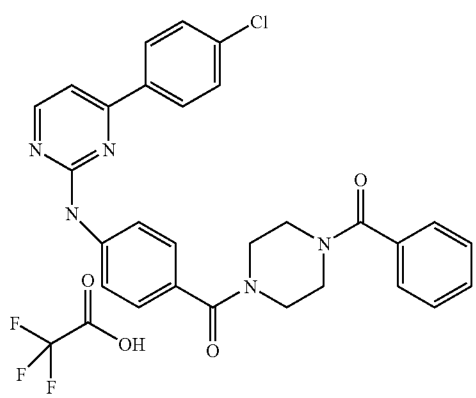 | 497.975 | 7.41 | 498 |
| 24-6 | 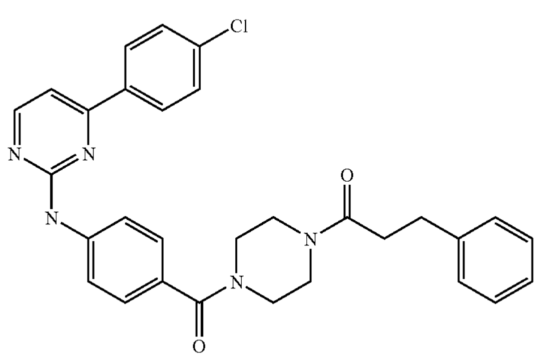 | 526.037 | 7.66 | 526 |

-continued

| Compound Number | Structure | MW | RT, min | M + 1 |
|---|---|---|---|---|
| 24-7 | 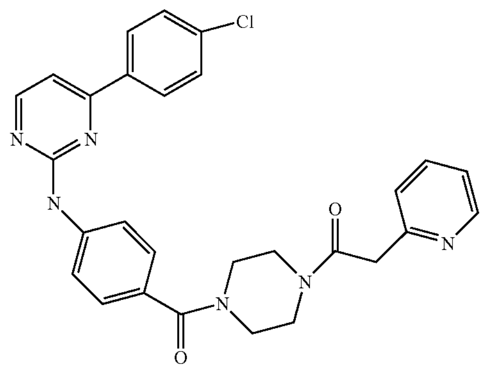 | 512.9985 | 8.350 | 513.4 |
| 24-8 | 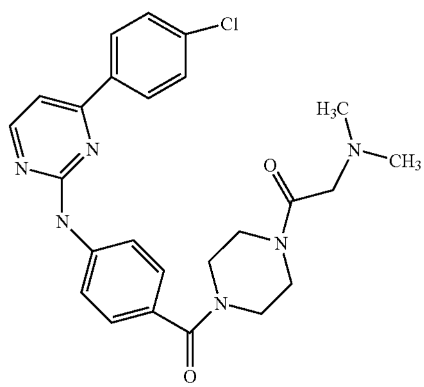 | 478.9813 | 7.533 | 479.4 |
| 24-9 | 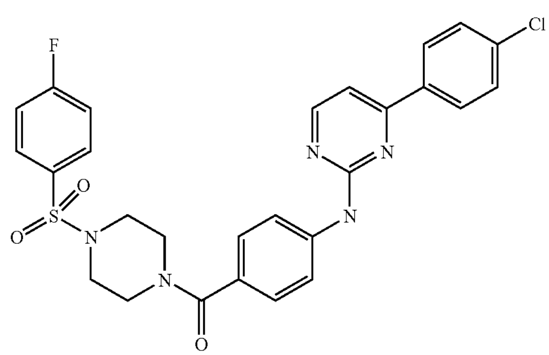 | 552.028 | 7.33 | 552.3 |
| 24-10 | 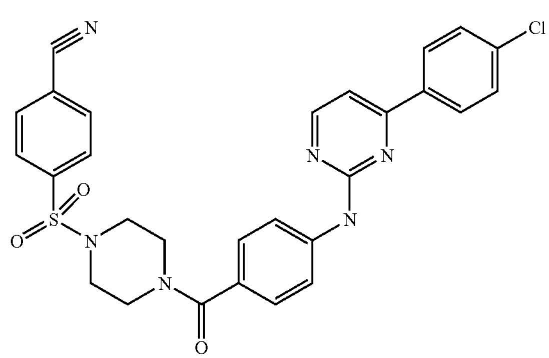 | 559.048 | 7.17 | 559.3 |

-continued
| Compound Number | Structure | MW | RT, min | M + 1 |
|---|---|---|---|---|
| 24-11 | 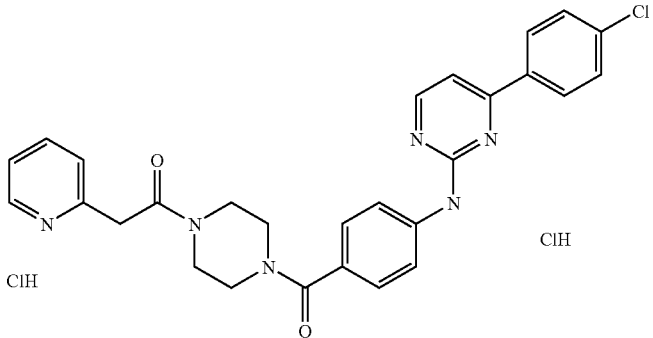 | 585.92 | 5.15 | 513.3 |
| 24-12 | 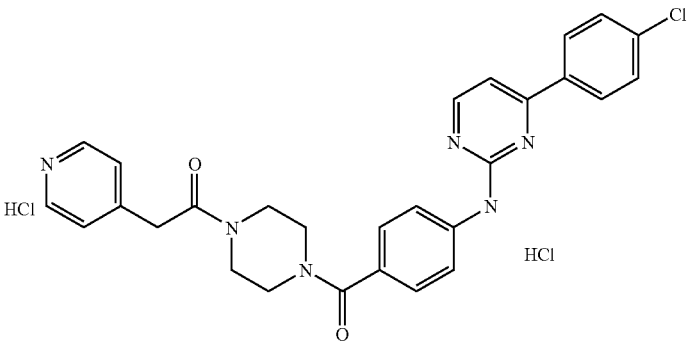 | 585.92 | 4.78 | 513 |
| 24-13 | 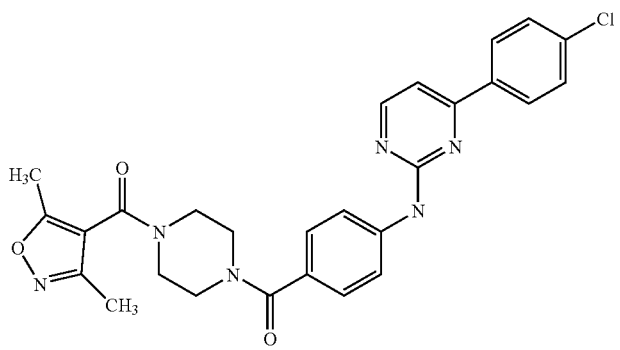 | 516.987 | 6.43 | 517.3 |
| 24-14 | 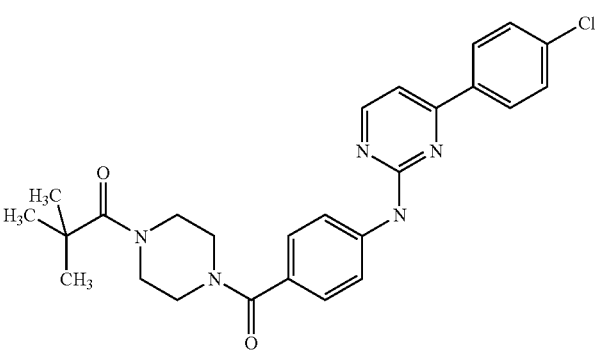 | 477.993 | 6.95 | 478.3 |

-continued

| Compound Number | Structure | MW | RT, min | M + 1 |
|---|---|---|---|---|
| 24-15 | 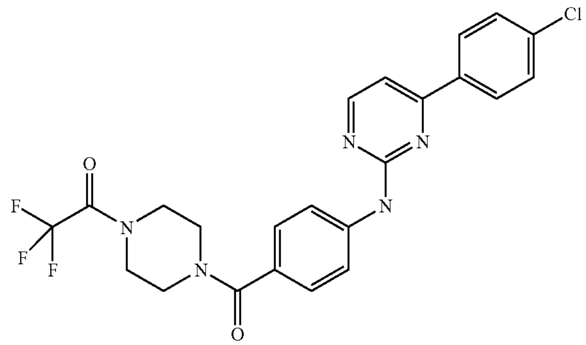 | 489.883 | 7.12 | 490.3 |
| 24-16 | 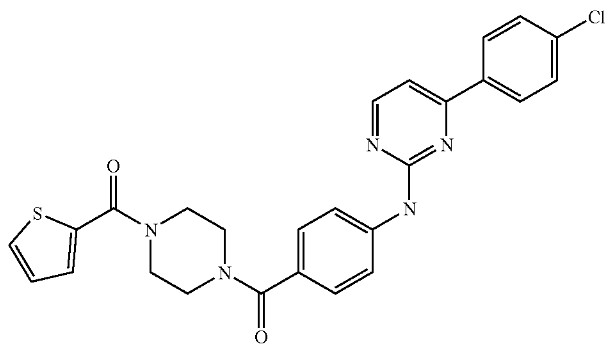 | 504.012 | 6.77 | 504.3 |
| 24-17 | 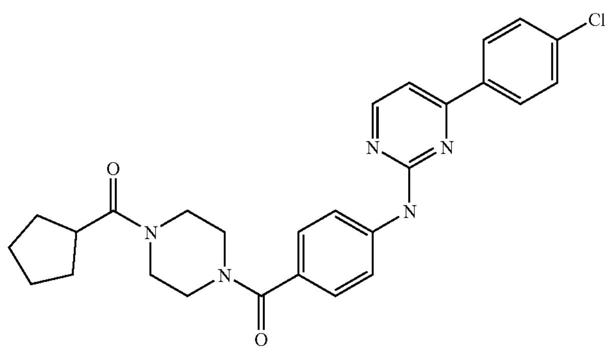 | 490.004 | 7.2 | 504.3 |
| 24-18 | 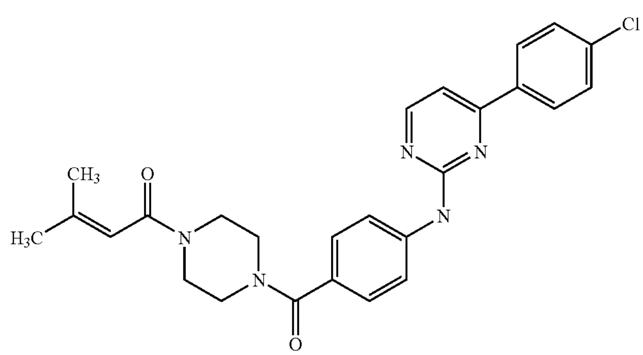 | 475.977 | 6.58 | 476.3 |

-continued

| Compound Number | Structure | MW | RT, min | M + 1 |
|---|---|---|---|---|
| 24-19 | 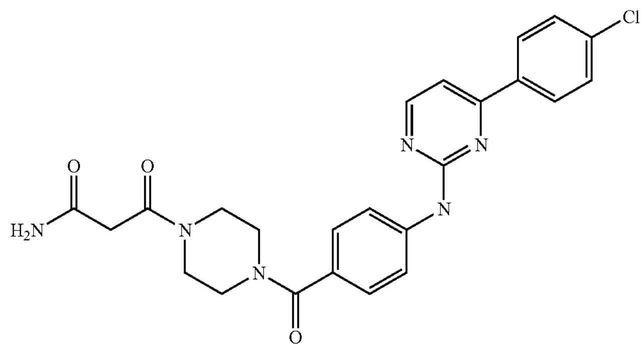 | 476.938 | 5.55 | 479.3 |
| 24-20 | 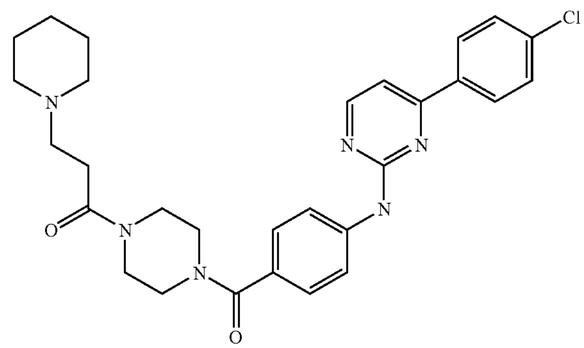 | 533.073 | 4.63 | 533.3 |
| 24-21 | 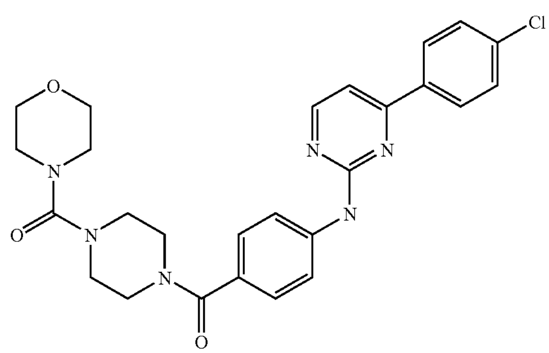 | 506.991 | 1.1 | 507.3 |
| 24-22 | 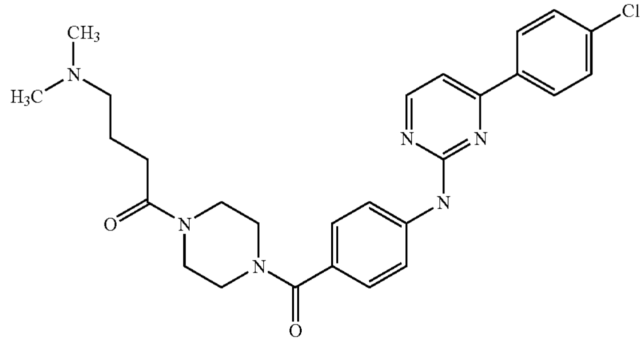 | 507.035 | 4.61 | 508.3 |

-continued

| Compound Number | Structure | MW | RT, min | M + 1 |
|---|---|---|---|---|
| 24-23 | 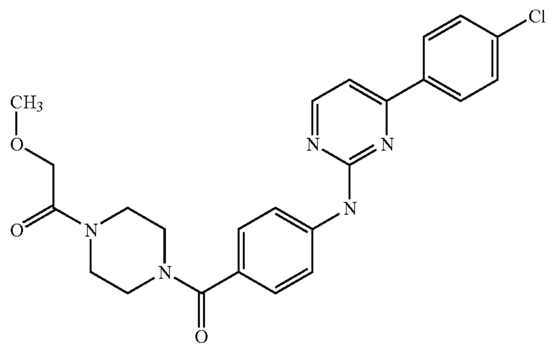 | 465.939 | 5.99 | 466.3 |
| 24-24 | 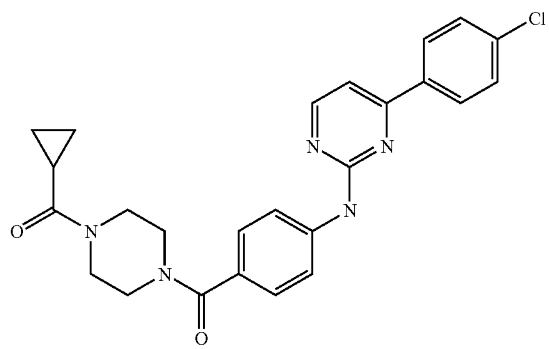 | 461.951 | 6.41 | 462.3 |
| 24-25 | 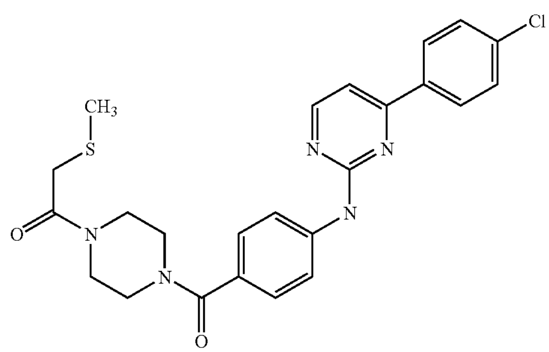 | 482.006 | 6.57 | 496.3 |
| 24-26 | 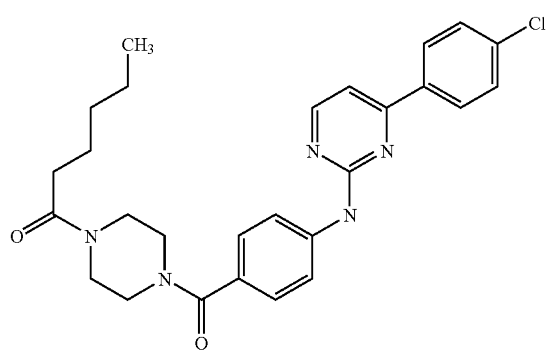 | 492.02 | 7.14 | 492.3 |

-continued

| Compound Number | Structure | MW | RT, min | M + 1 |
|---|---|---|---|---|
| 24-27 | 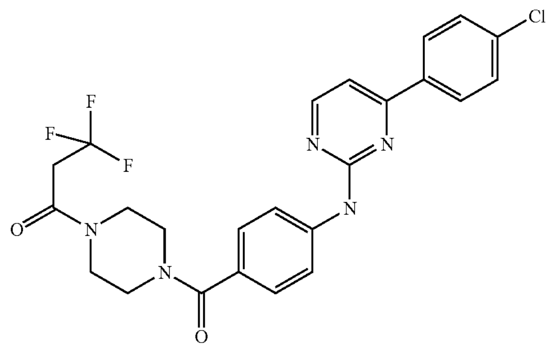 | 503.91 | 6.69 | 504.3 |
| 24-28 | 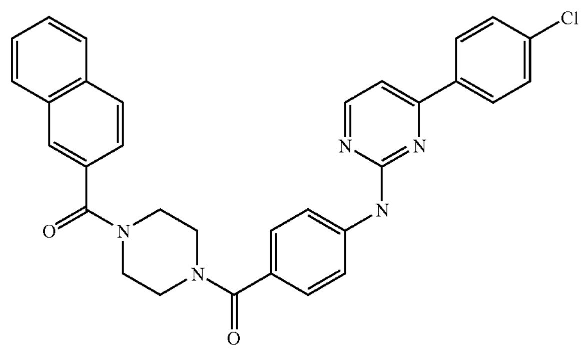 | 548.043 | 7.27 | 548.3 |
| 24-29 | 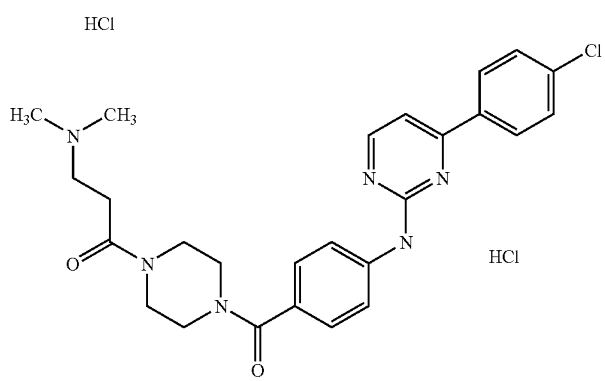 | 565.93 | 5.99 | 493.4 |
| 24-30 | 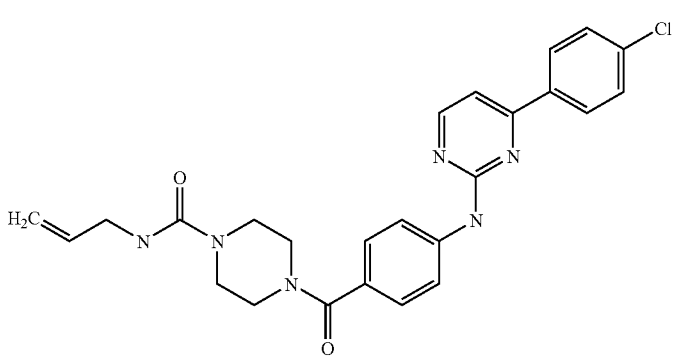 | 476.966 | 7.16 | 477.4 |

-continued

| Compound Number | Structure | MW | RT, min | M + 1 |
|---|---|---|---|---|
| 24-31 | 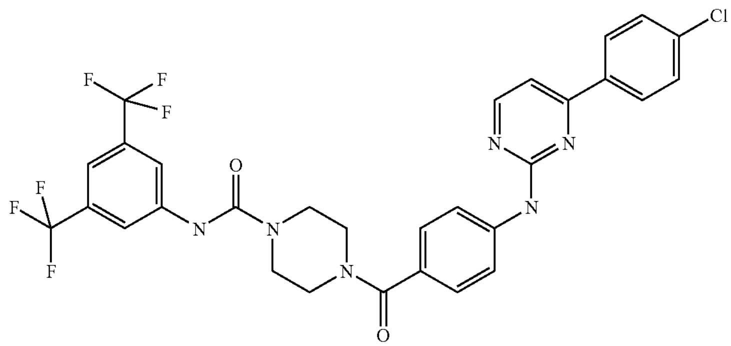 | 648.993 | 8.56 | 649.4 |
| 24-32 | 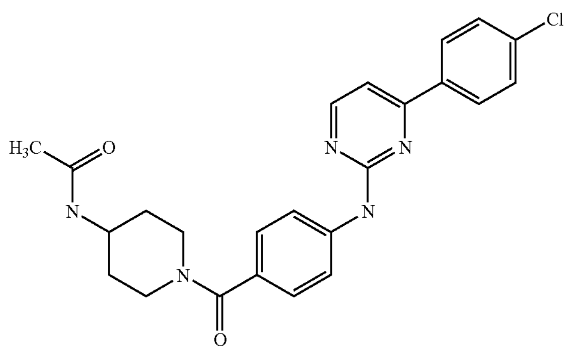 | 449.94 | 6.92 | 450.4 |
| 24-33 | 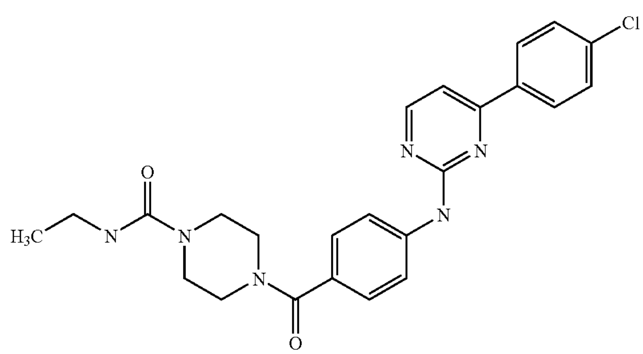 | 464.954 | 6.09 | 465.3 |
| 24-34 | 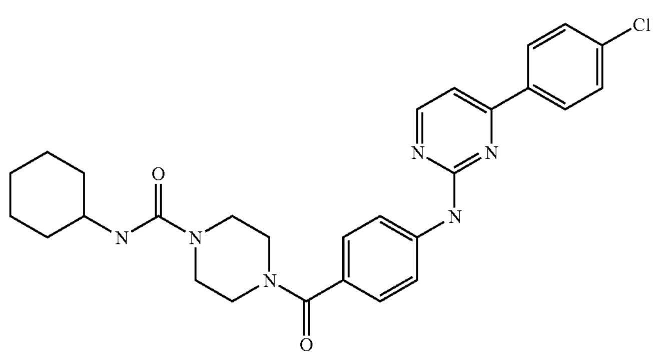 | 519.046 | 6.87 | 519.3 |

-continued

| Compound Number | Structure | MW | RT, min | M + 1 |
|---|---|---|---|---|
| 24-35 | 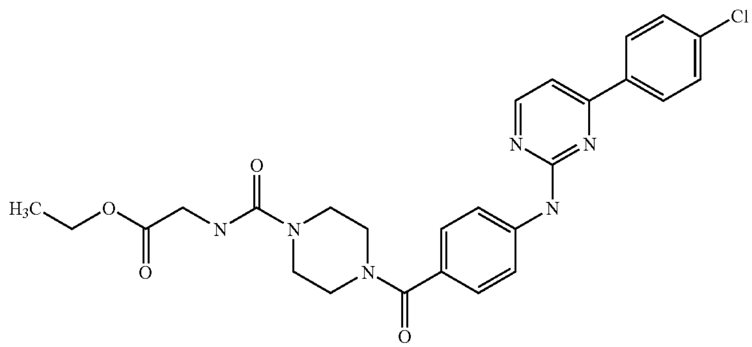 | 522.99 | 7.19 | 524.4 |
| 24-36 | 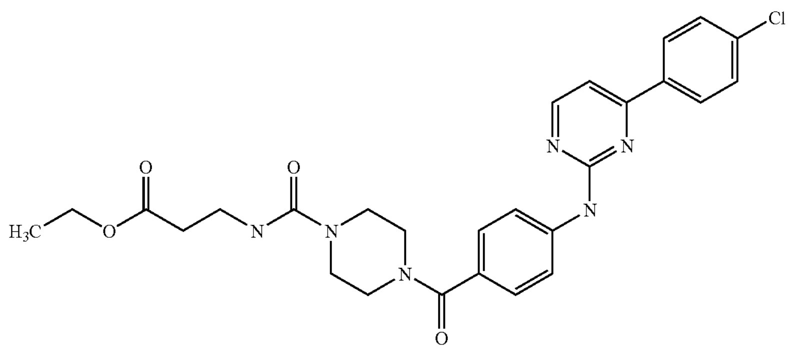 | 537.017 | 4.52 | 537.4 |
| 24-37 | 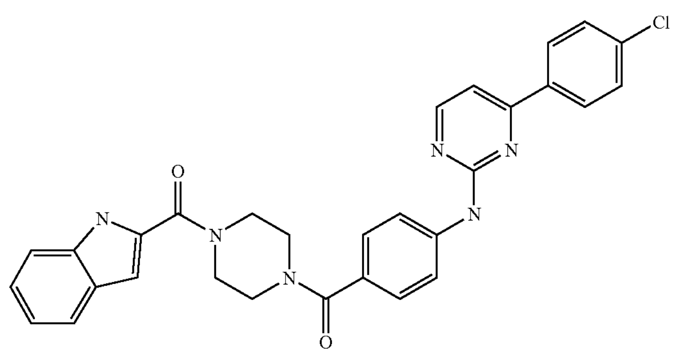 | 537.021 | 7.79 | 537.2 |
| 24-38 | 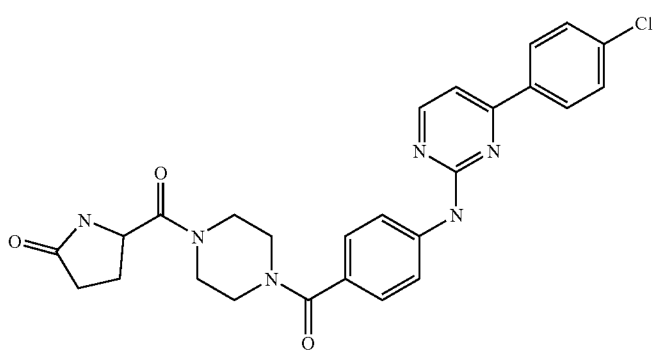 | 504.975 | 6.72 | 505.4 |

-continued

| Compound Number | Structure | MW | RT, min | M + 1 |
|---|---|---|---|---|
| 24-39 | 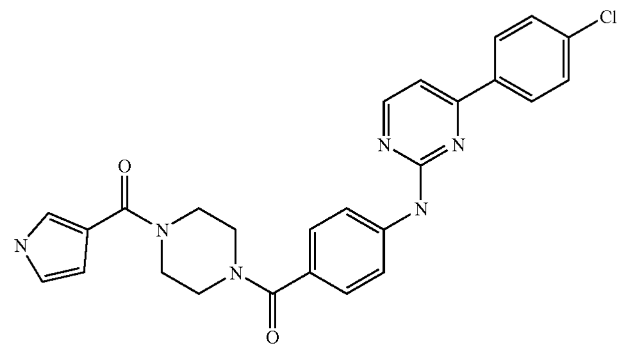 | 486.961 | 6.92 | 487.4 |
| 24-40 | 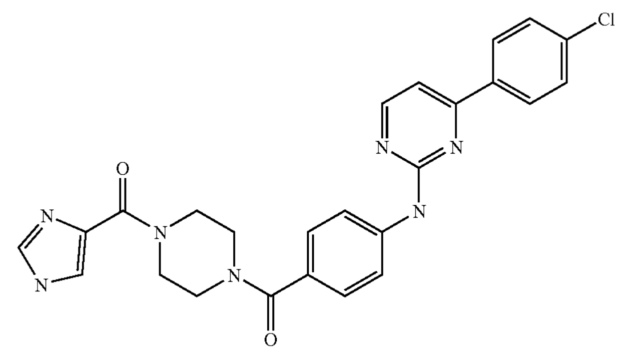 | 487.949 | 6.08 | 488.4 |
| 24-41 | 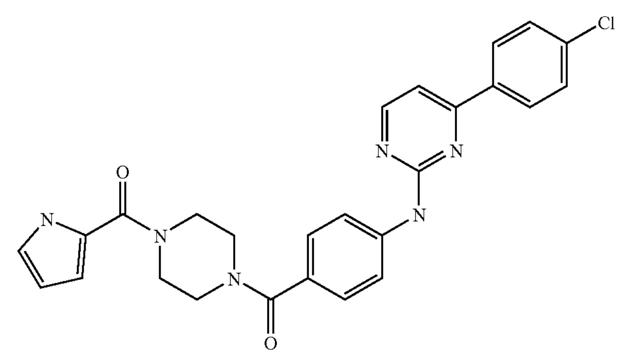 | 486.961 | 7.27 | 487.4 |
| 24-42 | 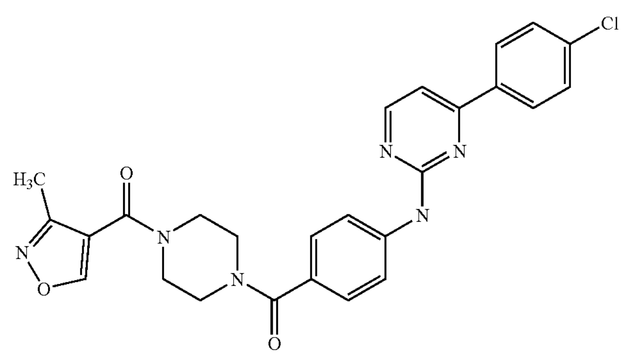 | 502.96 | 7.27 | 503.4 |

-continued
| Compound Number | Structure | MW | RT, min | M + 1 |
|---|---|---|---|---|
| 24-43 | 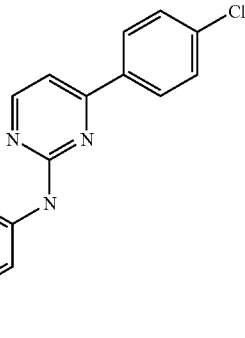 | 502.9597 | 7.27 | 503.4 |
| 24-44 | 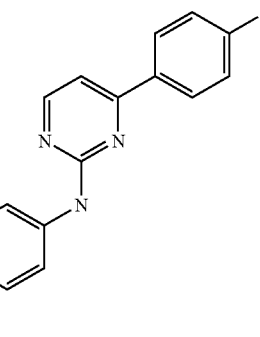 | 533.0535 | 7.19 | 533.2 |
| 24-45 | 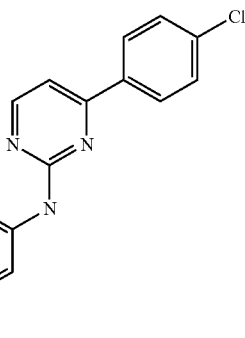 | 488.9329 | 7.09 | 489.4 |
| 24-46 | 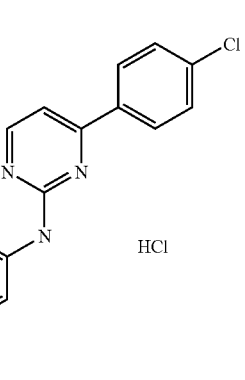 | 588.4076 | 3.25 | 478.3 |

| Compound Number | Structure | MW | RT, min | M + 1 |
|---|---|---|---|---|
| 24-47 | 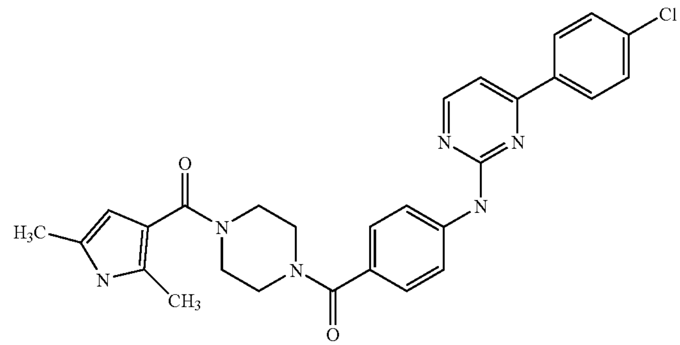 | 515.0143 | 7.16 | 515.4 |

Example 25

Synthesis of Sulfides

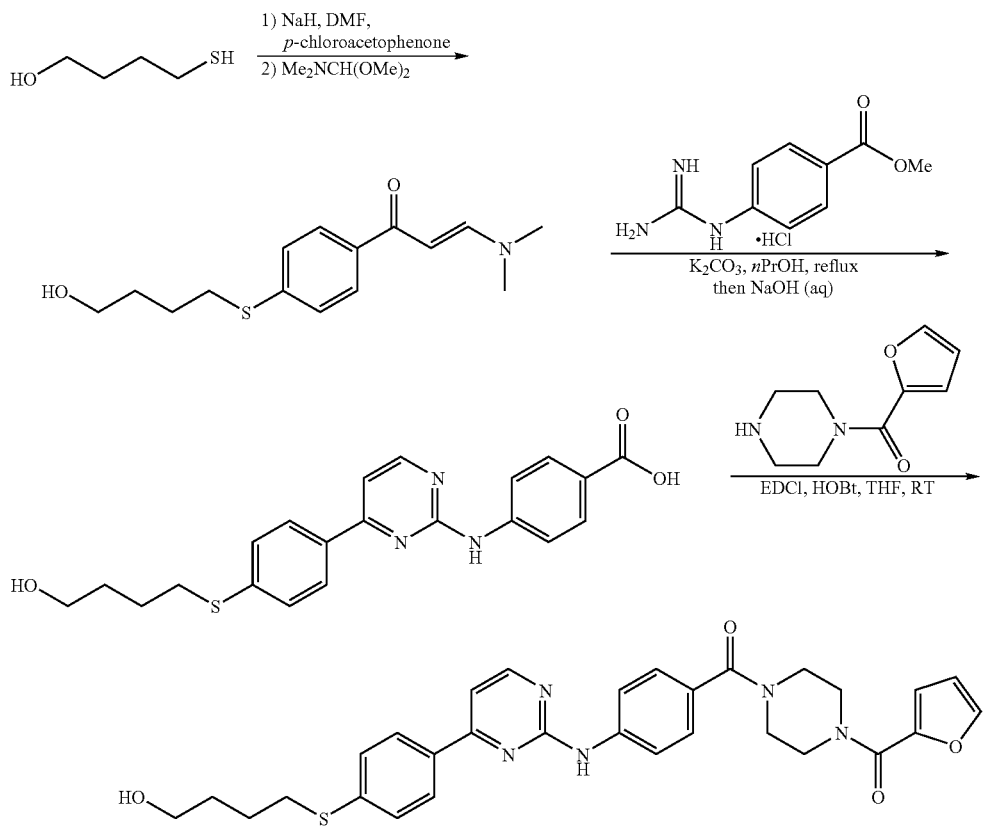

3-Dimethylamino-1-[4-(4-hydroxybutylsulfanyl)phenyl]propenone

To a stirred solution of 4-hydroxybutanethiol (5.0 g, 47 mmol) in DMF (100 mL) was added NaH (60% dispersion in mineral oil 2.1 g). After the effervescence had ceased, p-chloroacetophenone (4.3 mL, 33 mmol) was added. The solution was then stirred at 110° C. for 3 h. The mixture was cooled to RT and then diluted with ether (200 mL). The ethereal suspension was washed with 5% HCl (aq, 2×100 mL), water (100 mL), and then brine (50 mL). The ether extract was dried (MgSO$_4$), filtered and concentrated to afford crude 1-[4-(4-hydroxybutylsulfanyl)phenyl]ethanone, which was used without purification. 1-[4-(4-hydroxybutylsulfanyl)phenyl]ethanone was taken up in dimethylformamide dimethylacetal (100 mL) and stirred at reflux for 12 h. The mixture was cooled and then concentrated to about one half of the original volume. Hexane was added to precipitate 3-Dimethylamino- 1-[4-(4-hydroxybutylsulfanyl)phenyl]propenone. The mixture was filtered, washed with hexanes (50 mL), and dried to afford 3-Dimethylamino-1-[4-(4-hydroxy-butylsulfanyl)phenyl]propenone (6.4 g, 23 mmol): HPLC Retention Time; 5.58 min. (Method B) M+1; 279.8.

4-{4-[4-(4-Hydroxybutylsulfanyl)phenyl]pyrimidin-2-ylamino}benzoic Acid

3-Dimethylamino-1-[4-(4-hydroxybutylsulfanyl)-phenyl]propenone (6.4 g, 23 mmol) was, then taken up in nPrOH (150 mL). To this solution was added 4-guanidinobenzoic acid, methyl ester. hydrochloride salt (1.1 equiv, 5.4 g) and $K_2CO_3$ (3 equiv, 9.5 g). The mixture was stirred at reflux for 24 h. After this time, 10% NaOH (aq, 50 mL) was added, and the mixture was stirred at reflux for another 1 h. The mixture was then cooled to RT and concentrated to about half of the original volume. The pH of the mixture was then adjusted to pH 4-5 to 4-{4-[4-(4-Hydroxybutylsulfanyl)phenyl]pyrimidin-2-ylamino}benzoic acid. The acid was immediately filtered and washed with water (50 mL), cold EtOH (50 mL), and then dried (8.6 g, 21 mmol, 88%): HPLC Retention Time; 6.37 min. (Method B) M+1; 396.0.

[4-(Furan-2-carbonyl)piperazin-1-yl]-(4-{4-[4-4-(4-hydroxybutylsulfanyl)phenyl]pyrimidin-2-ylamino}phenyl)methanone 4-{4-[4-(4-Hydroxybutylsulfanyl)phenyl]pyrimidin-2-ylamino}benzoic acid (0.34 g, 0.86 mmol) was dissolved in THF (5 mL). To this solution was added 1-furoylpiperazine (0.170 g), EDCI (0.180 g), and HOBt (0.127 g). The mixture was stirred 12 h. The mixture was then diluted with $CH_2Cl_2$ (20 mL) and washed with 2% NaOH (aq, 30 mL), water (30 mL), and then brine (30 mL). The organic layer was dried ($Na_2SO_4$), filtered, and concentrated. The crude solid was subjected to preparatory HPLC (30-80 acetonitrile/water gradient, 20 min). The desired fractions were concentrated to remove most of the acetonitrile, and then the aqueous mixture was extracted with $CH_2Cl_2$/2% NaOH (aq). The organic layer was dried ($Na_2SO_4$), filtered, and concentrated to afford [4-(Furan-2-carbonyl)-piperazin-1-yl]-(4-{4-[4-(4-hydroxybutylsulfanyl)phenyl]pyrimidin-2-ylamino}phenyl)methanone (0.042 g, 9%): HPLC Retention Time; 10.07 min. (Method B) M+H=558.3.

Compounds listed below were prepared according to the above procedure.

| Compound Number | Structure | MW | RT, min | M + 1 |
|---|---|---|---|---|
| 25-1 | 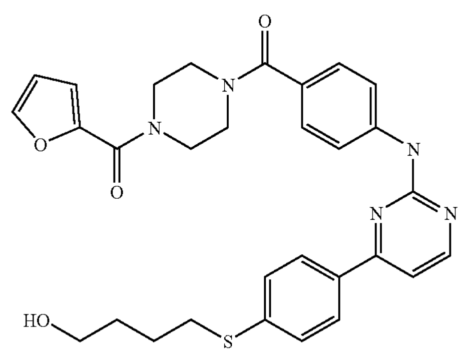 | 557.672 | 10.07 | 558.3 |
| 25-2 | 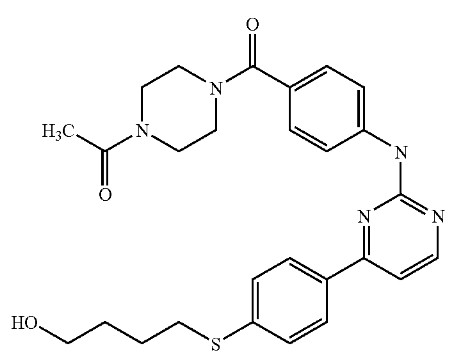 | 505.64 | 9.26 | 506.3 |

-continued

| Compound Number | Structure | MW | RT, min | M + 1 |
|---|---|---|---|---|
| 25-3 | 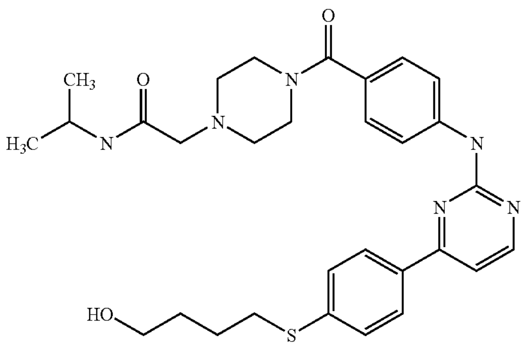 | 562.735 | 8.81 | 563.3 |
| 25-4 | (ClH salt) | 500.064 | 8.37 | 464.4 |
| 25-5 | 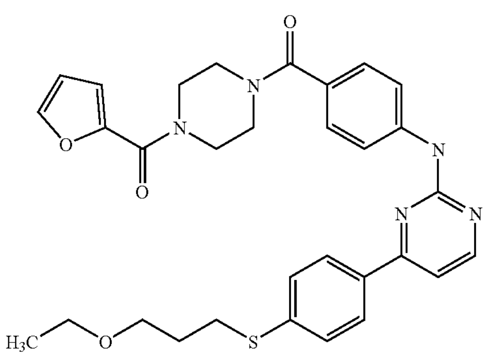 | 571.699 | 12.04 | 572.3 |
| 25-6 | 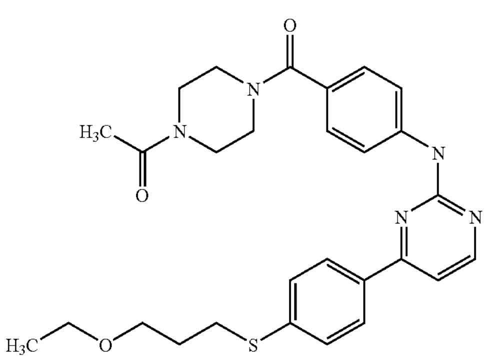 | 519.667 | 11.13 | 520.3 |

-continued

| Compound Number | Structure | MW | RT, min | M + 1 |
|---|---|---|---|---|
| 25-7 | 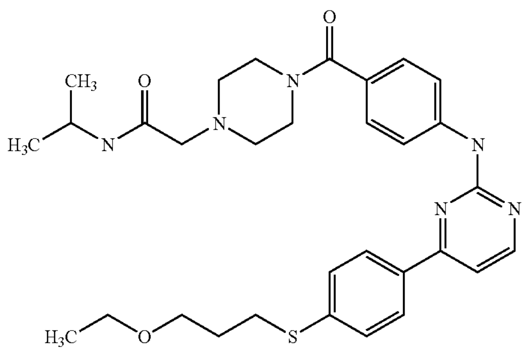 | 576.762 | 10.24 | 577.2 |
| 25-8 | 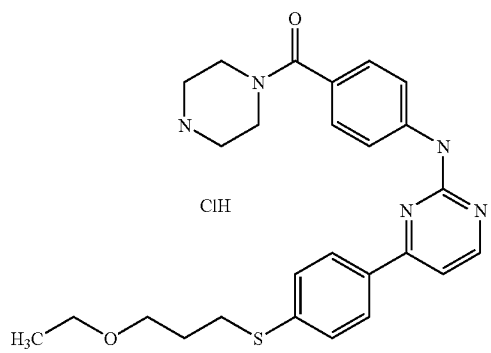 | 514.091 | 9.7 | 478.3 |
| 25-9 | 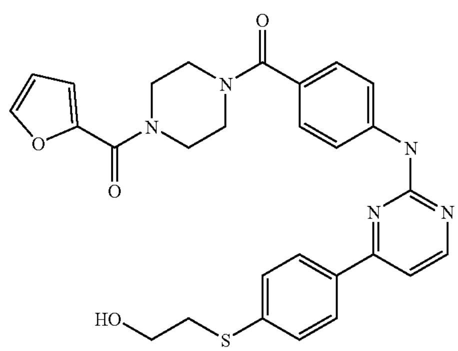 | 529.618 | 9.5 | 530.3 |
| 25-10 | 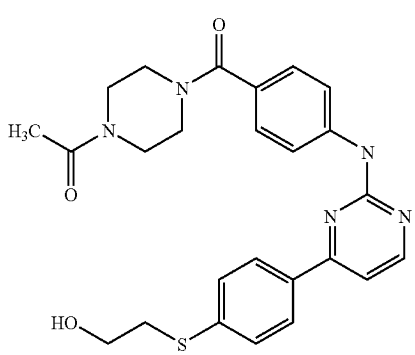 | 477.586 | 8.66 | 478.2 |

-continued

| Compound Number | Structure | MW | RT, min | M + 1 |
|---|---|---|---|---|
| 25-11 | 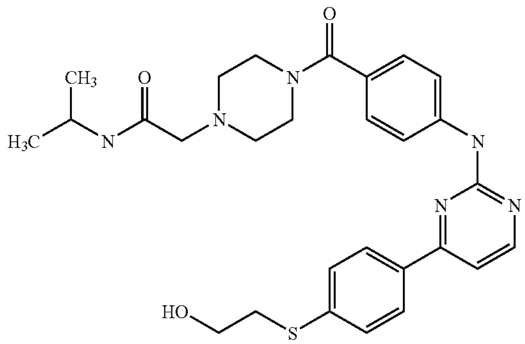 | 534.682 | 7.32 | 535.3 |
| 25-12 | 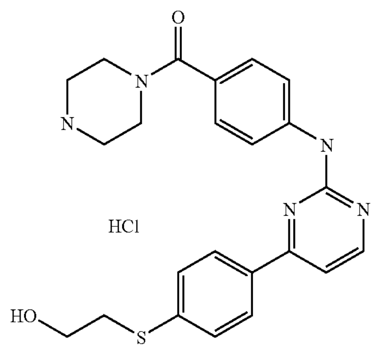 | 472.01 | 6.88 | 436.2 |
| 25-13 | 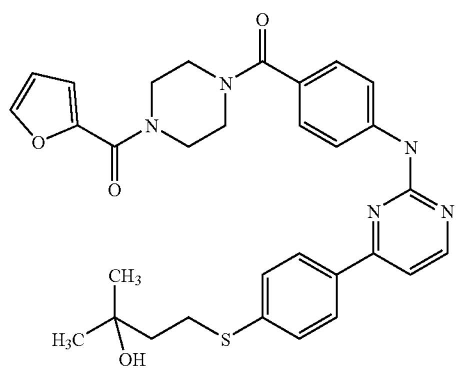 | 571.699 | 10.62 | 572.3 |
| 25-14 | 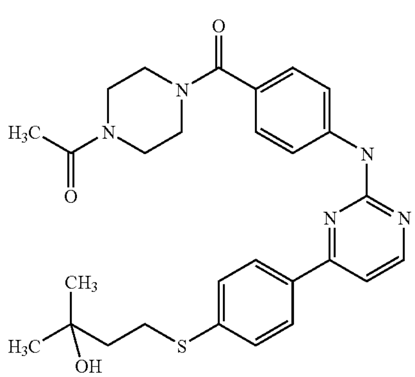 | 519.667 | 9.76 | 520.2 |

-continued

| Compound Number | Structure | MW | RT, min | M + 1 |
|---|---|---|---|---|
| 25-15 | 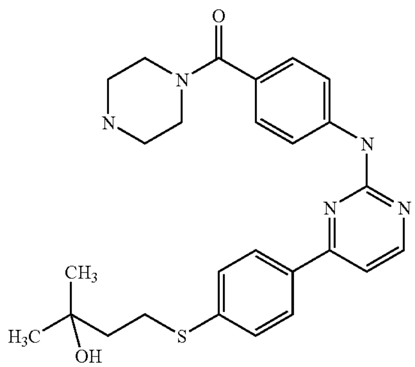 | 477.63 | 8.77 | 478.3 |
| 25-16 | 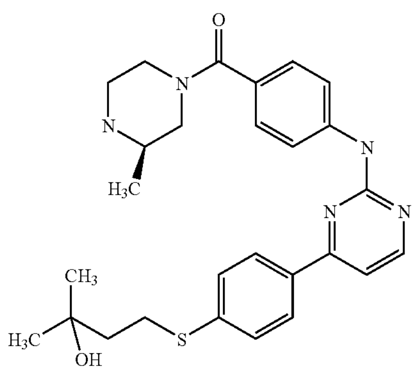 | 491.657 | 8.9 | 492.3 |
| 25-17 | 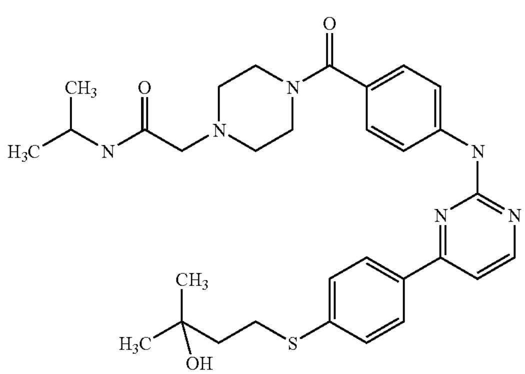 | 576.762 | 9.25 | 577.3 |
| 25-18 | 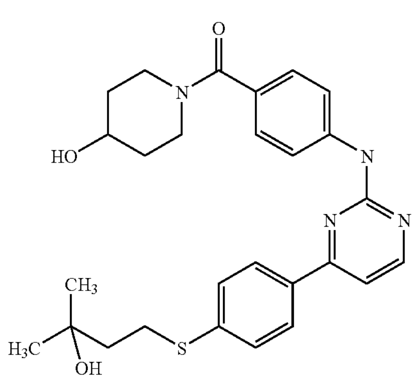 | 492.641 | 9.59 | 493.3 |

-continued

| Compound Number | Structure | MW | RT, min | M + 1 |
|---|---|---|---|---|
| 25-19 | 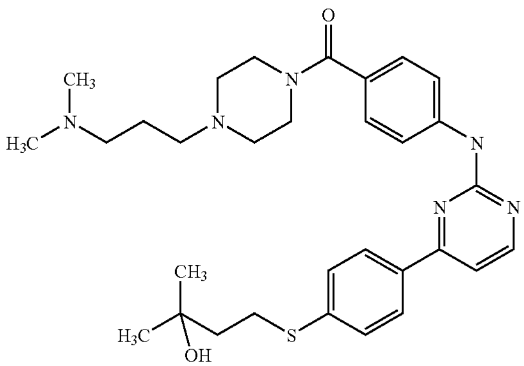 | 562.779 | 8.42 | 563.3 |
| 25-20 | 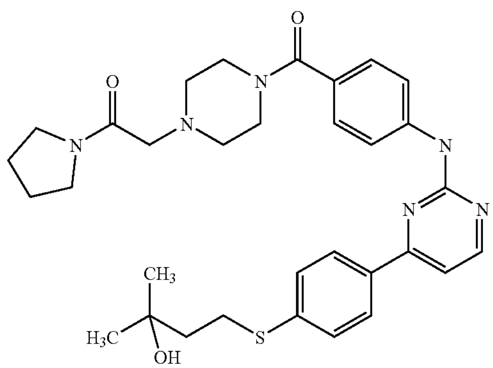 | 588.773 | 8.51 | 589.3 |
| 25-21 | 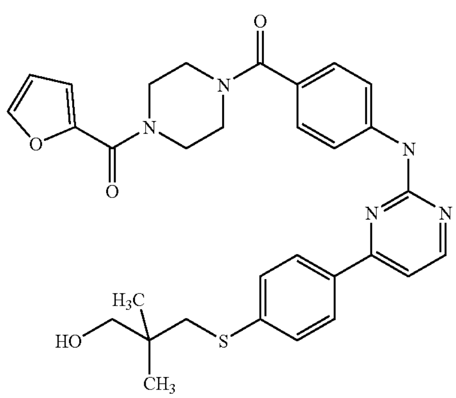 | 571.699 | 10.85 | 572.3 |
| 25-22 | 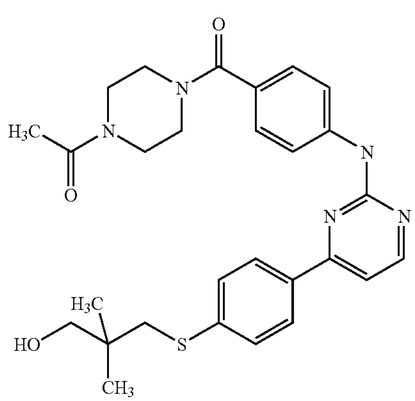 | 519.667 | 10.05 | 520.3 |

-continued

| Compound Number | Structure | MW | RT, min | M + 1 |
|---|---|---|---|---|
| 25-23 | 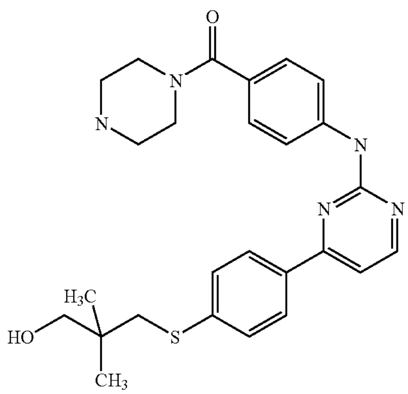 | 477.63 | 9 | 478.3 |
| 25-24 | 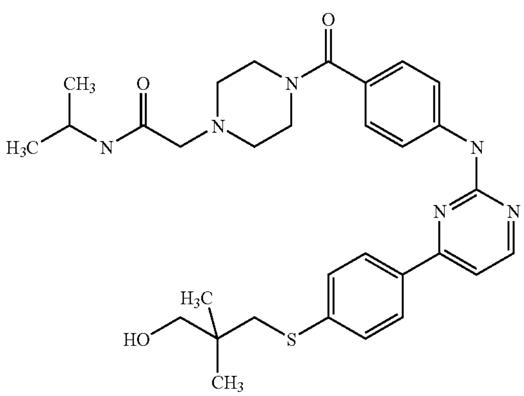 | 576.762 | 9.46 | 577.3 |
| 25-25 | 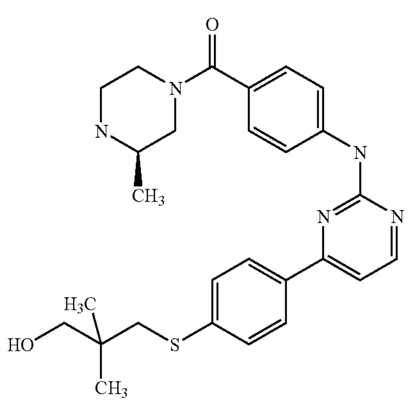 | 491.657 | 9.1 | 492.3 |

-continued

| Compound Number | Structure | MW | RT, min | M + 1 |
|---|---|---|---|---|
| 25-26 | 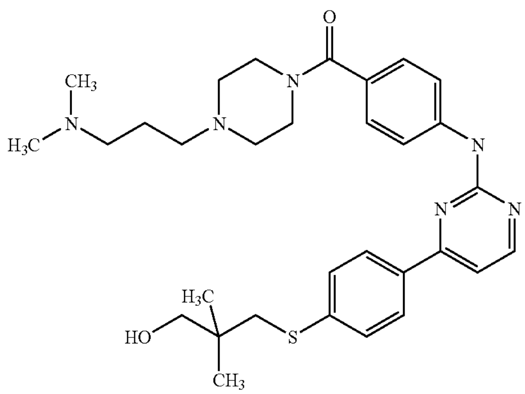 | 562.779 | 8.58 | 563.3 |
| 25-27 | 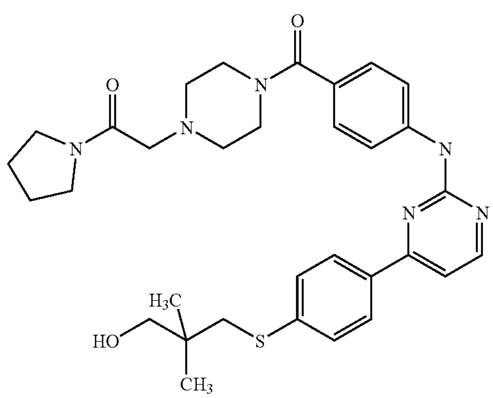 | 588.773 | 9.39 | 589.5 |
| 25-28 | 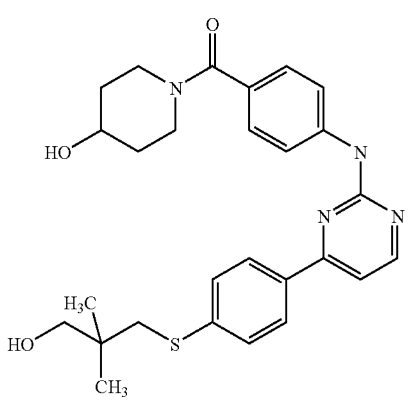 | 492.641 | 9.84 | 493.3 |

Example 26

Synthesis of Sulfonamides

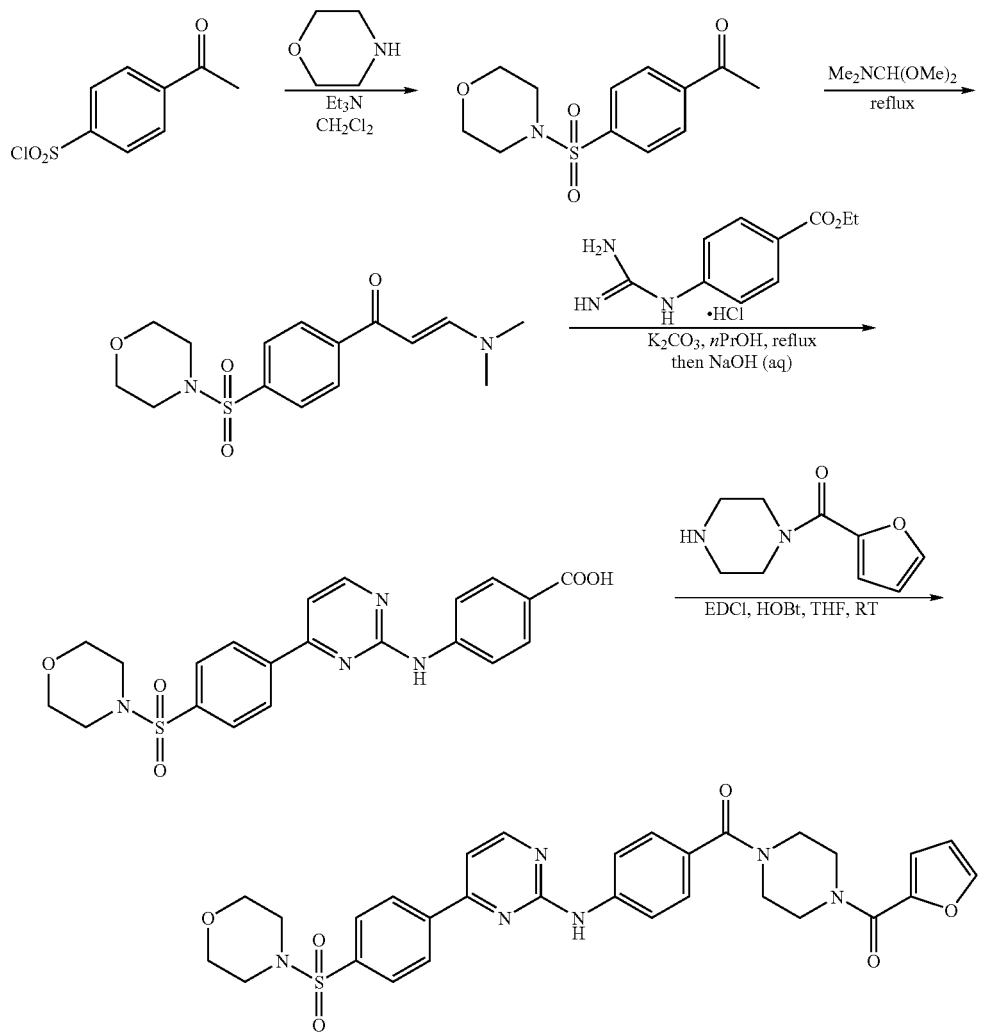

1-[4-(Morpholine-4-sulfonyl)phenyl]ethanone

To a suspension of 4-acetylbenzenesulfonyl chloride (5.5 g, 25 mmol) in $CH_2Cl_2$ (75 mL) and $Et_3N$ (2 equiv, 7.0 mL, 50 mmol) was added morpholine (1.5 equiv, 3.3 mL, 38 mmol) dropwise. The mixture was stirred at room temperature for 30 min. The mixture was then diluted with $CH_2Cl_2$ (100 mL) and washed with 5% HCl (2×50 mL), water (50 mL), and then brine (50 mL). The organic layer was dried ($Na_2SO_4$), filtered, and concentrated to afford crude 1-[4-(morpholine-4-sulfonyl)phenyl]ethanone (2) (4.78 g, 18 mmol, 71%): HPLC Retention Time; 5.82 min. (Method B) M+1, 270.0.

4-{4-[4-(Morpholine-4-sulfonyl)-phenyl]-pyrimidin-2-ylamino}benzoic Acid

Crude 1-[4-(morpholine-4-sulfonyl)phenyl]ethanone (4.78 g, 18 mmol) was suspended in dimethyformamide dimethylacetal (50 mL) and refluxed for 12 h. The reaction was allowed to cool and the mixture was concentrated to about half of the original volume. The solution was then titurated with hexanes to precipitate the eneamino ketone intermediate. The eneamino ketone was filtered and washed with hexanes (2×50 mL), dried under vacuum, and then taken up in nPrOH (150 mL). To this solution was added added 4-guanidinobenzoic acid, methyl ester, hydrochloride salt (1.1 equiv, 3.7 g) and $K_2CO_3$ (3 equiv, 6.4 g). The mixture was stirred at reflux for 24 h. After this time, 10% NaOH (aq, 50 mL) was added, and the mixture was stirred at reflux for another 1 h. The mixture was then cooled to RT and concentrated to about half of the original volume. The pH of the mixture was then adjusted to pH 4-5 to precipitate the acid. 4-{4-[4-(morpholine-4-sulfonyl)phenyl]pyrimidin-2-ylamino}benzoic acid was immediately filtered and washed with water (50 mL), cold EtOH (50 mL), and then dried (4.6 g, 10.5 mmol, 68%): HPLC Retention Time; 6.6 min. (Method B) M+1, 441.0.

[4-(Furan-2-carbonyl)-piperazin-1-yl](4-{4-[4-(morpholine-4-sulfonyl)phenyl]pyrimidin-2-ylamino}phenyl)methanone 4-{4-[4-(Morpholine-4-sulfonyl)-phenyl]-pyrimidin-2-ylamino}-benzoic acid (0.25 g, 0.57 mmol) was dissolved in THF (5 mL). To this solution was added 1-furoylpiperazine (0.123 g), EDCI (0.131 g), and HOBt (0.092 g). The mixture was stirred 12 h. The mixture was then diluted with $CH_2Cl_2$ (20 mL) and washed with 2% NaOH (aq, 30 mL), water (30 mL), and then brine (30 mL). The organic layer was dried ($Na_2SO_4$), filtered, and concentrated. The crude solid was subjected to preparatory HPLC (20-70 acetonitrile/water gradient, 20 min). The desired fractions were concentrated to remove most of the acetonitrile, and then the aqueous mixture was extracted with $CH_2Cl_2$/2% NaOH (aq). The organic layer was dried ($Na_2SO_4$), filtered, and concentrated to afford [4-(furan-2-carbonyl)piperazin-1-yl](4-{4-[4-(morpholine-4-sulfonyl)-phenyl]pyrimidin-2-ylamino}phenyl)methanone (0.177 g, 52%): HPLC Retention Time; 9.62 min. (Method B) M+H=603.3

Compounds listed below were prepared according to the above procedure.

| Compound Number | Structure | MW | RT, min | M+1 |
|---|---|---|---|---|
| 26-1 | 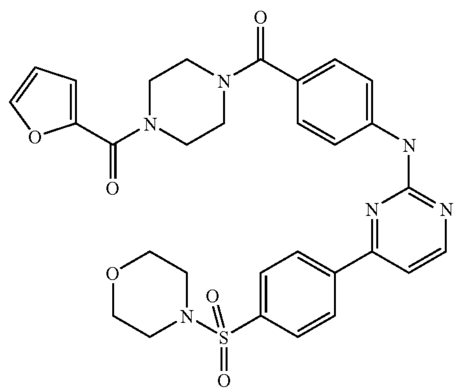 | 602.669 | 9.62 | 603.3 |
| 26-2 | 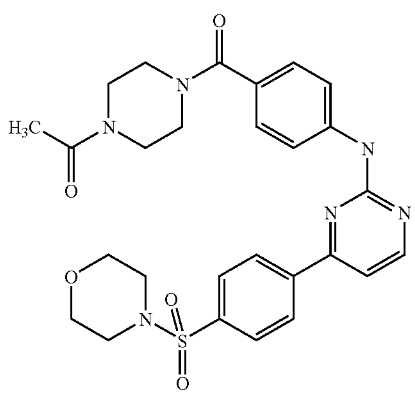 | 550.637 | 8.88 | 551.3 |
| 26-3 | 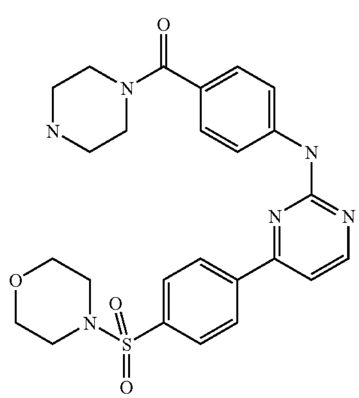 | 508.6 | 7.6 | 509.3 |

| Compound Number | Structure | MW | RT, min | M + 1 |
| --- | --- | --- | --- | --- |
| 26-4 | 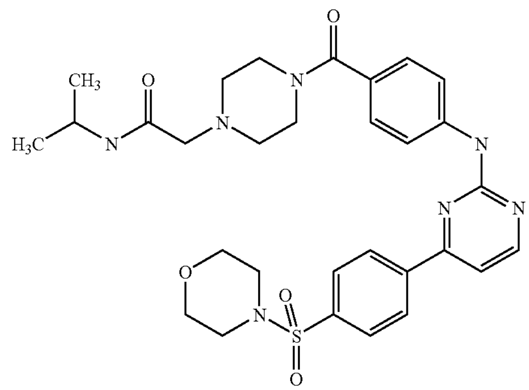 | 607.732 | 8.34 | 608.3 |
| 26-5 | 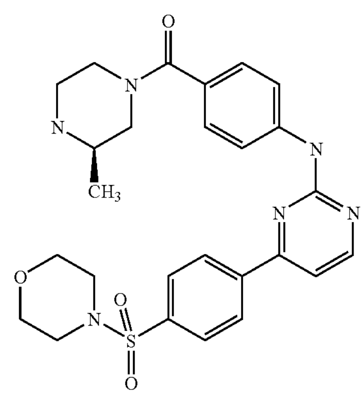 | 522.627 | 7.9 | 523.3 |
| 26-6 | 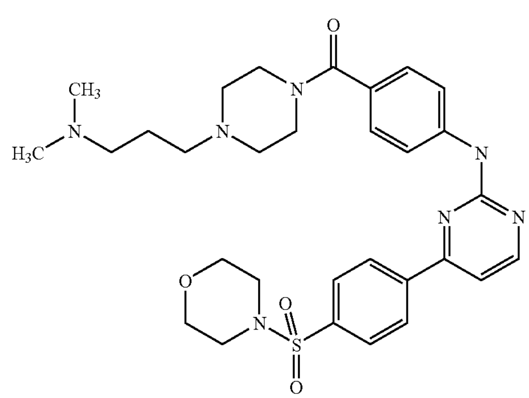 | 593.749 | 6.33 | 594.3 |

-continued

| Compound Number | Structure | MW | RT, min | M + 1 |
|---|---|---|---|---|
| 26-7 | 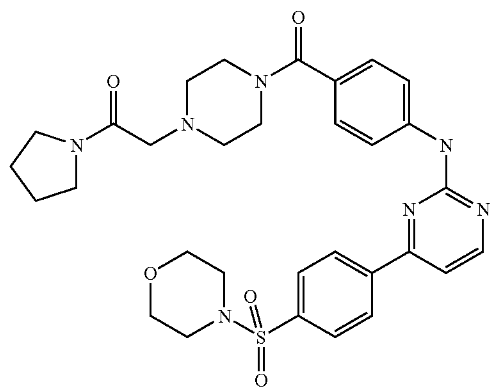 | 619.743 | 8.28 | 620.3 |
| 26-8 | 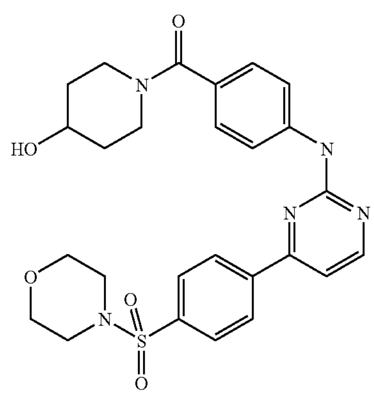 | 523.611 | 8.76 | 524.3 |
| 26-9 | 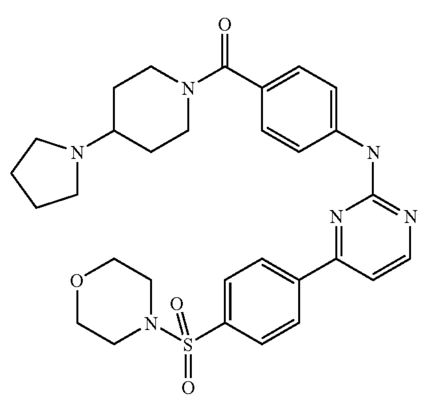 | 576.718 | 8.21 | 577.3 |

-continued
| Compound Number | Structure | MW | RT, min | M + 1 |
|---|---|---|---|---|
| 26-10 | 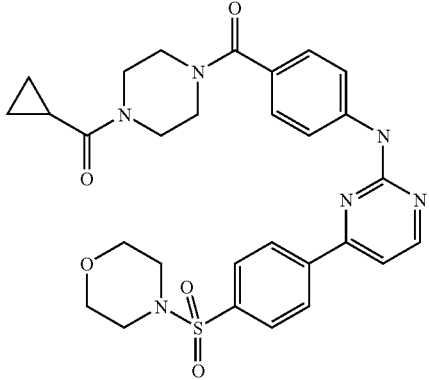 | 576.675 | 10.26 | 577.3 |
| 26-11 | 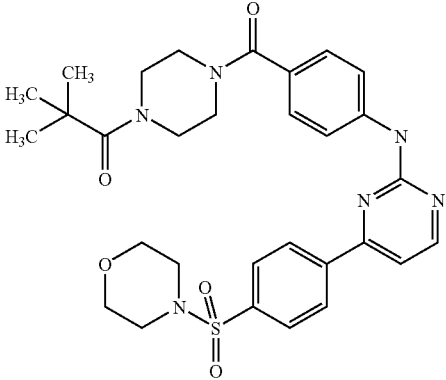 | 592.717 | 12.12 | 593.3 |
| 26-12 | 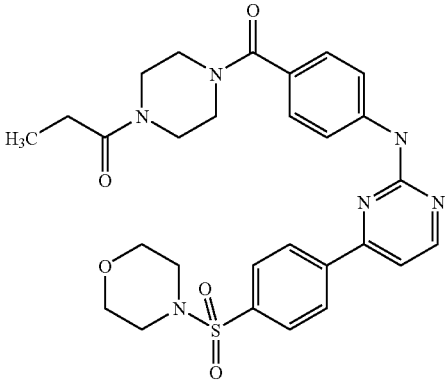 | 564.664 | 10.04 | 565.3 |

-continued
| Compound Number | Structure | MW | RT, min | M + 1 |
|---|---|---|---|---|
| 26-13 | 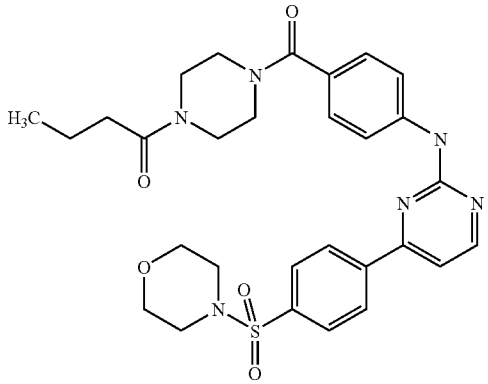 | 578.691 | 10.51 | 579.3 |
| 26-14 | 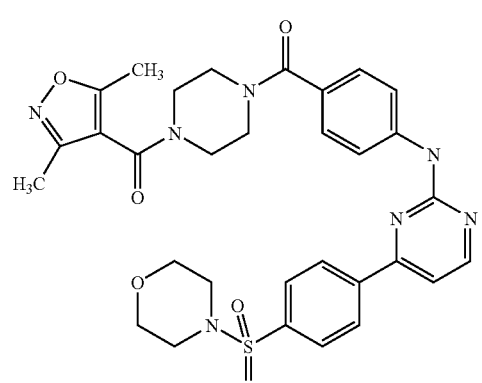 | 631.711 | 10.33 | 632.4 |
| 26-15 | 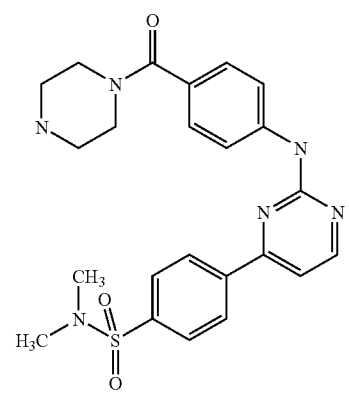 | 466.563 | 10.4 | 467.3 |

-continued

| Compound Number | Structure | MW | RT, min | M + 1 |
|---|---|---|---|---|
| 26-16 | 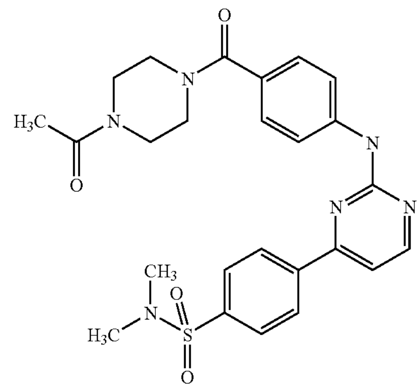 | 508.6 | 11.35 | 509.3 |
| 26-17 | 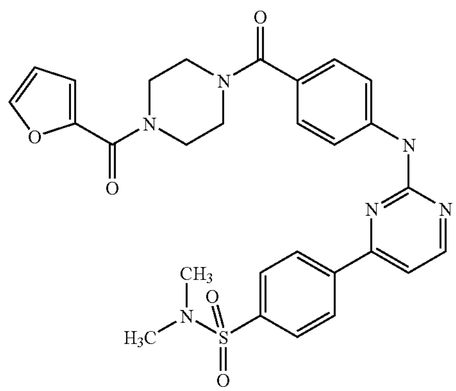 | 560.632 | 12 | 561.3 |
| 26-18 | 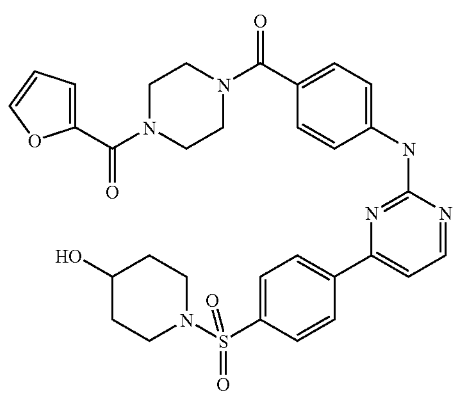 | 616.696 | 9.72 | 617.3 |
| 26-19 | 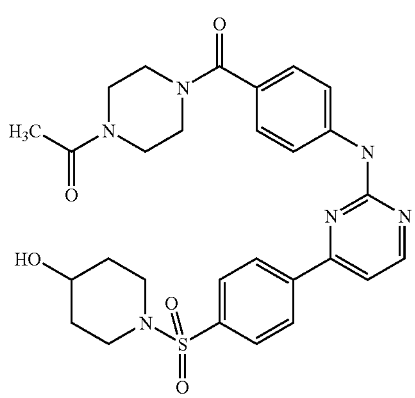 | 564.664 | 8.93 | 565.5 |

-continued
| Compound Number | Structure | MW | RT, min | M + 1 |
|---|---|---|---|---|
| 26-20 | 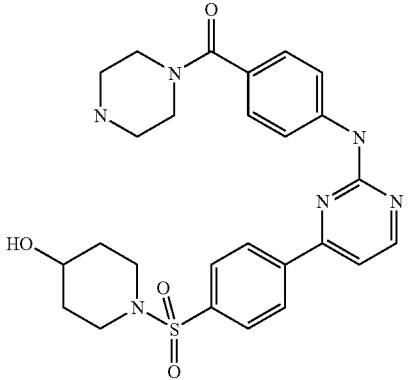 | 522.627 | 7.99 | 523.3 |
| 26-21 | 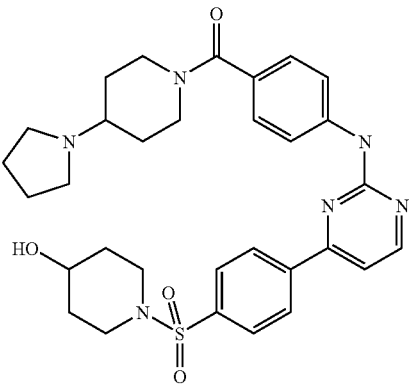 | 590.745 | 8.34 | 591.3 |
| 26-22 | 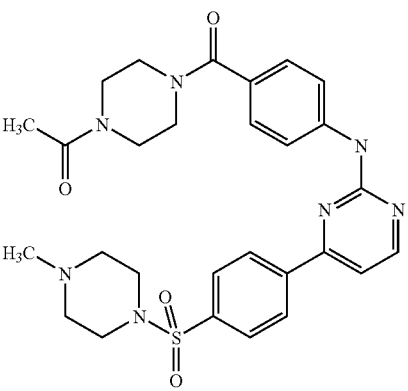 | 563.6797 | 8.05 | 564.3 |

| Compound Number | Structure | MW | RT, min | M + 1 |
|---|---|---|---|---|
| 26-23 | 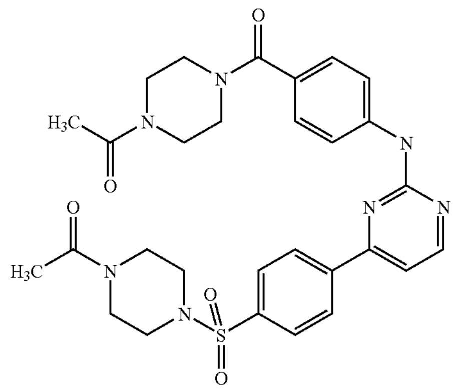 | 591.6897 | 9.01 | 592.3 |
| 26-24 | 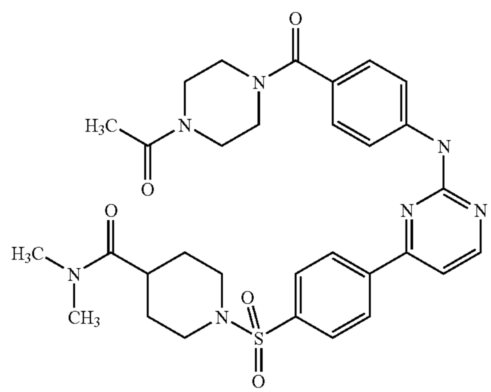 | 619.7433 | 9.25 | 620.3 |
| 26-25 | 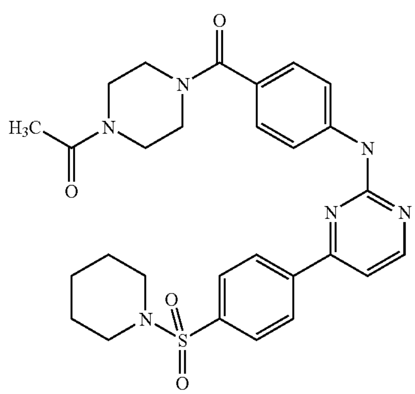 | 548.6648 | 10.88 | 549.5 |
| 26-26 | 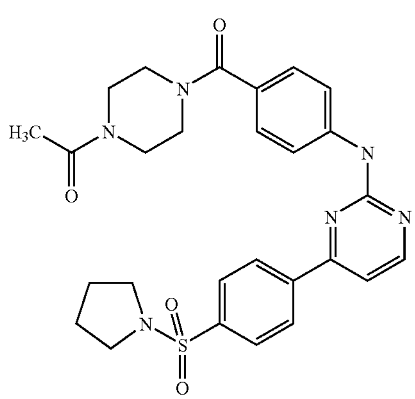 | 534.638 | 10 | 535.3 |

-continued

| Compound Number | Structure | MW | RT, min | M + 1 |
|---|---|---|---|---|
| 26-27 | 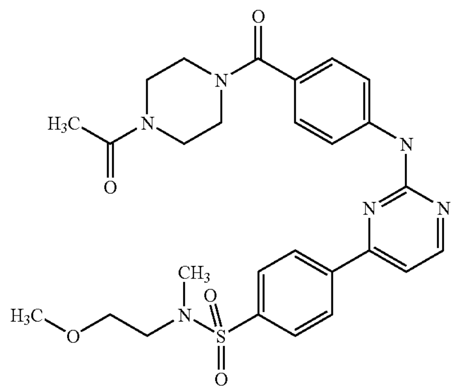 | 552.6528 | 6.82 | 553.3 |
| 26-28 | 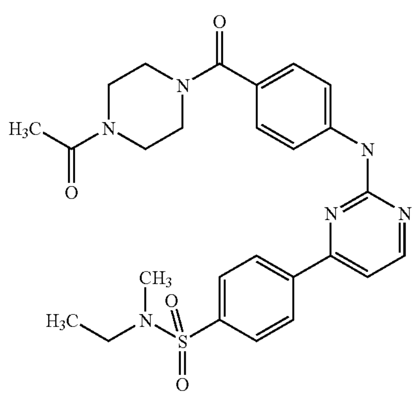 | 522.627 | 10.18 | 523.3 |
| 26-29 | 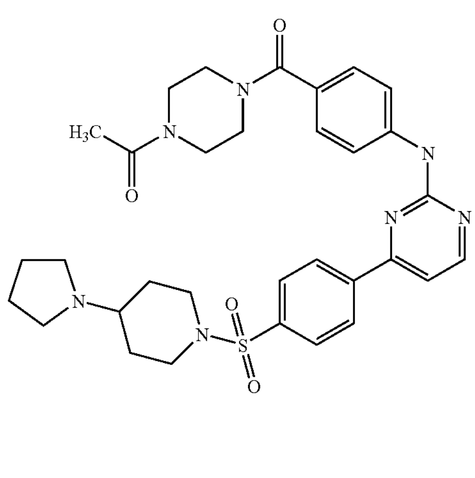 | 617.7711 | 8.31 | 618.5 |

-continued

| Compound Number | Structure | MW | RT, min | M + 1 |
|---|---|---|---|---|
| 26-30 | 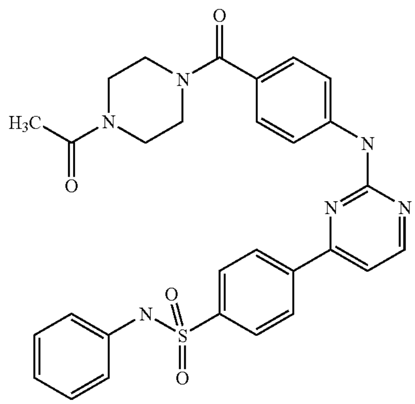 | 556.6442 | 10.29 | 557.2 |
| 26-31 | 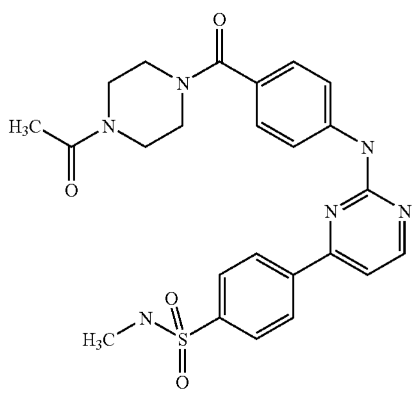 | 494.5734 | 8.96 | 495.3 |
| 26-32 | 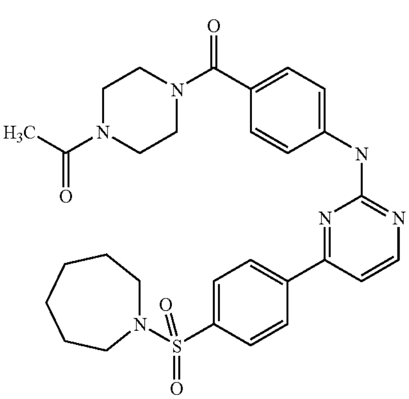 | 562.6916 | 11.36 | 563.4 |

-continued

| Compound Number | Structure | MW | RT, min | M + 1 |
|---|---|---|---|---|
| 26-33 | 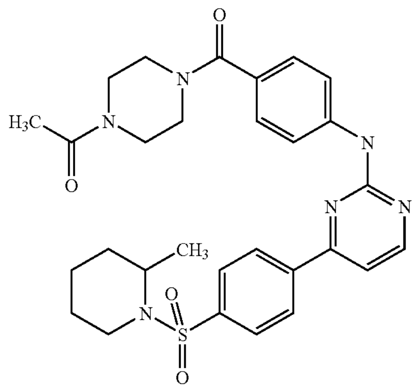 | 562.6916 | 11.2 | 563.4 |
| 26-34 | 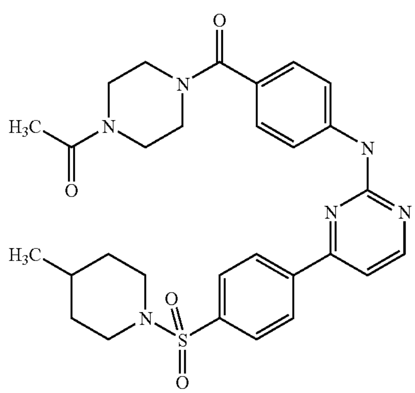 | 562.6916 | 11.52 | 563.4 |
| 26-35 | 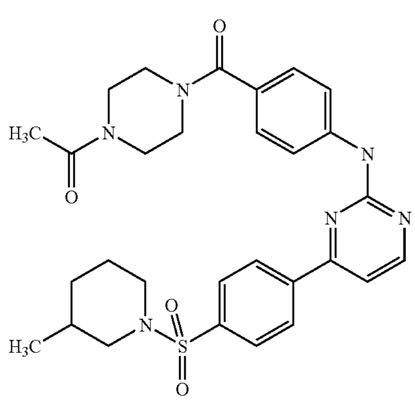 | 562.6916 | 11.5 | 563.4 |

-continued

| Compound Number | Structure | MW | RT, min | M + 1 |
|---|---|---|---|---|
| 26-36 | 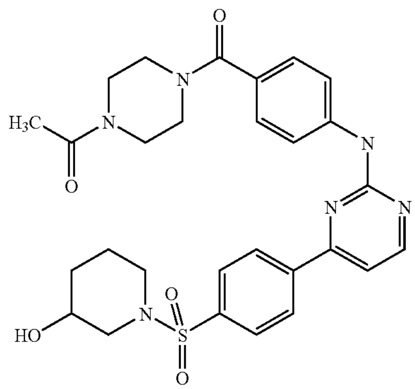 | 564.6638 | 9.14 | 565.4 |
| 26-37 | 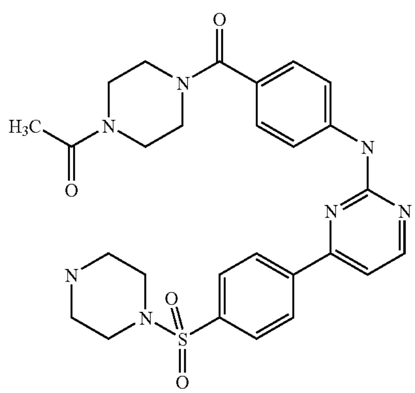 | 549.6529 | 8.04 | 550.4 |
| 26-38 | 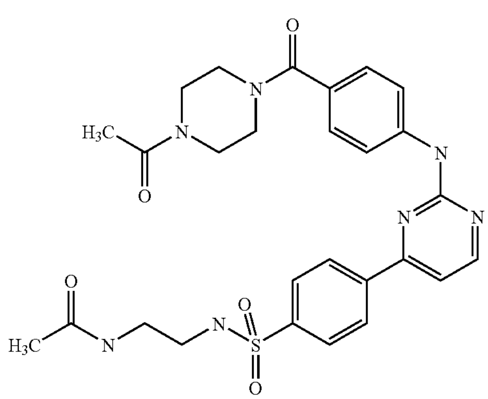 | 565.6519 | 8.26 | 566.3 |

-continued

| Compound Number | Structure | MW | RT, min | M + 1 |
|---|---|---|---|---|
| 26-39 | 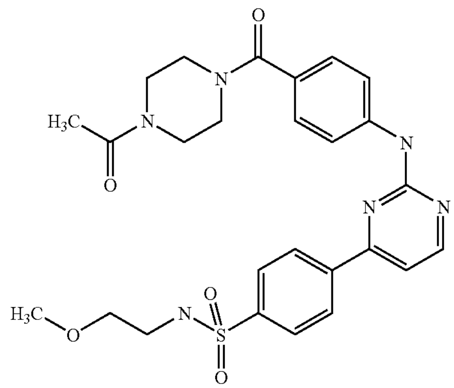 | 538.626 | 9.14 | 539.3 |
| 26-40 | 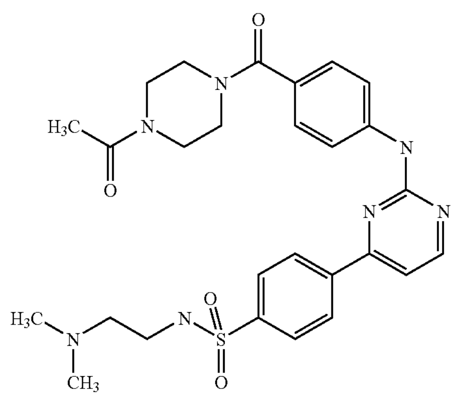 | 551.6687 | 7.77 | 552.3 |
| 26-41 | 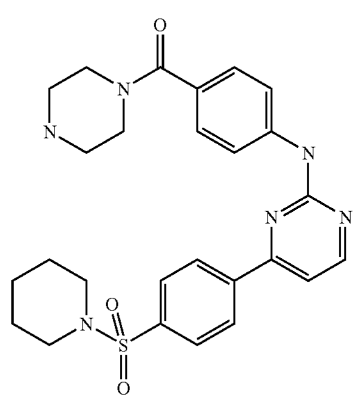 | 506.628 | 9.64 | 507.4 |

-continued

| Compound Number | Structure | MW | RT, min | M + 1 |
|---|---|---|---|---|
| 26-42 | 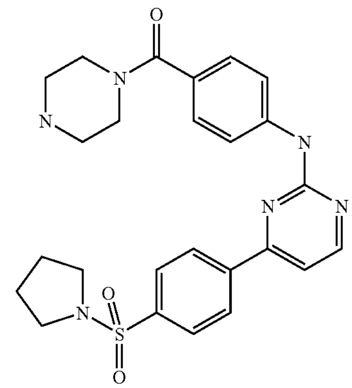 | 492.6012 | 9.08 | 493.4 |
| 26-43 | 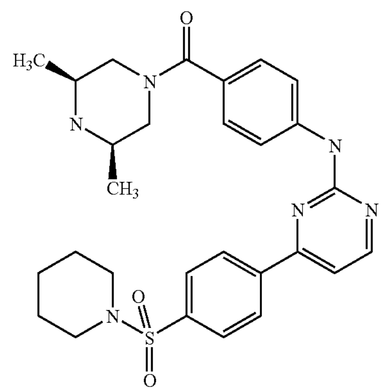 | 534.6816 | 9.9 | 535.3 |
| 26-44 | 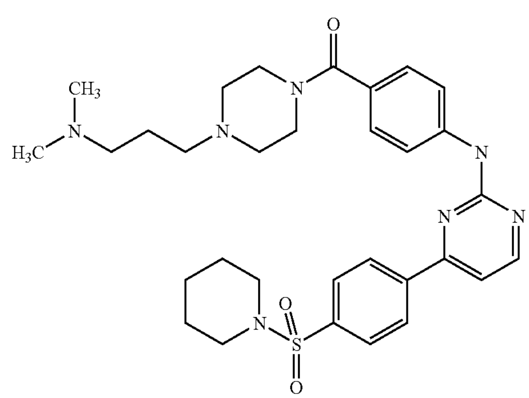 | 591.7769 | 9.16 | 592.5 |
| 26-45 | 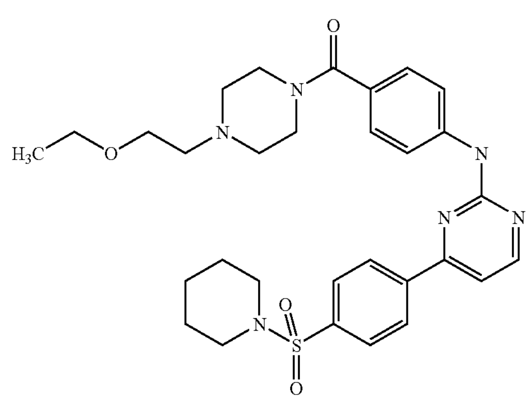 | 578.7342 | 10.25 | 579.5 |

-continued

| Compound Number | Structure | MW | RT, min | M + 1 |
|---|---|---|---|---|
| 26-46 | 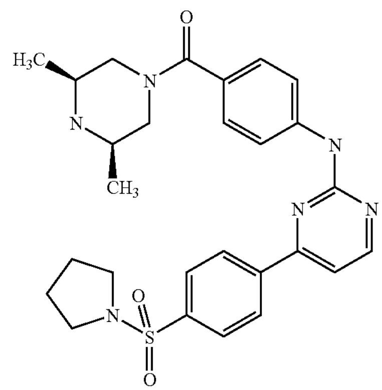 | 520.6548 | 9.32 | 521.5 |
| 26-47 | 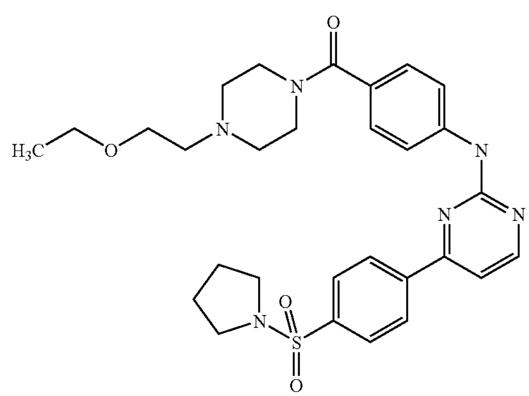 | 564.7074 | 9.7 | 565.5 |
| 26-48 | 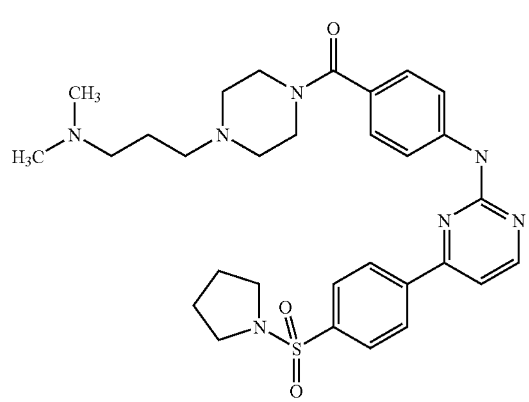 | 577.7501 | 8.66 | 578.5 |

| Compound Number | Structure | MW | RT, min | M + 1 |
|---|---|---|---|---|
| 26-49 | 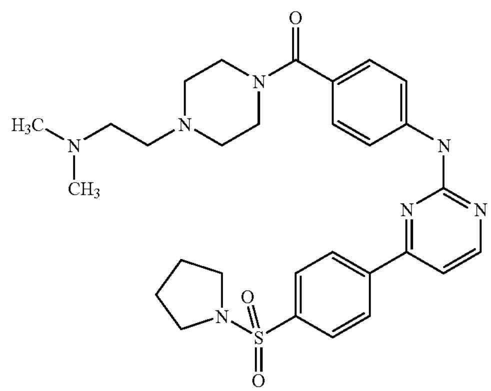 | 563.7233 | 8.77 | 564.5 |
| 26-50 | 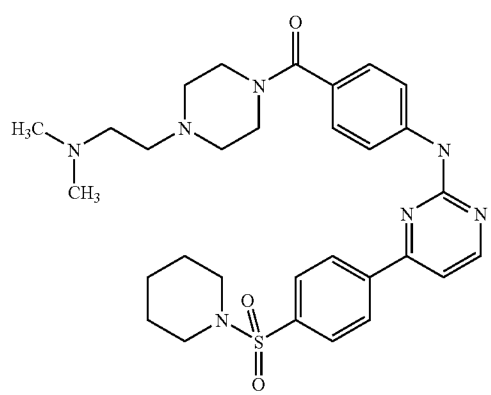 | 577.7501 | 9.28 | 578.5 |
| 26-51 | 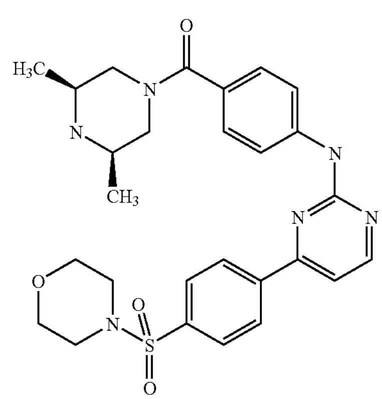 | 536.6538 | 8.89 | 537.5 |

-continued

| Compound Number | Structure | MW | RT, min | M + 1 |
|---|---|---|---|---|
| 26-52 | 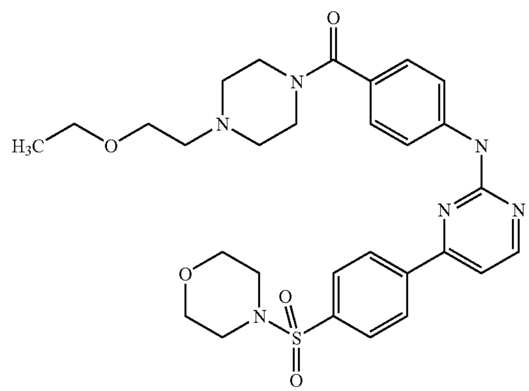 | 580.7064 | 9.29 | 581.4 |
| 26-53 | 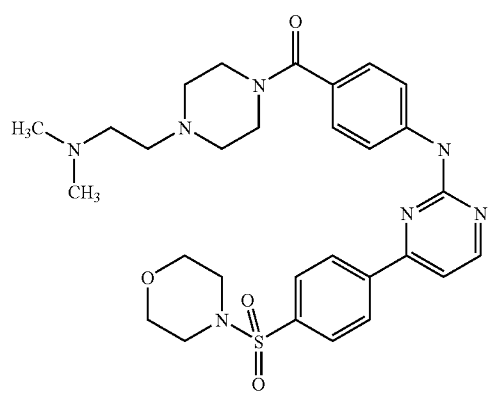 | 579.7223 | 8.4 | 580.5 |
| 26-54 | 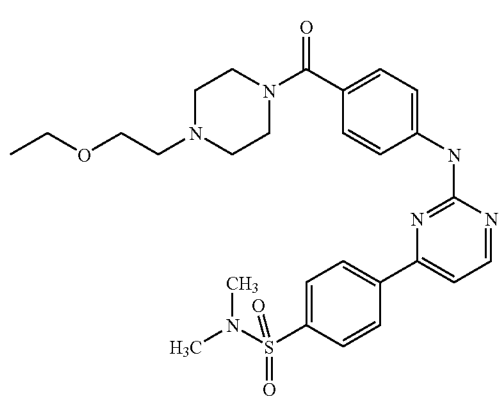 | 538.6629 | 9.44 | 539.3 |

| Compound Number | Structure | MW | RT, min | M + 1 |
|---|---|---|---|---|
| 26-55 | 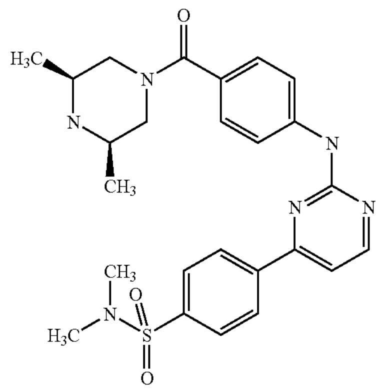 | 494.617 | 9.06 | 495.3 |
| 26-56 | 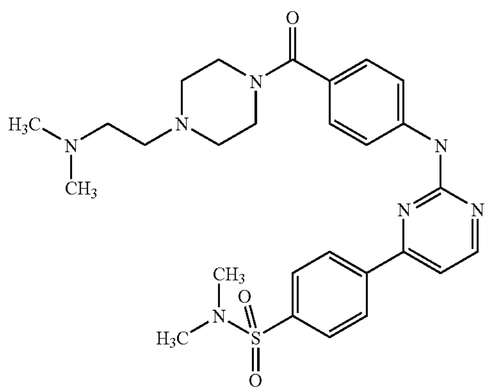 | 537.6855 | 8.56 | 538.5 |
| 26-57 | 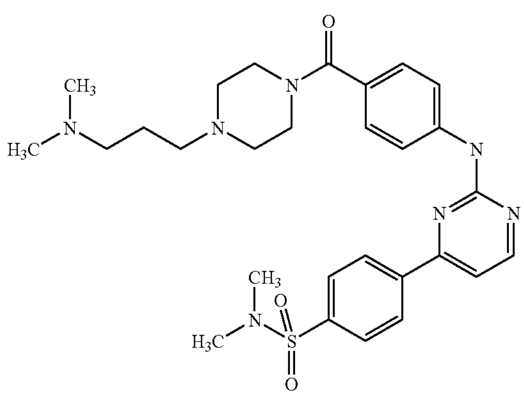 | 551.7123 | 8.47 | 552.5 |
| 26-58 | 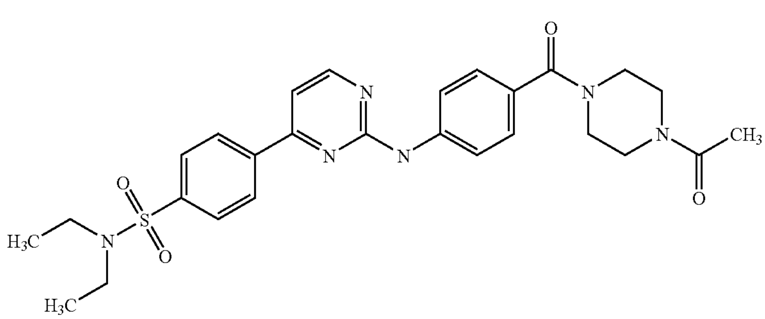 | 536.6538 | 10.64 | 537 |

-continued

| Compound Number | Structure | MW | RT, min | M + 1 |
|---|---|---|---|---|
| 26-59 | 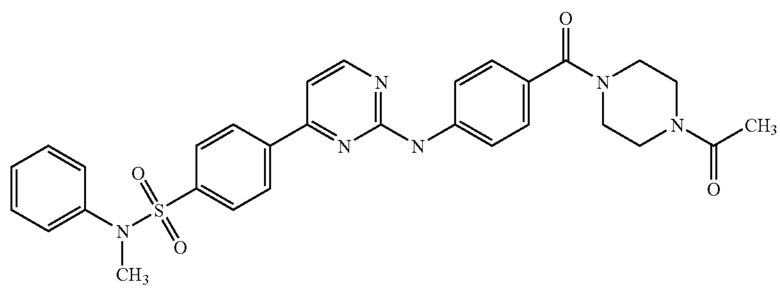 | 570.671 | 10.63 | 571 |
| 26-60 | 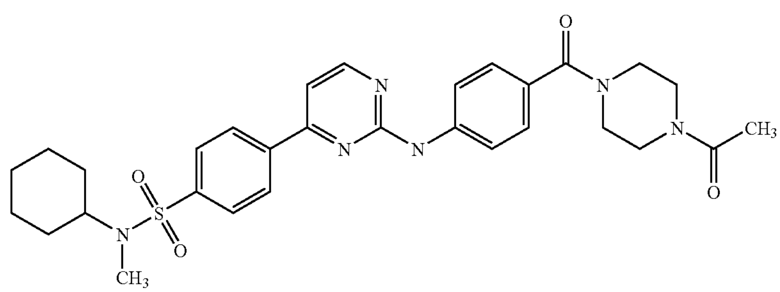 | 576.7184 | 11.43 | 577 |
| 26-61 | 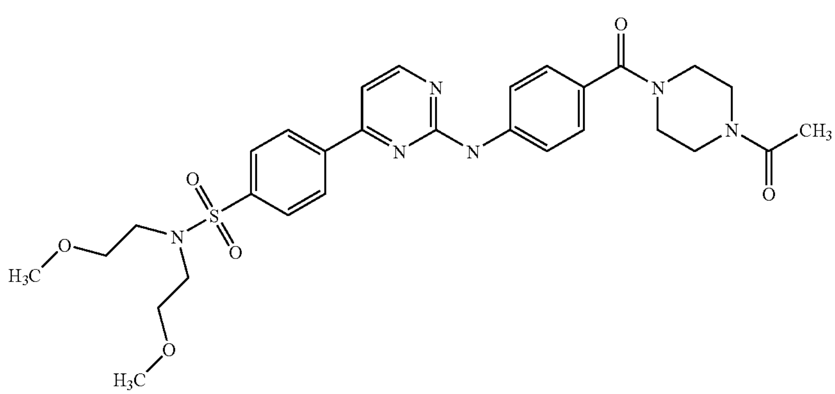 | 596.7054 | 10.01 | 597 |
| 26-62 | 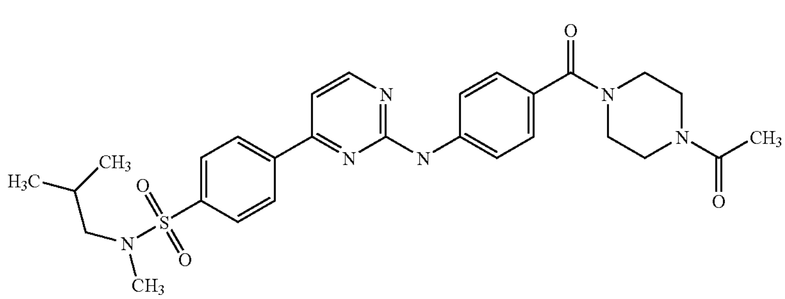 | 550.6806 | 11.75 | 551 |

| Compound Number | Structure | MW | RT, min | M + 1 |
|---|---|---|---|---|
| 26-63 | 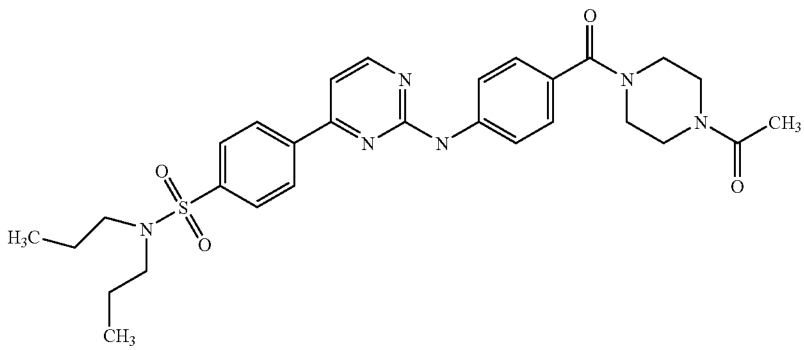 | 564.7074 | 11.82 | 565 |
| 26-64 | 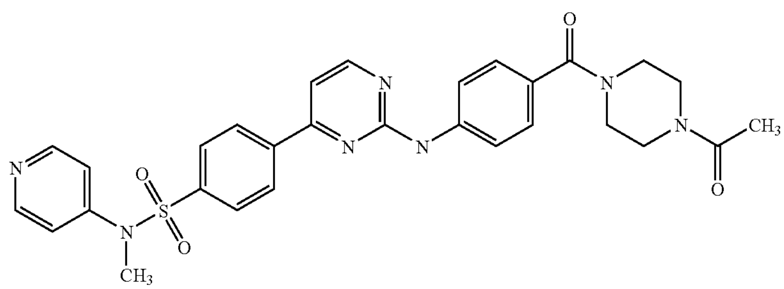 | 571.6591 | 8.11 | 572 |
| 26-65 | 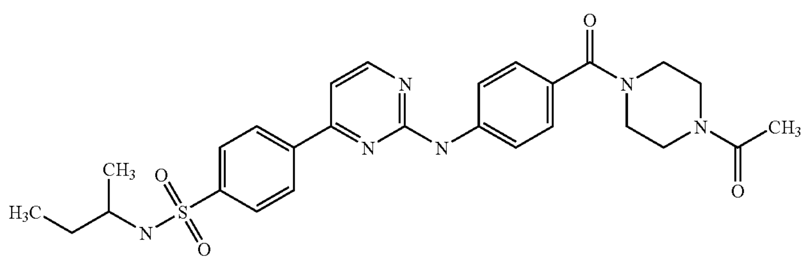 | 536.6538 | 10.28 | 537 |
| 26-66 | 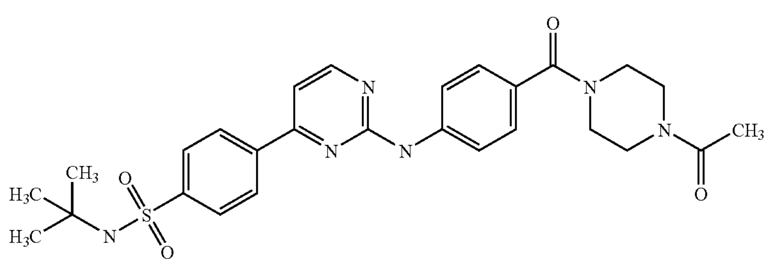 | 536.6538 | 10.24 | 537 |
| 26-67 | 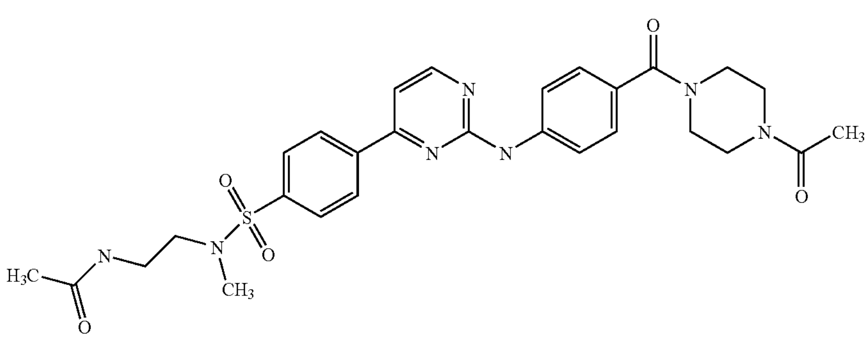 | 579.6787 | 8.71 | 580 |

| Compound Number | Structure | MW | RT, min | M + 1 |
| --- | --- | --- | --- | --- |
| 26-68 | 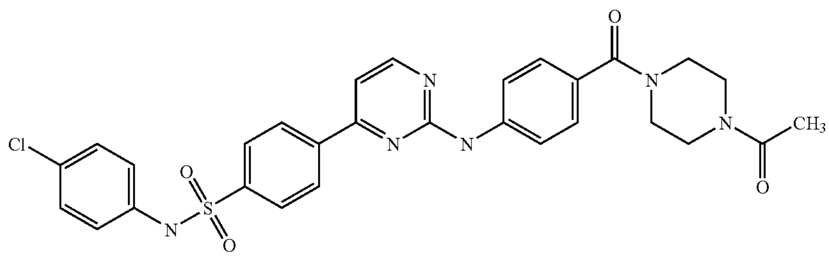 | 591.0893 | 11.07 | 591 |
| 26-69 | 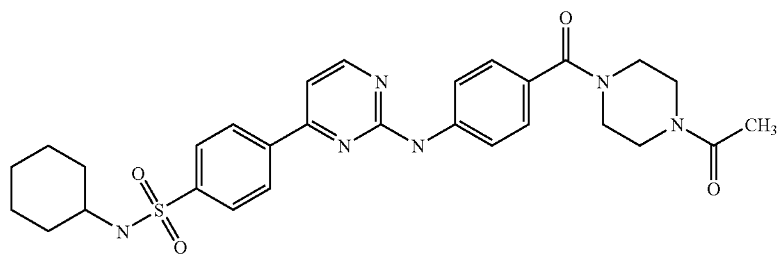 | 562.6916 | 10.9 | 563 |
| 26-70 | 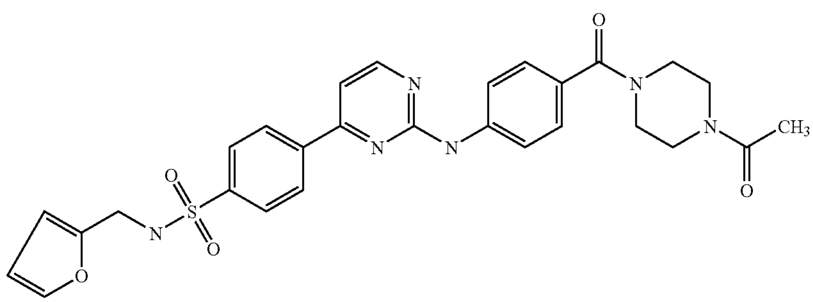 | 560.6322 | 10.74 | 561 |
Example 27
Synthesis of Sulfones
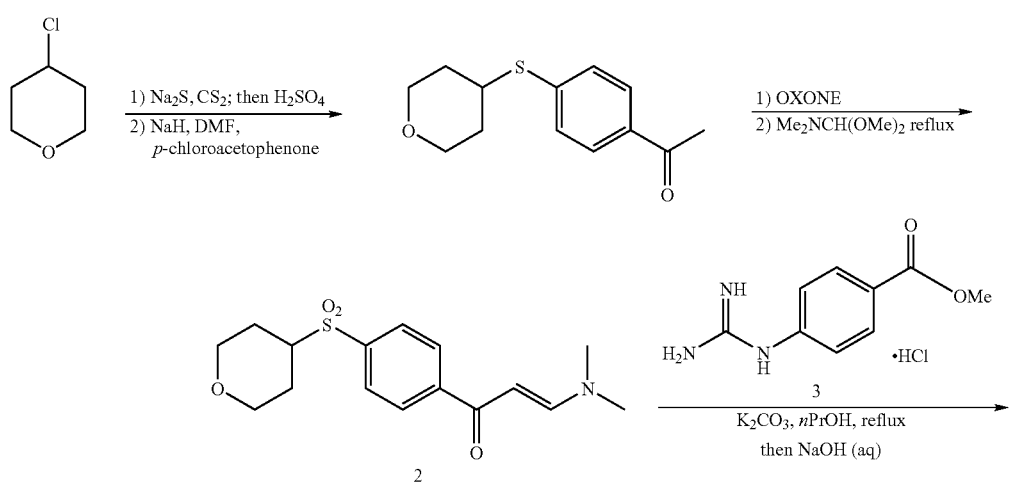

-continued

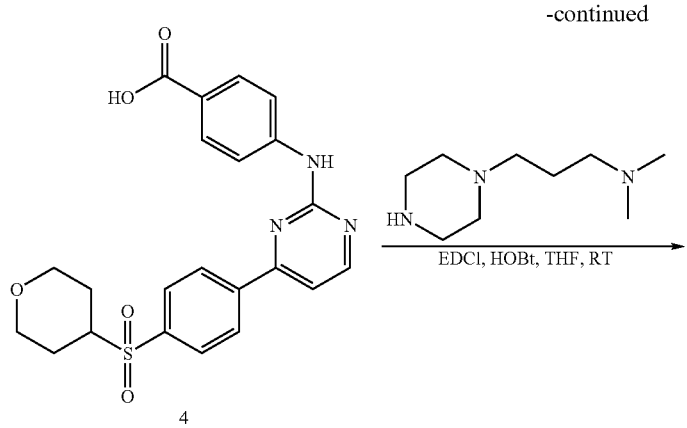 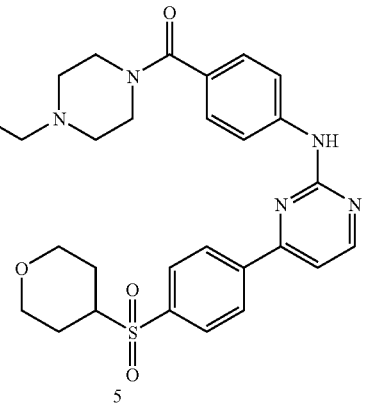

1-[4-(Tetrahydropyran-4-sulfanyl)phenyl]ethanone

To a stirred solution of $Na_2S$ (17.4 g, 0.22 mol) in water (26 mL) was added $CS_2$ (14.7 mL, 0.24 mol). The mixture was stirred at 60-70° C. for 6 h. To the resultant red solution of $Na_2CS_3$ was added 4-chlorotetrahydropyran (0.074 mol). The mixture was stirred for 12 h at 60-70° C. The mixture was then cooled to ~10° C. $H_2SO_4$ (conc.) was added to the mixture dropwise with stirring until a cloudy yellow color persisted. The mixture was then extracted with $CH_2Cl_2$ (3×50 mL). The aqueous layer was discarded and the $CH_2Cl_2$ layer was dried ($Na_2SO_4$) filtered, and concentrated. The crude thiol (47.5 mmol, ~64%) was dissolved in DMF (100 mL) and treated with NaH (1.9 g, 48 mmol). After the effervescence had ceased, p-chloroacetophenone (4.3 mL, 33 mmol) was added. The solution was then stirred at 110° C. for 3 h. The mixture was cooled to RT and then diluted with ether (200 mL). The ethereal suspension was washed with 5% HCl (aq, 2×100 mL), water (100 mL), and then brine (50 mL). The ether extract was dried ($MgSO_4$), filtered and concentrated to afford crude 1-[4-(tetrahydro-pyran-4-sulfanyl)-phenyl]-ethanone 1, which was purified by chromatography ($SiO_2$, 9:1 hex/EtOAc) to afford pure 1-[4-(tetrahydro-pyran-4-sulfanyl)phenyl]ethanone 1 (7.4 mmol, 16% from 4-chlorotetrahydropyran): HPLC Retention Time; 5.41 min. (Method B) M+1; 269.0.

3-Dimethylamino-1-[4-(tetrahydropyran-4-sulfonyl) phenyl]propenone

1-[4-(Tetrahydro-pyran-4-sulfanyl)-phenyl]-ethanone 1 (7.4 mmol) was dissolved in acetone/water (9:1 v/v, 100 mL). Oxone® (2.1 equiv, 9.1 g) was added to the solution. The reaction was stirred at room temperature for 5 h. The mixture was filtered and the majority of acetone was removed in vacuo. The solution was then diluted with water (50 mL) and extracted with $CH_2Cl_2$ (3×50 mL). The organic layer was dried ($Na_2SO_4$), filtered, and concentrated to afford the intermediate tetrahydropyranyl sulfone, which was taken up in dimethylformamide dimethylacetal (100 mL) and stirred at reflux for 12 h. The mixture was cooled and then concentrated to about one half of the original volume. Hexane was added to precipitate eneamino ketone intermediate. The mixture was filtered, washed with hexanes (50 mL), and dried to afford 3-dimethylamino-1-[4-(tetrahydro-pyran-4-sulfonyl)-phenyl]-propenone (2.2 g, 7 mmol): HPLC Retention Time; 5.18 min. (Method B) M+1; 324.0.

4-{4-[4-(Tetrahydropyran-4-sulfonyl)-phenyl]pyrimidin-2-ylamino}benzoic Acid 3-Dimethylamino-1-[4-(tetrahydro-pyran-4-sulfonyl)-phenyl]-propenone was then taken up in nPrOH (80 mL). To this solution was added 4-guanidinobenzoic acid, methyl ester, hydrochloride salt (1.1 equiv, 1.7 g) and $K_2CO_3$ (3 equiv, 2.9 g). The mixture was stirred at reflux for 24 h. After this time, 10% NaOH (aq, 50 mL) was added and the mixture was stirred at reflux for another 1 h. The mixture was then cooled to RT and concentrated to about half of the original volume. The pH of the mixture was then adjusted to pH 4-5 to precipitate 4-{4-[4-(tetrahydro-pyran-4-sulfonyl)-phenyl]-pyrimidin-2-ylamino}-benzoic acid 4. The acid was immediately filtered and washed with water (50 mL), cold EtOH (50 mL), and then dried (2.4 g, 5.5 mmol, 79% yield): HPLC Retention Time; 6.07 min. (Method B) M+1; 593.3.

[4-(3-Dimethylamino-propyl)-piperazin-1-yl]-(4-{4-[4-(tetrahydropyran-4-sulfonyl)phenyl]pyrimidin-2-ylamino}phenyl)methanone 4-{4-[4-(Tetrahydropyran-4-sulfonyl)-phenyl]pyrimidin-2-ylamino}benzoic acid 4 (0.26 g, 0.6 mmol) was dissolved in THF (5 mL). To this solution was added 1-(N,N-dimethylaminopropyl)piperazine (0.130 g). EDCI (0.136 g), and HOBt (0.096 g). The mixture was stirred 12 h. The mixture was then diluted with $CH_2Cl_2$ (20 mL) and washed with 2% NaOH (aq, 30 mL), water (30 mL), and then brine (30 mL). The organic layer was dried ($Na_2SO_4$), filtered, and concentrated. The crude solid was subjected to preparative HPLC (20-70 acetonitrile/water gradient, 20 min). The desired fractions were concentrated to remove most of the acetonitrile, and then the aqueous mixture was extracted with $CH_2Cl_2$/2% NaOH (aq). The organic layer was dried ($Na_2SO_4$), filtered, and concentrated to afford [4-(3-dimethylamino-propyl)piperazin 1-yl]-(4-{4-[4-(tetrahydropyran-4-sulfonyl)phenyl] pyrimidin-2-ylamino}phenyl)methanone 5 (0.079 g; 22%): HPLC Retention Time; 7.93 min. (Method B) M+1=593.3

Compounds listed below were prepared according to the above procedure.

| Compound Number | Structure | MW | RT, min | M + 1 |
|---|---|---|---|---|
| 27-1 | 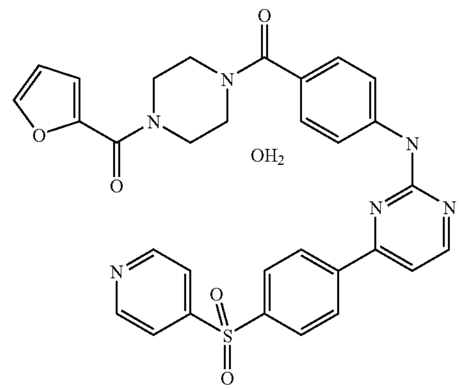 | 612.664 | 10.25 | 595.3 |
| 27-2 | 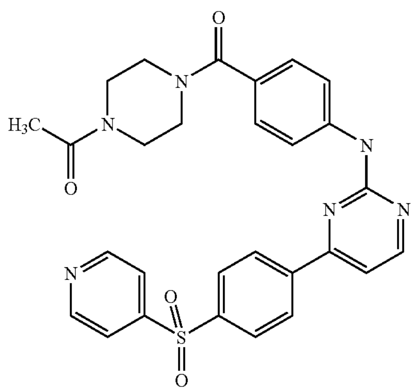 | 542.617 | 8.7 | 543.3 |
| 27-3 | 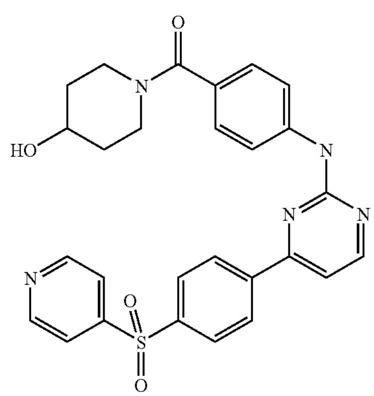 | 515.591 | 8.57 | 516.3 |
| 27-4 | 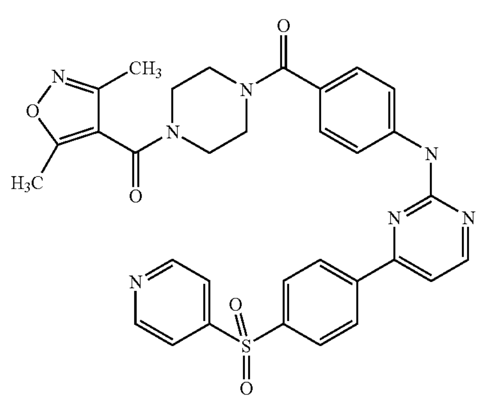 | 623.6911 | 9.36 | 624.3 |

-continued
| Compound Number | Structure | MW | RT, min | M + 1 |
|---|---|---|---|---|
| 27-4 | 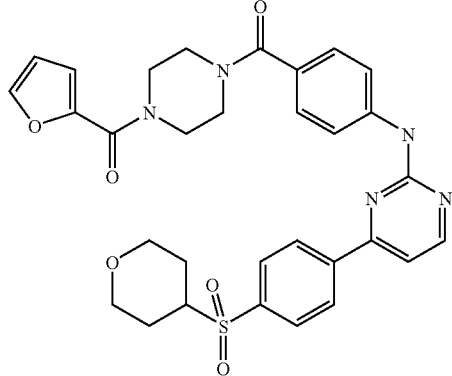 | 601.681 | 10.06 | 602.4 |
| 27-5 | 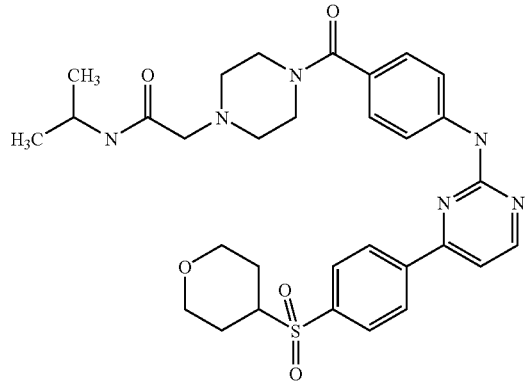 | 606.744 | 8.64 | 607.4 |
| 27-6 | 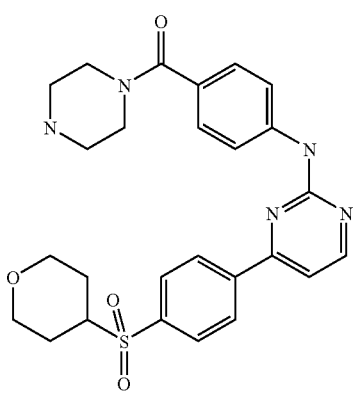 | 507.612 | 8.37 | 508.3 |

-continued

| Compound Number | Structure | MW | RT, min | M + 1 |
|---|---|---|---|---|
| 27-7 | 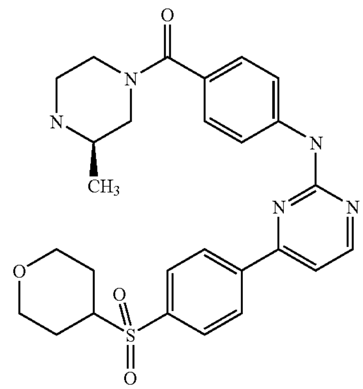 | 521.639 | 8.57 | 522.3 |
| 27-8 | 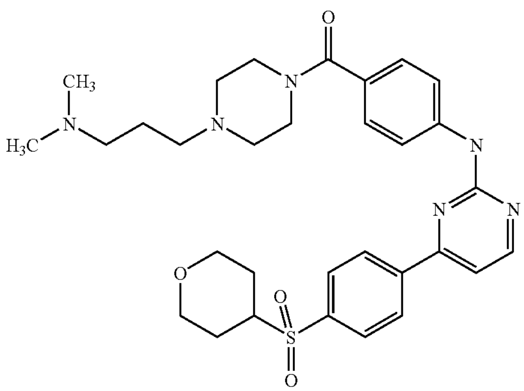 | 592.761 | 7.93 | 593.3 |
| 27-9 | 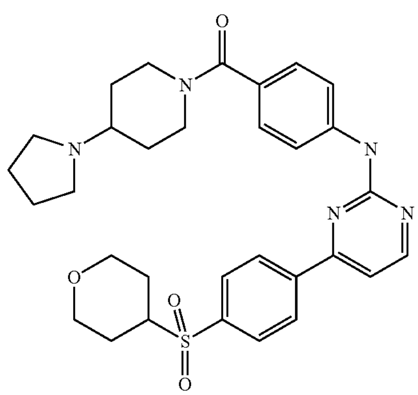 | 575.73 | 8.57 | 576.3 |
| 27-10 | 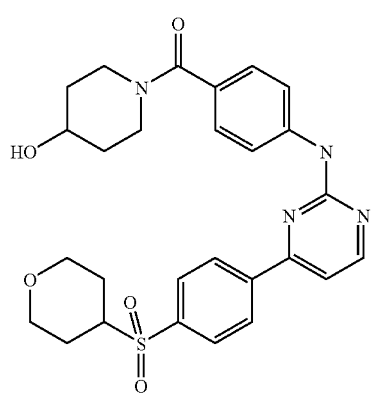 | 522.623 | 8.95 | 523.3 |

-continued

| Compound Number | Structure | MW | RT, min | M + 1 |
|---|---|---|---|---|
| 27-11 | 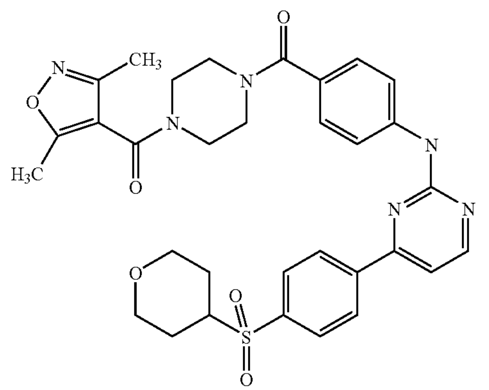 | 630.723 | 10.25 | 631.3 |
| 27-12 | 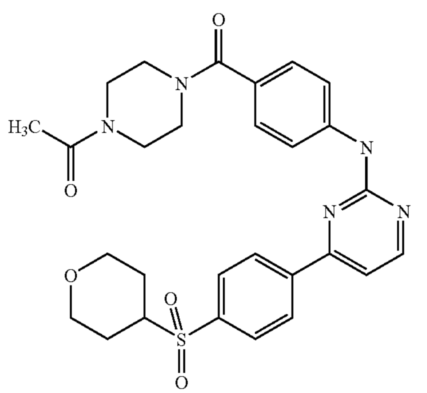 | 549.649 | 9.5 | 550 |
| 27-13 | 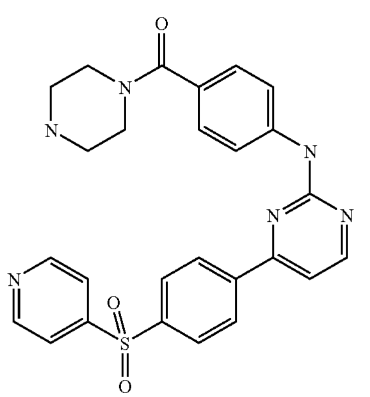 | 500.5806 | 8.8 | 501.3 |
| 27-14 | 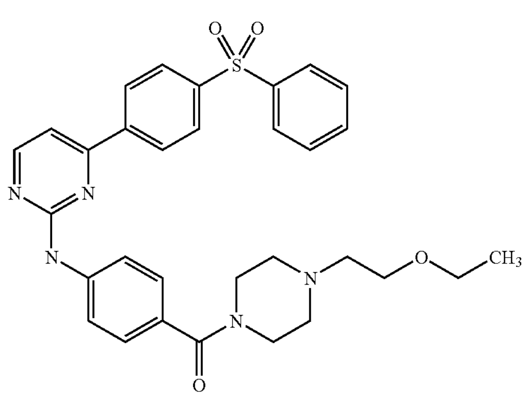 | 571.699 | 9.78 | 572.3 |

-continued

| Compound Number | Structure | MW | RT, min | M + 1 |
|---|---|---|---|---|
| 27-15 | 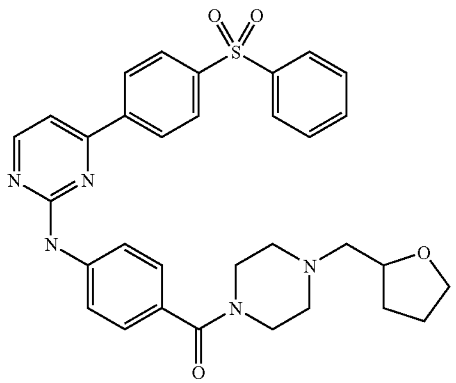 | 583.71 | 9.736 | 584.5 |
| 27-16 | 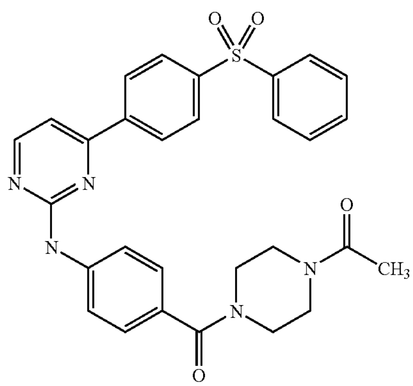 | 541.629 | 10.484 | 542.3 |
| 27-17 | 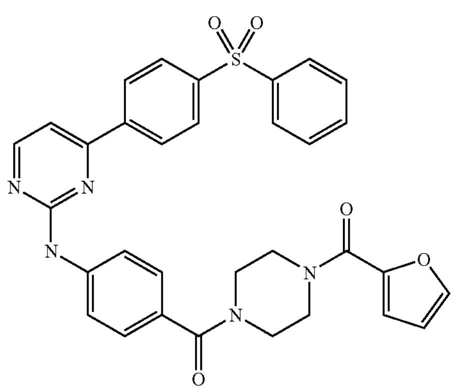 | 593.661 | 11.264 | 594.3 |
| 27-18 | 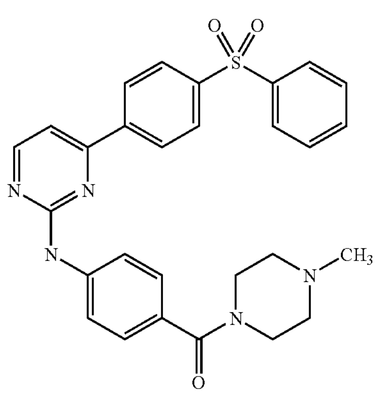 | 513.619 | 9.336 | 514.3 |

-continued
| Compound Number | Structure | MW | RT, min | M + 1 |
|---|---|---|---|---|
| 27-19 | 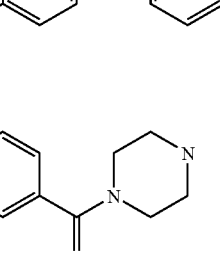 | 572.514 | 9.204 | 500 |
| 27-20 | 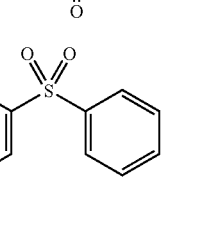 | 584.741 | 8.692 | 585.2 |
| 27-21 | 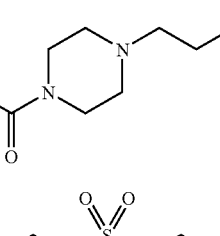 | 528.63 | 10.648 | 529.2 |
| 27-22 | 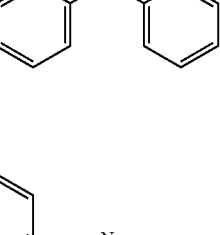 | 458.54 | 11.44 | 458.9 |

Example 28

Assays for Measuring Activity of Compounds

The Anilinopyrimidine Derivatives may be assayed for their activity according to the following procedures.

JNK2 Assay

To 10 µL of the test compound in 20%/DMSO/80% dilution buffer consisting of 20 mM HELPS (pH 7.6), 0.1 mM; EDTA, 2.5 mM magnesium chloride, 0.004% Triton×100, 2 µg/mL leupeptin, 20 mM β-glycerolphosphate, 0.1 mM sodium vanadate, and 2 mM DTT in water is added 30 µL of 50 ng His6-JNK2 in the same dilution buffer. The mixture is preincubated for 30 minutes at room temperature. Sixty microliter of 10 µg GST-c-Jun(1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton×100, 11 µM ATP, and 0.5 µCi γ-$^{32}$P ATP in water is added and the reaction is allowed to proceed for 1 hour at room temperature. The c-Jun phosphorylation is terminated by addition of 150 µL of 12.5% trichloroacetic acid. After 30 minutes, the precipitate is harvested onto a filter plate, diluted with 50 µL of the scintillation fluid and quantified by a counter. The $IC_{50}$ values are calculated as the concentration of the test compound at which the c-Jun phosphorylation is reduced to 50% of the control value. Preferred compounds of the present invention have all $IC_{50}$ valute ranging 0.01-10 µM in this assay.

JNK3 Assay

To 10 µL of the test compound in 20% DMSO/80% dilution buffer consisting of 20 mM HEPES (pH 7.6), 0.1 mM, EDTA, 2.5 mM magnesium chloride, 0.004% Triton×100, 2 µg/mL leupeptin, 20 mM β-glycerolphosphate, 0.1 mM sodium vanadate, and 2 mM DTT in water is added 30 µL of 200 ng His6-JNK3 in the same dilution buffer. The mixture is preincubated for 30 minutes at room temperature. Sixty microliter of 10 µg GST-c-Jun(1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton×100, 11 µM ATP, and 0.5 µCi γ-$^{32}$P ATP in water is added and the reaction is allowed to proceed for 1 hour at room temperature. The c-Jun phosphorylation is terminated b)y addition of 150 µL of 12.5% trichloroacetic acid. After 30 minutes, the precipitate is harvested onto a filter plate, diluted with 50 µL of the scintillation fluid and quantified by a counter. The $IC_{50}$ values are calculated as the concentration of the test compound at which the c-Jun phosphorylation is reduced to 50% of the control value. Preferred compounds of the present invention have an $IC_{50}$ value ranging 0.01-10 µM in this assay.

Jurkat T-cell II-2 Production Assay

Jurkat T cells (clone E6-1) are purchased from the American Tissue Culture Collection and maintained in growth media consisting of RPMI 1640 medium containing 2 mM L-glutamine (Mediatech), with 10% fetal bovine serum (Hyclone) and penicillin/streptomycin. All cells are cultured at 37° C. in 95% air and 5% $CO_2$. Cells are plated at a density of $0.2\times10^6$ cells per well in 200 µL of media. Compound stock (20 mM) is diluted in growth media and added to each well as a 10× concentrated solution in a volume of 25 µl, mixed, and allowed to pre-incubate with cells for 30 minutes. The compound vehicle (dimethylsulfoxide) is maintained at a final concentration of 0.5% in all samples. After 30 minutes the cells are activated with PMA (phorbol myristate acetate; final concentration 50 ng/mL) and PHA (phytohemagglutinin; final concentration 2 µg/mL). PMA and PHA are added as a 10× concentrated solution made up in growth media and added in a volume of 25 µL per well. Cell plates are cultured for 10 hours. Cells are pelleted by centrifugation and the media removed and stored at −20° C. Media aliquots are analyzed by sandwich ELISA for the presence of IL-2 as per the manufacturers instructions (Endogen). The $IC_{50}$ values are calculated as the concentration of the test compound at which the II-2 production was reduced to 50% of the control value. Preferred compounds of the present invention have an $IC_{50}$ value ranging 0.1-30 µM in this assay.

Rat in vivo LPS-induced TNF-α Production Assay

Male CD rats procured from Charles River Laboratories at 7 weeks of age are allowed to acclimate for one week prior to use. A lateral tail vein is cannulated percutanously with a 22-gage over-the-needle catheter under brief isoflurane anesthesia Rats are administered test compound either by intravenous injection via tile tail vein catheter or oral gavage 15 to 180 min prior to injection of 0.05 mg/kg LPS (E. Coli 055: B5). Catheters are flushed with 2.5 mL/kg of normal injectable saline. Blood is collected via cardiac puncture 90 minutes after LPS challenge. Plasma is prepared using lithium heparin separation tubes and frozen at −80° C. until analyzed. TNF-α are determined using a rat specific TNF-α ELISA kit (Busywork). The $ED_{50}$ values are calculated as the dose of the test compound at which the TNF-α production is reduced to 50% of the control value. Preferred compounds of the present invention have an $ED_{50}$ value ranging 1-30 mg/kg in this assay.

Detention of Phosphorylated c-Jun

Human umbilical vein endothelial cells (HUVEC) are cultured to 80% confluency and then pre-treated with compound (30 µM) at a final concentration of 0.5% DMSO. After 30 minutes, cells are stimulated with TNFα (30 ng/ml) for 20 minutes. Cells are washed, scraped from the plate, lyzed with 2× Laemmli buffer and heated to 100° C. for 5 minutes. Whole cell lysate (approx. 30 µg) is fractionated on Tris-glycine buffered 10% SDS-polyacrylamide gels (Novex, San Diego, Calif.) and transferred to nitrocellulose membrane (Amersham, Piscataway, N.J.). Membranes are blocked with 5% non-fat milk powder (BioRad, Hercules, Calif.) and incubated with antibody to phospho-cJun (1:1000 #91645) (New England Biolabs, Beverly, Mass.) and then donkey anti-rabbit horse radish peroxidase conjugated antibody (1:2500) (Amersham) in phosphate buffered saline with 0.1% Tween-20 and 5% non-fat milk powder. Immunoreactive proteins are detected with chemiluminescence and autoradiography (Amersham). Compounds are selected as inhibitors of the JNK pathway if they showed greater than 50% inhibition of cJun phosphorylation at 30 µM in this assay.

Example 29

Activity of Representative Compounds

Representative Anilinopyrimidine Derivatives were assayed for their ability to inhibit JNK2 by the assay set forth in Example 28. As noted above, preferred Anilinopyrimidine Derivatives have an $IC_{50}$ value ranging 0.01-10 µM in this assay. To this end, Anilinopyrimidine Derivative having an IC$_{50}$ value in the JNK Assay of 10 μM or less include Compound Nos. 1, 3-2, 3-4, 3-9, 3-10, 3-11, 3-12, 3-13, 3-14, 3-15, 3-16, 3-3-17, 3-22, 3-23, 3-24, 3-25, 3-26, 3-27, 3-29, 3-30, 3-34, 3-36, 3-37, 3-40, 17-2, 17-3, 17-6, 17-18, 17-20, 17-21, 17-22, 17-23, 17-24, 17-25, 17-26, 17-27, 17-28, 17-29, 17-30, 17-31, 17-32, 17-33, 17-34, 17-35, 17-37, 17-54, 17-86, 17-91, 17-106, 17-118, 17-119, 17-121, 17-127, 17-128, 17-129, 17-130, 17-131, 17-132, 17-133, 17-134, 17-135, 17-136, 17-137, 17-139, 17-140, 17-141, 17-142, 17-143, 17-144, 17-147, 17-148, 17-149, 17-150, 17-151, 17-152, 17-153, 17-154, 17-157, 17-158, 17-159, 17-160, 17-161, 17-162, 17-163, 17-164, 17-169, 17-171, 17-190, 17-215, 18, 20-1, 20-2, 20-3, 20-4, 20-5, 20-6, 22-10, 22-11 and 25-52. Preferred compounds of this invention have an IC$_{50}$ value in the JNK2 assay of 1 μM or less, and include Compound Nos. 3-2, 3-4, 3-9, 3-13, 3-14, 3-15, 3-23, 3-24, 3-25, 3-40, 17-20, 17-21, 17-22, 17-24, 17-29, 17-30, 17-31, 17-32, 17-33, 17-34, 17-37, 17-127, 17-129, 17-137, 17-141, 17-147, 17-154, 17-169, 17-171, 17-190, 18, 20-1, 20-3, 20-4, 22-10, 22-11, and 25-52.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed is:

1. A method for treating Type I diabetes, diabetes insipidus, diabetes mellitus, maturity-onset diabetes, juvenile diabetes, insulin-dependant diabetes, non-insulin dependant diabetes, malnutrition-related diabetes, ketosis-prone diabetes, or ketosis-resistant diabetes, comprising administering to a patient in need thereof an effective amount of a compound having the structure:

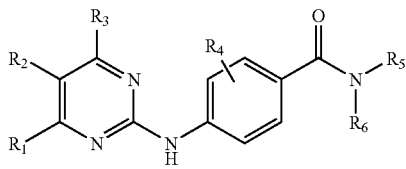

or a pharmaceutically acceptable salt thereof,
wherein:
$R_1$ is aryl optionally substituted with one to four substituents independently selected from $R_7$ or heteroaryl substituted with one to four substituents independently selected from $R_7$;
$R_2$ and $R_3$ are the same or different and are independently hydrogen or lower alkyl;
$R_4$ represents one to four optional substituents, wherein each substituent is the same or different and independently selected from halogen, hydroxy, lower alkyl or lower alkoxy;
$R_5$ and $R_6$ are the same or different and independently —$R_8$, —(CH$_2$)$_a$C(=O)R$_9$, —(CH$_2$)$_a$C(=O)OR$_9$, —(CH$_2$)$_a$C(=O)NR$_9$R$_{10}$, —(CH$_2$)$_a$C(=O)NR$_9$(CH$_2$)$_b$C(=O)R$_{10}$, —(CH$_2$)$_a$NR$_9$C(=O)R$_{10}$, —(CH$_2$)$_a$NR$_{11}$C(=O)NR$_9$R$_{10}$, —(CH$_2$)$_a$NR$_9$R$_{10}$, —(CH$_2$)$_a$OR$_9$, —(CH$_2$)$_a$SO$_c$R$_9$, or —(CH$_2$)$_a$SO$_2$NR$_9$R$_{10}$;

or $R_5$ and $R_6$ taken together with the nitrogen atom to which they are attached to form a heterocycle or substituted heterocycle;
$R_7$ is at each occurrence independently halogen, hydroxy, cyano, nitro, carboxy, alkyl, alkoxy, haloalkyl, acyloxy, thioalkyl, sulfinylakyl, sulfonylalkyl, hydroxyalkyl, aryl, substituted aryl, aralkyl, substituted aralkyl, heterocycle, substituted heterocycle, heterocyclealkyl, substituted heterocyclealkyl, —C(=O)OR$_8$, —OC(=O)R$_8$, —C(=O)NR$_8$R$_9$, —C(=O)NR$_8$OR$_9$, —SO$_c$R$_8$, —SO$_c$NR$_8$R$_9$, —NR$_8$SO$_c$R$_9$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;
$R_8$, $R_9$, $R_{10}$ and $R_{11}$ are the same or different and at each occurrence independently hydrogen, alkyl, substituted alkyl, aryl, substituted aryl, aralkyl, substituted arylalkyl, heterocycle, substituted heterocycle, heterocyclealkyl or substituted heterocyclealkyl;
or $R_8$ and $R_9$ taken together with the atom or atoms to which they are attached to form a heterocycle or substituted heterocycle;
a and b are the same or different and at each occurrence independently selected from 0, 1, 2, 3 or 4; and
c is at each occurrence 0, 1 or 2.

2. The method of claim 1, wherein the compound has the structure:

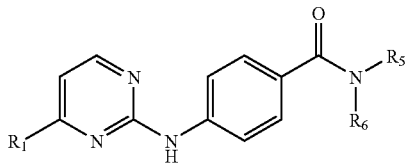

or a pharmaceutically acceptable salt thereof,
wherein:
$R_1$ is aryl optionally substituted with one to four substituents independently selected from $R_7$ or heteroaryl substituted with one to four substituents independently selected from $R_7$;
$R_5$ and $R_6$ are the same or different and independently $R_8$, —(CH$_2$)$_a$C(=O)R$_9$, —(CH$_2$)$_a$C(=O)OR$_9$, —(CH$_2$)$_a$C(=O)NR$_9$R$_{10}$, —(CH$_2$)$_a$C(=O)NR$_9$(CH$_2$)$_b$C(=O)R$_{10}$, (CH$_2$)$_a$NR$_9$C(=O)R$_{10}$, —(CH$_2$)$_a$NR$_{11}$C(=O)NR$_9$R$_{10}$, —(CH$_2$)$_a$NR$_9$R$_{10}$, —(CH$_2$)$_a$OR$_9$, —(CH$_2$)$_a$SO$_c$R$_9$, or —(CH$_2$)$_a$SO$_2$NR$_9$R$_{10}$;
or $R_5$ and $R_6$ taken together with the nitrogen atom to which they are attached to form a heterocycle or substituted heterocycle;
$R_7$ is at each occurrence independently halogen, hydroxy, cyano, nitro, carboxy, alkyl, alkoxy, haloalkyl, acyloxy, thioalkyl, sulfinylakyl, sulfonylalkyl, hydroxyalkyl, aryl, substituted aryl, aralkyl, substituted aralkyl, heterocycle, substituted heterocycle, heterocyclealkyl, substituted heterocyclealkyl, —C(=O)O$_8$, —OC(=O)R$_8$, —C(=O)NR$_8$R$_9$, —C(=O)NR$_8$OR$_9$, —SO$_c$R$_8$, —SO$_c$NR$_8$R$_9$, —NR$_8$SO$_c$R$_9$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;
$R_8$, $R_9$, $R_{10}$ and $R_{11}$ are the same or different and at each occurrence independently hydrogen, alkyl, substituted alkyl, aryl, substituted aryl, aralkyl, substituted arylalkyl, heterocycle, substituted heterocycle, heterocyclealkyl or substituted heterocyclealkyl;

or $R_8$ and $R_9$ taken together with the atom or atoms to which they are attached to form a heterocycle or substituted heterocycle;

a and b are the same or different and at each occurrence independently selected from 0, 1, 2, 3 or 4; and c is at each occurrence 0, 1 or 2.

3. The method of claim 1, wherein the compound has the structure:

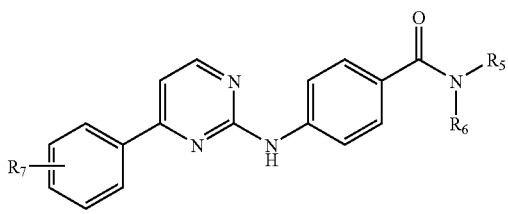

or a pharmaceutically acceptable salt thereof,
wherein:
$R_5$ and $R_6$ are the same or different and independently —$R_8$, —$(CH_2)_aC(=O)R_9$, —$(CH_2)_aC(=O)OR_9$, —$(CH_2)_aC(=O)NR_9R_{10}$, —$(CH_2)_aC(=O)NR_9(CH_2)_bC(=O)R_{10}$, —$(CH_2)_aNR_9C(=O)R_{10}$, —$(CH_2)_aNR_{11}C(=O)NR_9R_{10}$, —$(CH_2)_aNR_9R_{10}$, $(CH_2)_aOR_9$, —$(CH_2)_aSO_cR_9$, or —$(CH_2)_aSO_2NR_9R_{10}$;

or $R_5$ and $R_6$ taken together with the nitrogen atom to which they are attached to form a heterocycle or substituted heterocycle;

$R_7$ is at each occurrence independently halogen, hydroxy, cyano, nitro, carboxy, alkyl, alkoxy, haloalkyl, acyloxy, thioalkyl, sulfinylakyl, sulfonylalkyl, hydroxyalkyl, aryl, substituted aryl, aralkyl, substituted aralkyl, heterocycle, substituted heterocycle, heterocyclealkyl, substituted heterocyclealkyl, —$C(=O)OR_8$, —$OC(=O)R_8$, —$C(=O)NR_8R_9$, —$C(=O)NR_8OR_9$, —$SO_cR_8$, —$SO_cNR_8R_9$, —$NR_8SO_cR_9$, —$NR_8R_9$, —$NR_8C(=O)R_9$, —$NR_8C(=O)(CH_2)_bOR_9$, —$NR_8C(=O)(CH_2)_bR_9$, —$O(CH_2)_bNR_8R_9$, or heterocycle fused to phenyl;

$R_8$, $R_9$, $R_{10}$ and $R_{11}$ are the same or different and at each occurrence independently hydrogen, alkyl, substituted alkyl, aryl, substituted aryl, aralkyl, substituted arylalkyl, heterocycle, substituted heterocycle, heterocyclealkyl or substituted heterocyclealkyl;

or $R_8$ and $R_9$ taken together with the atom or atoms to which they are attached to form a heterocycle or substituted heterocycle;

a and b are the same or different and at each occurrence independently selected from 0, 1, 2, 3 or 4; and c is at each occurrence 0, 1 or 2.

4. The method of claim 3, wherein the compound has the structure:

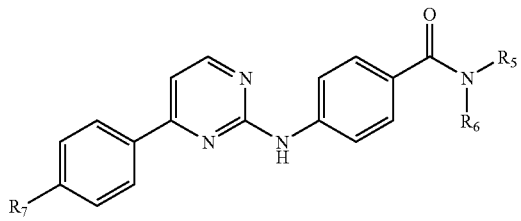

or a pharmaceutically acceptable salt thereof,
wherein:
$R_5$ and $R_6$ are the same or different and independently —$R_8$, —$(CH_2)_aC(=O)R_9$, —$(CH_2)_aC(=O)OR_9$, —$(CH_2)_aC(=O)NR_9R_{10}$, —$(CH_2)_aC(=O)NR_9(CH_2)_bC(=O)R_{10}$, —$(CH_2)_aNR_9C(=O)R_{10}$, —$(CH_2)_aNR_{11}C(=O)NR_9R_{10}$, —$(CH_2)_aNR_9R_{10}$, —$(CH_2)_aOR_9$, —$(CH_2)_aSO_cR_9$, or —$(CH_2)_aSO_2NR_9R_{10}$;

or $R_5$ and $R_6$ taken together with the nitrogen atom to which they are attached to form a heterocycle or substituted heterocycle;

$R_7$ is at each occurrence independently halogen, hydroxy, cyano, nitro, carboxy, alkyl, alkoxy, haloalkyl, acyloxy, thioalkyl, sulfinylakyl, sulfonylalkyl, hydroxyalkyl, aryl, substituted aryl, aralkyl, substituted aralkyl, heterocycle, substituted heterocycle, heterocyclealkyl, substituted heterocyclealkyl, —$C(=O)OR_8$, —$OC(=O)R_8$, —$C(=O)NR_8R_9$, —$C(=O)NR_8OR_9$, —$SO_cNR_8$, —$SO_cNR_8R_9$, —$NR_8SO_cR_9$, —$NR_8R_9$, —$NR_8C(=O)R_9$, —$NR_8C(=O)(CH_2)_bOR_9$, —$NR_8C(=O)(CH_2)_bR_9$, —$O(CH_2)_bNR_8R_9$, or heterocycle fused to phenyl;

$R_8$, $R_9$, $R_{10}$ and $R_{11}$ are the same or different and at each occurrence independently hydrogen, alkyl, substituted alkyl, aryl, substituted aryl, aralkyl, substituted arylalkyl, heterocycle, substituted heterocycle, heterocyclealkyl or substituted heterocyclealkyl;

or $R_8$ and $R_9$ taken together with the atom or atoms to which they are attached to form a heterocycle or substituted heterocycle;

a and b are the same or different and at each occurrence independently selected from 0, 1, 2, 3 or 4; and c is at each occurrence 0, 1 or 2.

* * * * *

UNITED STATES PATENT AND TRADEMARK OFFICE
CERTIFICATE OF CORRECTION

PATENT NO. : 7,429,599 B2
APPLICATION NO. : 10/395811
DATED : September 30, 2008
INVENTOR(S) : Satoh and Bhagwat It is certified that error appears in the above-identified patent and that said Letters Patent is hereby corrected as shown below:

At Claim 2, column 304, line 60, please replace "-C(=O)O$_8$" with -- -C(=O)OR$_8$ --.

Signed and Sealed this

Eleventh Day of November, 2008

JON W. DUDAS
*Director of the United States Patent and Trademark Office*